(12) United States Patent
Buchholz et al.

(10) Patent No.: US 9,462,808 B2
(45) Date of Patent: *Oct. 11, 2016

(54) PESTICIDAL COMPOSITIONS

(75) Inventors: Anke Buchholz, Stein (CH); Christoph Grimm, Stein (CH)

(73) Assignee: Syngenta Participants AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/701,454

(22) PCT Filed: May 26, 2011

(86) PCT No.: PCT/EP2011/058625
§ 371 (c)(1),
(2), (4) Date: Feb. 12, 2013

(87) PCT Pub. No.: WO2011/151247
PCT Pub. Date: Dec. 8, 2011

(65) Prior Publication Data
US 2013/0150394 A1  Jun. 13, 2013

(30) Foreign Application Priority Data
May 31, 2010 (EP) .................................. 10164501

(51) Int. Cl.
A01N 43/90 (2006.01)
C07D 471/10 (2006.01)

(52) U.S. Cl.
CPC ............. *A01N 43/90* (2013.01); *C07D 471/10* (2013.01)

(58) Field of Classification Search
None
See application file for complete search history.

(56) References Cited

U.S. PATENT DOCUMENTS 9,018,135 B2 * 4/2015 Buchholz ............... A01N 43/90
504/313

FOREIGN PATENT DOCUMENTS

| WO | 01/17972 | 3/2001 | |
|---|---|---|---|
| WO | 2009/049851 | 4/2009 | |
| WO | WO 2009049851 A1 * | 4/2009 | |
| WO | 2010/052161 | 5/2010 | |
| WO | WO 2010052161 A2 * | 5/2010 | |
| WO | 2010/063670 | 6/2010 | |
| WO | WO 2010066780 A1 * | 6/2010 | ............. A01N 43/90 |

OTHER PUBLICATIONS

Davies, Herbicide safeners—commercial products and tools for agrochemical research, Pestic. Outlook, Dec. 10-15, 2001.*
U.S. Appl. No. 13/989,341, filed May 2013, Buckholz.*
U.S. Appl. No. 13/701,460, filed Nov. 2012, Buckholz.*
International Search Report, International Application No. PCT/EP2011/058625, completion date: Dec. 1, 2011.

* cited by examiner

*Primary Examiner* — Svetlana M Ivanova
(74) *Attorney, Agent, or Firm* — Brian D. McAlhaney

(57) ABSTRACT

A pesticidal composition comprising a pesticidal effective amount of at least one compound of formula (I) in which the substituents are as defined as in claim 1, and a safener.

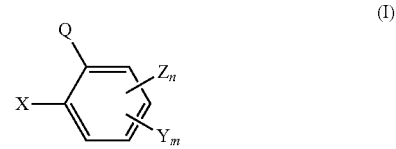

5 Claims, No Drawings

PESTICIDAL COMPOSITIONS

This application is a 371 of International Application No. PCT/EP2011/058625 filed May 26, 2011, which claims priority to EP 10164501.8 filed May 31, 2010, the contents of which are incorporated herein by reference.

The present invention relates to new pesticidal, in particular insecticidal, acaricidal, molluscicidal and nematicidal compositions and to methods of using them to combat and control pests such as insect, acarine, mollusc and nematode pests.

The application of pesticidal compositions to crop plants or the locus thereof can result in considerable damage being caused to crop plants, for example in dependence upon the concentration of the pesticide and the mode of its application, the crop plant, the nature of the soil and the climatic conditions, such as period of exposure to light, temperature and amounts of precipitation. In order to counter those problems, various substances have already been proposed as safeners that are capable of protecting the crop plant against the damaging action of the pesticide. It has been found that a given safener often has a very specific action both in respect of the crop plants and in respect of the pesticide and in some cases also in dependence upon the mode of application. This means that a specific safener is often suitable only for a specific crop plant and a particular class of pesticide or a specific pesticide.

Surprisingly, it has been found that the phytotoxic action of certain pesticidal cyclic dione compounds can be significantly reduced while the pesticidal action on the pests to be controlled is virtually unimpaired.

The present invention accordingly relates to a pesticidal composition comprising (a) a pesticidal effective amount of at least one compound of formula I

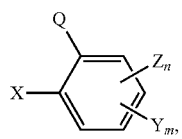
(I)

in which Q is
i or ii or iii

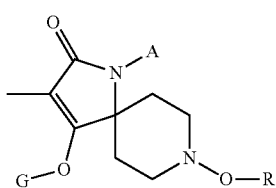
i

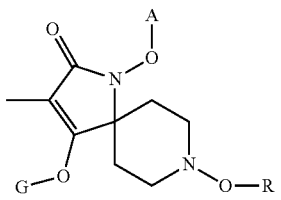
ii

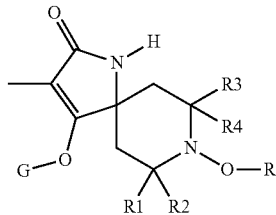
iii

X, Y and Z independently of each other are $C_{1-4}$alkyl, $C_{3-6}$cycloalkyl, $C_{1-4}$haloalkyl, $C_{1-4}$ alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, an ammonium, a sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy ($C_{1-4}$)alkyl or a group selected from G;

A is $C_{1-6}$alkyl, $C_{1-6}$haloalkyl, $C_{3-6}$cycloalkyl, $C_{3-6}$cycloalkyl ($C_{1-4}$)alkyl, or $C_{3-6}$cycloalkyl-($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$) alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio ($C_{1-4}$)alkyl, $C_{1-4}$alkylsulfinyl($C_{1-4}$)alkyl or $C_{1-4}$alkylsulfonyl($C_{1-4}$)alkyl; and when Q is ii A may also be hydrogen, furanyl-($C_{1-4}$)alkyl, tetrahydro-thiofuranyl, tetrahydro-thiopyranyl or 1-($C_{1-4}$)alkoxy-piperidin-4-yl; and $R_1$, $R_2$, $R_3$ and $R_4$, independently of each other, are hydrogen or methyl;

or an agrochemically acceptable salt or an N-oxide thereof, and (b) a safener, where the ratio of compound of formula I to safener is from 20:1 to 0.5:15.

In the compounds of the formula I, each alkyl moiety either alone or as part of a larger group is a straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups preferably have a preferred chain length of from 1 to 4 carbon atoms. Alkoxy is, for example, methoxy, ethoxy, propoxy, i-propoxy, n-butoxy, isobutoxy, sec-butoxy and tert-butoxy. Such groups can be part of a larger group such as alkoxyalkyl and alkoxyalkoxyalkyl. Alkoxyalkyl groups preferably have a chain length of 1 to 4 carbon atoms. Alkoxyalkyl is, for example, methoxymethyl, methoxyethyl, ethoxymethyl, ethoxyethyl, n-propoxymethyl, n-propoxyethyl or isopropoxymethyl.

Halogen is generally fluorine, chlorine, bromine or iodine. This also applies, correspondingly, to halogen in combination with other meanings, such as haloalkyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2- trichloroethyl; preferably trichloromethyl, difluorochloromethyl, difluoromethyl, trifluoromethyl and dichlorofluoromethyl.

The cycloalkyl groups preferably have from 3 to 6 ring carbon atoms, for example cyclopropyl, cyclobutyl, cyclopentyl and cyclohexyl. In these rings, a methylene group can be replaced by an oxygen and/or sulphur atom, which leads, for example, to oxetanyl, tetrahydrofuranyl, tetrahydropyranyl, furanyl, tetrahydro-thiofuranyl and tetrahydro-thiopyranyl rings.

Phenyl, also as part of a substituent such as benzyl, may be substituted, preferably by alkyl, haloalkyl or halogen groups. In this case, the substituents can be in ortho, meta and/or para position. The preferred substituent positions are the ortho and para positions to the ring attachment point.

The latentiating groups G are selected to allow its removal by one or a combination of biochemical, chemical or physical processes to afford compounds of formula I where G is hydrogen before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. Such latentiating groups are known in the art, for example, from WO08/071,405 and WO09/074,314, WO09/049,851, WO10/063,670 and WO10/066,780.

In particular, the latentiating group G is a group —C($X^a$)—$R^a$ or —C($X^b$)—$X^c$—$R^b$, and $X^a$, $R^a$, $X^b$, $X^c$ and $R^b$ are as defined above. wherein $X^a$, $X^b$ and $X^c$ are independently of each other oxygen or sulfur; $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, and $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_2$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro, heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro, It is preferred that G is hydrogen, a metal, preferably an alkali metal or alkaline earth metal, or an ammonium or sulfonium group, where hydrogen is especially preferred.

Depending on the nature of the substituents, compounds of formula I may exist in different isomeric forms. When G is hydrogen, for example, compounds of formula I may exist in different tautomeric forms:

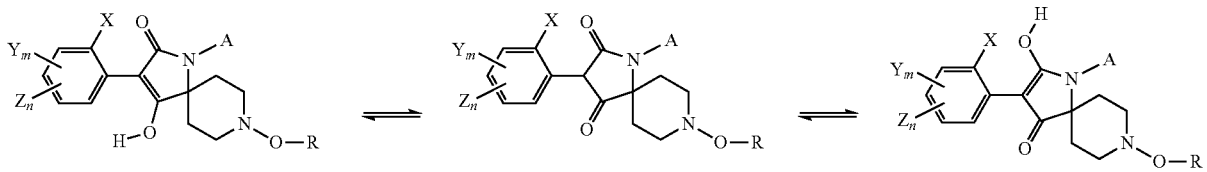

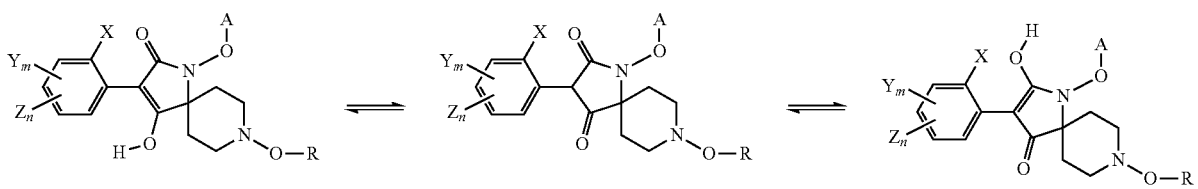

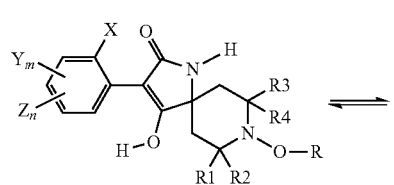 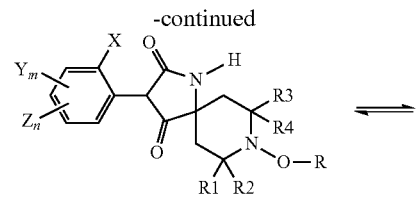 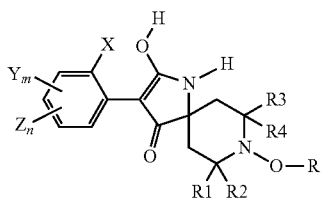

This invention covers all isomers and tautomers and mixtures thereof in all proportions. Also, when substituents contain double bonds, cis- and trans-isomers can exist. These isomers, too, are within the scope of the claimed compounds of the formula I.

The invention covers also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula $[N(R_a R_b R_c R_d)]OH$, wherein $R_a$, $R_b$, $R_c$, and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_e R_f R_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions. It should be understood that in those compounds of formula I, where G is a metal, ammonium or sulfonium as mentioned above and as such represents a cation, the corresponding negative charge is largely delocalised across the O—C═C—C═O unit.

The compounds of formula I also include hydrates which may be formed during the salt formation.

According to the present invention, the compounds of formula I are used in combination with safeners preferably selected from cloquintocet-mexyl, cloquintocet acid and salts thereof, fenchlorazole-ethyl, fenchlorazole acid and salts thereof, mefenpyr-diethyl, mefenpyr diacid, isoxadifen-ethyl, isoxadifen acid, furilazole, furilazole R isomer, benoxacor, dichlormid, AD-67, oxabetrinil, cyometrinil, cyometrinil Z-isomer, fenclorim, cyprosulfamide, naphthalic anhydride, flurazole, N-(2-methoxybenzoyl)-4-[(methylaminocarbonyl)amino]-benzenesulfonamide, CL 304,415, dicyclonon, fluxofenim, DKA-24, R-29148 and PPG-1292. A safening effect can also be observed for the mixtures compound of the formula I with dymron, MCPA, mecoprop and mecoprop-P. Thus, the preferred combinations of compound of formula I with safeners are the mixtures compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+N-(2-methoxybenzoyl)-4-[(methylaminocarbonyl)amino]-benzenesulfonamide, compound of formula I+CL 304,415, compound of formula I+dicyclonon, compound of formula I+fluxofenim, compound of formula I+DKA-24, compound of formula I+R-29148 and compound of formula I+PPG-1292, compound of formula I+dymron, compound of formula I+MCPA, compound of formula I+mecoprop and compound of formula I+mecoprop-P, where in these combinations the ratio of compound of formula I to safener ranges from 20:1 to 0.5:15.

The above-mentioned safeners are described, for example, in the Pesticide Manual, Twelfth Edition, British Crop Protection Council, 2000, or other readily available resources. R-29148 is described, for example by P. B. Goldsbrough et al., Plant Physiology, (2002), Vol. 130 pp. 1497-1505 and references, PPG-1292 is known from WO09211761 and N-(2-methoxybenzoyl)-4-[(methylaminocarbonyl)amino]benzenesulfonamide is known from EP365484. DKA-24 is known from DE-A-3426541 and CL304415 from EP-A-613654.

Preferably, in these mixtures, the compound of the formula I is one of those compounds listed in Tables 1 to 116, Tables 1ii-102ii and Tables 1iii-22iii, below.

Preferably, the ratio of formula I to safener is from 15:1 to 1:10. Preferably, in cereals, the ratio of formula I to safener is from 1:1 to 1:8, more preferably from 1:1 to 1:4. Preferably, in rice, the ratio of formula I to safener is from 15:1 to 1:1.

Preferably, the safeners used in the compositions according to the invention are cloquintocet-mexyl, cloquintocet acid and salts thereof, mefenpyr-diethyl, mefenpyr diacid, isoxadifen-ethyl, isoxadifen acid, cyprosulfamide or N-(2-methoxybenzoyl)-4-[(methylaminocarbonyl)amino]-benzenesulfonamide, and more preferably cloquintocet-mexyl, cloquintocet acid and salts thereof, mefenpyr-diethyl, mefenpyr diacid or N-(2-methoxybenzoyl)-4-[(methylaminocarbonyl)amino]-benzenesulfonamide.

Preferably, in the compounds of the formula I, the substituent R is hydrogen, $C_{1-6}$alkyl, $C_{1-6}$haloalkyl, $C_2$-$C_6$alkenyl, $C_3$-$C_6$alkynyl, benzyl or $C_{1-4}$alkoxy($C_{1-4}$)alkyl, in particular hydrogen, methyl, ethyl, trifluoromethyl, allyl, propargyl, benzyl, methoxymethyl, ethoxymethyl or methoxyethyl.

Preferably, X, Y and Z denote $C_1$-$C_4$alkyl, $C_3$-$C_6$cycloalkyl, $C_1$-$C_4$alkoxy or halogen, in particular methyl, ethyl, cyclopropyl, methoxy, fluoro, bromo or chloro, when m+n is 1-3, in particular, when m+n is 1-2.

Alternatively, Y and Z, independently of each other, denote $C_1$-$C_4$alkyl, $C_3$-$C_6$cycloalkyl, $C_{1-4}$alkoxy, halogen, phenyl or phenyl substituted by $C_{1-4}$alkyl or halogen, in particular methyl, ethyl, cyclopropyl, methoxy, fluoro, chloro, bromo, phenyl or phenyl substituted with halogen, in particular fluoro or chloro, in particular in 4-position, when m+n is 1-3, in particular, when m+n is 1-2.

In the compounds of the formula I, the substituent A is preferably $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{3-6}$alkynyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl or $C_{1-4}$alkylthio($C_{1-4}$)alkyl, in particular methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutylmethyl, cyclopentylmethyl, cyclohexylmethyl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, propargyl, benzyl, methoxymethyl, ethoxymethyl, methoxyethyl, methoxypropyl, methoxyethoxymethyl, methoxymethoxyethyl, oxetanyl-3-yl, tetrahydrofuran-2-yl, tetrahydropyran-2-yl, tetrahydrofuran-3-yl, tetrahydropyran-4-yl or methylthioethyl;
when Q is ii, A may also preferably be hydrogen, furanyl($C_{1-4}$)alkyl, tetrahydro-thiofuranyl, tetrahydro-thiopyranyl or 1-($C_{1-4}$)alkoxy-piperidin-4-yl, in particular hydrogen, furan-2-ylmethyl, furan-3-ylmethyl, tetrahydro-thiopyran-4-ylmethyl or 1-methoxy-piperidin-4-yl.

In another preferred group of compounds of the formula (I), R is hydrogen, methyl, ethyl, trifluoromethyl, allyl, propargyl, benzyl, methoxymethyl, ethoxymethyl or methoxyethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A has the meanings assigned to it above.

In a particularly preferred group of compounds of the formula (I), R is methyl, ethyl, allyl, propargyl, methoxymethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A has the meanings assigned to it above.

Preferably, Q is i or ii, more preferably i.

In a more preferred group of compounds of the formula (I), R is methyl, ethyl, methoxymethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A is methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutylmethyl, cyclopentylmethyl, cyclohexylmethyl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, propargyl, benzyl, methoxymethyl, ethoxymethyl, methoxyethyl, methoxypropyl, methoxyethoxymethyl, methoxymethoxyethyl, oxetanyl-3-yl, tetrahydrofuran-2-yl, tetrahydropyran-2-yl, tetrahydrofuran-3-yl, tetrahydropyran-4-yl or methylthioethyl;
and when Q is ii, A is also hydrogen, furan-2-ylmethyl, furan-3-ylmethyl, tetrahydro-thiopyran-4-ylmethyl or 1-methoxy-piperidin-4-yl.

Preferably, Q is i or iii, more preferably i.

It is preferred that when Q is iii, then $R_1$ to $R_4$ are hydrogen.

In another preferred group of compounds of the formula (I), R is methyl, X is methyl or methoxy, Y and Z, independently of each other, are methyl, ethyl, methoxy, chloro or bromo, G is hydrogen, methoxycarbonyl or propenyloxycarbonyl, and A is methyl, ethyl, methoxymethyl, tetrahydrofuran-2-yl or tetrahydrofuran-3-yl, and when Q is ii, A is also hydrogen.

The compounds of the invention may be made by a variety of methods as described in detail, for example, in WO09/049,851, WO10/063,670 and WO10/066,780.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable mi-croorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereose-lective or enantioselective synthesis, for example by carrying out the process according to the invention with starting materials of a suitable stereochemistry.

It is advantageous to isolate or synthesize in each case the biologically more effective iso-mer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables below can be prepared according to the methods described above.

TABLE 1

This table discloses the 132 compounds T1.001 to T1.132 of the formula Ia:

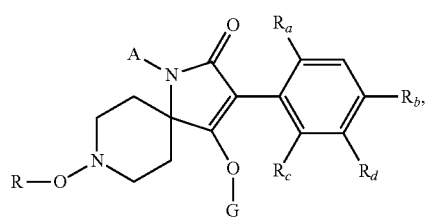

(Ia)

wherein R is $CH_3$, A is $CH_3$, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | $CH_3$ | H | H | H |
| T1.004 | $CH_2CH_3$ | H | H | H |
| T1.005 | $OCH_3$ | H | H | H |
| T1.006 | Br | Cl | H | H |
| T1.007 | Cl | Br | H | H |
| T1.008 | Cl | Cl | H | H |

TABLE 1-continued

This table discloses the 132 compounds T1.001 to T1.132 of the formula Ia:

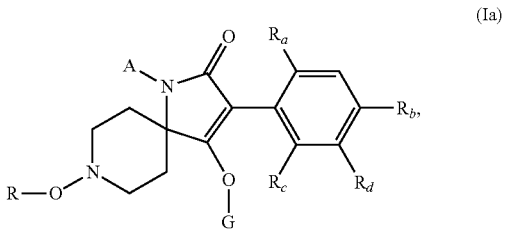

(Ia)

wherein R is $CH_3$, A is $CH_3$, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.009 | Cl | $CH_3$ | H | H |
| T1.010 | $CH_3$ | Cl | H | H |
| T1.011 | $CH_3$ | $CH_3$ | H | H |
| T1.012 | Cl | H | Cl | H |
| T1.013 | Cl | H | $CH_3$ | H |
| T1.014 | Cl | H | $CH_2CH_3$ | H |
| T1.015 | Cl | H | $OCH_3$ | H |
| T1.016 | $CH_3$ | H | $CH_3$ | H |
| T1.017 | $CH_3$ | H | $CH_2CH_3$ | H |
| T1.018 | $CH_3$ | H | $OCH_3$ | H |
| T1.019 | $CH_2CH_3$ | H | $CH_2CH_3$ | H |
| T1.020 | $CH_2CH_3$ | H | $OCH_3$ | H |
| T1.021 | $OCH_3$ | H | $OCH_3$ | H |
| T1.022 | Br | H | H | Cl |
| T1.023 | Br | H | H | $CH_3$ |
| T1.024 | Br | H | H | 4-Cl—$C_6H_4$ |
| T1.025 | Cl | H | H | Cl |
| T1.026 | Cl | H | H | $CH_3$ |
| T1.027 | Cl | H | H | 4-Cl—$C_6H_4$ |
| T1.028 | $CH_3$ | H | H | Br |
| T1.029 | $CH_3$ | H | H | Cl |
| T1.030 | $CH_3$ | H | H | $CH_3$ |
| T1.031 | $CH_3$ | H | H | $C_6H_5$ |
| T1.032 | $CH_3$ | H | H | 4-Cl—$C_6H_4$ |
| T1.033 | $CH_2CH_3$ | H | H | $CH_3$ |
| T1.034 | $CH_2CH_3$ | H | H | 4-Cl—$C_6H_4$ |
| T1.035 | $OCH_3$ | H | H | $CH_3$ |
| T1.036 | $OCH_3$ | H | H | 4-Cl—$C_6H_4$ |
| T1.037 | Cl | H | Cl | Br |
| T1.038 | $CH_3$ | H | $CH_3$ | Br |
| T1.039 | $CH_3$ | H | $CH_3$ | Cl |
| T1.040 | $CH_3$ | H | $CH_3$ | 4-Cl—$C_6H_4$ |
| T1.041 | Br | Cl | H | $CH_3$ |
| T1.042 | Br | $CH_3$ | H | $CH_3$ |
| T1.043 | Cl | Cl | H | Cl |
| T1.044 | Cl | Br | H | $CH_3$ |
| T1.045 | Cl | Cl | H | $CH_3$ |
| T1.046 | Cl | $CH_3$ | H | Cl |
| T1.047 | Cl | $CH_3$ | H | $CH_3$ |
| T1.048 | $CH_3$ | Br | H | $CH_3$ |
| T1.049 | $CH_3$ | Cl | H | $CH_3$ |
| T1.050 | $CH_3$ | $CH_3$ | H | $CH_3$ |
| T1.051 | $CH_3$ | $CH_3$ | H | 4-Cl—$C_6H_4$ |
| T1.052 | Br | Br | $CH_3$ | H |
| T1.053 | Br | Cl | $CH_3$ | H |
| T1.054 | Br | $CH_3$ | Br | H |
| T1.055 | Br | $CH_3$ | Cl | H |
| T1.056 | Cl | Br | $CH_3$ | H |
| T1.057 | Cl | Cl | Cl | H |
| T1.058 | Cl | Cl | $CH_3$ | H |
| T1.059 | Cl | $CH_3$ | Cl | H |
| T1.060 | Cl | $CH_3$ | $CH_2CH_3$ | H |
| T1.061 | Cl | $CH_3$ | $OCH_3$ | H |
| T1.062 | Cl | 4-Cl—$C_6H_4$ | Cl | H |
| T1.063 | Cl | 4-Cl—$C_6H_4$ | $CH_3$ | H |
| T1.064 | Cl | 4-Cl—$C_6H_4$ | $CH_2CH_3$ | H |
| T1.065 | Cl | 4-Cl—$C_6H_4$ | $OCH_3$ | H |
| T1.066 | $CH_3$ | Br | $CH_3$ | H |
| T1.067 | $CH_3$ | Cl | $CH_3$ | H |
| T1.068 | $CH_3$ | $CH_3$ | Br | H |
| T1.069 | $CH_3$ | $CH_3$ | Cl | H |

TABLE 1-continued

This table discloses the 132 compounds T1.001 to T1.132 of the formula Ia:

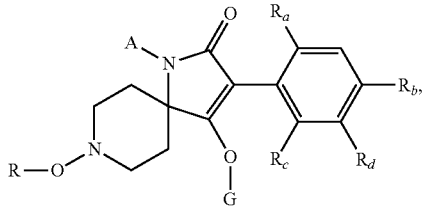

(Ia)

wherein R is CH₃, A is CH₃, G is hydrogen and Rₐ, R_b, R_c and R_d are as defined below:

| No. | Rₐ | R_b | R_c | R_d |
|---|---|---|---|---|
| T1.070 | CH₃ | CH₃ | CH₃ | H |
| T1.071 | CH₃ | CH₃ | CH₂CH₃ | H |
| T1.072 | CH₃ | CH₃ | OCH₃ | H |
| T1.073 | CH₃ | 4-Cl—C₆H₄ | CH₃ | H |
| T1.074 | CH₃ | 4-Cl—C₆H₄ | CH₂CH₃ | H |
| T1.075 | CH₃ | 4-Cl—C₆H₄ | OCH₃ | H |
| T1.076 | CH₂CH₃ | Br | Br | H |
| T1.077 | CH₂CH₃ | Br | Cl | H |
| T1.078 | CH₂CH₃ | Br | CH₃ | H |
| T1.079 | CH₂CH₃ | Br | CH₂CH₃ | H |
| T1.080 | CH₂CH₃ | Br | OCH₃ | H |
| T1.081 | CH₂CH₃ | Cl | Br | H |
| T1.082 | CH₂CH₃ | Cl | Cl | H |
| T1.083 | CH₂CH₃ | Cl | CH₃ | H |
| T1.084 | CH₂CH₃ | Cl | CH₂CH₃ | H |
| T1.085 | CH₂CH₃ | Cl | OCH₃ | H |
| T1.086 | CH₂CH₃ | CH₃ | Br | H |
| T1.087 | CH₂CH₃ | CH₃ | Cl | H |
| T1.088 | CH₂CH₃ | CH₃ | CH₂CH₃ | H |
| T1.089 | CH₂CH₃ | CH₃ | OCH₃ | H |
| T1.090 | CH₂CH₃ | CH₂CH₃ | CH₃ | H |
| T1.091 | CH₂CH₃ | CH₂CH₃ | CH₂CH₃ | H |
| T1.092 | CH₂CH₃ | 4-Cl—C₆H₄ | Br | H |
| T1.093 | CH₂CH₃ | 4-Cl—C₆H₄ | CH₂CH₃ | H |
| T1.094 | CH₂CH₃ | 4-Cl—C₆H₄ | OCH₃ | H |
| T1.095 | OCH₃ | Br | CH₃ | H |
| T1.096 | OCH₃ | Cl | CH₃ | H |
| T1.097 | OCH₃ | CH₃ | Br | H |
| T1.098 | OCH₃ | CH₃ | Cl | H |
| T1.099 | OCH₃ | CH₃ | OCH₃ | H |
| T1.100 | OCH₃ | 4-Cl—C₆H₄ | OCH₃ | H |
| T1.101 | CH₃ | CH₃ | CH₃ | F |
| T1.102 | CH₃ | CH₃ | CH₃ | Cl |
| T1.103 | CH₃ | CH₃ | CH₃ | Br |
| T1.104 | CH₃ | CH₃ | CH₃ | CH₃ |
| T1.105 | CH₃ | CH₃ | CH₃ | 4-Cl—C₆H₄ |
| T1.106 | Cl | CH₃ | CH₃ | CH₃ |
| T1.107 | CH₃ | Cl | CH₃ | CH₃ |
| T1.108 | CH₃ | CH₃ | Cl | CH₃ |
| T1.109 | CH₂CH₃ | CH₃ | CH₃ | CH₃ |
| T1.110 | OCH₃ | CH₃ | CH₃ | CH₃ |
| T1.111 | Cyclo-C3 | CH₃ | CH₃ | CH₃ |
| T1.112 | CH₃ | CH₃ | Cyclo-C3 | H |
| T1.113 | CH₃ | F | H | Br |
| T1.114 | CH₃ | CH₃ | H | Br |
| T1.115 | CH₂CH₃ | CH₃ | H | CH₃ |
| T1.116 | OCH₃ | CH₃ | H | CH₃ |
| T1.117 | Cyclo-C3 | CH₃ | H | CH₃ |
| T1.118 | CH₂CH₃ | Cl | H | CH₃ |
| T1.119 | OCH₃ | Cl | H | CH₃ |
| T1.120 | Cyclo-C3 | Cl | H | CH₃ |
| T1.121 | Cl | H | CH₃ | CH₃ |
| T1.122 | CH₃ | H | CH₃ | CH₃ |
| T1.123 | CH₂CH₃ | H | CH₃ | CH₃ |
| T1.124 | OCH₃ | H | CH₃ | CH₃ |
| T1.125 | Cyclo-C3 | H | CH₃ | CH₃ |
| T1.126 | F | H | Cl | CH₃ |
| T1.127 | Cl | H | F | CH₃ |
| T1.128 | H | CH₃ | CH₃ | CH₃ |
| T1.129 | Br | CH₃ | CH₃ | CH₃ |
| T1.130 | CH₃ | H | Cl | CH₃ |
| T1.131 | CH₃ | H | Br | CH₃ |
| T1.132 | Br | H | CH₃ | CH₃ |

Cyclo-C3 means cyclopropyl.

Table 2: This table discloses the 132 compounds T2.001 to T2.132 of the formula Ia, wherein R is CH₃, A is CH₂CH₃, G is hydrogen and Rₐ, R_b, R_c and R_d are as defined in Table 1.

Table 3: This table discloses the 132 compounds T3.001 to T3.132 of the formula Ia, wherein R is CH₃, A is n-C₃H₇, G is hydrogen and Rₐ, R_b, R_c, and R_d are as defined in Table 1.

Table 4: This table discloses the 132 compounds T4.001 to T4.132 of the formula Ia, wherein R is CH₃, A is i-C₃H₇, G is hydrogen and Rₐ, R_b, R_c, and R_d are as defined in Table 1.

Table 5: This table discloses the 132 compounds T5.001 to T5.132 of the formula Ia, wherein R is CH₃, A is n-C₄H₉, G is hydrogen and Rₐ, R_b, R_c, and R_d are as defined in Table 1.

Table 6: This table discloses the 132 compounds T6.001 to T6.132 of the formula Ia, wherein R is CH₃, A is i-C₄H₉, G is hydrogen and Rₐ, R_b, R_c, and R_d are as defined in Table 1.

Table 7: This table discloses the 132 compounds T7.001 to T7.132 of the formula Ia, wherein R is CH₃, A is t-C₄H₉, G is hydrogen and Rₐ, R_b, R_c, and R_d are as defined in Table 1.

Table 8: This table discloses the 132 compounds T8.001 to T8.132 of the formula Ia, wherein R is CH₃, A is cyclopropyl, G is hydrogen and Rₐ, R_b, R_c, and R_d are as defined in Table 1.

Table 9: This table discloses the 132 compounds T9.001 to T9.132 of the formula Ia, wherein R is CH₃, A is cyclopentyl, G is hydrogen and Rₐ, R_b, R_c, and R_d are as defined in Table 1.

Table 10: This table discloses the 132 compounds T10.001 to T10.132 of the formula Ia, wherein R is CH₃, A is cyclohexyl, G is hydrogen and Rₐ, R_b, R_c, and R_d are as defined in Table 1.

Table 11: This table discloses the 132 compounds T11.001 to T11.132 of the formula Ia, wherein R is CH₃, A is 2,2-(CH₃)-2-propyl, G is hydrogen and Rₐ, R_b, R_c, and R_d are as defined in Table 1.

Table 12: This table discloses the 132 compounds T12.001 to T12.132 of the formula Ia, wherein R is CH₃, A is allyl, G is hydrogen and Rₐ, R_b, R_c, and R_d are as defined in Table 1.

Table 13: This table discloses the 132 compounds T13.001 to T13.132 of the formula Ia, wherein R is $CH_3$, A is $CH_2-CH=C(CH_3)_2$, G is hydrogen and $R_a$, $R_b$, $R_c$, and $R_d$ are as defined in Table 1.

Table 14: This table discloses the 132 compounds T14.001 to T14.132 of the formula Ia, wherein R is $CH_3$, A is $CH_2-CH=C(Cl)_2$, G is hydrogen and $R_a$, $R_b$, $R_c$, and $R_d$ are as defined in Table 1.

Table 15: This table discloses the 132 compounds T15.001 to T15.132 of the formula Ia, wherein R is $CH_3$, A is propargyl, G is hydrogen and $R_a$, $R_b$, $R_c$, and $R_d$ are as defined in Table 1.

Table 16: This table discloses the 132 compounds T16.001 to T16.132 of the formula Ia, wherein R is $CH_3$, A is $CH_2C\equiv CCH_3$, G is hydrogen and $R_a$, $R_b$, $R_c$, and $R_d$ are as defined in Table 1.

Table 17: This table discloses the 132 compounds T17.001 to T17.132 of the formula Ia, wherein R is $CH_3$, A is $CH_2$-cyclopropyl, G is hydrogen and $R_a$, $R_b$, $R_c$, and $R_d$ are as defined in Table 1.

Table 18: This table discloses the 132 compounds T18.001 to T18.132 of the formula Ia, wherein R is $CH_3$, A is $CH_2CN$, G is hydrogen and $R_a$, $R_b$, $R_c$, and $R_d$ are as defined in Table 1.

Table 19: This table discloses the 132 compounds T19.001 to T19.132 of the formula Ia, wherein R is $CH_3$, A is $CH_2OCH_3$, G is hydrogen and $R_a$, $R_b$, $R_c$, and $R_d$ are as defined in Table 1.

Table 20: This table discloses the 132 compounds T20.001 to T20.132 of the formula Ia, wherein R is $CH_3$, A is $CH_2OCH_2CH_3$, G is hydrogen and $R_a$, $R_b$, $R_c$, and $R_d$ are as defined in Table 1.

Table 21: This table discloses the 132 compounds T21.001 to T21.132 of the formula Ia, wherein R is $CH_3$, A is $CH_2CH_2OCH_3$, G is hydrogen and $R_a$, $R_b$, $R_c$, and $R_d$ are as defined in Table 1.

Table 22: This table discloses the 132 compounds T22.001 to T22.132 of the formula Ia, wherein R is $CH_3$, A is $CH_2OCH_2CH_2OCH_3$, G is hydrogen and $R_a$, $R_b$, $R_c$, and $R_d$ are as defined in Table 1.

Table 23: This table discloses the 132 compounds T23.001 to T23.132 of the formula Ia, wherein R is $CH_3$, A is $CH_2CH_2OCH_2OCH_3$, G is hydrogen and $R_a$, $R_b$, $R_c$, and $R_d$ are as defined in Table 1.

Table 24: This table discloses the 132 compounds T24.001 to T24.132 of the formula Ia, wherein R is $CH_3$, A is oxetan-3-yl, G is hydrogen and $R_a$, $R_b$, $R_c$, and $R_d$ are as defined in Table 1.

Table 25: This table discloses the 132 compounds T25.001 to T25.132 of the formula Ia, wherein R is $CH_3$, A is tetrahydrofuran-2-yl, G is hydrogen and $R_a$, $R_b$, $R_c$, and $R_d$ are as defined in Table 1.

Table 26: This table discloses the 132 compounds T26.001 to T26.132 of the formula Ia, wherein R is $CH_3$, A is tetrahydrofuran-3-yl, G is hydrogen and $R_a$, $R_b$, $R_c$, and $R_d$ are as defined in Table 1.

Table 27: This table discloses the 132 compounds T27.001 to T27.132 of the formula Ia, wherein R is $CH_3$, A is tetrahydropyran-2-yl, G is hydrogen and $R_a$, $R_b$, $R_c$, and $R_d$ are as defined in Table 1.

Table 28: This table discloses the 132 compounds T28.001 to T28.132 of the formula Ia, wherein R is $CH_3$, A is tetrahydropyran-4-yl, G is hydrogen and $R_a$, $R_b$, $R_c$, and $R_d$ are as defined in Table 1.

Table 29: This table discloses the 132 compounds T29.001 to T29.132 of the formula Ia, wherein R is $CH_3$, A is $CH_2CH_2F$, G is hydrogen and $R_a$, $R_b$, $R_c$, and $R_d$ are as defined in Table 1.

Table 30: This table discloses the 132 compounds T30.001 to T30.132 of the formula Ia, wherein R is $CH_3$, A is $CH_2CHF_2$, G is hydrogen and $R_a$, $R_b$, $R_c$, and $R_d$ are as defined in Table 1.

Table 31: This table discloses the 132 compounds T31.001 to T31.132 of the formula Ia, wherein R is $CH_3$, A is $CH_2CF_3$, G is hydrogen and $R_a$, $R_b$, $R_c$, and $R_d$ are as defined in Table 1.

Table 32: This table discloses the 132 compounds T32.001 to T32.132 of the formula Ia, wherein R is $CH_3$, A is benzyl, G is hydrogen and $R_a$, $R_b$, $R_c$, and $R_d$ are as defined in Table 1.

Table 33: This table discloses the 132 compounds T33.001 to T33.132 of the formula Ia, wherein R is $CH_3$, A is $C(O)-CH_3$, G is hydrogen and $R_a$, $R_b$, $R_c$, and $R_d$ are as defined in Table 1.

Table 34: This table discloses the 132 compounds T34.001 to T34.132 of the formula Ia, wherein R is $CH_3$, A is $C(O)-OCH_3$, G is hydrogen and $R_a$, $R_b$, $R_c$, and $R_d$ are as defined in Table 1.

Table 35: This table discloses the 132 compounds T35.001 to T35.132 of the formula Ia, wherein R is $CH_3$, A is C(O)-cyclopropyl, G is hydrogen and $R_a$, $R_b$, $R_c$, and $R_d$ are as defined in Table 1.

Table 36: This table discloses the 132 compounds T36.001 to T36.132 of the formula Ia, wherein R is $CH_3$, A is $C(O)-N(CH_3)_2$, G is hydrogen and $R_a$, $R_b$, $R_c$, and $R_d$ are as defined in Table 1.

Table 37: This table discloses the 132 compounds T37.001 to T37.132 of the formula Ia, wherein R is $CH_3$, A is $C(O)-C_6H_5$, G is hydrogen and $R_a$, $R_b$, $R_c$, and $R_d$ are as defined in Table 1.

Table 38: This table discloses the 132 compounds T38.001 to T38.132 of the formula Ia, wherein R is $CH_3$, A is $SO_2CH_3$, G is hydrogen and $R_a$, $R_b$, $R_c$, and $R_d$ are as defined in Table 1.

Table 39: This table discloses the 132 compounds T39.001 to T39.132 of the formula Ia, wherein R is $CH_3$, A is $SO_2C_6H_5$, G is hydrogen and $R_a$, $R_b$, $R_c$, and $R_d$ are as defined in Table 1.

Table 40: This table discloses the 132 compounds T40.001 to T40.132 of the formula Ia, wherein R is hydrogen, A is $CH_3$, G is hydrogen and $R_a$, $R_b$, $R_c$, and $R_d$ are as defined in Table 1.

Table 41: This table discloses the 132 compounds T41.001 to T41.132 of the formula Ia, wherein R is hydrogen, A is $CH_2CH_3$, G is hydrogen and $R_a$, $R_b$, $R_c$, and $R_d$ are as defined in Table 1.

Table 42: This table discloses the 132 compounds T42.001 to T42.132 of the formula Ia, wherein R is hydrogen, A is $i-C_3H_7$, G is hydrogen and $R_a$, $R_b$, $R_c$, and $R_d$ are as defined in Table 1.

Table 43: This table discloses the 132 compounds T43.001 to T43.132 of the formula Ia, wherein R is hydrogen, A is cyclopropyl, G is hydrogen and $R_a$, $R_b$, $R_c$, and $R_d$ are as defined in Table 1.

Table 44: This table discloses the 132 compounds T44.001 to T44.132 of the formula Ia, wherein R is hydrogen, A is $CH_2$-cyclopropyl, G is hydrogen and $R_a$, $R_b$, $R_c$, and $R_d$ are as defined in Table 1.

Table 45: This table discloses the 132 compounds T45.001 to T45.132 of the formula Ia, wherein R is hydrogen, A is $CH_2OCH_3$, G is hydrogen and $R_a$, $R_b$, $R_c$, and $R_d$ are as defined in Table 1.

Table 46: This table discloses the 132 compounds T46.001 to T46.132 of the formula Ia, wherein R is hydrogen, A is $CH_2CH_2OCH_3$, G is hydrogen and $R_a$, $R_b$, $R_c$, and $R_d$ are as defined in Table 1.

Table 47: This table discloses the 132 compounds T47.001 to T47.132 of the formula Ia, wherein R is hydrogen, A is $CH_2OCH_2CH_2OCH_3$, G is hydrogen and $R_a$, $R_b$, $R_c$, and $R_d$ are as defined in Table 1.

Table 48: This table discloses the 132 compounds T48.001 to T48.132 of the formula Ia, wherein R is hydrogen, A is $CH_2CH_2OCH_2OCH_3$, G is hydrogen and $R_a$, $R_b$, $R_c$, and $R_d$ are as defined in Table 1.

Table 49: This table discloses the 132 compounds T49.001 to T49.132 of the formula Ia, wherein R is hydrogen, A is oxetan-3-yl, G is hydrogen and $R_a$, $R_b$, $R_c$, and $R_d$ are as defined in Table 1.

Table 50: This table discloses the 132 compounds T50.001 to T50.132 of the formula Ia, wherein R is hydrogen, A is $CH_2CHF_2$, G is hydrogen and $R_a$, $R_b$, $R_c$, and $R_d$ are as defined in Table 1.

Table 51: This table discloses the 132 compounds T51.001 to T51.132 of the formula Ia, wherein R is hydrogen, A is $CH_2CF_3$, G is hydrogen and $R_a$, $R_b$, $R_c$, and $R_d$ are as defined in Table 1.

Table 52: This table discloses the 132 compounds T52.001 to T52.132 of the formula Ia, wherein R is hydrogen, A is benzyl, G is hydrogen and $R_a$, $R_b$, $R_c$, and $R_d$ are as defined in Table 1.

Table 53: This table discloses the 132 compounds T53.001 to T53.132 of the formula Ia, wherein R is $CH_2CH_3$, A is $CH_3$, G is hydrogen and $R_a$, $R_b$, $R_c$, and $R_d$ are as defined in Table 1.

Table 54: This table discloses the 132 compounds T54.001 to T54.132 of the formula Ia, wherein R is $CH_2CH_3$, A is $CH_2CH_3$, G is hydrogen and $R_a$, $R_b$, $R_c$, and $R_d$ are as defined in Table 1.

Table 55: This table discloses the 132 compounds T55.001 to T55.132 of the formula Ia, wherein R is $CH_2CH_3$, A is i-$C_3H_7$, G is hydrogen and $R_a$, $R_b$, $R_c$, and $R_d$ are as defined in Table 1.

Table 56: This table discloses the 132 compounds T56.001 to T56.132 of the formula Ia, wherein R is $CH_2CH_3$, A is cyclopropyl, G is hydrogen and $R_a$, $R_b$, $R_c$, and $R_d$ are as defined in Table 1.

Table 57: This table discloses the 132 compounds T57.001 to T57.132 of the formula Ia, wherein R is $CH_2CH_3$, A is $CH_2$-cyclopropyl, G is hydrogen and $R_a$, $R_b$, $R_c$, and $R_d$ are as defined in Table 1.

Table 58: This table discloses the 132 compounds T58.001 to T58.132 of the formula Ia, wherein R is $CH_2CH_3$, A is $CH_2OCH_3$, G is hydrogen and $R_a$, $R_b$, $R_c$, and $R_d$ are as defined in Table 1.

Table 59: This table discloses the 132 compounds T59.001 to T59.132 of the formula Ia, wherein R is $CH_2CH_3$, A is $CH_2CH_2OCH_3$, G is hydrogen and $R_a$, $R_b$, $R_c$, and $R_d$ are as defined in Table 1.

Table 60: This table discloses the 132 compounds T60.001 to T60.132 of the formula Ia, wherein R is $CH_2CH_3$, A is $CH_2OCH_2CH_2OCH_3$, G is hydrogen and $R_a$, $R_b$, $R_c$, and $R_d$ are as defined in Table 1.

Table 61: This table discloses the 132 compounds T61.001 to T61.132 of the formula Ia, wherein R is $CH_2CH_3$, A is $CH_2CH_2OCH_2OCH_3$, G is hydrogen and $R_a$, $R_b$, $R_c$, and $R_d$ are as defined in Table 1.

Table 62: This table discloses the 132 compounds T62.001 to T62.132 of the formula Ia, wherein R is $CH_2CH_3$, A is oxetan-3-yl, G is hydrogen and $R_a$, $R_b$, $R_c$, and $R_d$ are as defined in Table 1.

Table 63: This table discloses the 132 compounds T63.001 to T63.132 of the formula Ia, wherein R is $CH_2CH_3$, A is $CH_2CHF_2$, G is hydrogen and $R_a$, $R_b$, $R_c$, and $R_d$ are as defined in Table 1.

Table 64: This table discloses the 132 compounds T64.001 to T64.132 of the formula Ia, wherein R is $CH_2CH_3$, A is $CH_2CF_3$, G is hydrogen and $R_a$, $R_b$, $R_c$, and $R_d$ are as defined in Table 1.

Table 65: This table discloses the 132 compounds T65.001 to T65.132 of the formula Ia, wherein R is $CH_2CH_3$, A is benzyl, G is hydrogen and $R_a$, $R_b$, $R_c$, and $R_d$ are as defined in Table 1.

Table 66: This table discloses the 132 compounds T66.001 to T66.132 of the formula Ia, wherein R is $CH_2OCH_3$, A is $CH_3$, G is hydrogen and $R_a$, $R_b$, $R_c$, and $R_d$ are as defined in Table 1.

Table 67: This table discloses the 132 compounds T67.001 to T67.132 of the formula Ia, wherein R is $CH_2OCH_3$, A is $CH_2CH_3$, G is hydrogen and $R_a$, $R_b$, $R_c$, and $R_d$ are as defined in Table 1.

Table 68: This table discloses the 132 compounds T68.001 to T68.132 of the formula Ia, wherein R is $CH_2OCH_3$, A is i-$C_3H_7$, G is hydrogen and $R_a$, $R_b$, $R_c$, and $R_d$ are as defined in Table 1.

Table 69: This table discloses the 132 compounds T69.001 to T69.132 of the formula Ia, wherein R is $CH_2OCH_3$, A is cyclopropyl, G is hydrogen and $R_a$, $R_b$, $R_c$, and $R_d$ are as defined in Table 1.

Table 70: This table discloses the 132 compounds T70.001 to T70.132 of the formula Ia, wherein R is $CH_2OCH_3$, A is $CH_2$-cyclopropyl, G is hydrogen and $R_a$, $R_b$, $R_c$, and $R_d$ are as defined in Table 1.

Table 71: This table discloses the 132 compounds T71.001 to T71.132 of the formula Ia, wherein R is $CH_2OCH_3$, A is $CH_2OCH_3$, G is hydrogen and $R_a$, $R_b$, $R_c$, and $R_d$ are as defined in Table 1.

Table 72: This table discloses the 132 compounds T72.001 to T72.132 of the formula Ia, wherein R is $CH_2OCH_3$, A is $CH_2CH_2OCH_3$, G is hydrogen and $R_a$, $R_b$, $R_c$, and $R_d$ are as defined in Table 1.

Table 73: This table discloses the 132 compounds T73.001 to T73.132 of the formula Ia, wherein R is $CH_2OCH_3$, A is $CH_2OCH_2CH_2OCH_3$, G is hydrogen and $R_a$, $R_b$, $R_c$, and $R_d$ are as defined in Table 1.

Table 74: This table discloses the 132 compounds T74.001 to T74.132 of the formula Ia, wherein R is $CH_2OCH_3$, A is $CH_2CH_2OCH_2OCH_3$, G is hydrogen and $R_a$, $R_b$, $R_c$, and $R_d$ are as defined in Table 1.

Table 75: This table discloses the 132 compounds T75.001 to T75.132 of the formula Ia, wherein R is $CH_2OCH_3$, A is oxetan-3-yl, G is hydrogen and $R_a$, $R_b$, $R_c$, and $R_d$ are as defined in Table 1.

Table 76: This table discloses the 132 compounds T76.001 to T76.132 of the formula Ia, wherein R is $CH_2OCH_3$, A is $CH_2CHF_2$, G is hydrogen and $R_a$, $R_b$, $R_c$, and $R_d$ are as defined in Table 1.

Table 77: This table discloses the 132 compounds T77.001 to T77.132 of the formula Ia, wherein R is $CH_2OCH_3$, A is $CH_2CF_3$, G is hydrogen and $R_a$, $R_b$, $R_c$, and $R_d$ are as defined in Table 1.

Table 78: This table discloses the 132 compounds T78.001 to T78.132 of the formula Ia, wherein R is $CH_2OCH_3$, A is benzyl, G is hydrogen and $R_a$, $R_b$, $R_c$, and $R_d$ are as defined in Table 1.

Table 79: This table discloses the 132 compounds T79.001 to T79.132 of the formula Ia, wherein R is $CH_2CH_2OCH_3$, A is $CH_3$, G is hydrogen and $R_a$, $R_b$, $R_c$, and $R_d$ are as defined in Table 1.

Table 80: This table discloses the 132 compounds T80.001 to T80.132 of the formula Ia, wherein R is $CH_2CH_2OCH_3$, A is $CH_2CH_3$, G is hydrogen and $R_a$, $R_b$, $R_c$, and $R_d$ are as defined in Table 1.

Table 81: This table discloses the 132 compounds T81.001 to T81.132 of the formula Ia, wherein R is $CH_2CH_2OCH_3$, A is $i\text{-}C_3H_7$, G is hydrogen and $R_a$, $R_b$, $R_c$, and $R_d$ are as defined in Table 1.

Table 82: This table discloses the 132 compounds T82.001 to T82.132 of the formula Ia, wherein R is $CH_2CH_2OCH_3$, A is cyclopropyl, G is hydrogen and $R_a$, $R_b$, $R_c$, and $R_d$ are as defined in Table 1.

Table 83: This table discloses the 132 compounds T83.001 to T83.132 of the formula Ia, wherein R is $CH_2CH_2OCH_3$, A is $CH_2$-cyclopropyl, G is hydrogen and $R_a$, $R_b$, $R_c$, and $R_d$ are as defined in Table 1.

Table 84: This table discloses the 132 compounds T84.001 to T84.132 of the formula Ia, wherein R is $CH_2CH_2OCH_3$, A is $CH_2OCH_3$, G is hydrogen and $R_a$, $R_b$, $R_c$, and $R_d$ are as defined in Table 1.

Table 85: This table discloses the 132 compounds T85.001 to T85.132 of the formula Ia, wherein R is $CH_2CH_2OCH_3$, A is $CH_2CH_2OCH_3$, G is hydrogen and $R_a$, $R_b$, $R_c$, and $R_d$ are as defined in Table 1.

Table 86: This table discloses the 132 compounds T86.001 to T86.132 of the formula Ia, wherein R is $CH_2CH_2OCH_3$, A is $CH_2OCH_2CH_2OCH_3$, G is hydrogen and $R_a$, $R_b$, $R_c$ and $R_d$ are as defined in Table 1.

Table 87: This table discloses the 132 compounds T87.001 to T87.132 of the formula Ia, wherein R is $CH_2CH_2OCH_3$, A is $CH_2CH_2OCH_2OCH_3$, G is hydrogen and $R_a$, $R_b$, $R_c$ and $R_d$ are as defined in Table 1.

Table 88: This table discloses the 132 compounds T88.001 to T88.132 of the formula Ia, wherein R is $CH_2CH_2OCH_3$, A is oxetan-3-yl, G is hydrogen and $R_a$, $R_b$, $R_c$, and $R_d$ are as defined in Table 1.

Table 89: This table discloses the 132 compounds T89.001 to T89.132 of the formula Ia, wherein R is $CH_2CH_2OCH_3$, A is $CH_2CHF_2$, G is hydrogen and $R_a$, $R_b$, $R_c$, and $R_d$ are as defined in Table 1.

Table 90: This table discloses the 132 compounds T90.001 to T90.132 of the formula Ia, wherein R is $CH_2CH_2OCH_3$, A is $CH_2CF_3$, G is hydrogen and $R_a$, $R_b$, $R_c$, and $R_d$ are as defined in Table 1.

Table 91: This table discloses the 132 compounds T91.001 to T91.132 of the formula Ia, wherein R is $CH_2CH_2OCH_3$, A is benzyl, G is hydrogen and $R_a$, $R_b$, $R_c$, and $R_d$ are as defined in Table 1.

Table 92: This table discloses the 132 compounds T92.001 to T92.132 of the formula Ia, wherein R is benzyl, A is $CH_3$, G is hydrogen and $R_a$, $R_b$, $R_c$, and $R_d$ are as defined in Table 1.

Table 93: This table discloses the 132 compounds T93.001 to T93.132 of the formula Ia, wherein R is benzyl, A is $CH_2CH_3$, G is hydrogen and $R_a$, $R_b$, $R_c$, and $R_d$ are as defined in Table 1.

Table 94: This table discloses the 132 compounds T94.001 to T94.132 of the formula Ia, wherein R is benzyl, A is $i\text{-}C_3H_7$, G is hydrogen and $R_a$, $R_b$, $R_c$, and $R_d$ are as defined in Table 1.

Table 95: This table discloses the 132 compounds T95.001 to T95.132 of the formula Ia, wherein R is benzyl, A is cyclopropyl, G is hydrogen and $R_a$, $R_b$, $R_c$, and $R_d$ are as defined in Table 1.

Table 96: This table discloses the 132 compounds T96.001 to T96.132 of the formula Ia, wherein R is benzyl, A is $CH_2$-cyclopropyl, G is hydrogen and $R_a$, $R_b$, $R_c$, and $R_d$ are as defined in Table 1.

Table 97: This table discloses the 132 compounds T97.001 to T97.132 of the formula Ia, wherein R is benzyl, A is $CH_2OCH_3$, G is hydrogen and $R_a$, $R_b$, $R_c$, and $R_d$ are as defined in Table 1.

Table 98: This table discloses the 132 compounds T98.001 to T98.132 of the formula Ia, wherein R is benzyl, A is $CH_2CH_2OCH_3$, G is hydrogen and $R_a$, $R_b$, $R_c$, and $R_d$ are as defined in Table 1.

Table 99: This table discloses the 132 compounds T99.001 to T99.132 of the formula Ia, wherein R is benzyl, A is $CH_2OCH_2CH_2OCH_3$, G is hydrogen and $R_a$, $R_b$, $R_c$, and $R_d$ are as defined in Table 1.

Table 100: This table discloses the 132 compounds T100.001 to T100.132 of the formula Ia, wherein R is benzyl, A is $CH_2CH_2OCH_2OCH_3$, G is hydrogen and $R_a$, $R_b$, $R_c$, and $R_d$ are as defined in Table 1.

Table 101: This table discloses the 132 compounds T101.001 to T101.132 of the formula Ia, wherein R is benzyl, A is oxetan-3-yl, G is hydrogen and $R_a$, $R_b$, $R_c$, and $R_d$ are as defined in Table 1.

Table 102: This table discloses the 132 compounds T102.001 to T102.132 of the formula Ia, wherein R is benzyl, A is $CH_2CHF_2$, G is hydrogen and $R_a$, $R_b$, $R_c$, and $R_d$ are as defined in Table 1.

Table 103: This table discloses the 132 compounds T103.001 to T103.132 of the formula Ia, wherein R is benzyl, A is $CH_2CF_3$, G is hydrogen and $R_a$, $R_b$, $R_c$, and $R_d$ are as defined in Table 1.

Table 104: This table discloses the 132 compounds T104.001 to T104.132 of the formula Ia, wherein R is benzyl, A is benzyl, G is hydrogen and $R_a$, $R_b$, $R_c$, and $R_d$ are as defined in Table 1.

Table 105: This table discloses the 132 compounds T105.001 to T105.132 of the formula Ia, wherein R is $CH_3$, A is methoxypropyl, G is hydrogen and $R_a$, $R_b$, $R_c$, and $R_d$ are as defined in Table 1.

Table 106: This table discloses the 132 compounds T106.001 to T106.132 of the formula Ia, wherein R is $CH_3$, A is oxetan-3-ylmethyl, G is hydrogen and $R_a$, $R_b$, $R_c$, and $R_d$ are as defined in Table 1.

Table 107: This table discloses the 132 compounds T107.001 to T107.132 of the formula Ia, wherein R is $CH_3$, A is tetrahydrofuran-2-ylmethyl, G is hydrogen and $R_a$, $R_b$, $R_c$ and $R_d$ are as defined in Table 1.

Table 108: This table discloses the 132 compounds T108.001 to T108.132 of the formula Ia, wherein R is $CH_3$, A is tetrahydrofuran-3-ylmethyl, G is hydrogen and $R_a$, $R_b$, $R_c$ and $R_d$ are as defined in Table 1.

Table 109: This table discloses the 132 compounds T109.001 to T109.132 of the formula Ia, wherein R is CH₃, A is tetrahydropyran-4-ylmethyl, G is hydrogen and $R_a$, $R_b$, $R_c$ and $R_d$ are as defined in Table 1.

Table 110: This table discloses the 132 compounds T110.001 to T110.132 of the formula Ia, wherein R is CH₃, A is methylthioethyl, G is hydrogen and $R_a$, $R_b$, $R_c$, and $R_d$ are as defined in Table 1.

Table 111: This table discloses the 132 compounds T111.001 to T111.132 of the formula Ia, wherein R is H, A is methoxypropyl, G is hydrogen and $R_a$, $R_b$, $R_c$, and $R_d$ are as defined in Table 1.

Table 112: This table discloses the 132 compounds T112.001 to T112.132 of the formula Ia, wherein R is CH₂CH₃, A is methoxypropyl, G is hydrogen and $R_a$, $R_b$, $R_c$, and $R_d$ are as defined in Table 1.

Table 113: This table discloses the 132 compounds T113.001 to T113.132 of the formula Ia, wherein R is CH₂CH₂OCH₃, A is methoxypropyl, G is hydrogen and $R_a$, $R_b$, $R_c$ and $R_d$ are as defined in Table 1.

Table 114: This table discloses the 132 compounds T114.001 to T114.132 of the formula Ia, wherein R is H, A is tetrahydrofuran-2-ylmethyl, G is hydrogen and $R_a$, $R_b$, $R_c$, and $R_d$ are as defined in Table 1.

Table 115: This table discloses the 132 compounds T115.001 to T115.132 of the formula Ia, wherein R is CH₂CH₃, A is tetrahydrofuran-2-ylmethyl, G is hydrogen and $R_a$, $R_b$, $R_c$, and $R_d$ are as defined in Table 1.

Table 116: This table discloses the 132 compounds T116.001 to T116.132 of the formula Ia, wherein R is CH₂CH₂OCH₃, A is tetrahydrofuran-2-ylmethyl, G is hydrogen and $R_a$, $R_b$, $R_c$, and $R_d$ are as defined in Table 1.

TABLE 1ii

This table discloses the 132 compounds T1ii.001 to T1ii.132 of the formula Ib:

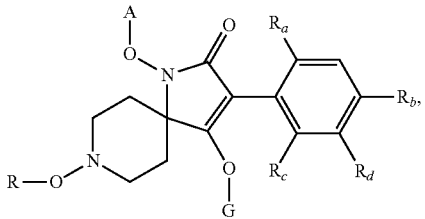

(Ib)

wherein R is CH₃, A is hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1ii.001 | Br | H | H | H |
| T1ii.002 | Cl | H | H | H |
| T1ii.003 | CH₃ | H | H | H |
| T1ii.004 | CH₂CH₃ | H | H | H |
| T1ii.005 | OCH₃ | H | H | H |
| T1ii.006 | Br | Cl | H | H |
| T1ii.007 | Cl | Br | H | H |
| T1ii.008 | Cl | Cl | H | H |
| T1ii.009 | Cl | CH₃ | H | H |
| T1ii.010 | CH₃ | Cl | H | H |
| T1ii.011 | CH₃ | CH₃ | H | H |
| T1ii.012 | Cl | H | Cl | H |
| T1ii.013 | Cl | H | CH₃ | H |
| T1ii.014 | Cl | H | CH₂CH₃ | H |
| T1ii.015 | Cl | H | OCH₃ | H |
| T1ii.016 | CH₃ | H | CH₃ | H |
| T1ii.017 | CH₃ | H | CH₂CH₃ | H |
| T1ii.018 | CH₃ | H | OCH₃ | H |

TABLE 1ii-continued

This table discloses the 132 compounds T1ii.001 to T1ii.132 of the formula Ib:

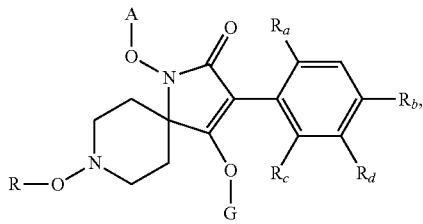

(Ib)

wherein R is CH₃, A is hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1ii.019 | CH₂CH₃ | H | CH₂CH₃ | H |
| T1ii.020 | CH₂CH₃ | H | OCH₃ | H |
| T1ii.021 | OCH₃ | H | OCH₃ | H |
| T1ii.022 | Br | H | H | Cl |
| T1ii.023 | Br | H | H | CH₃ |
| T1ii.024 | Br | H | H | 4-Cl—C₆H₄ |
| T1ii.025 | Cl | H | H | Cl |
| T1ii.026 | Cl | H | H | CH₃ |
| T1ii.027 | Cl | H | H | 4-Cl—C₆H₄ |
| T1ii.028 | CH₃ | H | H | Br |
| T1ii.029 | CH₃ | H | H | Cl |
| T1ii.030 | CH₃ | H | H | CH₃ |
| T1ii.031 | CH₃ | H | H | C₆H₅ |
| T1ii.032 | CH₃ | H | H | 4-Cl—C₆H₄ |
| T1ii.033 | CH₂CH₃ | H | H | CH₃ |
| T1ii.034 | CH₂CH₃ | H | H | 4-Cl—C₆H₄ |
| T1ii.035 | OCH₃ | H | H | CH₃ |
| T1ii.036 | OCH₃ | H | H | 4-Cl—C₆H₄ |
| T1ii.037 | Cl | H | Cl | Br |
| T1ii.038 | CH₃ | H | CH₃ | Br |
| T1ii.039 | CH₃ | H | CH₃ | Cl |
| T1ii.040 | CH₃ | H | CH₃ | 4-Cl—C₆H₄ |
| T1ii.041 | Br | Cl | H | CH₃ |
| T1ii.042 | Br | CH₃ | H | CH₃ |
| T1ii.043 | Cl | Cl | H | Cl |
| T1ii.044 | Cl | Br | H | CH₃ |
| T1ii.045 | Cl | Cl | H | CH₃ |
| T1ii.046 | Cl | CH₃ | H | Cl |
| T1ii.047 | Cl | CH₃ | H | CH₃ |
| T1ii.048 | CH₃ | Br | H | CH₃ |
| T1ii.049 | CH₃ | Cl | H | CH₃ |
| T1ii.050 | CH₃ | CH₃ | H | CH₃ |
| T1ii.051 | CH₃ | CH₃ | H | 4-Cl—C₆H₄ |
| T1ii.052 | Br | Br | CH₃ | H |
| T1ii.053 | Br | Cl | CH₃ | H |
| T1ii.054 | Br | CH₃ | Br | H |
| T1ii.055 | Br | CH₃ | Cl | H |
| T1ii.056 | Cl | Br | CH₃ | H |
| T1ii.057 | Cl | Cl | Cl | H |
| T1ii.058 | Cl | Cl | CH₃ | H |
| T1ii.059 | Cl | CH₃ | Cl | H |
| T1ii.060 | Cl | CH₃ | CH₂CH₃ | H |
| T1ii.061 | Cl | CH₃ | OCH₃ | H |
| T1ii.062 | Cl | 4-Cl—C₆H₄ | Cl | H |
| T1ii.063 | Cl | 4-Cl—C₆H₄ | CH₃ | H |
| T1ii.064 | Cl | 4-Cl—C₆H₄ | CH₂CH₃ | H |
| T1ii.065 | Cl | 4-Cl—C₆H₄ | OCH₃ | H |
| T1ii.066 | CH₃ | Br | CH₃ | H |
| T1ii.067 | CH₃ | Cl | CH₃ | H |
| T1ii.068 | CH₃ | CH₃ | Br | H |
| T1ii.069 | CH₃ | CH₃ | Cl | H |
| T1ii.070 | CH₃ | CH₃ | CH₃ | H |
| T1ii.071 | CH₃ | CH₃ | CH₂CH₃ | H |
| T1ii.072 | CH₃ | CH₃ | OCH₃ | H |
| T1ii.073 | CH₃ | 4-Cl—C₆H₄ | CH₃ | H |
| T1ii.074 | CH₃ | 4-Cl—C₆H₄ | CH₂CH₃ | H |
| T1ii.075 | CH₃ | 4-Cl—C₆H₄ | OCH₃ | H |
| T1ii.076 | CH₂CH₃ | Br | Br | H |
| T1ii.077 | CH₂CH₃ | Br | Cl | H |

TABLE 1ii-continued

This table discloses the 132 compounds T1ii.001 to T1ii.132 of the formula Ib:

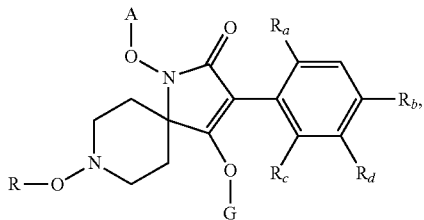

(Ib)

wherein R is $CH_3$, A is hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1ii.078 | $CH_2CH_3$ | Br | $CH_3$ | H |
| T1ii.079 | $CH_2CH_3$ | Br | $CH_2CH_3$ | H |
| T1ii.080 | $CH_2CH_3$ | Br | $OCH_3$ | H |
| T1ii.081 | $CH_2CH_3$ | Cl | Br | H |
| T1ii.082 | $CH_2CH_3$ | Cl | Cl | H |
| T1ii.083 | $CH_2CH_3$ | Cl | $CH_3$ | H |
| T1ii.084 | $CH_2CH_3$ | Cl | $CH_2CH_3$ | H |
| T1ii.085 | $CH_2CH_3$ | Cl | $OCH_3$ | H |
| T1ii.086 | $CH_2CH_3$ | $CH_3$ | Br | H |
| T1ii.087 | $CH_2CH_3$ | $CH_3$ | Cl | H |
| T1ii.088 | $CH_2CH_3$ | $CH_3$ | $CH_2CH_3$ | H |
| T1ii.089 | $CH_2CH_3$ | $CH_3$ | $OCH_3$ | H |
| T1ii.090 | $CH_2CH_3$ | $CH_2CH_3$ | $CH_3$ | H |
| T1ii.091 | $CH_2CH_3$ | $CH_2CH_3$ | $CH_2CH_3$ | H |
| T1ii.092 | $CH_2CH_3$ | 4-Cl—$C_6H_4$ | Br | H |
| T1ii.093 | $CH_2CH_3$ | 4-Cl—$C_6H_4$ | $CH_2CH_3$ | H |
| T1ii.094 | $CH_2CH_3$ | 4-Cl—$C_6H_4$ | $OCH_3$ | H |
| T1ii.095 | $OCH_3$ | Br | $CH_3$ | H |
| T1ii.096 | $OCH_3$ | Cl | $CH_3$ | H |
| T1ii.097 | $OCH_3$ | $CH_3$ | Br | H |
| T1ii.098 | $OCH_3$ | $CH_3$ | Cl | H |
| T1ii.099 | $OCH_3$ | $CH_3$ | $OCH_3$ | H |
| T1ii.100 | $OCH_3$ | 4-Cl—$C_6H_4$ | $OCH_3$ | H |
| T1ii.101 | $CH_3$ | $CH_3$ | $CH_3$ | F |
| T1ii.102 | $CH_3$ | $CH_3$ | $CH_3$ | Cl |
| T1ii.103 | $CH_3$ | $CH_3$ | $CH_3$ | Br |
| T1ii.104 | $CH_3$ | $CH_3$ | $CH_3$ | $CH_3$ |
| T1ii.105 | $CH_3$ | $CH_3$ | $CH_3$ | 4-Cl—$C_6H_4$ |
| T1ii.106 | Cl | $CH_3$ | $CH_3$ | $CH_3$ |
| T1ii.107 | $CH_3$ | Cl | $CH_3$ | $CH_3$ |
| T1ii.108 | $CH_3$ | $CH_3$ | Cl | $CH_3$ |
| T1ii.109 | $CH_2CH_3$ | $CH_3$ | $CH_3$ | $CH_3$ |
| T1ii.110 | $OCH_3$ | $CH_3$ | $CH_3$ | $CH_3$ |
| T1ii.111 | Cyclo-C3 | $CH_3$ | $CH_3$ | $CH_3$ |
| T1ii.112 | $CH_3$ | $CH_3$ | Cyclo-C3 | H |
| T1ii.113 | $CH_3$ | F | H | Br |
| T1ii.114 | $CH_3$ | $CH_3$ | H | Br |
| T1ii.115 | $CH_2CH_3$ | $CH_3$ | H | $CH_3$ |
| T1ii.116 | $OCH_3$ | $CH_3$ | H | $CH_3$ |
| T1ii.117 | Cyclo-C3 | $CH_3$ | H | $CH_3$ |
| T1ii.118 | $CH_2CH_3$ | Cl | H | $CH_3$ |
| T1ii.119 | $OCH_3$ | Cl | H | $CH_3$ |
| T1ii.120 | Cyclo-C3 | Cl | H | $CH_3$ |
| T1ii.121 | Cl | H | $CH_3$ | $CH_3$ |
| T1ii.122 | $CH_3$ | H | $CH_3$ | $CH_3$ |
| T1ii.123 | $CH_2CH_3$ | H | $CH_3$ | $CH_3$ |
| T1ii.124 | $OCH_3$ | H | $CH_3$ | $CH_3$ |
| T1ii.125 | Cyclo-C3 | H | $CH_3$ | $CH_3$ |
| T1ii.126 | F | H | Cl | $CH_3$ |
| T1ii.127 | Cl | H | F | $CH_3$ |
| T1ii.128 | H | $CH_3$ | $CH_3$ | $CH_3$ |
| T1ii.129 | Br | $CH_3$ | $CH_3$ | $CH_3$ |
| T1ii.130 | $CH_3$ | H | Cl | $CH_3$ |
| T1ii.131 | $CH_3$ | H | Br | $CH_3$ |
| T1ii.132 | Br | H | $CH_3$ | $CH_3$ |

Cyclo-C3 means cyclopropyl.

Table 2ii: This table discloses the 132 compounds T2ii.001 to T2ii. 132 of the formula Ib, wherein R is $CH_3$, A is $CH_3$, G is hydrogen and $R_a$, $R_b$, $R_c$ and $R_d$ are as defined in Table 1.

Table 3ii: This table discloses the 132 compounds T3ii.001 to T3ii. 132 of the formula Ib, wherein R is $CH_3$, A is $CH_2CH_3$, G is hydrogen and $R_a$, $R_b$, $R_c$ and $R_d$ are as defined in Table 1.

Table 4ii: This table discloses the 132 compounds T4ii.001 to T4ii. 132 of the formula Ib, wherein R is $CH_3$, A is n-$C_3H_7$, G is hydrogen and $R_a$, $R_b$, $R_c$ and $R_d$ are as defined in Table 1.

Table 5ii: This table discloses the 132 compounds T5ii.001 to T5ii. 132 of the formula Ib, wherein R is $CH_3$, A is i-$C_3H_7$, G is hydrogen and $R_a$, $R_b$, $R_c$ and $R_d$ are as defined in Table 1.

Table 6ii: This table discloses the 132 compounds T6ii.001 to T6ii. 132 of the formula Ib, wherein R is $CH_3$, A is n-$C_4H_9$, G is hydrogen and $R_a$, $R_b$, $R_c$, and $R_d$ are as defined in Table 1.

Table 7ii: This table discloses the 132 compounds T7ii.001 to T7ii. 132 of the formula Ib, wherein R is $CH_3$, A is i-$C_4H_9$, G is hydrogen and $R_a$, $R_b$, $R_c$, and $R_d$ are as defined in Table 1.

Table 8ii: This table discloses the 132 compounds T8ii.001 to T8ii. 132 of the formula Ib, wherein R is $CH_3$, A is t-$C_4H_9$, G is hydrogen and $R_a$, $R_b$, $R_c$, and $R_d$ are as defined in Table 1.

Table 9ii: This table discloses the 132 compounds T9ii.001 to T9ii. 132 of the formula Ib, wherein R is $CH_3$, A is cyclopropyl, G is hydrogen and $R_a$, $R_b$, $R_c$, and $R_d$ are as defined in Table 1.

Table 10ii: This table discloses the 132 compounds T10ii.001 to T10ii. 132 of the formula Ib, wherein R is $CH_3$, A is cyclopentyl, G is hydrogen and $R_a$, $R_b$, $R_c$, and $R_d$ are as defined in Table 1.

Table 11ii: This table discloses the 132 compounds T11ii.001 to T11ii. 132 of the formula Ib, wherein R is $CH_3$, A is cyclohexyl, G is hydrogen and $R_a$, $R_b$, $R_c$, and $R_d$ are as defined in Table 1.

Table 12ii: This table discloses the 132 compounds T12ii.001 to T12ii. 132 of the formula Ib, wherein R is $CH_3$, A is 2,2-$(CH_3)_2$-propyl, G is hydrogen and $R_a$, $R_b$, $R_c$, and $R_d$ are as defined in Table 1.

Table 13ii: This table discloses the 132 compounds T13ii.001 to T13ii. 132 of the formula Ib, wherein R is $CH_3$, A is allyl, G is hydrogen and $R_a$, $R_b$, $R_c$, and $R_d$ are as defined in Table 1.

Table 14ii: This table discloses the 132 compounds T14ii.001 to T14ii. 132 of the formula Ib, wherein R is $CH_3$, A is $CH_2$—CH=$C(CH_3)_2$, G is hydrogen and $R_a$, $R_b$, $R_c$, and $R_d$ are as defined in Table 1.

Table 15ii: This table discloses the 132 compounds T15ii.001 to T15ii. 132 of the formula Ib, wherein R is $CH_3$, A is $CH_2$—CH=$C(Cl)_2$, G is hydrogen and $R_a$, $R_b$, $R_c$, and $R_d$ are as defined in Table 1.

Table 16ii: This table discloses the 132 compounds T16ii.001 to T16ii. 132 of the formula Ib, wherein R is $CH_3$, A is propargyl, G is hydrogen and $R_a$, $R_b$, $R_c$, and $R_d$ are as defined in Table 1.

Table 17ii: This table discloses the 132 compounds T17ii.001 to T17ii. 132 of the formula Ib, wherein R is $CH_3$, A is $CH_2C{\equiv}CCH_3$, G is hydrogen and $R_a$, $R_b$, $R_c$, and $R_d$ are as defined in Table 1.

Table 18ii: This table discloses the 132 compounds T18ii.001 to T18ii. 132 of the formula Ib, wherein R is $CH_3$, A is $CH_2$-cyclopropyl, G is hydrogen and $R_a$, $R_b$, $R_c$, and $R_d$ are as defined in Table 1.

Table 19ii: This table discloses the 132 compounds T19ii.001 to T19ii. 132 of the formula Ib, wherein R is $CH_3$, A is $CH_2CN$, G is hydrogen and $R_a$, $R_b$, $R_c$, and $R_d$ are as defined in Table 1.

Table 20ii: This table discloses the 132 compounds T20ii.001 to T20ii. 132 of the formula Ib, wherein R is $CH_3$, A is $CH_2OCH_3$, G is hydrogen and $R_a$, $R_b$, $R_c$, and $R_d$ are as defined in Table 1.

Table 21ii: This table discloses the 132 compounds T21ii.001 to T21ii. 132 of the formula Ib, wherein R is $CH_3$, A is $CH_2OCH_2CH_3$, G is hydrogen and $R_a$, $R_b$, $R_c$, and $R_d$ are as defined in Table 1.

Table 22ii: This table discloses the 132 compounds T22ii.001 to T22ii. 132 of the formula Ib, wherein R is $CH_3$, A is $CH_2CH_2OCH_3$, G is hydrogen and $R_a$, $R_b$, $R_c$, and $R_d$ are as defined in Table 1.

Table 23ii: This table discloses the 132 compounds T23ii.001 to T23ii. 132 of the formula Ib, wherein R is $CH_3$, A is $CH_2OCH_2CH_2OCH_3$, G is hydrogen and $R_a$, $R_b$, $R_c$, and $R_d$ are as defined in Table 1.

Table 24ii: This table discloses the 132 compounds T24ii.001 to T24ii. 132 of the formula Ib, wherein R is $CH_3$, A is oxetan-3-yl, G is hydrogen and $R_a$, $R_b$, $R_c$, and $R_d$ are as defined in Table 1.

Table 25ii: This table discloses the 132 compounds T25ii.001 to T25ii. 132 of the formula Ib, wherein R is $CH_3$, A is tetrahydrofuran-2-yl, G is hydrogen and $R_a$, $R_b$, $R_c$, and $R_d$ are as defined in Table 1.

Table 26ii: This table discloses the 132 compounds T26ii.001 to T26ii. 132 of the formula Ib, wherein R is $CH_3$, A is tetrahydrofuran-3-yl, G is hydrogen and $R_a$, $R_b$, $R_c$, and $R_d$ are as defined in Table 1.

Table 27ii: This table discloses the 132 compounds T27ii.001 to T27ii. 132 of the formula Ib, wherein R is $CH_3$, A is tetrahydropyran-2-yl, G is hydrogen and $R_a$, $R_b$, $R_c$, and $R_d$ are as defined in Table 1.

Table 28ii: This table discloses the 132 compounds T28ii.001 to T28ii. 132 of the formula Ib, wherein R is $CH_3$, A is tetrahydropyran-4-yl, G is hydrogen and $R_a$, $R_b$, $R_c$, and $R_d$ are as defined in Table 1.

Table 29ii: This table discloses the 132 compounds T29ii.001 to T29ii. 132 of the formula Ib, wherein R is $CH_3$, A is $CH_2CHF_2$, G is hydrogen and $R_a$, $R_b$, $R_c$, and $R_d$ are as defined in Table 1.

Table 30ii: This table discloses the 132 compounds T30ii.001 to T30ii. 132 of the formula Ib, wherein R is $CH_3$, A is $CH_2C(O)$—$CH_3$, G is hydrogen and $R_a$, $R_b$, $R_c$, and $R_d$ are as defined in Table 1.

Table 31ii: This table discloses the 132 compounds T31ii.001 to T31ii. 132 of the formula Ib, wherein R is $CH_3$, A is $CH_2C(O)$—$CH_2CH_3$, G is hydrogen and $R_a$, $R_b$, $R_c$, and $R_d$ are as defined in Table 1.

Table 32ii: This table discloses the 132 compounds T32ii.001 to T32ii. 132 of the formula Ib, wherein R is $CH_3$, A is $CH(CH_3)C(O)$—$CH_3$, G is hydrogen and $R_a$, $R_b$, $R_c$, and $R_d$ are as defined in Table 1.

Table 33ii: This table discloses the 132 compounds T33ii.001 to T33ii. 132 of the formula Ib, wherein R is $CH_3$, A is $C(CH_3)_2C(O)$—$CH_3$, G is hydrogen and $R_a$, $R_b$, $R_c$, and $R_d$ are as defined in Table 1.

Table 34ii: This table discloses the 132 compounds T34ii.001 to T34ii. 132 of the formula Ib, wherein R is $CH_3$, A is benzyl, G is hydrogen and $R_a$, $R_b$, $R_c$, and $R_d$ are as defined in Table 1.

Table 35ii: This table discloses the 132 compounds T35ii.001 to T35ii. 132 of the formula Ib, wherein R is $CH_3$, A is $C(O)$—$CH_3$, G is hydrogen and $R_a$, $R_b$, $R_c$, and $R_d$ are as defined in Table 1.

Table 36ii: This table discloses the 132 compounds T36ii.001 to T36ii. 132 of the formula Ib, wherein R is $CH_3$, A is $C(O)$—$OCH_3$, G is hydrogen and $R_a$, $R_b$, $R_c$, and $R_d$ are as defined in Table 1.

Table 37ii: This table discloses the 132 compounds T37ii.001 to T37ii. 132 of the formula Ib, wherein R is $CH_3$, A is $C(O)$-cyclopropyl, G is hydrogen and $R_a$, $R_b$, $R_c$, and $R_d$ are as defined in Table 1.

Table 38ii: This table discloses the 132 compounds T37ii.001 to T37ii. 132 of the formula Ib, wherein R is $CH_3$, A is $C(O)$—$N(CH_3)_2$, G is hydrogen and $R_a$, $R_b$, $R_c$, and $R_d$ are as defined in Table 1.

Table 39ii: This table discloses the 132 compounds T39ii.001 to T39ii. 132 of the formula Ib, wherein R is hydrogen, A is hydrogen, G is hydrogen and $R_a$, $R_b$, $R_c$, and $R_d$ are as defined in Table 1.

Table 40ii: This table discloses the 132 compounds T40ii.001 to T40ii. 132 of the formula Ib, wherein R is hydrogen, A is $CH_3$, G is hydrogen and $R_a$, $R_b$, $R_c$, and $R_d$ are as defined in Table 1.

Table 41ii: This table discloses the 132 compounds T41ii.001 to T41ii. 132 of the formula Ib, wherein R is hydrogen, A is $CH_2OCH_3$, G is hydrogen and $R_a$, $R_b$, $R_c$, and $R_d$ are as defined in Table 1.

Table 42ii: This table discloses the 132 compounds T42ii.001 to T42ii. 132 of the formula Ib, wherein R is hydrogen, A is $CH_2CH_2OCH_3$, G is hydrogen and $R_a$, $R_b$, $R_c$, and $R_d$ are as defined in Table 1.

Table 43ii: This table discloses the 132 compounds T43ii.001 to T43ii. 132 of the formula Ib, wherein R is hydrogen, A is propargyl, G is hydrogen and $R_a$, $R_b$, $R_c$, and $R_d$ are as defined in Table 1.

Table 44ii: This table discloses the 132 compounds T44ii.001 to T44ii. 132 of the formula Ib, wherein R is $CH_2CH_3$, A is hydrogen, G is hydrogen and $R_a$, $R_b$, $R_c$, and $R_d$ are as defined in Table 1.

Table 45ii: This table discloses the 132 compounds T45ii.001 to T45ii. 132 of the formula Ib, wherein R is $CH_2CH_3$, A is $CH_3$, G is hydrogen and $R_a$, $R_b$, $R_c$, and $R_d$ are as defined in Table 1.

Table 46ii: This table discloses the 132 compounds T46ii.001 to T46ii. 132 of the formula Ib, wherein R is $CH_2CH_3$, A is $CH_2OCH_3$, G is hydrogen and $R_a$, $R_b$, $R_c$, and $R_d$ are as defined in Table 1.

Table 47ii: This table discloses the 132 compounds T47ii.001 to T47ii. 132 of the formula Ib, wherein R is $CH_2CH_3$, A is $CH_2CH_2OCH_3$, G is hydrogen and $R_a$, $R_b$, $R_c$, and $R_d$ are as defined in Table 1.

Table 48ii: This table discloses the 132 compounds T48ii.001 to T48ii. 132 of the formula Ib, wherein R is $CH_2CH_3$, A is propargyl, G is hydrogen and $R_a$, $R_b$, $R_c$, and $R_d$ are as defined in Table 1.

Table 49ii: This table discloses the 132 compounds T49ii.001 to T49ii. 132 of the formula Ib, wherein R is $CH_2OCH_3$, A is hydrogen, G is hydrogen and $R_a$, $R_b$, $R_c$, and $R_d$ are as defined in Table 1.

Table 50ii: This table discloses the 132 compounds T50ii.001 to T50ii.132 of the formula Ib, wherein R is $CH_2OCH_3$, A is $CH_3$, G is hydrogen and $R_a$, $R_b$, $R_c$, and $R_d$ are as defined in Table 1.

Table 51ii: This table discloses the 132 compounds T51ii.001 to T51ii.132 of the formula Ib, wherein R is $CH_2OCH_3$, A is $CH_2OCH_3$, G is hydrogen and $R_a$, $R_b$, $R_c$, and $R_d$ are as defined in Table 1.

Table 52ii: This table discloses the 132 compounds T52ii.001 to T52ii.132 of the formula Ib, wherein R is $CH_2OCH_3$, A is $CH_2CH_2OCH_3$, G is hydrogen and $R_a$, $R_b$, $R_c$, and $R_d$ are as defined in Table 1.

Table 53ii: This table discloses the 132 compounds T53ii.001 to T53ii.132 of the formula Ib, wherein R is $CH_2OCH_3$, A is propargyl, G is hydrogen and $R_a$, $R_b$, $R_c$, and $R_d$ are as defined in Table 1.

Table 54ii: This table discloses the 132 compounds T54ii.001 to T54ii.132 of the formula Ib, wherein R is $CH_2CH_2OCH_3$, A is hydrogen, G is hydrogen and $R_a$, $R_b$, $R_c$, and $R_d$ are as defined in Table 1.

Table 55ii: This table discloses the 132 compounds T55ii.001 to T55ii.132 of the formula Ib, wherein R is $CH_2CH_2OCH_3$, A is $CH_3$, G is hydrogen and $R_a$, $R_b$, $R_c$, and $R_d$ are as defined in Table 1.

Table 56ii: This table discloses the 132 compounds T56ii.001 to T56ii.132 of the formula Ib, wherein R is $CH_2CH_2OCH_3$, A is $CH_2OCH_3$, G is hydrogen and $R_a$, $R_b$, $R_c$, and $R_d$ are as defined in Table 1.

Table 57ii: This table discloses the 132 compounds T57ii.001 to T57ii.132 of the formula Ib, wherein R is $CH_2CH_2OCH_3$, A is $CH_2CH_2OCH_3$, G is hydrogen and $R_a$, $R_b$, $R_c$, and $R_d$ are as defined in Table 1.

Table 58ii: This table discloses the 132 compounds T58ii.001 to T58ii.132 of the formula Ib, wherein R is $CH_2CH_2OCH_3$, A is propargyl, G is hydrogen and $R_a$, $R_b$, $R_c$, and $R_d$ are as defined in Table 1.

Table 59ii: This table discloses the 132 compounds T59ii.001 to T59ii.132 of the formula Ib, wherein R is benzyl, A is hydrogen, G is hydrogen and $R_a$, $R_b$, $R_c$, and $R_d$ are as defined in Table 1.

Table 60ii: This table discloses the 132 compounds T60ii.001 to T60ii.132 of the formula Ib, wherein R is benzyl, A is $CH_3$, G is hydrogen and $R_a$, $R_b$, $R_c$, and $R_d$ are as defined in Table 1.

Table 61ii: This table discloses the 132 compounds T61ii.001 to T61ii.132 of the formula Ib, wherein R is benzyl, A is $CH_2OCH_3$, G is hydrogen and $R_a$, $R_b$, $R_c$, and $R_d$ are as defined in Table 1.

Table 62ii: This table discloses the 132 compounds T62ii.001 to T62ii.132 of the formula Ib, wherein R is benzyl, A is $CH_2CH_2OCH_3$, G is hydrogen and $R_a$, $R_b$, $R_c$, and $R_d$ are as defined in Table 1.

Table 63ii: This table discloses the 132 compounds T63ii.001 to T63ii.132 of the formula Ib, wherein R is benzyl, A is propargyl, G is hydrogen and $R_a$, $R_b$, $R_c$, and $R_d$ are as defined in Table 1.

Table 64ii: This table discloses the 132 compounds T64ii.001 to T64ii.132 of the formula Ib, wherein R is $CH_3$, A is cyclobutyl, G is hydrogen and $R_a$, $R_b$, $R_c$, and $R_d$ are as defined in Table 1.

Table 65ii: This table discloses the 132 compounds T65ii.001 to T65ii.132 of the formula Ib, wherein R is $CH_3$, A is $CH_2CH_2CH_2OCH_3$, G is hydrogen and $R_a$, $R_b$, $R_c$, and $R_d$ are as defined in Table 1.

Table 66ii: This table discloses the 132 compounds T66ii.001 to T66ii.132 of the formula Ib, wherein R is $CH_3$, A is $CH_2CH_2O$(tetrahydrofuran-2-yl), G is hydrogen and $R_a$, $R_b$, $R_c$ and $R_d$ are as defined in Table 1.

Table 67ii: This table discloses the 132 compounds T67ii.001 to T67ii.132 of the formula Ib, wherein R is $CH_3$, A is $CH_2CH_2O$(tetrahydropyran-2-yl), G is hydrogen and $R_a$, $R_b$, R and $R_d$ are as defined in Table 1.

Table 68ii: This table discloses the 132 compounds T68ii.001 to T68ii.132 of the formula Ib, wherein R is $CH_3$, A is $CH_2$(oxetan-3-yl), G is hydrogen and $R_a$, $R_b$, $R_c$, and $R_d$ are as defined in Table 1.

Table 69ii: This table discloses the 132 compounds T69ii.001 to T69ii.132 of the formula Ib, wherein R is $CH_3$, A is $CH_2$(3-methyl-oxetan-3-yl), G is hydrogen and $R_a$, $R_b$, $R_c$, and $R_d$ are as defined in Table 1.

Table 70ii: This table discloses the 132 compounds T70ii.001 to T70ii.132 of the formula Ib, wherein R is $CH_3$, A is $CH_2$(tetrahydrofuran-2-yl), G is hydrogen and $R_a$, $R_b$, $R_c$, and $R_d$ are as defined in Table 1.

Table 71ii: This table discloses the 132 compounds T71ii.001 to T71ii.132 of the formula Ib, wherein R is $CH_3$, A is $CH_2$(tetrahydrofuran-3-yl), G is hydrogen and $R_a$, $R_b$, $R_c$, and $R_d$ are as defined in Table 1.

Table 72ii: This table discloses the 132 compounds T72ii.001 to T72ii.132 of the formula Ib, wherein R is $CH_3$, A is $CH_2$(tetrahydropyran-2-yl), G is hydrogen and $R_a$, $R_b$, $R_c$, and $R_d$ are as defined in Table 1.

Table 73ii: This table discloses the 132 compounds T73ii.001 to T73ii.132 of the formula Ib, wherein R is $CH_3$, A is $CH_2$(tetrahydropyran-3-yl), G is hydrogen and $R_a$, $R_b$, $R_c$, and $R_d$ are as defined in Table 1.

Table 74ii: This table discloses the 132 compounds T74ii.001 to T74ii.132 of the formula Ib, wherein R is $CH_3$, A is $CH_2$(tetrahydropyran-4-yl), G is hydrogen and $R_a$, $R_b$, $R_c$, and $R_d$ are as defined in Table 1.

Table 75ii: This table discloses the 132 compounds T75ii.001 to T75ii.132 of the formula Ib, wherein R is hydrogen, A is $CH_2CH_3$, G is hydrogen and $R_a$, $R_b$, $R_c$, and $R_d$ are as defined in Table 1.

Table 76ii: This table discloses the 132 compounds T76ii.001 to T76ii.132 of the formula Ib, wherein R is hydrogen, A is allyl, G is hydrogen and $R_a$, $R_b$, $R_c$, and $R_d$ are as defined in Table 1.

Table 77ii: This table discloses the 132 compounds T77ii.001 to T77ii.132 of the formula Ib, wherein R is hydrogen, A is tetrahydrofuran-2-yl, G is hydrogen and $R_a$, $R_b$, $R_c$, and $R_d$ are as defined in Table 1.

Table 78ii: This table discloses the 132 compounds T78ii.001 to T78ii.132 of the formula Ib, wherein R is hydrogen, A is tetrahydropyran-2-yl, G is hydrogen and $R_a$, $R_b$, $R_c$, and $R_d$ are as defined in Table 1.

Table 79ii: This table discloses the 132 compounds T79ii.001 to T79ii.132 of the formula Ib, wherein R is $CH_2CH_3$, A is $CH_2CH_3$, G is hydrogen and $R_a$, $R_b$, $R_c$, and $R_d$ are as defined in Table 1.

Table 80ii: This table discloses the 132 compounds T80ii.001 to T80ii.132 of the formula Ib, wherein R is $CH_2CH_3$, A is allyl, G is hydrogen and $R_a$, $R_b$, $R_c$, and $R_d$ are as defined in Table 1.

Table 81ii: This table discloses the 132 compounds T81ii.001 to T81ii.132 of the formula Ib, wherein R is $CH_2CH_3$, A is tetrahydrofuran-2-yl, G is hydrogen and $R_a$, $R_b$, $R_c$, and $R_d$ are as defined in Table 1.

Table 82ii: This table discloses the 132 compounds T82ii.001 to T82ii.132 of the formula Ib, wherein R is $CH_2CH_3$, A is tetrahydropyran-2-yl, G is hydrogen and $R_a$, $R_b$, $R_c$, and $R_d$ are as defined in Table 1.

Table 83ii: This table discloses the 132 compounds T83ii.001 to T83ii.132 of the formula Ib, wherein R is CH$_2$OCH$_3$, A is CH$_2$CH$_3$, G is hydrogen and R$_a$, R$_b$, R$_c$, and R$_d$ are as defined in Table 1.

Table 84ii: This table discloses the 132 compounds T84ii.001 to T84ii.132 of the formula Ib, wherein R is CH$_2$OCH$_3$, A is allyl, G is hydrogen and R$_a$, R$_b$, R$_c$, and R$_d$ are as defined in Table 1.

Table 85ii: This table discloses the 132 compounds T85ii.001 to T85ii.132 of the formula Ib, wherein R is CH$_2$OCH$_3$, A is tetrahydrofuran-2-yl, G is hydrogen and R$_a$, R$_b$, R$_c$, and R$_d$ are as defined in Table 1.

Table 86ii: This table discloses the 132 compounds T86ii.001 to T86ii.132 of the formula Ib, wherein R is CH$_2$OCH$_3$, A is tetrahydropyran-2-yl, G is hydrogen and R$_a$, R$_b$, R$_c$, and R$_d$ are as defined in Table 1.

Table 87ii: This table discloses the 132 compounds T87ii.001 to T87ii.132 of the formula Ib, wherein R is CH$_2$CH$_2$OCH$_3$, A is CH$_2$CH$_3$, G is hydrogen and R$_a$, R$_b$, R$_c$, and R$_d$ are as defined in Table 1.

Table 88ii: This table discloses the 132 compounds T88ii.001 to T88ii.132 of the formula Ib, wherein R is CH$_2$CH$_2$OCH$_3$, A is allyl, G is hydrogen and R$_a$, R$_b$, R$_c$, and R$_d$ are as defined in Table 1.

Table 89ii: This table discloses the 132 compounds T89ii.001 to T89ii.132 of the formula Ib, wherein R is CH$_2$CH$_2$OCH$_3$, A is tetrahydrofuran-2-yl, G is hydrogen and R$_a$, R$_b$, R$_c$ and R$_d$ are as defined in Table 1.

Table 90ii: This table discloses the 132 compounds T90ii.001 to T90ii.132 of the formula Ib, wherein R is CH$_2$CH$_2$OCH$_3$, A is tetrahydropyran-2-yl, G is hydrogen and R$_a$, R$_b$, R$_c$ and R$_d$ are as defined in Table 1.

Table 91ii: This table discloses the 132 compounds T91ii.001 to T91ii.132 of the formula Ib, wherein R is CH$_3$, A is CH$_2$-cyclobutyl, G is hydrogen and R$_a$, R$_b$, R$_c$, and R$_d$ are as defined in Table 1.

Table 92ii: This table discloses the 132 compounds T92ii.001 to T92ii.132 of the formula Ib, wherein R is CH$_3$, A is CH$_2$-cyclopentyl, G is hydrogen and R$_a$, R$_b$, R$_c$, and R$_d$ are as defined in Table 1.

Table 93ii: This table discloses the 132 compounds T93ii.001 to T93ii.132 of the formula Ib, wherein R is CH$_3$, A is CH$_2$-cyclohexyl, G is hydrogen and R$_a$, R$_b$, R$_c$, and R$_d$ are as defined in Table 1.

Table 94ii: This table discloses the 132 compounds T94ii.001 to T94ii.132 of the formula Ib, wherein R is CH$_3$, A is CH$_2$(3-ethyl-oxetan-3-yl), G is hydrogen and R$_a$, R$_b$, R$_c$, and R$_d$ are as defined in Table 1.

Table 95ii: This table discloses the 132 compounds T95ii.001 to T95ii.132 of the formula Ib, wherein R is CH$_3$, A is CH$_2$(furan-2-yl), G is hydrogen and R$_a$, R$_b$, R$_c$, and R$_d$ are as defined in Table 1.

Table 96ii: This table discloses the 132 compounds T96ii.001 to T96ii.132 of the formula Ib, wherein R is CH$_3$, A is CH$_2$(furan-3-yl), G is hydrogen and R$_a$, R$_b$, R$_c$, and R$_d$ are as defined in Table 1.

Table 97ii: This table discloses the 132 compounds T97ii.001 to T97ii.132 of the formula Ib, wherein R is CH$_3$, A is CH$_2$(tetrahydro-thiopyran-4-yl), G is hydrogen and R$_a$, R$_b$, R$_c$ and R$_d$ are as defined in Table 1.

Table 98ii: This table discloses the 132 compounds T98ii.001 to T98ii.132 of the formula Ib, wherein R is CH$_3$, A is C(O)—OCH$_2$CH$_3$, G is hydrogen and R$_a$, R$_b$, R$_c$, and R$_d$ are as defined in Table 1.

Table 99ii: This table discloses the 132 compounds T99ii.001 to T99ii.132 of the formula Ib, wherein R is CH$_3$, A is CH$_2$CH$_2$SCH$_3$, G is hydrogen and R$_a$, R$_b$, R$_c$, and R$_d$ are as defined in Table 1.

Table 100ii: This table discloses the 132 compounds T100ii.001 to T100ii.132 of the formula Ib, wherein R is CH$_3$, A is CH$_2$CH$_2$S(O)CH$_3$, G is hydrogen and R$_a$, R$_b$, R$_c$ and R$_d$ are as defined in Table 1.

Table 101ii: This table discloses the 132 compounds T101ii.001 to T101ii.132 of the formula Ib, wherein R is CH$_3$, A is CH$_2$CH$_2$S(O)$_2$CH$_3$, G is hydrogen and R$_a$, R$_b$, R$_c$ and R$_d$ are as defined in Table 1.

Table 102ii: This table discloses the 132 compounds T102ii.001 to T102ii.132 of the formula Ib, wherein R is CH$_3$, A is 1-methoxy-piperidin-4-yl, G is hydrogen and R$_a$, R$_b$, R$_c$ and R$_d$ are as defined in Table 1.

TABLE 1iii

This table discloses the 105 compounds T1iii.001 to T1iii.105 of the formula Ic:

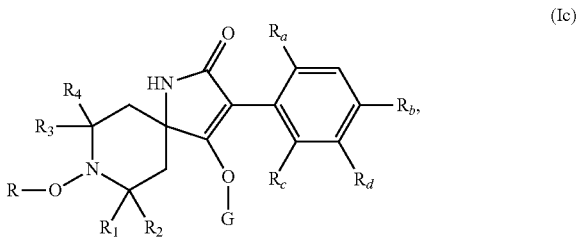

(Ic)

wherein R is CH$_3$, R$_1$, R$_2$, R$_3$ and R$_4$ are hydrogen, G is hydrogen and R$_a$, R$_b$, R$_c$ and R$_d$ are as defined below:

| No. | R$_a$ | R$_b$ | R$_c$ | R$_d$ |
| --- | --- | --- | --- | --- |
| T1iii.001 | Br | H | H | H |
| T1iii.002 | Cl | H | H | H |
| T1iii.003 | CH$_3$ | H | H | H |
| T1iii.004 | CH$_2$CH$_3$ | H | H | H |
| T1iii.005 | OCH$_3$ | H | H | H |
| T1iii.006 | Br | Cl | H | H |
| T1iii.007 | Cl | Br | H | H |
| T1iii.008 | Cl | Cl | H | H |
| T1iii.009 | Cl | CH$_3$ | H | H |
| T1iii.010 | CH$_3$ | Cl | H | H |

TABLE 1iii-continued

This table discloses the 105 compounds T1iii.001 to T1iii.105 of the formula Ic:

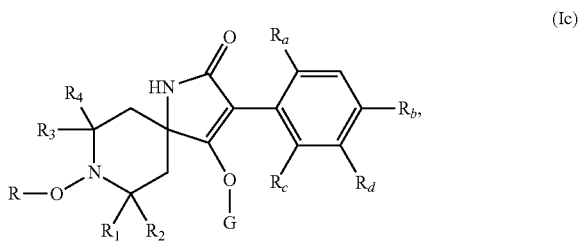
(Ic)

wherein R is CH₃, R₁, R₂, R₃ and R₄ are hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1iii.011 | CH₃ | CH₃ | H | H |
| T1iii.012 | Cl | H | Cl | H |
| T1iii.013 | Cl | H | CH₃ | H |
| T1iii.014 | Cl | H | CH₂CH₃ | H |
| T1iii.015 | Cl | H | OCH₃ | H |
| T1iii.016 | CH₃ | H | CH₃ | H |
| T1iii.017 | CH₃ | H | CH₂CH₃ | H |
| T1iii.018 | CH₃ | H | OCH₃ | H |
| T1iii.019 | CH₂CH₃ | H | CH₂CH₃ | H |
| T1iii.020 | CH₂CH₃ | H | OCH₃ | H |
| T1iii.021 | OCH₃ | H | OCH₃ | H |
| T1iii.022 | Br | H | H | Cl |
| T1iii.023 | Br | H | H | CH₃ |
| T1iii.024 | Br | H | H | 4-Cl—C₆H₄ |
| T1iii.025 | Cl | H | H | Cl |
| T1iii.026 | Cl | H | H | CH₃ |
| T1iii.027 | Cl | H | H | 4-Cl—C₆H₄ |
| T1iii.028 | CH₃ | H | H | Br |
| T1iii.029 | CH₃ | H | H | Cl |
| T1iii.030 | CH₃ | H | H | CH₃ |
| T1iii.031 | CH₃ | H | H | C₆H₅ |
| T1iii.032 | CH₃ | H | H | 4-Cl—C₆H₄ |
| T1iii.033 | CH₂CH₃ | H | H | CH₃ |
| T1iii.034 | CH₂CH₃ | H | H | 4-Cl—C₆H₄ |
| T1iii.035 | OCH₃ | H | H | CH₃ |
| T1iii.036 | OCH₃ | H | H | 4-Cl—C₆H₄ |
| T1iii.037 | Cl | H | Cl | Br |
| T1iii.038 | CH₃ | H | CH₃ | Br |
| T1iii.039 | CH₃ | H | CH₃ | Cl |
| T1iii.040 | CH₃ | H | CH₃ | 4-Cl—C₆H₄ |
| T1iii.041 | Br | Cl | H | CH₃ |
| T1iii.042 | Br | CH₃ | H | CH₃ |
| T1iii.043 | Cl | Cl | H | Cl |
| T1iii.044 | Cl | Br | H | CH₃ |
| T1iii.045 | Cl | Cl | H | CH₃ |
| T1iii.046 | Cl | CH₃ | H | Cl |
| T1iii.047 | Cl | CH₃ | H | CH₃ |
| T1iii.048 | CH₃ | Br | H | CH₃ |
| T1iii.049 | CH₃ | Cl | H | CH₃ |
| T1iii.050 | CH₃ | CH₃ | H | CH₃ |
| T1iii.051 | CH₃ | CH₃ | H | 4-Cl—C₆H₄ |
| T1iii.052 | Br | Br | CH₃ | H |
| T1iii.053 | Br | Cl | CH₃ | H |
| T1iii.054 | Br | CH₃ | Br | H |
| T1iii.055 | Br | CH₃ | Cl | H |
| T1iii.056 | Cl | Br | CH₃ | H |
| T1iii.057 | Cl | Cl | Cl | H |
| T1iii.058 | Cl | Cl | CH₃ | H |
| T1iii.059 | Cl | CH₃ | Cl | H |
| T1iii.060 | Cl | CH₃ | CH₂CH₃ | H |
| T1iii.061 | Cl | CH₃ | OCH₃ | H |
| T1iii.062 | Cl | 4-Cl—C₆H₄ | Cl | H |
| T1iii.063 | Cl | 4-Cl—C₆H₄ | CH₃ | H |
| T1iii.064 | Cl | 4-Cl—C₆H₄ | CH₂CH₃ | H |
| T1iii.065 | Cl | 4-Cl—C₆H₄ | OCH₃ | H |
| T1iii.066 | CH₃ | Br | CH₃ | H |
| T1iii.067 | CH₃ | Cl | CH₃ | H |
| T1iii.068 | CH₃ | CH₃ | Br | H |
| T1iii.069 | CH₃ | CH₃ | Cl | H |
| T1iii.070 | CH₃ | CH₃ | CH₃ | H |

TABLE 1iii-continued

This table discloses the 105 compounds T1iii.001 to T1iii.105 of the formula Ic:

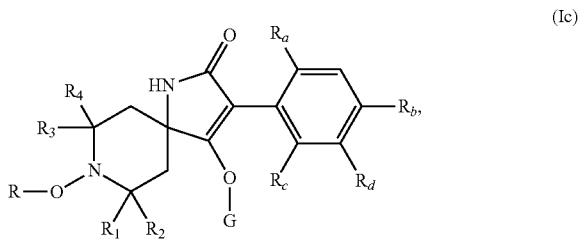

(Ic)

wherein R is $CH_3$, $R_1$, $R_2$, $R_3$ and $R_4$ are hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1iii.071 | $CH_3$ | $CH_3$ | $CH_2CH_3$ | H |
| T1iii.072 | $CH_3$ | $CH_3$ | $OCH_3$ | H |
| T1iii.073 | $CH_3$ | $4\text{-}Cl\text{—}C_6H_4$ | $CH_3$ | H |
| T1iii.074 | $CH_3$ | $4\text{-}Cl\text{—}C_6H_4$ | $CH_2CH_3$ | H |
| T1iii.075 | $CH_3$ | $4\text{-}Cl\text{—}C_6H_4$ | $OCH_3$ | H |
| T1iii.076 | $CH_2CH_3$ | Br | Br | H |
| T1iii.077 | $CH_2CH_3$ | Br | Cl | H |
| T1iii.078 | $CH_2CH_3$ | Br | $CH_3$ | H |
| T1iii.079 | $CH_2CH_3$ | Br | $CH_2CH_3$ | H |
| T1iii.080 | $CH_2CH_3$ | Br | $OCH_3$ | H |
| T1iii.081 | $CH_2CH_3$ | Cl | Br | H |
| T1iii.082 | $CH_2CH_3$ | Cl | Cl | H |
| T1iii.083 | $CH_2CH_3$ | Cl | $CH_3$ | H |
| T1iii.084 | $CH_2CH_3$ | Cl | $CH_2CH_3$ | H |
| T1iii.085 | $CH_2CH_3$ | Cl | $OCH_3$ | H |
| T1iii.086 | $CH_2CH_3$ | $CH_3$ | Br | H |
| T1iii.087 | $CH_2CH_3$ | $CH_3$ | Cl | H |
| T1iii.088 | $CH_2CH_3$ | $CH_3$ | $CH_2CH_3$ | H |
| T1iii.089 | $CH_2CH_3$ | $CH_3$ | $OCH_3$ | H |
| T1iii.090 | $CH_2CH_3$ | $CH_2CH_3$ | $CH_3$ | H |
| T1iii.091 | $CH_2CH_3$ | $CH_2CH_3$ | $CH_2CH_3$ | H |
| T1iii.092 | $CH_2CH_3$ | $4\text{-}Cl\text{—}C_6H_4$ | Br | H |
| T1iii.093 | $CH_2CH_3$ | $4\text{-}Cl\text{—}C_6H_4$ | $CH_2CH_3$ | H |
| T1iii.094 | $CH_2CH_3$ | $4\text{-}Cl\text{—}C_6H_4$ | $OCH_3$ | H |
| T1iii.095 | $OCH_3$ | Br | $CH_3$ | H |
| T1iii.096 | $OCH_3$ | Cl | $CH_3$ | H |
| T1iii.097 | $OCH_3$ | $CH_3$ | Br | H |
| T1iii.098 | $OCH_3$ | $CH_3$ | Cl | H |
| T1iii.099 | $OCH_3$ | $CH_3$ | $OCH_3$ | H |
| T1iii.100 | $OCH_3$ | $4\text{-}Cl\text{—}C_6H_4$ | $OCH_3$ | H |
| T1iii.101 | $CH_3$ | $CH_3$ | $CH_3$ | F |
| T1iii.102 | $CH_3$ | $CH_3$ | $CH_3$ | Cl |
| T1iii.103 | $CH_3$ | $CH_3$ | $CH_3$ | Br |
| T1iii.104 | $CH_3$ | $CH_3$ | $CH_3$ | $CH_3$ |
| T1iii.105 | $CH_3$ | $CH_3$ | $CH_3$ | $4\text{-}Cl\text{—}C_6H_4$ |

Table 2iii: This table discloses the 105 compounds T2iii.001 to T2iii. 105 of the formula Ic, wherein R is $CH_2CH_3$, $R_1$, $R_2$, $R_3$ and $R_4$ are hydrogen, G is hydrogen and $R_a$, $R_b$, $R_c$ and $R_d$ are as defined in Table 1.

Table 3iii: This table discloses the 105 compounds T3iii.001 to T3iii. 105 of the formula Ic, wherein R is n-$C_3H_7$, $R_1$, $R_2$, $R_3$ and $R_4$ are hydrogen, G is hydrogen and $R_a$, $R_b$, $R_c$ and $R_d$ are as defined in Table 1.

Table 4iii: This table discloses the 105 compounds T4iii.001 to T4iii. 105 of the formula Ic, wherein R is i-$C_3H_7$, $R_1$, $R_2$, $R_3$ and $R_4$ are hydrogen, G is hydrogen and $R_a$, $R_b$, $R_c$ and $R_d$ are as defined in Table 1.

Table 5ii: This table discloses the 105 compounds T5iii.001 to T5iii. 105 of the formula Ic, wherein R is allyl, $R_1$, $R_2$, $R_3$ and $R_4$ are hydrogen, G is hydrogen and $R_a$, $R_b$, $R_c$, and $R_d$ are as defined in Table 1.

Table 6ii: This table discloses the 105 compounds T6iii.001 to T6iii. 105 of the formula Ic, wherein R is benzyl, $R_1$, $R_2$, $R_3$ and $R_4$ are hydrogen, G is hydrogen and $R_a$, $R_b$, $R_c$ and $R_d$ are as defined in Table 1.

Table 7iii: This table discloses the 105 compounds T7iii.001 to T7iii. 105 of the formula Ic, wherein R is C(=O)—$CH_3$, $R_1$, $R_2$, $R_3$ and $R_4$ are hydrogen, G is hydrogen and $R_a$, $R_b$, $R_c$, and $R_d$ are as defined in Table 1.

Table 8iii: This table discloses the 105 compounds T8iii.001 to T8iii. 105 of the formula Ic, wherein R is C(=O)—$CH_2CH_3$, $R_1$, $R_2$, $R_3$ and $R_4$ are hydrogen, G is hydrogen and $R_a$, $R_b$, $R_c$ and $R_d$ are as defined in Table 1.

Table 9iii: This table discloses the 105 compounds T9iii.001 to T9iii. 105 of the formula Ic, wherein R is C(=O)-n-$C_3H_7$, $R_1$, $R_2$, $R_3$ and $R_4$ are hydrogen, G is hydrogen and $R_a$, $R_b$, $R_c$ and $R_d$ are as defined in Table 1.

Table 10iii: This table discloses the 105 compounds T10iii.001 to T10iii. 105 of the formula Ic, wherein R is C(=O)O—$CH_3$, $R_1$, $R_2$, $R_3$ and $R_4$ are hydrogen, G is hydrogen and $R_a$, $R_b$, $R_c$ and $R_d$ are as defined in Table 1.

Table 11 iii: This table discloses the 105 compounds T11 iii.001 to T11iii. 105 of the formula Ic, wherein R is C(=O)O—$CH_2CH_3$, $R_1$, $R_2$, $R_3$ and $R_4$ are hydrogen, G is hydrogen and $R_a$, $R_b$, $R_c$, and $R_d$ are as defined in Table 1.

Table 12iii: This table discloses the 105 compounds T12iii.001 to T12iii. 105 of the formula Ic, wherein R is C(=O)O-n-$C_3H_7$, $R_1$, $R_2$, $R_3$ and $R_4$ are hydrogen, G is hydrogen and $R_a$, $R_b$, $R_c$, and $R_d$ are as defined in Table 1.

Table 13iii: This table discloses the 105 compounds T13iii.001 to T13iii. 105 of the formula Ic, wherein R is C(=O)NH—$CH_3$, $R_1$, $R_2$, $R_3$ and $R_4$ are hydrogen, G is hydrogen and $R_a$, $R_b$, $R_c$, and $R_d$ are as defined in Table 1.

Table 14iii: This table discloses the 105 compounds T14iii.001 to T14iii. 105 of the formula Ic, wherein R is C(=O)NH—$CH_2CH_3$, $R_1$, $R_2$, $R_3$ and $R_4$ are hydrogen, G is hydrogen and $R_a$, $R_b$, $R_c$, and $R_d$ are as defined in Table 1.

Table 15iii: This table discloses the 105 compounds T15iii.001 to T15iii. 105 of the formula Ic, wherein R is C(=O)NH-n-$C_3H_7$, $R_1$, $R_2$, $R_3$ and $R_4$ are hydrogen, G is hydrogen and $R_a$, $R_b$, $R_c$, and $R_d$ are as defined in Table 1.

Table 16iii: This table discloses the 105 compounds T16iii.001 to T16iii. 105 of the formula Ic, wherein R is hydrogen, $R_1$, $R_2$, $R_3$ and $R_4$ are hydrogen, G is hydrogen and $R_a$, $R_b$, $R_c$ and $R_d$ are as defined in Table 1.

Table 17iii: This table discloses the 105 compounds T17iii.001 to T17iii. 105 of the formula Ic, wherein R is $CH_2$—O—$CH_3$, $R_1$, $R_2$, $R_3$ and $R_4$ are hydrogen, G is hydrogen and $R_a$, $R_b$, $R_c$ and $R_d$ are as defined in Table 1.

Table 18iii: This table discloses the 105 compounds T18iii.001 to T18iii. 105 of the formula Ic, wherein R is $CH_2$—O—$C_2H_5$, $R_1$, $R_2$, $R_3$ and $R_4$ are hydrogen, G is hydrogen and $R_a$, $R_b$, $R_c$ and $R_d$ are as defined in Table 1.

Table 19iii: This table discloses the 105 compounds T19iii.001 to T19iii. 105 of the formula Ic, wherein R is $CH_2$—O—$C_2H_4$—O—$CH_3$, $R_1$, $R_2$, $R_3$ and $R_4$ are hydrogen, G is hydrogen and $R_a$, $R_b$, $R_c$, and $R_d$ are as defined in Table 1.

Table 20iii: This table discloses the 105 compounds T20iii.001 to T20iii. 105 of the formula Ic, wherein R is hydrogen, $R_1$, $R_2$, $R_3$ and $R_4$ are $CH_3$, G is hydrogen and $R_a$, $R_b$, $R_c$ and $R_d$ are as defined in Table 1.

Table 21 iii: This table discloses the 105 compounds T21 iii.001 to T21iii. 105 of the formula Ic, wherein R is $CH_3$, $R_1$, $R_2$, $R_3$ and $R_4$ are $CH_3$, G is hydrogen and $R_a$, $R_b$, $R_c$ and $R_d$ are as defined in Table 1.

Table 22iii: This table discloses the 105 compounds T22iii.001 to T22iii. 105 of the formula Ic, wherein R is $C_2H_5$, $R_1$, $R_2$, $R_3$ and $R_4$ are $CH_3$, G is hydrogen and $R_a$, $R_b$, $R_c$, and $R_d$ are as defined in Table 1.

Pest control may be achieved in a range of crops. Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as bedding plants, flowering plants, shrubs, and trees). Preferably the crop plants are selected from the group consisting of corn, wheat, rice, soybean and also ornamentals.

The compositions according to the invention are preferably applied to monocotylendonous crops. The term "crops" is to be understood as including also crops that have been rendered tolerant to herbicides like bromoxynil or classes of herbicides (such as, for example, HPPD inhibitors like isoxazoles like isoxaflutole and isoxachlortol, and triones like mesotrione and sulcotrione, ALS inhibitors, for example sulfonylurea like primisulfuron, prosulfuron, trifloxysulfuron, imidazolinones, triazolopyrimidines, phthalides and pyrimidyloxybenzoates, ACCase inhibitors such as aryloxyphenoxyalkanecarboxylic acids and cyclohexadiones, PROTOX inhibitors such as diphenyl ether, cyclic imides, phenyl pyrazoles, pyridines and oxadiazoles, EPSPS (5-enol-pyrovyl-shikimate-3-phosphate-synthase) inhibitors, GS (glutamine synthetase) inhibitors), as well as inhibitors of phosphinothricin acetyltransferase, O-methyl transferase, adenylosuccinate lyase and synthase, anthranilate synthase, nitrilase, glyphosate oxidoreductase as described in Tables 1 to 3 of US2010/0130561.

An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard 1® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

The compositions according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compositions can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compositions according to the invention include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp.(citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Examples of the abovementioned pests are:
from the order Acarina, for example,
*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,
*Haematopinus* spp., *Linognathus* spp., *Pediculus* spp., *Pemphigus* spp. and *Phylloxera* spp.;

from the order Coleoptera, for example,
*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,
*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,
*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euschistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotino-phara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttala, Amritodus atkinsoni, Aonidiella* spp., *Aphididae, Aphis* spp., *Aspidiotus* spp., *Aulacorthum solani, Bactericera cockerelli, Bemisia* spp., *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis*

*brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;*
from the order Hymenoptera, for example,
*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;
from the order Isoptera, for example,
*Coptotermes* spp, *Corniternes cumulans, Incisitermes* spp, *Macrotermes* spp, *Mastotermes* spp, *Microtermes* spp, *Reticulitermes* spp.; *Solenopsis* geminate,
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;
from the order Mallophaga, for example,
*Damalinea* spp. and *Trichodectes* spp.;

from the order Orthoptera, for example,
*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;
from the order Thysanura, for example,
*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

Depending on the plant species or plant varieties, their location and growth conditions (soils, climate, vegetation period, diet), the treatment according to the invention may also result in superadditive effects. Thus, for example, reduced application rates and/or widening of the activity spectrum and/or an increase in the activity of the compositions according to the invention and compositions which lead to better plant growth, increased tolerance to high or lower temperatures, increased tolerance to drought or to water or soil salt content, increased flowering performance, easier harvesting accelerated maturation, higher harvest yields, better quality and/or higher nutritional value of the harvested products, better storage ability and/or processability of the harvested products are possible which exceed the effects which were actually to be expected.

The compounds of formula I and safeners are generally applied as compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo¬ lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propy¬ lene glycol unit. Examples which may be mentioned are nonylphenoxypolyethoxyethanol, castor oil polyglycol ether, polypropylene glycol/polyethylene oxide adducts, tributylpheno¬ xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl¬ ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl) phosphate, tris-n-octyl phosphate and tris-butoxyethyl phosphate, where tris-(2-ethylhexyl) phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037,373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyloxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE®(Syngenta Crop Protection Canada.)

In addition to the oil additives listed above, in order to enhance the activity of the composi-tions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO08/017,388, which can enhance the efficacy of the inventively used compounds; or other active ingredients for achieving specific effects, for example ammonium or phosphonium salts, in particular halides, (hydrogen)sulphates, nitrates, (hydrogen)carbonates, citrates, tartrates, formiates and acetates, as described in WO07/068,427 and WO07/068, 428, which also can enhance the efficacy of the inventively used compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

In another aspect the present invention provides a method of combating and controlling pests which comprises treating the pests or the locus of the pests or the plant susceptible to attack by a pest with an insecticidally, nematicidally or mollusicidally effective amount of a composition according to this invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing.

Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Further methods of application of the compositions according to the invention comprise drip application onto the soil, dipping of parts of plants such as roots bulbs or tubers, drenching the soil, as well as soil injection. These methods are known in the art.

In order to apply compositions according to the invention as an insecticide, acaricide, nematicide, or molluscicide to a pest, a locus of pest, or to a plant susceptible to attack by a pest, a compound of formula I and the safener is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula I. The composition is generally used for the control of pests such that a compound of formula I is applied at a rate of from 0.1 g to 10 kg per hectare, preferably from 1 g to 6 kg per hectare, more preferably from 1 g to 1 kg per hectare.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I and, optionally, the safener.

Dustable powders (DP) may be prepared by mixing a compound of formula I and, optionally, the safener, with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I and, optionally, the safener, with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I and, optionally, the safener, with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and, optionally, the safener, and one or more powdered solid diluents or carriers, or from pre-formed blank granules by absorbing a compound of formula I and, optionally, the safener (or a solution thereof, in a suitable agent) in a porous granular material (such as pumice, attapulgite clays, fuller's earth, kieselguhr, diatomaceous earths or ground corn cobs) or by adsorbing a compound of formula I and, optionally, the safener (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula I and, optionally, the safener in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I and, optionally, the safener, in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I and, optionally, the safener, either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula I and, optionally, the safener, is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I and, optionally, the safener. SCs may be prepared by ball or bead milling the solid compounds in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I and, optionally, the safener, may be dry milled and added to water, containing agents hereinbefore described, to produce the desired end product.

Oil-based suspension concentrate (OD) may be prepared similarly by suspending finely divided insoluble solid particles of a compound of formula I and, optionally the safener, in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, anti-oxidants, dyestuffs, and/or inert filler materials. An OD is intended and suitable for dilution with water before use to produce a spray solution with sufficient stability to allow spray application through appropriate equipment.

Aerosol formulations comprise a compound of formula I and safener and a suitable propellant (for example n-butane). A compound of formula I and safener may also be dissolved or dispersed in a suitable medium (for example water or a water miscible liquid, such as n-propanol) to provide compositions for use in non-pressurised, hand-actuated spray pumps.

A compound of formula I and safener may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I, optionally the safener, and, optionally, a carrier or diluent therefor. The polymeric shell may be produced by either an interfacial polycondensation reaction or by a coacervation procedure. The compositions may provide for controlled release of the compound of formula I and safener and they may be used for seed treatment. A compound of formula I and safener may also be formulated in a biodegradable polymeric matrix to provide a slow, controlled release of the compound.

A compound of formula I and safener may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier).

A composition used according to the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A composition according to the invention may be applied by any of the known means of applying pesticidal compounds. For example, it may be applied to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A composition according to the invention may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A composition according to the invention may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

The invention therefore also provides a fertiliser composition comprising a fertiliser and a compound of formula I and a safener.

The compositions of this invention may contain other compounds having biological activity, for example micronutrients, saccharides, amino acids, flavonoids, quinines; or other plant activators and/or stimulators and/or growth regulators like for example natural or synthetic hormones, auxins, brassinosteroids, gibberellins, polyamines, abscisic acid, cytokinins, jasmonates, cis-jasmonates, strigolactones, salicylic acid, ethylene, 1-methylcyclopropene, or derivatives thereof; or compounds which possess fungicidal, herbicidal, safening, insecticidal, nematicidal or acaricidal activity.

Methods for applying or treating pesticidal active ingredients on to plant propagation material, especially seeds, are known in the art, and include dressing, coating, pelleting and soaking application methods of the propagation material. It is preferred that the plant propagation material is a seed.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the compound and adherence thereof to the seeds is desired during propagation material treatment. Treatment could vary from a thin film (dressing) of a formulation containing the compound, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable into the controlled release material or applied between layers of materials, or both.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the compound. In particular, seed coating or seed pelleting are preferred in the treatment of the compound. As a result of the treatment, the compound is adhered on to the seed and therefore available for pest control.

The treated seeds can be stored, handled, sowed and tilled in the same manner as any other active ingredient treated seed.

The invention is illustrated by the following preparation examples. The H-NMR data of certain compounds of this invention show line broadening at room temperature, suggesting the existence of plural conformational isomers due to, for example keto-enol tautomerism, hindered rotation, ring inversion in the piperidine moiety or nitrogen inversion at the piperidine N—OR center. Broad signals have been labeled with 'br' accordingly.

EXAMPLE 1

Preparation of Carbonic acid ethyl ester 8-methoxy-1-methyl-2-oxo-3-(2,4,6-trimethyl-phenyl)-1,8-diaza-spiro[4.5]dec-3-en-4-yl ester (Compound P1.2)

Step 1: Preparation of 4-hydroxy-8-methoxy-1-methyl-3-(2,4,6-trimethyl-phenyl)-1,8-diaza-spiro[4.5]dec-3-en-2-one (Compound P2.2)

[Two-Steps (Amide N-Alkylation and Cyclisation), One-Pot Procedure]

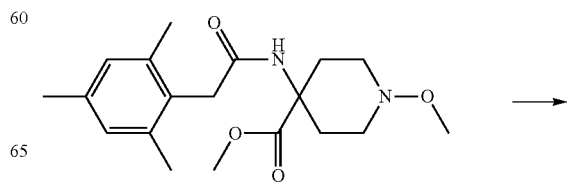

-continued

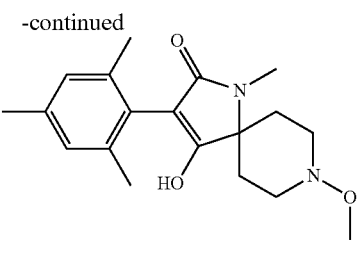

To a solution of 1-methoxy-4-[2-(2,4,6-trimethyl-phenyl)-acetylamino]-piperidine-4-carboxylic acid methyl ester [prepared according to WO09/049,851](850 mg, 2.44 mmol) in dimethylformamide (20 ml) at 0° C. was added sodium hydride (122 mg, 55% w/w dispersion in mineral oil, 2.81 mmol) in two portions. The reaction mixture was stirred at 0° C. for one hour, treated with methyl iodide (0.175 ml, 398 mg, 2.81 mmol) dropwise, and further stirred at 0° C. for one hour and at room temperature for 3 hours. To the mixture recooled at 0° C. was added sodium methoxide (198 mg, 3.66 mmol) in one portion, and stirring continued at room temperature for 2 hours, at 40° C. for 30 minutes and after further addition of sodium methoxide (~20 mg) at 50° C. for 45 minutes. The reaction mixture was poured on iced aqueous ammonium chloride, acidified to pH 5-6 with an aqueous HCl solution and thoroughly extracted with ethyl acetate. The combined organic layers were washed with brine, dried over sodium sulfate and concentrated. The crude oily product was purified by chromatography on silica gel (ethyl acetate), and further triturated with cold diethyl ether, filtered and dried. Yield: 338 mg of 4-hydroxy-8-methoxy-1-methyl-3-(2,4,6-trimethyl-phenyl)-1,8-diaza-spiro[4.5]dec-3-en-2-one (compound P2.2) as a solid, mp 241-243° C.

$^1$H-NMR (CD$_3$OD): 1.44 (br m, 1H), 1.72 (br m, 1H), 2.10 (s, 6H), 2.25 (s, 3H), 2.33 (br m, 1H), 2.48 (br m, 1H), 2.89 (br signal, 3H), 3.20 (br m, 1H), 3.27-3.43 (br signals, total 3H), 3.54 (s, 3H), 6.89 (s, 2H).

LC/MS (ES+): 331 (M+H)$^+$, LC/MS (ES−): 329 (M−H)$^−$

Step 2: Preparation of carbonic acid ethyl ester 8-methoxy-1-methyl-2-oxo-3-(2,4,6-trimethyl-phenyl)-1,8-diaza-spiro[4.5]dec-3-en-4-yl ester (title Compound P1.2)

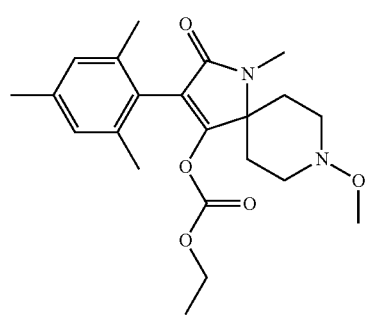

To a solution of 4-hydroxy-8-methoxy-1-methyl-3-(2,4,6-trimethyl-phenyl)-1,8-diaza-spiro[4.5]dec-3-en-2-one (238 mg, 0.72 mmol), triethylamine (0.15 ml, 109 mg, 1.08 mmol) and 4-dimethylaminopyridine (2 mg) in tetrahydrofuran (10 ml) at 0° C. was added ethyl chloroformate (0.075 ml, 85 mg, 0.79 mmol) dropwise. The suspension was stirred at 0° C. for one hour. The reaction mixture was diluted with ethyl acetate and water, the layers separated, the aqueous phase extracted with ethyl acetate, the combined organic phases washed with brine, dried over sodium sulfate and concentrated. The residue was purified by chromatography on silica gel (ethyl acetate/heptane 5:1). Yield: 145 mg of carbonic acid ethyl ester 8-methoxy-1-methyl-2-oxo-3-(2,4,6-trimethyl-phenyl)-1,8-diaza-spiro[4.5]dec-3-en-4-yl ester (title compound P1.2) as a white solid, mp 134-136° C.

$^1$H-NMR (CDCl$_3$): 1.05 (t, 3H), 1.59 (br m, 1H), 1.83 (br m, 1H), 2.15 (s, 6H), 2.25 (s, 3H), 2.36 (br m, 2H), 2.88 (br m, 1H), 2.95 (br s, 3H), 3.22 (br m, 1H), 3.38 (m, 2H), 3.55 (s, 3H), 3.98 (q, 2H), 6.84 (s, 2H).

LC/MS (ES+): 403 (M+H)$^+$

EXAMPLE 2

Preparation of 4-Hydroxy-8-methoxy-1-methyl-3-(2,4,6-trimethyl-phenyl)-1,8-diaza-spiro[4.5]dec-3-en-2-one (Compound P2.2)

Step 1: Preparation of 4-benzyloxy-8-methoxy-3-(2,4,6-trimethyl-phenyl)-1,8-diaza-spiro[4.5]dec-3-en-2-one (Compound P3.4)

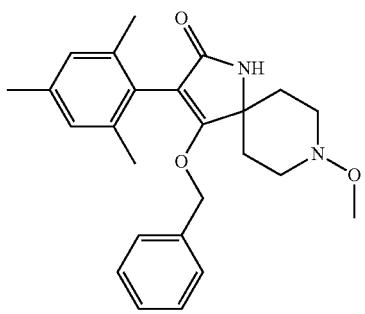

To a suspension of 4-hydroxy-8-methoxy-3-(2,4,6-trimethyl-phenyl)-1,8-diaza-spiro[4.5]dec-3-en-2-one [prepared according to WO09/049,851](67.0 g, 211.7 mmol) in acetone (900 ml) was added potassium carbonate (35.1 g, 254.1 mmol), followed by benzyl bromide (35.3 ml, 50.7 g, 296.4 mmol) dropwise. The suspension was stirred at reflux for one hour, then poured on ice water and ethyl acetate. The resulting precipitate was filtered off, dissolved in methylene chloride, dried over sodium sulfate, concentrated and dried over phosphorus pentoxide under vacuum at 50° C. overnight to afford a first crop of product as a white solid (55.8 g). The layers of the mother liquor were separated, the aqueous phase extracted with ethyl acetate, the combined organic phases washed with brine, dried over sodium sulfate and concentrated. The residue was suspended in diethyl ether, filtered and dried to further deliver 22.6 g of product. Yield: 78.4 g of 4-benzyloxy-8-methoxy-3-(2,4,6-trimethyl-phenyl)-1,8-diaza-spiro[4.5]dec-3-en-2-one (compound P3.4) as a solid, mp 184-186° C.

$^1$H-NMR (CDCl$_3$): 1.66 (m, 2H), 2.11 (s, 6H), 2.28 (s, 3H), 2.33 (m, 2H), 2.47 (m, 2H), 3.45 (m, 2H), 3.55 (s, 3H), 4.68 (s, 2H), 6.13 (br s, 1H), 6.87 (s, 2H), 7.04 (m, 2H), 7.28 (m, 3H).

LC/MS (ES+): 407 (M+H)$^+$

Step 2: Preparation of 4-benzyloxy-8-methoxy-1-methyl-3-(2,4,6-trimethyl-phenyl)-1,8-diaza-spiro[4.5]dec-3-en-2-one (Compound P3.5)

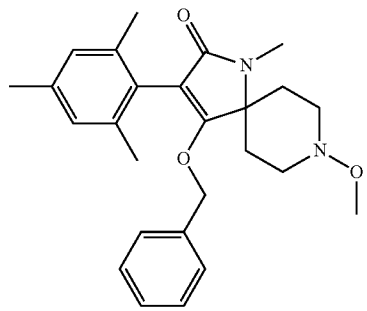

To a solution of 4-benzyloxy-8-methoxy-3-(2,4,6-trimethyl-phenyl)-1,8-diaza-spiro[4.5]dec-3-en-2-one (40.0 g, 98.4 mmol) in tetrahydrofuran (500 ml) at 0° C. was added a 1.0 M solution of lithium bis(trimethylsilyl)amide in tetrahydrofuran (108.3 ml, 108.3 mmol) dropwise over one hour. The mixture was stirred at 0° C. for 30 minutes and at room temperature for 30 minutes, then treated with methyl iodide (6.75 ml, 15.4 g, 108.2 mmol) dropwise at 0° C. over minutes. Stirring was continued at room temperature overnight and the reaction mixture was quenched with cold saturated aqueous ammonium chloride. The layers were separated, the aqueous phase extracted twice with ethyl acetate, the combined organic phases washed with brine, dried over sodium sulfate and concentrated. The residue was suspended in diethyl ether, stirred for 30 minutes, filtered and dried. Yield: 28.6 g of 4-benzyloxy-8-methoxy-1-methyl-3-(2,4,6-trimethyl-phenyl)-1,8-diaza-spiro[4.5]dec-3-en-2-one (compound P3.5) as a solid, mp 139-141° C.
$^1$H-NMR (CDCl$_3$): 1.52 (br m, 1H), 1.74 (br m, 1H), 2.11 (br s, 6H), 2.28 (s, 3H), 2.34 (br m, 2H), 2.92 (br signal, 3H), 3.12 (br m, 1H), 3.30 (m, 3H), 3.52 (s, 3H), 4.67 (br signal, 2H), 6.85 (s, 2H), 7.04 (m, 2H), 7.28 (m, 3H).
LC/MS (ES+): 421 (M+H)$^+$ Step 3: Preparation of 4-hydroxy-8-methoxy-1-methyl-3-(2,4,6-trimethyl-phenyl)-1,8-diaza-spiro[4.5]dec-3-en-2-one (Title Compound P2.2)

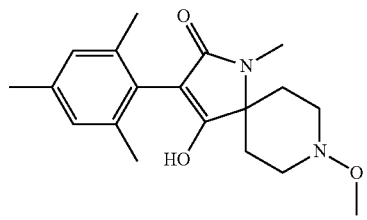

To a solution of 4-benzyloxy-8-methoxy-1-methyl-3-(2,4,6-trimethyl-phenyl)-1,8-diaza-spiro[4.5]dec-3-en-2-one (22.6 g, 53.7 mmol) in methanol (226 ml) and water (22.6 ml) in a Parr shaker type hydrogenator was added 5% Pd/C (22.6 g). After hydrogenation under 4 bars H$_2$ at 36° C. for 22 hours, the reaction mixture was filtered and concentrated. The residue was diluted with ethyl acetate and extracted with saturated aqueous sodium carbonate under ice cooling. The organic layer was discarded, the aqueous alkaline phase acidified with cooling to pH 5-6 with an aqueous HCl solution and thoroughly extracted with ethyl acetate. The combined organic layers were washed with brine, dried over sodium sulfate and concentrated. Yield: 13.0 g of 4-hydroxy-8-methoxy-1-methyl-3-(2,4,6-trimethyl-phenyl)-1,8-diaza-spiro[4.5]dec-3-en-2-one (title compound P2.2) as a solid, mp 239-241° C. The spectral data were identical to those described above under preparation example 1, step 1.

EXAMPLE 3

Preparation of 1-Cyclopropylmethyl-4-hydroxy-8-methoxy-3-(2,4,6-trimethyl-phenyl)-1,8-diaza-spiro[4.5]dec-3-en-2-one (Compound P2.8)

Step 1: Preparation of 4-benzyloxy-1-cyclopropylmethyl-8-methoxy-3-(2,4,6-trimethyl-phenyl)-1,8-diaza-spiro[4.5]dec-3-en-2-one (Compound P3.8)

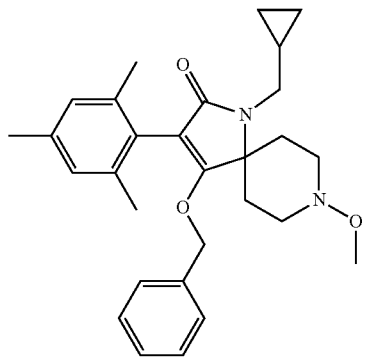

To a solution of 4-benzyloxy-8-methoxy-3-(2,4,6-trimethyl-phenyl)-1,8-diaza-spiro[4.5]dec-3-en-2-one (compound P3.4) (1.0 g, 2.46 mmol) in dioxane (40 ml) was added bromomethyl-cyclopropane (1.257 ml, 1.78 g, 13.16 mmol) and potassium tert-butoxide (1.50 g, 13.37 mmol). The reaction mixture was stirred at 100° C. for 5 days, then poured on water and extracted with ethyl acetate. The combined organic phases were washed with brine, dried over sodium sulfate and concentrated. The residue was suspended in ethyl acetate/heptane 1:5, stirred overnight, filtered and dried to afford a first crop of product as a white solid (350 mg). The mother liquor was concentrated, and the residue purified by chromatography on silica gel (dichloromethane/acetone 10:1) to further deliver 205 mg of product. Yield: 555 mg of 4-benzyloxy-1-cyclopropylmethyl-8-methoxy-3-(2,4,6-trimethyl-phenyl)-1,8-diaza-spiro[4.5]dec-3-en-2-one (compound P3.8) as a solid, mp 119-121° C.
$^1$H-NMR (CD$_3$OD): 0.34 (m, 2H), 0.52 (m, 2H), 1.10 (m, 1H), 1.48 (br m, 1H), 1.83 (br m, 1H), 2.11 (br s, 6H), 2.29 (s, 3H), 2.41 (br m, 1H), 2.60 (br m, 1H), 3.12 (br m, 1H), 3.23 (m, 2H), 3.24-3.41 (br signals, total 3H), 3.50 (s, 3H), 4.72 (br signal, 2H), 6.91 (s, 2H), 7.06 (m, 2H), 7.29 (m, 3H).
LC/MS (ES+): 461 (M+H)$^+$ Step 2: Preparation of 1-cyclopropylmethyl-4-hydroxy-8-methoxy-3-(2,4,6-trimethyl-phenyl)-1,8-diaza-spiro[4.5]dec-3-en-2-one (Title Compound P2.8)

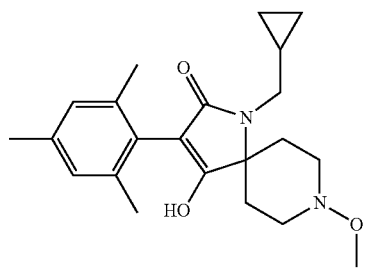

Debenzylation was conducted using an H-Cube® continuous-flow hydrogenator: 4-benzyloxy-1-cyclopropylmethyl-8-methoxy-3-(2,4,6-trimethyl-phenyl)-1,8-diaza-spiro[4.5]dec-3-en-2-one (546 mg, 1.34 mmol) was dissolved in methanol (47 ml) and this substrate solution (0.029 M) pumped twice through a 5% Pd/C filled cartridge at a flow-rate of 1 mL/min, a temperature of 35° C. and a pressure of 2-3 bars. The collected product solution was concentrated, and the residue purified by chromatography on silica gel (ethyl acetate/heptane 1:1). Yield: 215 mg of 1-cyclopropylmethyl-4-hydroxy-8-methoxy-3-(2,4,6-trimethyl-phenyl)-1,8-diaza-spiro[4.5]dec-3-en-2-one (title compound P2.8) as a white solid, mp 223-225° C.

$^1$H-NMR (CD$_3$OD): 0.34 (m, 2H), 0.52 (m, 2H), 1.11 (m, 1H), 1.43 (br m, 1H), 1.78 (br m, 1H), 2.11 (s, 6H), 2.25 (s, 3H), 2.41 (br m, 1H), 2.62 (br m, 1H), 3.23 (br signal, total 3H), 3.28-3.45 (br signals, total 3H), 3.55 (s, 3H), 6.90 (s, 2H).

LC/MS (ES$^+$): 371 (M+H)$^+$, 369 (M−H)

EXAMPLE 4

Preparation of 4-Hydroxy-8-methoxy-1-methyl-3-(2,4,6-trimethyl-phenyl)-1,8-diaza-spiro[4.5]dec-3-en-2-one (Compound P2.2)

Step 1: Preparation of 1-methoxy-4-methylamino-piperidine-4-carbonitrile (Compound P5.1)

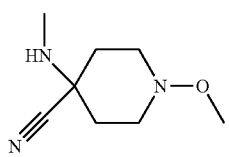

To a solution of 1-methoxy-piperidin-4-one [prepared according to Journal of Organic Chemistry (1961), 26, 1867-74] (100 g, 0.77 mol), aqueous methylamine (40 wt. % in H$_2$O, 86 ml) and methylamine hydrochloride (57.5 g, 0.85 mol) in water (700 ml) at 0° C. was added a solution of potassium cyanide (55.5 g, 0.85 mol) in water (150 ml) dropwise over one hour. The reaction mixture was stirred at room temperature for two days. Over the next five days, the mixture was further treated with methylamine hydrochloride (5×2.6 g, total 13.0 g), aqueous methylamine (5×4.3 ml, total 21.5 ml) and potassium cyanide (5×2.5 g, total 12.5 g), and stirring continued at room temperature until the reaction was judged complete by thin layer chromatography. The aqueous reaction mixture was extracted with dichloromethane (1×500 ml, and 4×200 ml), the combined organic phases dried over sodium sulfate and evaporated. Yield: 113.0 g of 1-methoxy-4-methylamino-piperidine-4-carbonitrile (compound P5.1) as a red liquid. This material was used without further purification in the next step.

$^1$H-NMR (CDCl$_3$): 1.36 (br s, 1H), 1.62-2.22 (br signals, total 4H), 2.51 (s, 3H), 2.63-3.41 (br signals, total 4H), 3.51 (s, 3H).

IR(CN): ν 2220 cm$^{-1}$. LC/MS (ES+): 170 (M+H)$^+$

Step 2: Preparation of N-(4-cyano-1-methoxy-piperidin-4-yl)-N-methyl-2-(2,4,6-trimethyl-phenyl)-acetamide (Compound P4.1)

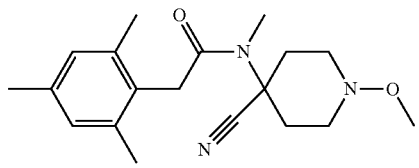

Method A: To a solution of 1-methoxy-4-methylamino-piperidine-4-carbonitrile (20.0 g, 118.2 mmol), triethylamine (24.6 ml, 17.9 g, 177.3 mmol) and 4-dimethylaminopyridine (DMAP, 0.1 g) in tetrahydrofuran (250 ml) at 0-5° C. was added a solution of (2,4,6-trimethyl-phenyl)-acetyl chloride (25.6 g, 130.0 mmol) in THF (25 ml) dropwise over 1.5 hour. The reaction mixture was stirred at room temperature for a total of three hours, during which it was further treated with (2,4,6-trimethyl-phenyl)-acetyl chloride (5.4 g) and triethylamine (7 ml). The reaction mixture was diluted with ethyl acetate and water, the layers separated, the aqueous phase extracted twice with ethyl acetate, the combined organic phases washed twice with saturated aqueous sodium hydrogen carbonate and brine, dried over sodium sulfate and concentrated. The solid residue was suspended in diethyl ether (500 ml), stirred overnight at room temperature, filtered and dried. Yield: 27.5 g of N-(4-cyano-1-methoxy-piperidin-4-yl)-N-methyl-2-(2,4,6-trimethyl-phenyl)-acetamide (compound P4.1) as a white solid, mp 171-178° C. This material was used without further purification in the next step.

$^1$H-NMR (CDCl$_3$): 2.01 (br m, 1H), 2.11 (br m, 1H), 2.20 (s, 6H), 2.25 (s, 3H), 2.34 (br m, 1H), 2.57 (br m, 1H), 2.83 (br m, 1H), 3.12 (s, 3H), 3.20 (br m, 1H), 3.34 (br m, 2H), 3.50 (br s, 3H), 3.66 (s, 2H), 6.85 (s, 2H).

IR(CN): ν 2231 cm$^{-1}$. LC/MS (ES+): 330 (M+H)$^+$

Method B: To a solution of 1-methoxy-4-methylamino-piperidine-4-carbonitrile (20.0 g, 118.2 mmol) in pyridine (250 ml) was added (2,4,6-trimethyl-phenyl)-acetyl chloride (25.6 g, 130.0 mmol) dropwise at 0° C. The reaction mixture was stirred at 0° C. for one hour and at room temperature overnight, poured on ice water and acidified to pH 7 with an aqueous 2N HCl solution. The resulting thick precipitate was filtered, washed with cold water, dissolved in dichloromethane, dried over sodium sulfate and concentrated. The solid residue was suspended in hexane, stirred at room temperature, filtered and dried. Yield: 32.7 g of N-(4-cyano-1-methoxy-piperidin-4-yl)-N-methyl-2-(2,4,6-trimethylphenyl)-acetamide (compound P4.1) as a pale yellow solid, mp 175-177° C. The spectral data of this material were identical to those described above under preparation example 4, step 2, Method A.

Step 3: Preparation of 1-methoxy-4-{methyl-[2-(2, 4,6-trimethyl-phenyl)-acetyl]-amino}-piperidine-4-carboxylic acid methyl ester (Compound P4.2)

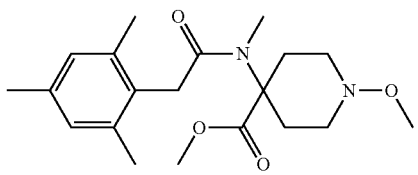

To a suspension of N-(4-cyano-1-methoxy-piperidin-4-yl)-N-methyl-2-(2,4,6-trimethyl-phenyl)-acetamide (106.0 g, 0.322 mol) in methanol (222 ml) at 15-20° C. was added concentrated sulfuric acid (85.7 ml, 157.8 g, 1.609 mol) dropwise over 75 minutes and the reaction mixture was stirred at room temperature for one hour. The mixture was poured on ice (1 kg), stirred for one hour, then neutralised carefully with 30% aqueous sodium hydroxide to pH 5-5.5 (external ice cooling). The thick pasty mixture was diluted with water (1000 ml) and filtered. The solid residue was washed with water and hexane, air-dried and further dried over phosphorus pentoxide under vacuum at 40° C. for two hours. In order to eliminate inorganic impurities (sodium sulfate!), the solid material was diluted with dichloromethane (600 ml), washed with water (2×300 ml), the aqueous phases extracted once with dichloromethane, the combined organic phases dried over sodium sulfate and evaporated. Yield: 85.4 g of 1-methoxy-4-{methyl-[2-(2,4,6-trimethyl-phenyl)-acetyl]-amino}-piperidine-4-carboxylic acid methyl ester (compound P4.2) as a white solid, mp 133-135° C.

$^1$H-NMR (CDCl$_3$): 1.92 (br m, 1H), 2.04 (br m, 1H), 2.16 (s, 6H), 2.23 (s, 3H), 2.27-2.49 (br m, 2H), 2.82 (br m, 2H), 3.14 (br m, 2H), 3.22 (br s, 3H), 3.52 (s, 3H), 3.62 (br s, 5H), 6.82 (s, 2H).

LC/MS (ES+): 363 (M+H)$^+$

Step 4: Preparation of 4-hydroxy-8-methoxy-1-methyl-3-(2,4,6-trimethyl-phenyl)-1,8-diaza-spiro[4.5]dec-3-en-2-one (Title Compound P2.2)

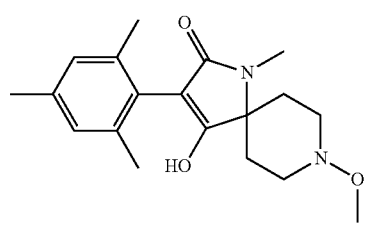

To a solution of 1-methoxy-4-{methyl-[2-(2,4,6-trimethyl-phenyl)-acetyl]-amino}-piperidine-4-carboxylic acid methyl ester (85.0 g, 234.5 mmol) in dimethylformamide (800 ml) at 0° C. was added sodium methoxide (38.0 g, 703.5 mmol) in four portions and stirring continued at 0° C. for 30 minutes, then at room temperature for 1 hour. The reaction mixture was poured on ice and saturated aqueous ammonium chloride, acidified to pH 5-6 with concentrated HCl and thoroughly extracted with ethyl acetate. The combined organic layers were washed with water and brine, dried over sodium sulfate, concentrated and the residue dried in vacuo. Yield: 72.7 g of 4-hydroxy-8-methoxy-1-methyl-3-(2,4,6-trimethyl-phenyl)-1,8-diaza-spiro[4.5]dec-3-en-2-one (title compound P2.2) as a solid.

The spectral data of this crude material were identical to those described above under preparation example 1, step 1.

EXAMPLE 5

Preparation of 4-Cyclopropylamino-1-methoxy-piperidine-4-carbonitrile (Compound P5.2)

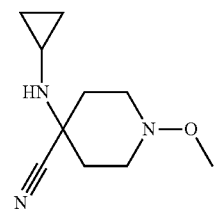

To a solution of cyclopropylamine (1.4 ml, 1.14 g, 20.0 mmol) in methanol (20 ml) at 0° C. was added 1N hydrochloric acid (20 ml, 20.0 mmol) dropwise and the mixture was stirred at room temperature for 30 minutes. 1-Methoxy-piperidin-4-one [prepared according to Journal of Organic Chemistry (1961), 26, 1867-74](2.58 g, 20.0 mmol), followed 10 minutes later by potassium cyanide (1.3 g, 20.0 mmol) in water (10 ml) were then added dropwise at 0° C. The reaction mixture was warmed to room temperature and stirred overnight, diluted with water and diethyl ether, the layers separated and the aqueous phase thoroughly extracted with diethyl ether. The combined organic layers were washed with brine, dried over sodium sulfate and evaporated. Yield: 3.19 g of 4-cyclopropylamino-1-methoxy-piperidine-4-carbonitrile (title compound P5.2) as an oil. This material was used without further purification in the next step.

$^1$H-NMR (CDCl$_3$): 0.42 (br m, 2H), 0.56 (m, 2H), 1.57-2.30 (br signals, total 5H), 2.31 (m, 1H), 2.63-3.41 (br signals, total 4H), 3.51 (br s, 3H).

IR(CN): ν 2223 cm$^{-1}$. LC/MS (ES$^+$): 196 (M+H)+

EXAMPLE 6

Preparation of 1-Methoxy-4-methylamino-piperidine-4-carboxylic acid methyl ester (Compound P5.4)

Step 1: Preparation of 8-methoxy-1-methyl-1,3,8-triaza-spiro[4.5]decane-2,4-dione (Compound P5.6)

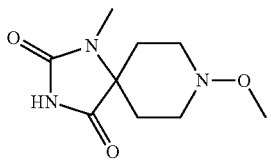

To a solution of 1-methoxy-4-methylamino-piperidine-4-carbonitrile (compound P5.1) (10.0 g, 59.09 mmol) in dichloromethane (180 ml) was added chlorosulfonyl isocyanate (5.14 ml, 8.36 g, 59.05 mmol) dropwise over 15 minutes at 20-30° C. The yellowish suspension was stirred at room temperature for 30 minutes and concentrated to generate a pale yellow solid. This material was dissolved in aqueous 1N hydrochloric acid (180 ml), heated at reflux for one hour, cooled to 0° C. and acidified to pH 5.5 with an aqueous 4N NaOH solution. The aqueous phase was extracted with ethyl acetate (4×), the combined organic layers were washed with brine, dried over sodium sulfate and concentrated. The residue was purified by chromatography on silica gel (ethyl acetate/heptane 1:1). Yield: 3.86 g of 8-methoxy-1-methyl-1,3,8-triaza-spiro[4.5]decane-2,4-dione (compound P5.6) as a solid.

$^1$H-NMR (CDCl$_3$): 1.33-2.41 (br signals, total 4H), 2.86 (br s, 3H), 3.09-3.42 (br signals, total 4H), 3.52 (br s, 3H), 7.76 (br s, 1H).

LC/MS (ES+): 214 (M+H)$^+$

Step 2: Preparation of
1-methoxy-4-methylamino-piperidine-4-carboxylic
acid methyl ester (Title Compound P5.4)

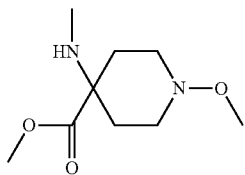

To a suspension of 8-methoxy-1-methyl-1,3,8-triaza-spiro[4.5]decane-2,4-dione (3.36 g, 15.76 mmol) in water (100 ml) was added sodium hydroxide (0.63 g, 15.75 mmol) and the mixture was heated in a microwave apparatus at 190° C. for 30 minutes, at 200° C. for one hour and further at 210° C. for one hour until judged complete by LC-MS analysis. The reaction mixture was acidified to pH 3 (ice cooling) with an aqueous HCl solution, concentrated in vacuo, the solid residue taken up in warm methanol (40° C.), filtered and the filtrate evaporated. The residue was dried over phosphorus pentoxide at 40° C. overnight. Yield: 2.08 g of 1-methoxy-4-methylamino-piperidine-4-carboxylic acid hydrochloride salt. LC/MS (ES+): 189 (M+H)$^+$ of the free base.

To a suspension of 1-methoxy-4-methylamino-piperidine-4-carboxylic acid hydrochloride salt (2.08 g, 9.26 mmol) in methanol (20 ml) at 0-5° C. was added thionyl chloride (2.41 ml, 3.97 g, 33.40 mmol) and the reaction mixture was heated at reflux for 7 days. After cooling, the mixture was concentrated, the residue diluted with ice water and neutralised with aqueous sodium bicarbonate. The aqueous phase was extracted with ethyl acetate (4×), the combined organic layers washed with brine, dried over sodium sulfate and concentrated. The residue was purified by chromatography on silica gel (gradient ethyl acetate→ethyl acetate/methanol 20:1). Yield: 76 mg of 1-methoxy-4-methylamino-piperidine-4-carboxylic acid methyl ester (title compound P5.4) as an oil.

$^1$H-NMR (CDCl$_3$): 1.46-2.33 (br signals, total 5H), 2.22 (br s, 3H), 2.51-3.31 (br signals, total 4H), 3.51 (s, 3H), 3.72 (br s, 3H).

IR(COOMe): ν 1726 cm$^{-1}$. LC/MS (ES+): 203 (M+H)$^+$

EXAMPLE 7

Preparation of 3-(2-Chloro-4,5-dimethyl-phenyl)-4-hydroxy-8-methoxy-1-methyl-1,8-diaza-spiro[4.5]dec-3-en-2-one (Compound P2.26)

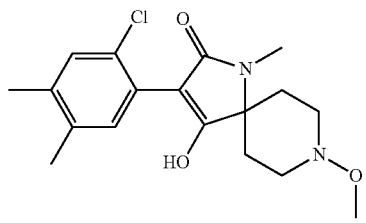

To a solution of 2-(2-chloro-4,5-dimethyl-phenyl)-N-(4-cyano-1-methoxy-piperidin-4-yl)-N-methyl-acetamide (compound P4.27) (1.15 g, 3.29 mmol) in methanol (~3 ml) at 10° C. was added concentrated sulfuric acid (0.876 ml, 16.43 mmol) dropwise and the reaction mixture was stirred at room temperature overnight. After further treatment with concentrated sulfuric acid (0.876 ml, 16.43 mmol) and stirring at 80° C. overnight, additional concentrated sulfuric acid (0.876 ml, 16.43 mmol) was added and stirring continued at 90° C. over another night. The mixture was poured on ice, neutralised carefully with 30% aqueous sodium hydroxide to pH 5-6, the resulting precipitate filtered and dried to afford a first crop of product as a beige solid (225 mg). The mother liquor was concentrated, and the residue purified by chromatography on silica gel (ethyl acetate) to further deliver 462 mg of product as a yellowish solid. Yield: 687 mg of 3-(2-chloro-4,5-dimethyl-phenyl)-4-hydroxy-8-methoxy-1-methyl-1,8-diaza-spiro[4.5]dec-3-en-2-one (title compound P2.26) as a solid, mp 191-192° C.

$^1$H-NMR (CD$_3$Cl$_3$): 1.49-2.57 (br signals, total 4H), 2.20 (s, 3H), 2.21 (s, 3H), 2.79-3.46 (br signals, total 4H), 3.00 (br s, 3H), 3.52 (br s, 3H), 4.40 (br s, 1H), 6.87 (s, 1H), 7.16 (s, 1H).

LC/MS (ES$^+$): 351/353 (M+H)$^+$

EXAMPLE 8

Alternative Preparation of 4-Hydroxy-8-methoxy-1-methyl-3-(2,4,6-trimethyl-phenyl)-1,8-diaza-spiro[4.5]dec-3-en-2-one (Compound P2.2)

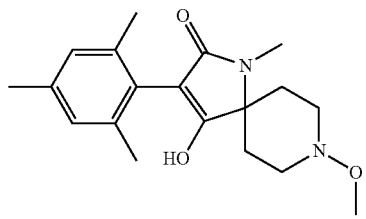

To a solution of 4-hydroxy-8-methoxy-3-(2,4,6-trimethyl-phenyl)-1,8-diaza-spiro[4.5]dec-3-en-2-one [starting material (SM) prepared according to WO09/049,851](500 mg, 1.58 mmol) in tetrahydrofuran (20 ml) at 0° C. was added a 1.0 M lithium bis(trimethylsilyl)amide solution in hexanes (3.32 ml, 3.32 mmol) dropwise over 15 minutes. The mixture was stirred one hour at 0° C., treated with methyl iodide (0.099 ml, 225 mg, 1.59 mmol) dropwise over 10 minutes, and further stirred at 0° C. for 30 minutes and at room temperature for one hour. The reaction mixture was quenched over cold saturated aqueous ammonium chloride and extracted with tert-butyl methyl ether (3×), the combined organic phases washed with brine, dried over sodium sulfate and concentrated. The residue (210 mg) was suspended in hexane, stirred at room temperature for 10 minutes, filtered and dried. Yield: 171 mg of a clean mixture of starting material (SM) and 4-hydroxy-8-methoxy-1-methyl-3-(2,4,6-trimethyl-phenyl)-1,8-diaza-spiro[4.5]dec-3-en-2-one (title compound P2.2) as a beige solid. $^1$H-NMR and LC-MS analysis of the crude material indicated a ~1:2.5 ratio of this mixture SM/compound P2.2.

$^1$H-NMR (CD$_3$OD, selected signals only): 6.86 (s, 2H, H$_{arom}$ SM), 6.89 (s, 2H, H$_{arom}$ compound P2.2); both signals in a ratio 1:2.6.

LC/MS (ES+): 317 (M+H)$^+$; R$_t$=1.40 min for SM. LC/MS (ES$^+$): 331 (M+H)$^+$; R$_t$=1.46 min for compound P2.2. Both signals in a ratio 1:2.5 considering UV peak areas at 220 nm.

EXAMPLE 9

Preparation of 2,2-Dimethyl-propionic acid 8-methoxy-1-methyl-2-oxo-3-(2,4,6-trimethyl-phenyl)-1,8-diaza-spiro[4.5]dec-3-en-4-yl ester (Compound P1.31)

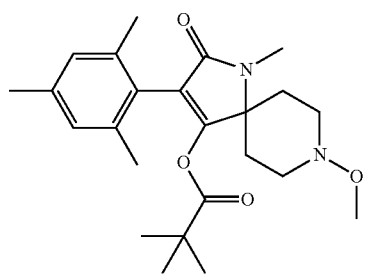

To a solution of 4-hydroxy-8-methoxy-1-methyl-3-(2,4,6-trimethyl-phenyl)-1,8-diaza-spiro[4.5]dec-3-en-2-one (compound P2.2) (350 mg, 1.06 mmol) and triethylamine (0.221 ml, 160.7 mg, 1.59 mmol) in tetrahydrofuran (10 ml) at 0° C. was added pivaloyl chloride (0.143 ml, 140.1 mg, 1.16 mmol) dropwise. The suspension was stirred at 0° C. for two hours. The reaction mixture was diluted with ethyl acetate and water, the layers separated, the aqueous phase extracted with ethyl acetate, the combined organic phases washed with brine, dried over sodium sulfate and concentrated. The residue was purified by chromatography on silica gel (ethyl acetate). Yield: 344 mg of 2,2-dimethyl-propionic acid 8-methoxy-1-methyl-2-oxo-3-(2,4,6-trimethyl-phenyl)-1,8-diaza-spiro[4.5]dec-3-en-4-yl ester (compound P1.31) as a colorless gum.

$^1$H-NMR (CDCl$_3$): 1.02 (br s, 9H), 1.46-2.51 (br signals, total 4H), 2.14 (s, 6H), 2.23 (s, 3H), 2.70-3.46 (br signals, total 4H), 2.95 (br s, 3H), 3.54 (s, 3H), 6.82 (s, 2H).

LC/MS (ES+): 415 (M+H)$^+$

EXAMPLE 10

Preparation of 4-{[2-(2,5-Dimethyl-phenyl)-acetyl]-methyl-amino}-1-methoxy-piperidine-4-carboxylic acid methyl ester (Compound P4.46)

Step 1: Preparation of 1-methoxy-4-methylamino-piperidine-4-carboxylic acid (Compound P5.7)

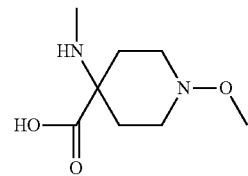

1-Methoxy-4-methylamino-piperidine-4-carbonitrile (compound P5.1) (3.0 g, 17.73 mmol) was added in two portions to concentrated sulfuric acid (30 ml) at 0° C. After stirring for 20 minutes, a yellow solution was obtained which was kept at room temperature overnight. The reaction mixture was carefully diluted with ice water (60 ml), heated at reflux for 4 hours, then poured on ice (50 g) and neutralised with 25% aqueous ammonia under cooling to pH 7-8. The reaction mixture was evaporated and the white solid residue triturated with warm (40° C.) methanol (3×50 ml), filtered and the combined methanol phases concentrated. The residue was treated with toluene (3×50 ml) to remove water azeotropically until constant weight, then triturated with tetrahydrofuran, filtered and dried. Yield: 2.30 g of 1-methoxy-4-methylamino-piperidine-4-carboxylic acid (compound P5.7) as a white solid, mp>250° C.

$^1$H-NMR (D$_2$O): 1.73 (m, 1H), 2.02 (m, 2H), 2.32 (m, 1H), 2.54 (appar. d, 3H), 2.69 (m, 1H), 2.99 (m, 1H), 3.18 (m, 1H), 3.33 (m, 1H), 3.49 (appar. d, 3H). The spectral data are suggesting two major conformers in a 1:1 ratio.

LC/MS (ES+): 189 (M+H)$^+$

Step 2: Preparation of 1-methoxy-4-methylamino-piperidine-4-carboxylic acid methyl ester (Compound P5.4)

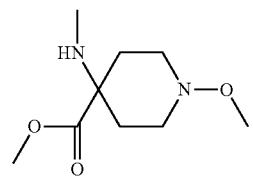

To a suspension of 1-methoxy-4-methylamino-piperidine-4-carboxylic acid (2.0 g, 10.63 mmol) in methanol (50 ml) at 0-10° C. was added thionyl chloride (2.29 ml, 3.76 g, 31.57 mmol) and the reaction mixture was heated at reflux overnight. After cooling, the mixture was concentrated, the residue diluted with ice water (20 ml) and neutralised with aqueous sodium bicarbonate. The aqueous phase was extracted with ethyl acetate (4×25 ml) and dichloromethane (4×50 ml), the combined organic layers washed with aqueous sodium bicarbonate (15 ml) and brine (15 ml), dried over sodium sulfate and concentrated. Yield: 0.76 g of 1-methoxy-4-methylamino-piperidine-4-carboxylic acid methyl ester (compound P5.4) as a viscous, orange oil. The spectral data of this crude material were identical to those described above under preparation example 6, step 2.

LC/MS (ES+): 203 (M+H)+

Step 3: Preparation of 4-{[2-(2,5-dimethyl-phenyl)-acetyl]-methyl-amino}-1-methoxy-piperidine-4-carboxylic acid methyl ester (Title Compound P4.46)

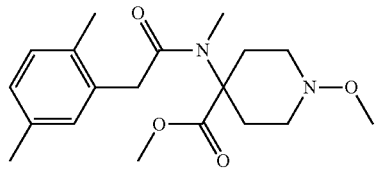

To a solution of 1-methoxy-4-methylamino-piperidine-4-carboxylic acid methyl ester (200 mg, 0.99 mmol) in pyridine (5 ml) was added (2,5-dimethyl-phenyl)-acetyl chloride (240 mg, 1.31 mmol) dropwise at 0° C. The reaction mixture was stirred at 0° C. for one hour and at room temperature for 6 hours, poured on ice water, acidified to pH 7 with an aqueous 2N HCl solution and diluted with ethyl acetate (50 ml). The layers were separated, the aqueous phase extracted with ethyl acetate (3×25 ml), the combined organic phases washed with water (3×15 ml) and brine, dried over sodium sulfate and concentrated. The residue was purified by chromatography on silica gel (cyclohexane/ethyl acetate 2:1). Yield: 170 mg of 4-{[2-(2,5-dimethyl-phenyl)-acetyl]-methyl-amino}-1-methoxy-piperidine-4-carboxylic acid methyl ester (title compound P4.46) as a colorless gum.

$^1$H-NMR (CD$_3$OD): 1.99 (br m, 2H), 2.17 (s, 3H), 2.26 (s, 3H), 2.36 (br m, 2H), 2.79 (br m, 1H), 2.93 (br m, 1H), 3.06 (appar. d, 3H), 3.21 (br m, 2H), 3.50 (s, 3H), 3.67 (s, 3H), 3.68 (br s, 2H), 6.91 (br s, 1H), 6.95 (d, 1H), 7.04 (d, 1H).

LC/MS (ES+): 349 (M+H)+

Compounds of the formula I from Table P1, compounds of the formula II from Table P2 and intermediates listed in Tables P3, P4 and P5 can be prepared by analogous procedures. Either one of the following LC-MS methods was used to characterize the compounds:

Method A
MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Ångström, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B
MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 μm particle size, 110 Ångström, 30×3 mm, Temp: 60° C.; DAD Wavelength range (nm): 200 to 500; Solvent gradient: A=water+0.05% v/v HCOOH, B=Acetonitril/Methanol (4:1, v:v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

The characteristic values obtained for each compound were the retention time ("R$_t$", recorded in minutes) and the molecular ion as listed in Table P1, Table P2, Table P3, Table P4 and in Table P5.

TABLE P1

Physical data of compounds of formula I:

| Compound No. | Structures | Melting Point | MS/NMR |
|---|---|---|---|
| P1.1 | 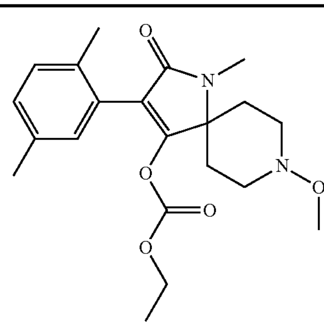 | 96-110° C. | LC/MS: 389 (M + H)+<br>R$_t$ = 1.82 min |

TABLE P1-continued

Physical data of compounds of formula I:

| Compound No. | Structures | Melting Point | MS/NMR |
|---|---|---|---|
| P1.2 | EXAMPLE 1, step 2 | 134-136° C. | LC/MS: 403 (M + H)+<br>R$_r$ = 1.81 min |
| P1.3 | 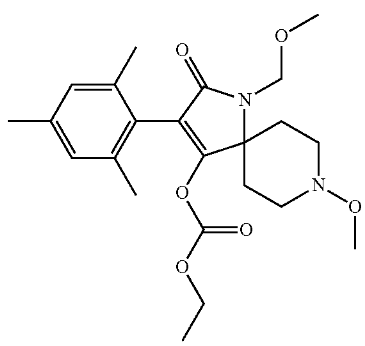 | gum | $^1$H-NMR (CD3OD, selected signals only):<br>1.03 (t, 3H, OCH$_2$CH$_3$), 2.14 (s, 6H, mesityl CH$_3$), 2.26 (s, 3H, mesityl CH$_3$), 3.34 (br s, 3H, CH$_2$OCH$_3$), 3.55 (s, 3H, NOCH$_3$), 4.01 (q, 2H, OCH$_2$CH$_3$), 6.89 (s, 2H, H$_{arom}$). |
| P1.4 | 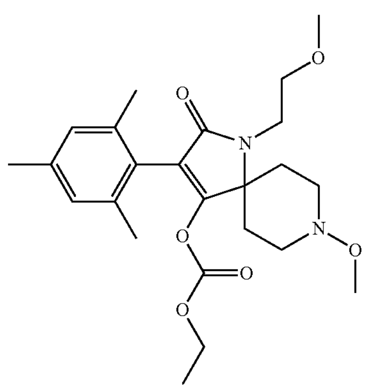 | solid | LC/MS: 447 (M + H)+<br>R$_r$ = 1.94 min |
| P1.5 | 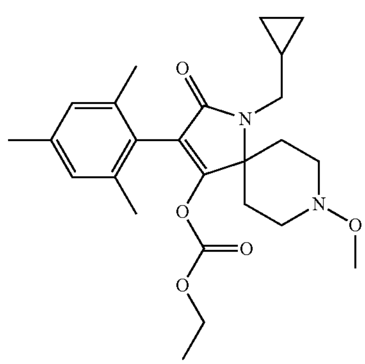 | gum | $^1$H-NMR (CD$_3$OD):<br>0.38 (m, 2H), 0.55 (m, 2H), 1.02 (t, 3H), 1.15 (m, 1H), 1.54 (br m, 1H), 1.88 (br m, 1H), 2.13 (s, 6H), 2.25 (s, 3H), 2.48 (br m, 1H), 2.66 (br m, 1H), 2.83 (br m, 1H), 3.18 (br m, 1H), 3.30 (br m, 2H), 3.41 (br m, 2H), 3.55 (s, 3H), 4.00 (q, 2H), 6.87 (s, 2H).<br>LC/MS (ES+):<br>443 (M + H)+; R$_r$ = 2.06 min |

TABLE P1-continued

Physical data of compounds of formula I:

| Compound No. | Structures | Melting Point | MS/NMR |
|---|---|---|---|
| P1.6 | 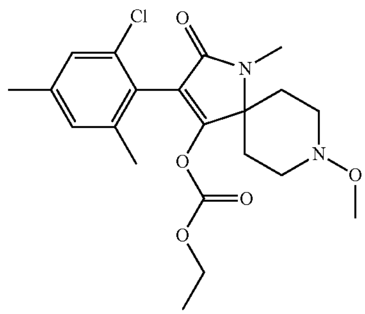 | 164-167° C. | LC/MS: 423/425 (M + H)$^+$<br>$R_t$ = 1.82 min |
| P1.7 | 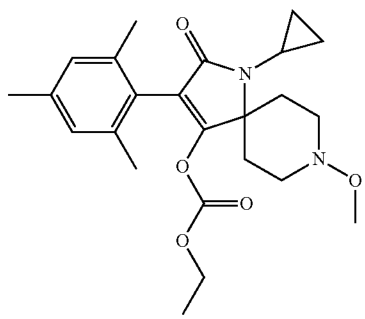 | gum | LC/MS: 429 (M + H)$^+$<br>$R_t$ = 1.93 min |
| P1.8 | 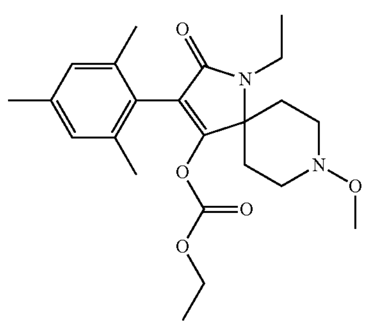 | 101-103° C. | LC/MS: 417 (M + H)$^+$<br>$R_t$ = 1.91 min |
| P1.9 | 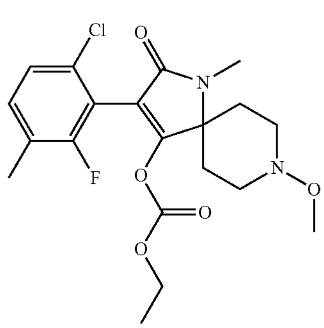 [SMILES: CCOC(=O)OC1=C(c2c(Cl)ccc(C)c2F)C(=O)N(C)C12CCN(OC)CC2] | solid | LC/MS: 427/429 (M + H)$^+$<br>$R_t$ = 1.75 min |

TABLE P1-continued

Physical data of compounds of formula I:

| Compound No. | Structures | Melting Point | MS/NMR |
|---|---|---|---|
| P1.10 | 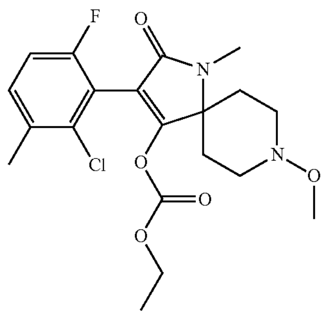 | 47-50° C. | LC/MS: 427/429 (M + H)+<br>$R_t$ = 1.73 min |
| P1.11 | 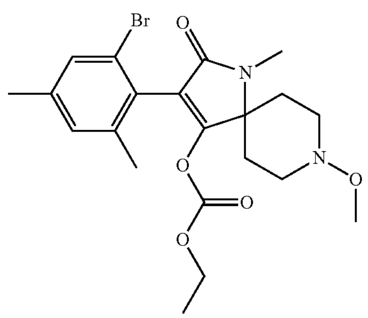 | 163-167° C. | LC/MS: 467/469 (M + H)+<br>$R_t$ = 1.83 min |
| P1.12 | 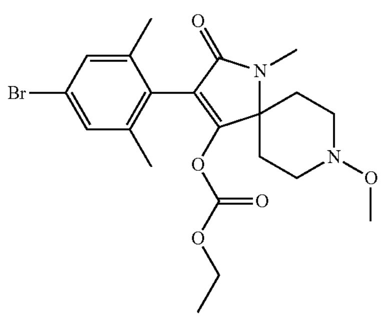 | 126-127° C. | LC/MS: 467/469 (M + H)+<br>$R_t$ = 1.89 min |
| P1.13 | 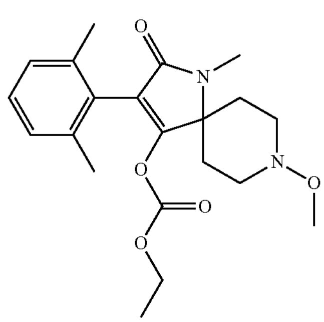 [SMILES: CCOC(=O)OC1=C(c2c(C)cccc2C)C(=O)N(C)C12CCN(OC)CC2] | 106-109° C. | LC/MS: 389 (M + H)+<br>$R_t$ = 1.74 min |

TABLE P1-continued

Physical data of compounds of formula I:

| Compound No. | Structures | Melting Point | MS/NMR |
|---|---|---|---|
| P1.14 | 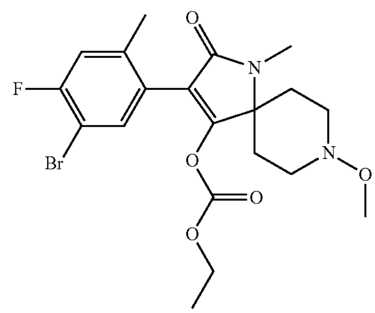 [SMILES: CCOC(=O)OC1=C(c2cc(Br)c(F)cc2C)C(=O)N(C)C12CCN(OC)CC2] | gum | LC/MS: 471/473 (M + H)+<br>$R_t$ = 1.81 min |
| P1.15 | 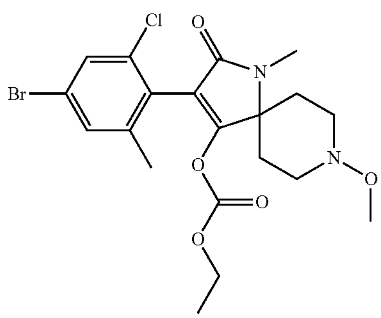 | 87-89° C. | LC/MS: 473/475/477 (M + H)+<br>$R_t$ = 1.80 min |
| P1.16 | 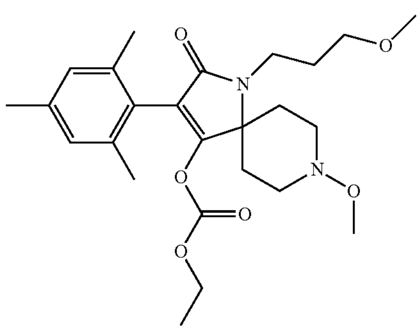 | gum | LC/MS: 461 (M + H)+<br>$R_t$ = 1.91 min |
| P1.17 | 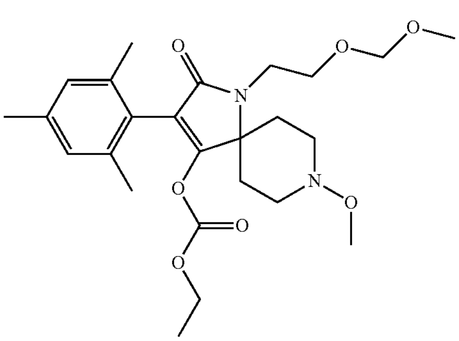 | gum | LC/MS: 477 (M + H)+<br>$R_t$ = 1.89 min |

TABLE P1-continued

Physical data of compounds of formula I:

| Compound No. | Structures | Melting Point | MS/NMR |
|---|---|---|---|
| P1.18 | 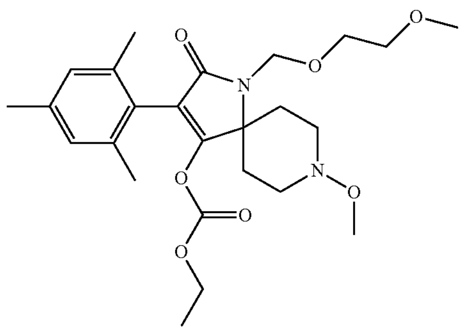 | gum | LC/MS: 477 (M + H)+<br>R$_t$ = 1.91 min |
| P1.19 | 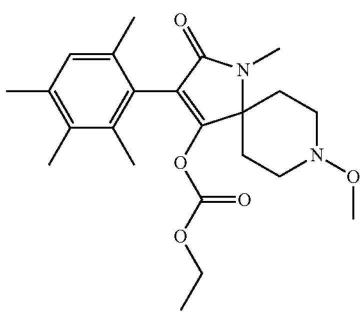 | solid | LC/MS: 417 (M + H)+<br>R$_t$ = 1.86 min |
| P1.20 | 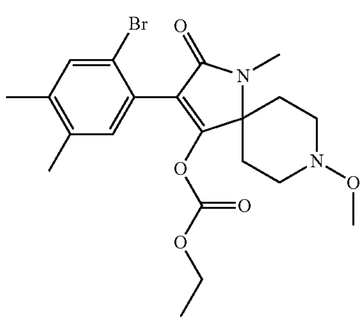 | 158-159° C. | $^1$H-NMR(CDCl$_3$, selected signals only):<br>1.16 (t, 3H, OCH$_2$CH$_3$), 2.20 (s, 3H, phenyl CH$_3$), 2.22 (s, 3H, phenyl CH$_3$), 2.94 (br s, 3H, N—CH$_3$; overlapping signal with piperidinyl Hs), 3.56 (s, 3H, NOCH$_3$), 4.09 (q, 2H, OCH$_2$CH$_3$), 7.07 (s, 1H, H$_{arom}$), 7.35 (s, 1H, H$_{arom}$). |
| P1.21 | 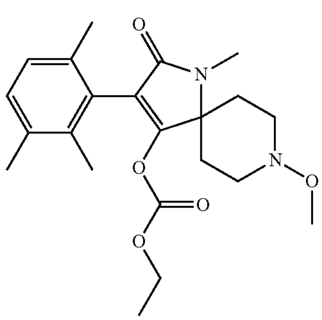 [SMILES: CCOC(=O)OC1=C(c2c(C)ccc(C)c2C)C(=O)N(C)C12CCN(OC)CC2] | gum | LC/MS: 403 (M + H)+<br>R$_t$ = 1.81 min |

TABLE P1-continued

Physical data of compounds of formula I:

| Compound No. | Structures | Melting Point | MS/NMR |
|---|---|---|---|
| P1.22 | 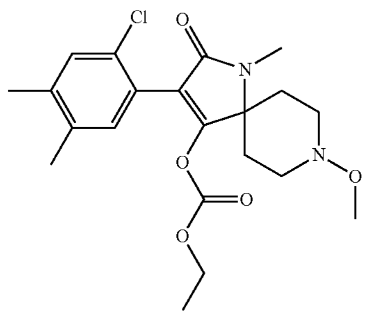 | 149-150° C. | LC/MS: 423/425 (M + H)+<br>$R_t$ = 1.91 min |
| P1.23 | 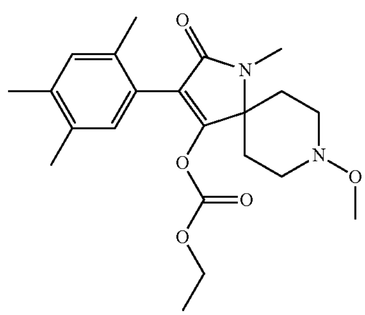 | gum | LC/MS: 403 (M + H)+<br>$R_t$ = 1.83 min |
| P1.24 | 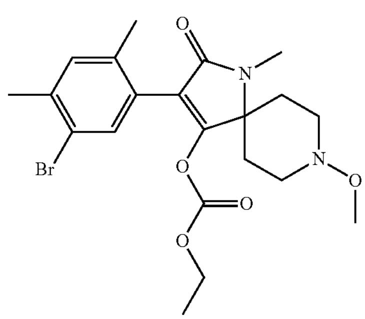 | solid | LC/MS: 467/469 (M + H)+<br>$R_t$ = 1.88 min |
| P1.25 | 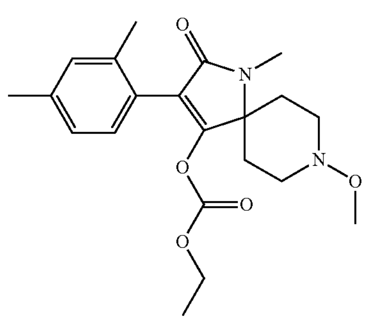 | solid | LC/MS: 389 (M + H)+<br>$R_t$ = 1.77 min |

TABLE P1-continued

Physical data of compounds of formula I:

| Compound No. | Structures | Melting Point | MS/NMR |
|---|---|---|---|
| P1.26 | 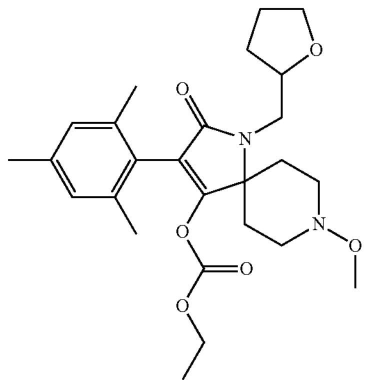 | gum | LC/MS: 473 (M + H)+<br>R$_t$ = 1.96 min |
| P1.27 | 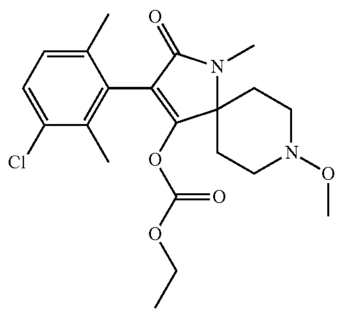 [SMILES: CCOC(=O)OC1=C(c2c(C)ccc(Cl)c2C)C(=O)N(C)C12CCN(OC)CC2] | gum | LC/MS: 423/425 (M + H)+<br>R$_t$ = 1.84 min |
| P1.28 | 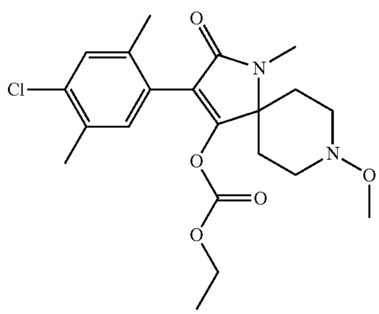 [SMILES: CCOC(=O)OC1=C(c2cc(C)c(Cl)cc2C)C(=O)N(C)C12CCN(OC)CC2] | gum | LC/MS: 423/425 (M + H)+<br>R$_t$ = 1.86 min |
| P1.29 | 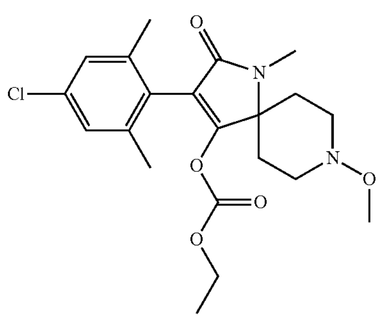 [SMILES: CCOC(=O)OC1=C(c2c(C)cc(Cl)cc2C)C(=O)N(C)C12CCN(OC)CC2] | 130-132° C. | LC/MS: 423/425 (M + H)+<br>R$_t$ = 1.86 min |
| P1.30 | 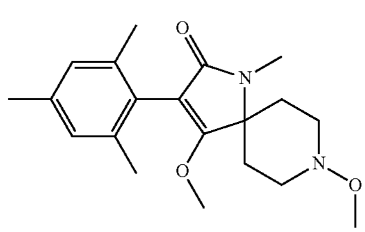 | | LC/MS: 345 (M + H)+<br>R$_t$ = 1.77 min |

TABLE P1-continued

Physical data of compounds of formula I:

| Compound No. | Structures | Melting Point | MS/NMR |
|---|---|---|---|
| P1.31 | (structure shown) EXAMPLE 9 | gum | LC/MS: 415 (M + H)+<br>R$_t$ = 2.00 min |

TABLE P2

Physical data of compounds of formula II:

| Compound No. | Structures | Melting Point | MS/NMR |
|---|---|---|---|
| P2.1 | (structure shown) | 121-123° C. | LC/MS: 317 (M + H)+<br>R$_t$ = 1.49 min |
| P2.2 | (structure shown)<br>EXAMPLE 1, step 1<br>EXAMPLE 2, step 3<br>EXAMPLE 4, step 4 | 241-243° C. | LC/MS: 331 (M + H)+<br>R$_t$ = 1.44 min |
| P2.3 | (structure shown) | solid | $^1$H-NMR (400 MHz, CDCl$_3$):<br>1.75 (m, 2H), 2.31 (m, 2H),<br>2.48 (m, 2H), 3.47 (m, 2H),<br>3.58 (s, 3H), 3.93 (m, 2H),<br>5.90 (m, 1H), 6.30 (br s,<br>1H), 7.25-7.32 (m, 2H), 7.40<br>(m, 1H). |
| P2.4 | (structure shown) | solid | $^1$H-NMR (400 MHz, CDCl$_3$,<br>selected signals only):<br>3.57 (s, 3H, NOCH$_3$), 5.85<br>(m, 1H, CHF$_2$), 6.52 (br s,<br>1H) , 7.27-7.35 (m, 2H,<br>H$_{arom}$), 7.49 (d, 1H, H$_{arom}$). |

TABLE P2-continued

Physical data of compounds of formula II:

| Compound No. | Structures | Melting Point | MS/NMR |
|---|---|---|---|
| P2.5 | 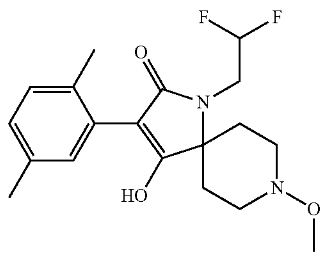 [SMILES: CON1CCC2(CC1)C(O)=C(c1cc(C)ccc1C)C(=O)N2CC(F)F] | solid | ¹H-NMR (400 MHz, CDCl₃, selected signals only): 2.18 (s, 3H, phenyl CH$_3$), 2.31 (s, 3H, phenyl CH$_3$), 3.39 (s, 3H, NOCH$_3$), 5.78 (m, 1H, CHF$_2$), 6.19 (br s, 1H), 7.00 (s, 1H, H$_{arom}$), 7.08 (d, 1H, H$_{arom}$), 7.12 (d, 1H, H$_{arom}$). |
| P2.6 | 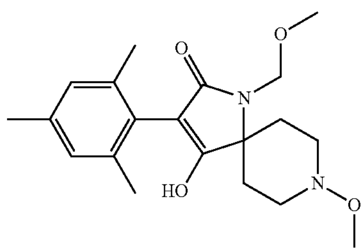 | 205-207° C. | LC/MS: 361 (M + H)$^+$ R$_t$ = 1.47 min |
| P2.7 | 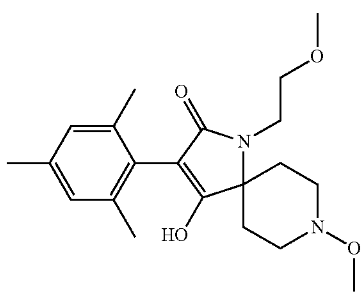 | solid | LC/MS: 375 (M + H)$^+$ R$_t$ = 1.58 min |
| P2.8 | EXAMPLE 3, step 2 | 223-225° C. | LC/MS: 371 (M + H)$^+$ R$_t$ = 1.76 min |
| P2.9 | 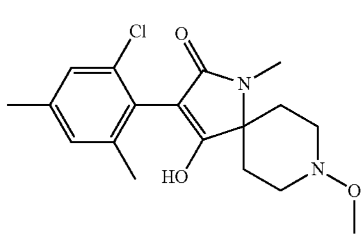 | >240° C. | LC/MS: 351/353 (M + H)$^+$ R$_t$ = 1.48 min |

TABLE P2-continued

Physical data of compounds of formula II:

| Compound No. | Structures | Melting Point | MS/NMR |
|---|---|---|---|
| P2.10 | 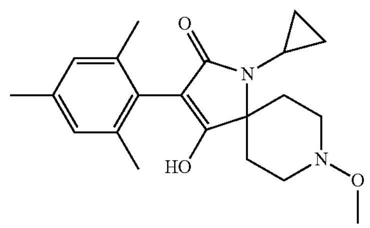 | 208-211° C. | LC/MS: 357 (M + H)+ $R_t$ = 1.61 min |
| P2.11 | 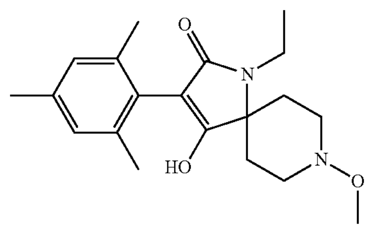 | 218-221° C. | LC/MS: 345 (M + H)+ $R_t$ = 1.58 min |
| P2.12 | 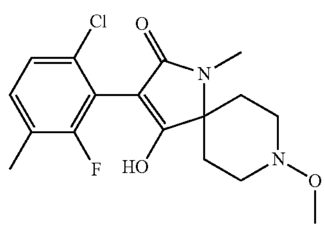 [SMILES: CON1CCC2(CC1)C(O)=C(c1c(Cl)ccc(C)c1F)C(=O)N2C] | solid | LC/MS: 355/357 (M + H)+ $R_t$ = 1.52 min |
| P2.13 | 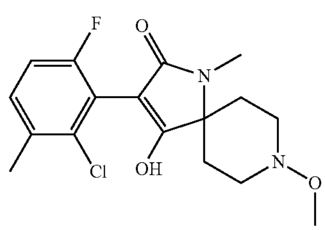 [SMILES: CON1CCC2(CC1)C(O)=C(c1c(F)ccc(C)c1Cl)C(=O)N2C] | 54-57° C. | LC/MS: 355/357 (M + H)+ $R_t$ = 1.49 min |
| P2.14 | 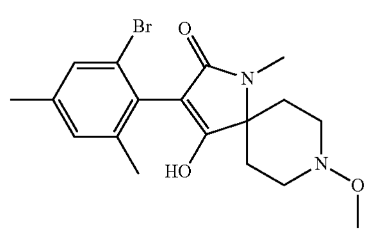 | solid | LC/MS: 395/397 (M + H)+ $R_t$ = 1.48 min |
| P2.15 | 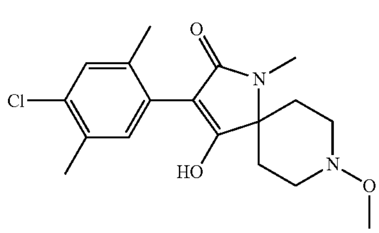 [SMILES: CON1CCC2(CC1)C(O)=C(c1cc(C)c(Cl)cc1C)C(=O)N2C] | 191-195° C. | LC/MS: 351/353 (M + H)+ $R_t$ = 1.58 min |

TABLE P2-continued

Physical data of compounds of formula II:

| Compound No. | Structures | Melting Point | MS/NMR |
|---|---|---|---|
| P2.16 | 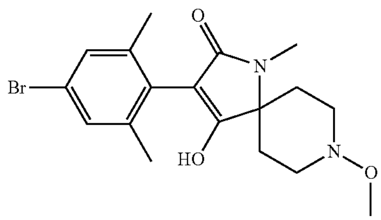 | 234-235° C. | LC/MS: 395/397 (M + H)+<br>R$_t$ = 1.54 min |
| P2.17 | 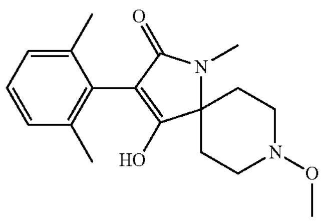 [SMILES: CON1CCC2(CC1)C(O)=C(c1c(C)cccc1C)C(=O)N2C] | 202-204° C. | LC/MS: 317 (M + H)+<br>R$_t$ = 1.36 min |
| P2.18 | 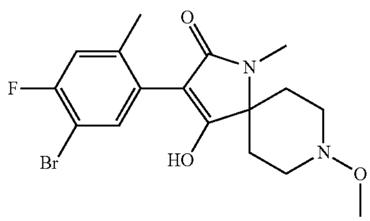 [SMILES: CON1CCC2(CC1)C(O)=C(c1cc(Br)c(F)cc1C)C(=O)N2C] | gum | LC/MS: 399/401 (M + H)+<br>R$_t$ = 1.54 min |
| P2.19 | 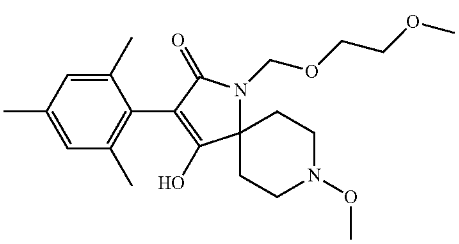 | 80-82° C. | $^1$H-NMR (CD3OD, selected signals only): 2.12 (s, 6H, mesityl CH$_3$), 2.27 (s, 3H, mesityl CH$_3$), 3.37 (s, 3H, CH$_2$CH$_2$OCH$_3$), 3.47 (t, 2H, CH$_2$CH$_2$OMe), 3.55 (s, 3H, NOCH$_3$), 3.65 (t, 2H, CH$_2$CH$_2$OMe), 6.91 (s, 2H, H$_{arom}$). |
| P2.20 | 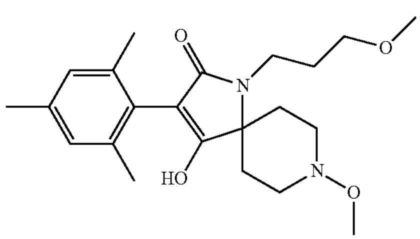 | 79-81° C. | LC/MS: 389 (M + H)+<br>R$_t$ = 1.62 min |
| P2.21 | 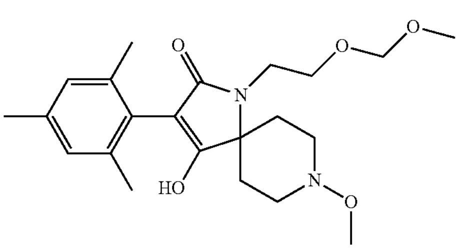 | 181-183° C. | LC/MS: 405 (M + H)+<br>R$_t$ = 1.60 min |

TABLE P2-continued

Physical data of compounds of formula II:

| Compound No. | Structures | Melting Point | MS/NMR |
|---|---|---|---|
| P2.22 | 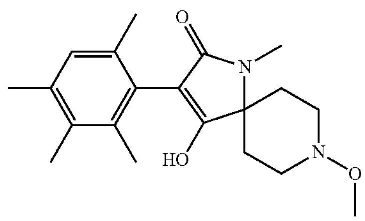 | solid | LC/MS: 345 (M + H)+ $R_t$ = 1.55 min |
| P2.23 | 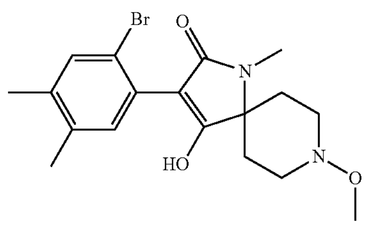 | 191-193° C. | LC/MS: 395/397 (M + H)+ $R_t$ = 1.59 min |
| P2.24 | 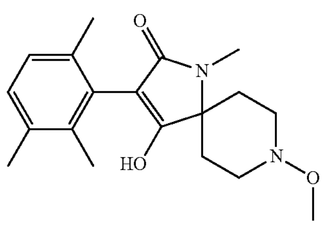 [SMILES: CON1CCC2(CC1)C(O)=C(c1c(C)ccc(C)c1C)C(=O)N2C] | 192-194° C. | LC/MS: 331 (M + H)+ $R_t$ = 1.41 min |
| P2.25 | 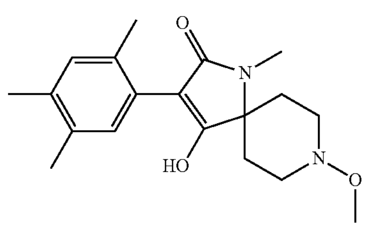 | 183-186° C. | LC/MS: 331 (M + H)+ $R_t$ = 1.56 min |
| P2.26 | EXAMPLE 7 | 191-192° C. | LC/MS: 351/353 (M + H)+ $R_t$ = 1.60 min |
| P2.27 | 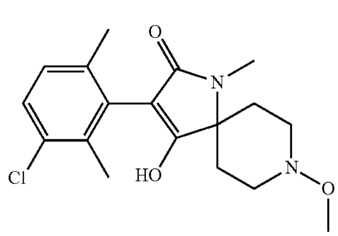 [SMILES: CON1CCC2(CC1)C(O)=C(c1c(C)ccc(Cl)c1C)C(=O)N2C] | 138-142° C. | LC/MS: 351/353 (M + H)+ $R_t$ = 1.49 min |

TABLE P2-continued

Physical data of compounds of formula II:

| Compound No. | Structures | Melting Point | MS/NMR |
|---|---|---|---|
| P2.28 | 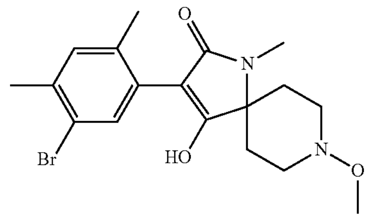 | 182-183° C. | LC/MS: 395/397 (M + H)⁺<br>$R_t$ = 1.62 min |
| P2.29 | 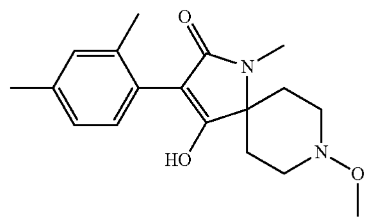 | solid | LC/MS: 317 (M + H)⁺<br>$R_t$ = 1.47 min |
| P2.30 | 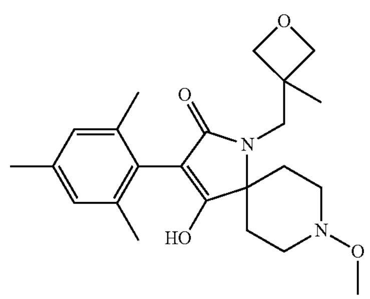 | 180-182° C. | LC/MS: 401 (M + H)⁺<br>$R_t$ = 1.50 min |
| P2.31 | 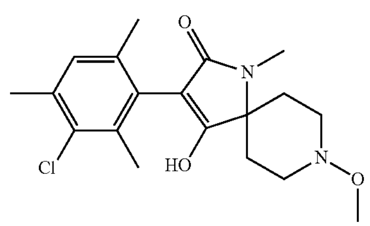 | gum | LC/MS: 365/367 (M + H)⁺<br>$R_t$ = 1.59 min |
| P2.32 | 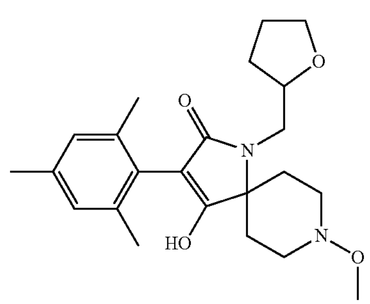 | 211-213° C. | LC/MS: 401 (M + H)⁺<br>$R_t$ = 1.60 min |
| P2.33 | 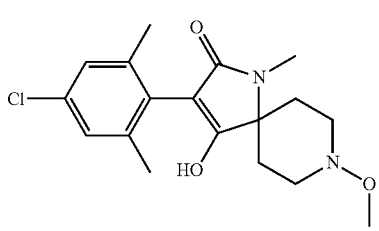 [SMILES: CON1CCC2(CC1)C(O)=C(c1c(C)cc(Cl)cc1C)C(=O)N2C] | solid | LC/MS: 351/353 (M + H)⁺<br>$R_t$ = 1.50 min |

TABLE P2-continued

Physical data of compounds of formula II:

| Compound No. | Structures | Melting Point | MS/NMR |
|---|---|---|---|
| P2.34 | (structure) | >200° C. | LC/MS: 415/417/419 (M + H)+ $R_t$ = 1.54 min |

Intermediates of the formula XIII or XIV from Table P3 can be prepared by analogous procedures.

TABLE P3

Physical data of intermediates of formula XIII or XIV:

| Compound No. | Structures | Melting Point | MS/NMR |
|---|---|---|---|
| P3.1 | (structure) | 128-131° C. | Described in WO09/049851 |
| P3.2 | (structure) | 180-183° C. | Described in WO09/049851 |

TABLE P3-continued

Physical data of intermediates of formula XIII or XIV:

| Compound No. | Structures | Melting Point | MS/NMR |
|---|---|---|---|
| P3.3 | (structure: 3-(2,4-dichlorophenyl)-4-((4-methoxybenzyl)oxy)-1'-methoxyspiro pyrrolinone) | 111-113° C. | Described in WO09/049851 |
| P3.4 | (structure: 3-mesityl-4-(benzyloxy)-1'-methoxyspiro pyrrolinone, NH) EXAMPLE 2, step 1 | 184-186 | LC/MS: 407 (M + H)+ $R_t$ = 2.02 min |
| P3.5 | (structure: N-methyl analog) EXAMPLE 2, step 2 | 139-141° C. | LC/MS: 421 (M + H)+ $R_t$ = 2.04 min |
| P3.6 | (structure: N-methoxymethyl analog) | solid | LC/MS: 451 (M + H)+ $R_t$ = 2.08 min |

TABLE P3-continued
Physical data of intermediates of formula XIII or XIV:
| Compound No. | Structures | Melting Point | MS/NMR |
|---|---|---|---|
| P3.7 | 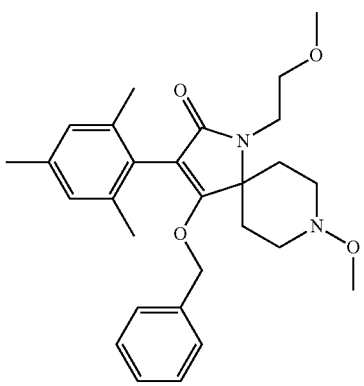 | solid | LC/MS: 465 (M + H)+<br>R$_t$ = 2.05 min |
| P3.8 | 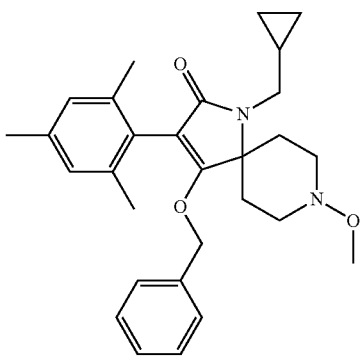<br>EXAMPLE 3, step 1 | 119-121° C. | LC/MS: 461 (M + H)+<br>R$_t$ = 2.19 min |
| P3.9 | 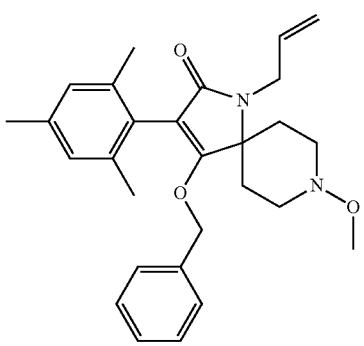 | 134-136° C. | LC/MS: 447 (M + H)+<br>R$_t$ = 2.14 min |
| P3.10 | 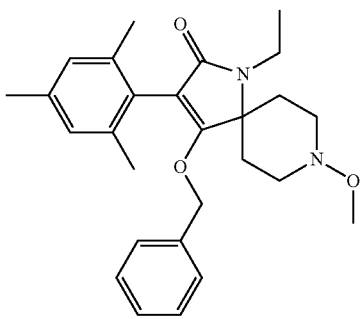 | solid | LC/MS: 435 (M + H)+<br>R$_t$ = 2.07 min |

TABLE P3-continued
Physical data of intermediates of formula XIII or XIV:
| Compound No. | Structures | Melting Point | MS/NMR |
|---|---|---|---|
| P3.11 | 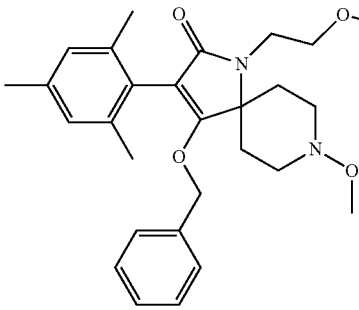 | 90-92° C. | LC/MS: 495 (M + H)$^+$<br>R$_t$ = 2.06 min |
| P3.12 | 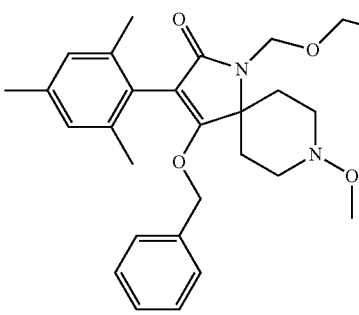 | 68-70° C. | LC/MS: 495 (M + H)$^+$<br>R$_t$ = 2.05 min |
| P3.13 | 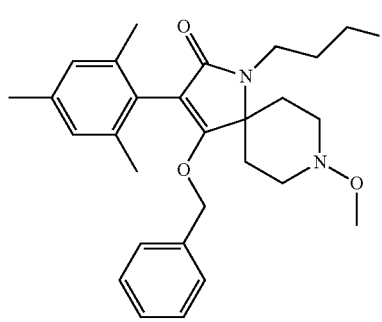 | solid | LC/MS: 479 (M + H)$^+$<br>R$_t$ = 2.07 min |
| P3.14 | 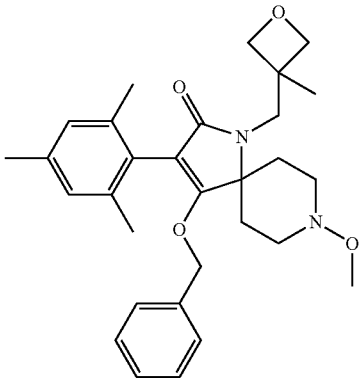 | | LC/MS: 491 (M + H)$^+$<br>R$_t$ = 2.04 min |
Intermediates of the formula IV or XI from Table P4 can be prepared by analogous procedures.

TABLE P4
Physical data of intermediates of formula IV or XI:
| Compound No. | Structures | Melting Point | MS/NMR |
|---|---|---|---|
| P4.1 | 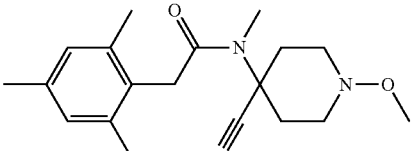<br>EXAMPLE 4, step 2 | 175-177° C. | LC/MS: 330 (M + H)+<br>$R_t$ = 1.78 min |
| P4.2 | 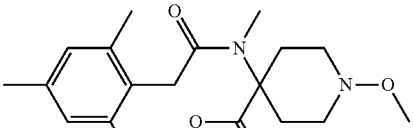<br>EXAMPLE 4, step 3 | 133-135° C. | LC/MS: 363 (M + H)+<br>$R_t$ = 1.79 min |
| P4.3 | 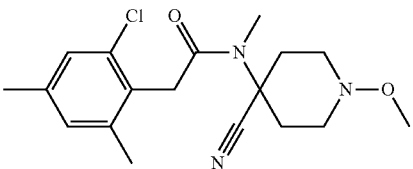 | | LC/MS: 350/352 (M + H)+<br>$R_t$ = 1.78 min |
| P4.4 | 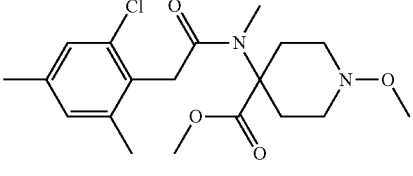 | | LC/MS: 383/385 (M + H)+<br>$R_t$ = 1.79 min |
| P4.5 | 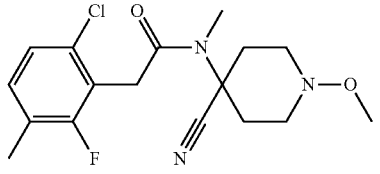 [SMILES: CON1CCC(C#N)(N(C)C(=O)Cc2c(F)ccc(C)c2Cl)CC1] | | LC/MS: 354/356 (M + H)+<br>$R_t$ = 1.71 min |
| P4.6 | 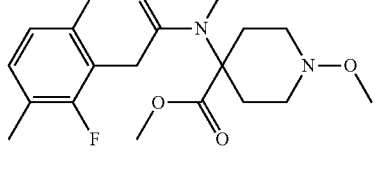 | | LC/MS: 387/389 (M + H)+<br>$R_t$ = 1.73 min |
| P4.7 | 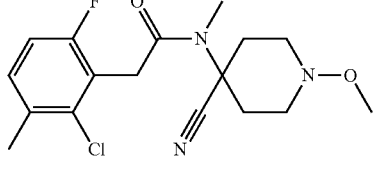 | | LC/MS: 354/356 (M + H)+<br>$R_t$ = 1.70 min |
| P4.8 | 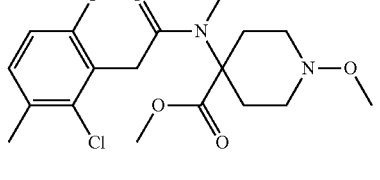 | | LC/MS: 387/389 (M + H)+<br>$R_t$ = 1.71 min |

TABLE P4-continued

Physical data of intermediates of formula IV or XI:

| Compound No. | Structures | Melting Point | MS/NMR |
|---|---|---|---|
| P4.9 | 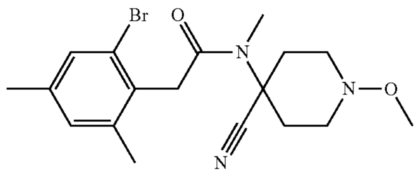 | | LC/MS: 394/396 (M + H)+<br>R$_t$ = 1.78 min |
| P4.10 | 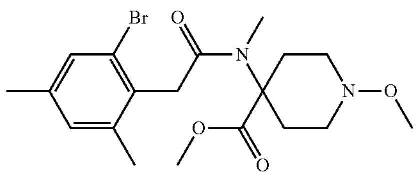 | | LC/MS: 427/429 (M + H)+<br>R$_t$ = 1.81 min |
| P4.11 | 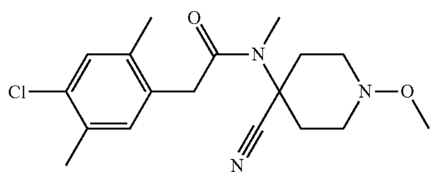 [SMILES: CON1CCC(C#N)(N(C)C(=O)Cc2cc(C)c(Cl)cc2C)CC1] | | LC/MS: 350/352 (M + H)+<br>R$_t$ = 1.78 min |
| P4.12 | 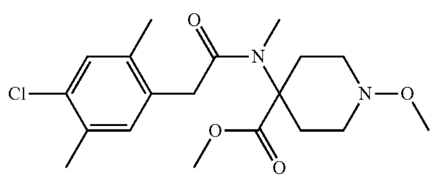 [SMILES: COC(=O)C1(N(C)C(=O)Cc2cc(C)c(Cl)cc2C)CCN(OC)CC1] | | LC/MS: 383/385 (M + H)+<br>R$_t$ = 1.78 min |
| P4.13 | 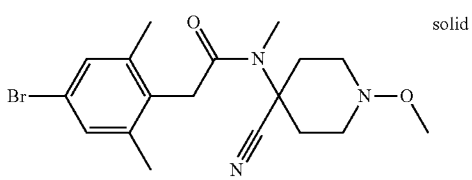 | solid | LC/MS: 394/396 (M + H)+<br>R$_t$ = 1.78 min |
| P4.14 | 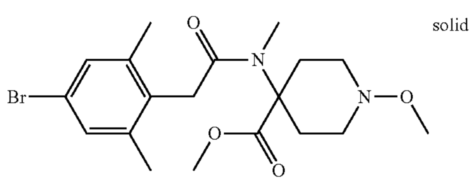 | solid | LC/MS: 427/429 (M + H)+<br>R$_t$ = 1.80 min |
| P4.15 | 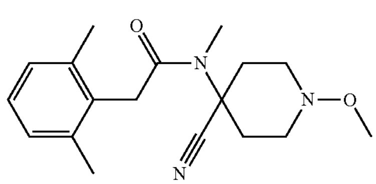 [SMILES: CON1CCC(C#N)(N(C)C(=O)Cc2c(C)cccc2C)CC1] | 171-174° C. | LC/MS: 316 (M + H)+<br>R$_t$ = 1.64 min |
| P4.16 | 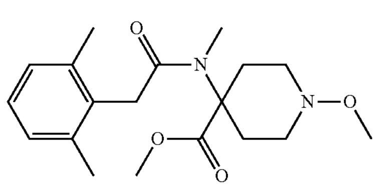 [SMILES: COC(=O)C1(N(C)C(=O)Cc2c(C)cccc2C)CCN(OC)CC1] | 139-141° C. | LC/MS: 349 (M + H)+<br>R$_t$ = 1.64 min |

TABLE P4-continued

Physical data of intermediates of formula IV or XI:

| Compound No. | Structures | Melting Point | MS/NMR |
|---|---|---|---|
| P4.17 | 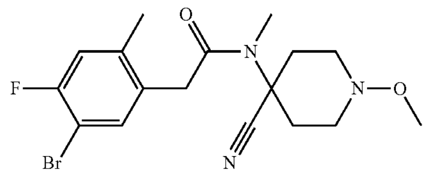 [SMILES: CON1CCC(C#N)(N(C)C(=O)Cc2cc(Br)c(F)cc2C)CC1] | gum | LC/MS: 398/400 (M + H)$^+$<br>R$_t$ = 1.71 min |
| P4.18 | 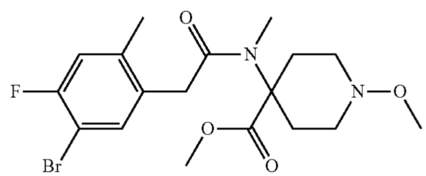 [SMILES: COC(=O)C1(N(C)C(=O)Cc2cc(Br)c(F)cc2C)CCN(OC)CC1] | solid | LC/MS: 431/433 (M + H)$^+$<br>R$_t$ = 1.75 min |
| P4.19 | 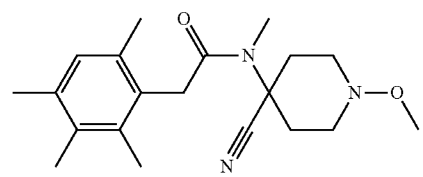 | | $^1$H-NMR (CDCl$_3$, selected signals only):<br>3.15 (s, 3H, N—CH$_3$), 3.50 (br s, 3H, NOCH$_3$), 3.75 (s, 2H, PhCH$_2$CO), 6.89 (s, 1H, H$_{arom}$). |
| P4.20 | 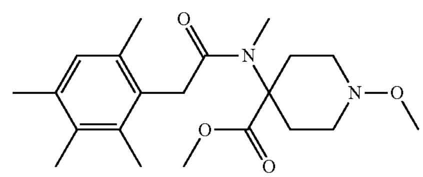 | | LC/MS: 377 (M + H)$^+$<br>R$_t$ = 1.81 min |
| P4.21 | 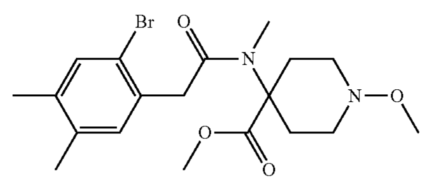 | gum | LC/MS: 427/429 (M + H)$^+$<br>R$_t$ = 1.82 min |
| P4.22 | 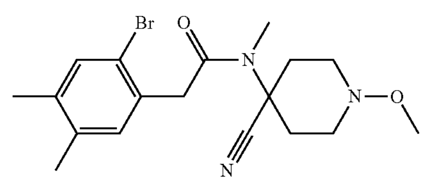 | 123-126° C. | LC/MS: 394/396 (M + H)$^+$<br>R$_t$ = 1.82 min |
| P4.23 | 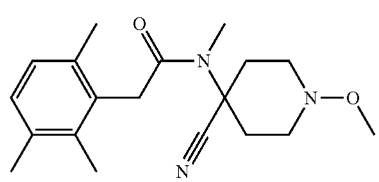 [SMILES: CON1CCC(C#N)(N(C)C(=O)Cc2c(C)ccc(C)c2C)CC1] | | $^1$H-NMR (CDCl$_3$, selected signals only):<br>2.13 (s, 3H, phenyl CH$_3$), 2.22 (s, 3H, phenyl CH$_3$), 2.25 (s, 3H, phenyl CH$_3$), 3.14 (s, 3H, N—CH$_3$), 3.51 (br s, 3H, NOCH$_3$), 3.73 (s, 2H, PhCH$_2$CO). |
| P4.24 | 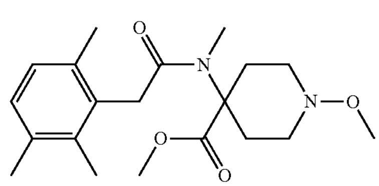 [SMILES: COC(=O)C1(N(C)C(=O)Cc2c(C)ccc(C)c2C)CCN(OC)CC1] | | $^1$H-NMR (CDCl$_3$, selected signals only):<br>3.52 (br s, 3H, NOCH$_3$). |

TABLE P4-continued

Physical data of intermediates of formula IV or XI:

| Compound No. | Structures | Melting Point | MS/NMR |
|---|---|---|---|
| P4.25 | 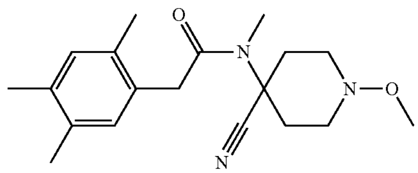 | | LC/MS: 330 (M + H)+<br>R$_t$ = 1.78 min |
| P4.26 | 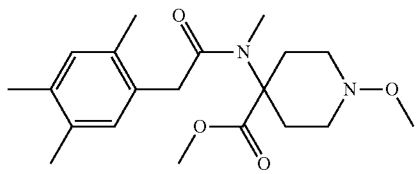 | | LC/MS: 363 (M + H)+<br>R$_t$ = 1.77 min |
| P4.27 | 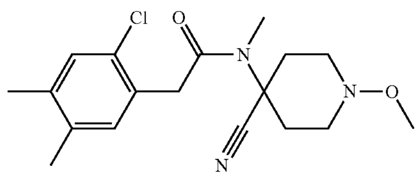 | solid | LC/MS: 350/352 (M + H)+<br>R$_t$ = 1.54 min |
| P4.28 | 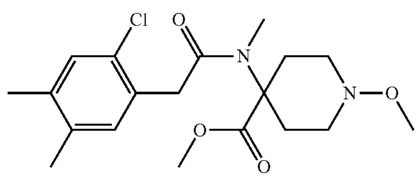 | | |
| P4.29 | 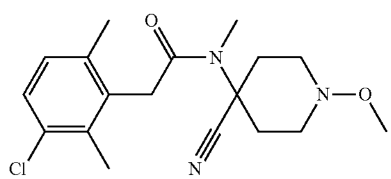 [SMILES: CON1CCC(C#N)(N(C)C(=O)Cc2c(C)ccc(Cl)c2C)CC1] | | |
| P4.30 | 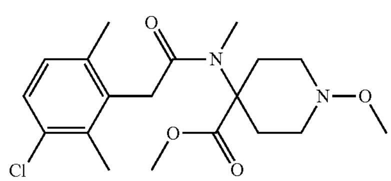 [SMILES: COC(=O)C1(N(C)C(=O)Cc2c(C)ccc(Cl)c2C)CCN(OC)CC1] | | |
| P4.31 | 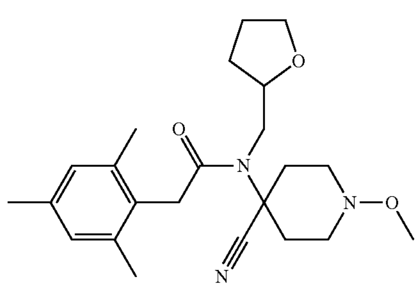 | 134-136° C. | LC/MS: 400 (M + H)+<br>R$_t$ = 1.87 min |

TABLE P4-continued

Physical data of intermediates of formula IV or XI:

| Compound No. | Structures | Melting Point | MS/NMR |
|---|---|---|---|
| P4.32 | 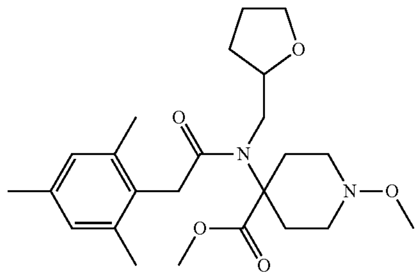 | 132-134° C. | LC/MS: 433 (M + H)+<br>$R_t$ = 1.87 min |
| P4.33 | 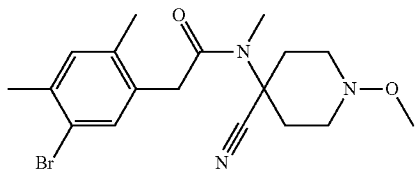 | 144-146° C. | LC/MS: 394/396 (M + H)+<br>$R_t$ = 1.82 min |
| P4.34 | 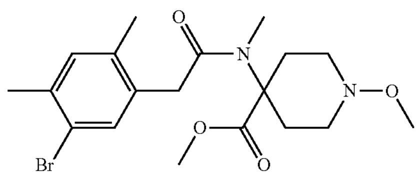 | gum | LC/MS: 427/429 (M + H)+<br>$R_t$ = 1.84 min |
| P4.35 | 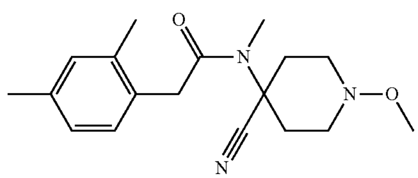 | solid | LC/MS: 316 (M + H)+<br>$R_t$ = 1.66 min |
| P4.36 | 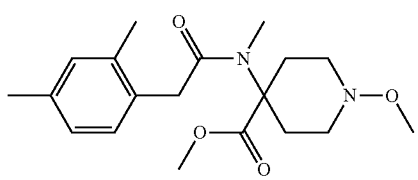 | solid | LC/MS: 349 (M + H)+<br>$R_t$ = 1.67 min |
| P4.37 | 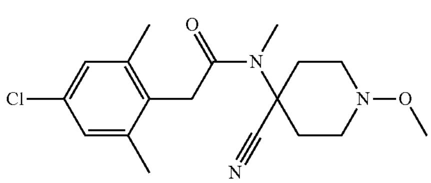 [SMILES: CON1CCC(C#N)(N(C)C(=O)Cc2c(C)cc(Cl)cc2C)CC1] | 188-192° C. | LC/MS: 350/352 (M + H)+<br>$R_t$ = 1.75 min |
| P4.38 | 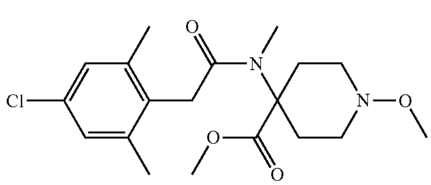 [SMILES: COC(=O)C1(N(C)C(=O)Cc2c(C)cc(Cl)cc2C)CCN(OC)CC1] | 150-152° C. | LC/MS: 383/385 (M + H)+<br>$R_t$ = 1.77 min |

TABLE P4-continued

Physical data of intermediates of formula IV or XI:

| Compound No. | Structures | Melting Point | MS/NMR |
|---|---|---|---|
| P4.39 | 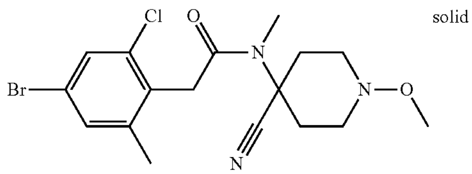 | solid | LC/MS: 414/416/418 (M + H)+ $R_t$ = 1.78 min |
| P4.40 | 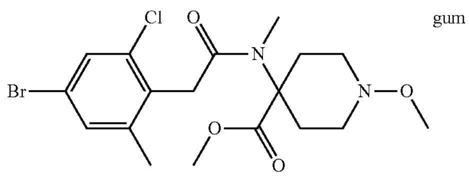 | gum | LC/MS: 447/449/451 (M + H)+ $R_t$ = 1.82 min |
| P4.41 | 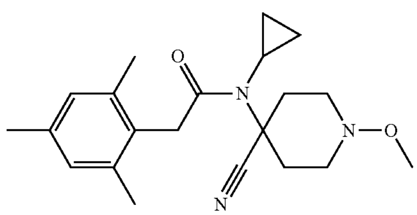 | | LC/MS: 356 (M + H)+ $R_t$ = 1.87 min |
| P4.42 | 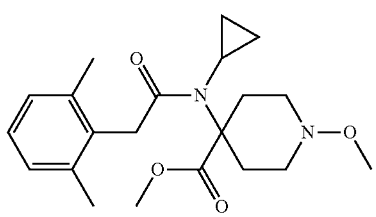 | | LC/MS: 389 (M + H)+ $R_t$ = 1.89 min |
| P4.43 | 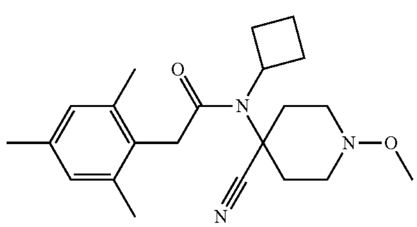 | gum | LC/MS: 370 (M + H)+ $R_t$ = 1.99 min |
| P4.44 | 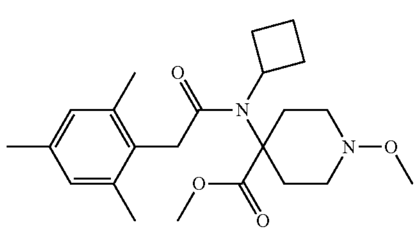 | | |
| P4.45 | 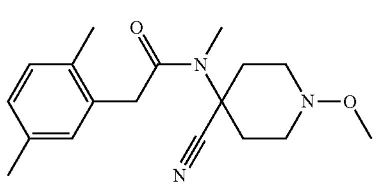 [SMILES: CON1CCC(C#N)(N(C)C(=O)Cc2cc(C)ccc2C)CC1] | | |

TABLE P4-continued

Physical data of intermediates of formula IV or XI:

| Compound No. | Structures | Melting Point | MS/NMR |
|---|---|---|---|
| P4.46 | EXAMPLE 10, step 3 | gum | LC/MS: 349 (M + H)$^+$<br>R$_t$ = 1.66 min |

Intermediates of the formula V, VII, VIII or IX from Table P5 can be prepared by analogous procedures.

TABLE P5

Physical data of intermediates of formula V, VII, VIII or IX:

| Compound No. | Structures | Melting Point | MS/NMR/IR |
|---|---|---|---|
| P5.1 | EXAMPLE 4, step 1 | liquid | $^1$H-NMR (CDCl$_3$):<br>1.36 (br s, 1H), 1.62-2.22 (br signals, total 4H), 2.51 (s, 3H), 2.63-3.41 (br signals, total 4H), 3.51 (s, 3H).<br>LC/MS (ES+):<br>170 (M + H)$^+$; R$_t$ = 0.25 min |
| P5.2 | EXAMPLE 5 | | LC/MS: 196 (M + H)$^+$<br>R$_t$ = 1.14 min<br>IR (CN): ν 2223 cm$^{-1}$ |
| P5.3 | 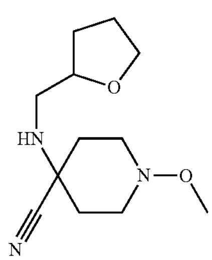 [SMILES: CON1CCC(C#N)(NCC2CCCO2)CC1] | oil | LC/MS: 240 (M + H)$^+$<br>R$_t$ = 1.18 min |
| P5.4 | EXAMPLE 6, step 2<br>EXAMPLE 10, step 2 | oil | $^1$H-NMR (CDCl$_3$):<br>1.46-2.33 (br signals, total 5H), 2.22 (br s, 3H), 2.51-3.31 (br signals, total 4H), 3.51 (s, 3H), 3.72 (br s, 3H).<br>LC/MS (ES+):<br>203 (M + H)$^+$; R$_t$ = 0.20 min |

TABLE P5-continued

Physical data of intermediates of formula V, VII, VIII or IX:

| Compound No. | Structures | Melting Point | MS/NMR/IR |
|---|---|---|---|
| P5.5 | (structure shown) | | LC/MS: 210 (M + H)$^+$<br>$R_t$ = 1.10 min<br>IR (CN): ν 2222 cm$^{-1}$ |
| P5.6 | (structure shown)<br>EXAMPLE 6, step 1 | solid | LC/MS: 214 (M + H)$^+$<br>$R_t$ = 0.75 min |
| P5.7 | (structure shown)<br>EXAMPLE 10, step 1 | >250° C. | $^1$H-NMR (D$_2$O):<br>1.73 (m, 1H), 2.02 (m, 2H),<br>2.32 (m, 1H), 2.54 (appar.<br>d, 3H), 2.69 (m, 1H), 2.99<br>(m, 1H), 3.18 (m, 1H), 3.33<br>(m, 1H), 3.49 (appar. d, 3H).<br>LC/MS (ES+):<br>189 (M + H)$^+$; $R_t$ = 0.21<br>min |

EXAMPLE 11

Preparation of Carbonic acid 3-(2,5-dimethyl-phenyl)-8-methoxy-1-methoxy-methoxy-2-oxo-1,8-diaza-spiro[4.5]dec-3-en-4-yl ester ethyl ester (Compound P1ii.2)

Step 1: Preparation of 1-methoxy-piperidin-4-one oxime

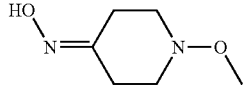

To a solution of 1-methoxy-piperidin-4-one [prepared according to Journal of Organic Chemistry (1961), 26, 1867-74](258 g, 2.0 mol) and triethylamine (305.2 ml, 221.9 g, 4.4 mol) in methanol (3000 ml) was added hydroxylamine hydrochloride (277.6 g, 4.0 mol), and the reaction mixture heated at reflux for 1.5 hours. The solvent was evaporated, the residue diluted with diethyl ether and the suspension filtered. The filtrate was washed with water and brine, dried over sodium sulfate and concentrated. Yield: 286.25 g of 1-methoxy-piperidin-4-one oxime as a colorless, viscous oil. This material was used without further purification in the next step.

$^1$H-NMR (CDCl$_3$): 2.2-3.45 (br signals, total 8H), 3.55 (s, 3H), 8.65 (br s, 1H).

LC/MS (ES+): 145 (M+H)$^+$

Step 2: Preparation of 4-hydroxyamino-1-methoxy-piperidine-4-carbonitrile (Compound P4ii.1)

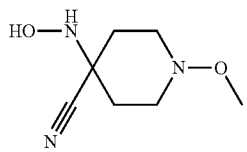

To a suspension of 1-methoxy-piperidin-4-one oxime (240 g, 1.66 mol) and potassium dihydrogen phosphate (792.9 g, 5.83 mol) in water (200 ml) at 0-5° C. was added a solution of potassium cyanide (195.1 g, 3.0 mol) in water (200 ml) dropwise (caution!). The reaction mixture was stirred at room temperature overnight (stoppered flask), treated with another portion of potassium dihydrogen phosphate (79.3 g, 0.58 mol) and further stirred at room temperature over another night. The mixture was flushed with nitrogen, the semi-solid removed by filtration and dissolved in ethyl acetate. The aqueous layer was extracted twice with ethyl acetate, all organic layers combined, washed with water and brine, dried over sodium sulfate and concentrated. The residue was triturated with cold diethyl ether, filtered and dried. Yield: 230.8 g of 4-hydroxyamino-1-methoxy-piperidine-4-carbonitrile as a tan solid, mp 130-131° C.

$^1$H-NMR (CDCl$_3$): 1.55-2.35 (br signals, total 4H), 2.60-3.45 (br signals, total 4H), 3.52 (s, 3H), 5.19 (br s, 1H), 5.42 (br s, 1H).

IR(CN): ν 2227.8 cm$^{-1}$. LC/MS (ES+): 172 (M+H)$^+$

Step 3: Preparation of 4-hydroxyamino-1-methoxy-piperidine-4-carboxylic acid methyl ester (Compound 4ii.2)

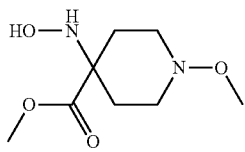

To a suspension of 4-hydroxyamino-1-methoxy-piperidine-4-carbonitrile (230 g, 1.34 mol) in dichloromethane (2400 ml) at room temperature was added concentrated sulfuric acid (358 ml, 658.8 g, 6.72 mol) dropwise, and the reaction mixture was stirred at 40° C. for one hour. Methanol (925.1 ml, 731.7 g, 22.8 mol) was added at 40° C. dropwise, and the mixture stirred at 40° C. for 4 hours. The dichloromethane was distilled off allowing to heat the reaction mixture at 60° C. for 24 hours. The reaction mixture was poured on ice (3 kg) and neutralized by careful addition of concentrated aqueous sodium hydroxide first, followed by saturated aqueous sodium hydrogen carbonate. The aqueous phase was saturated with sodium chloride, extracted with ter-butyl methyl ether (10×300 ml), the combined organic layers washed with brine, dried over sodium sulfate and concentrated to afford a first crop of product (163.8 g). Further extraction of the aqueous layer with ethyl acetate delivered another 35 g of crude product. Yield: 198.8 g of 4-hydroxyamino-1-methoxy-piperidine-4-carboxylic acid methyl ester as a red-brown, viscous oil. This material was used without further purification in the next step.

$^1$H-NMR (CDCl$_3$): 1.50-2.40 (br signals, total 4H), 2.76 (br m, 2H), 3.01-3.32 (br m, 2H), 3.52 (s, 3H), 3.76 (s, 3H), 5.58 (br s, 2H).

IR(COOMe): ν 1731.3 cm$^{-1}$. LC/MS (ES$^+$): 205 (M+H)+

Step 4: Preparation of 4-{[2-(2,5-dimethyl-phenyl)-acetyl]-hydroxy-amino}-1-methoxy-piperidine-4-carboxylic acid methyl ester (Compound P3ii.1)

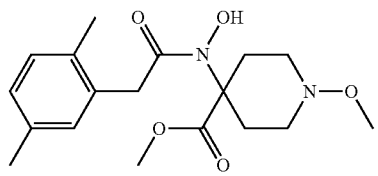 [SMILES: COC(=O)C1(N(O)C(=O)Cc2cc(C)ccc2C)CCN(OC)CC1]

To a solution of 4-hydroxyamino-1-methoxy-piperidine-4-carboxylic acid methyl ester (50 g, 244.8 mmol) in tetrahydrofuran (500 ml) at 0° C. was added sodium hydrogen carbonate (34.96 g, 416.2 mmol), followed by a solution of (2,5-dimethyl-phenyl)-acetyl chloride [prepared by treatment (2,5-dimethyl-phenyl)-acetic acid with oxalyl chloride in dichloromethane under standard conditions](44.72 g, 244.8 mmol) in tetrahydrofuran (500 ml) dropwise. The reaction mixture was stirred at 0° C. for one hour and at room temperature for two hours. The solvent was evaporated, the residue diluted with water and ethyl acetate and the layers separated. The aqueous phase was extracted with ethyl acetate (6×250 ml), the combined organic layers washed with an aqueous sodium hydrogen carbonate solution and brine, dried over sodium sulfate and concentrated. The crude product was triturated with a cold diethyl ether/hexane 1:1 solution, filtered and dried to afford 36.4 g as a white solid. The mother liquor was concentrated and purified by chromatography on silica gel (ethyl acetate/hexane 1:1) to further afford 4.2 g of product. Yield: 40.6 g of 4-{[2-(2,5-dimethyl-phenyl)-acetyl]-hydroxy-amino}-1-methoxy-piperidine-4-carboxylic acid methyl ester (compound P3ii.1), mp 137-139° C.

$^1$H-NMR (CDCl$_3$): 1.99-3.32 (br signals, total 8H), 2.23 (s, 3H), 2.29 (s, 3H), 3.53 (s, 3H), 3.72 (s, 3H), 3.83 (s, 2H), 6.43 (br s, 1H), 6.98 (d, 1H), 6.99 (s, 1H), 7.06 (d, 1H).

LC/MS (ES+): 351 (M+H)$^+$

Step 5: Preparation of 3-(2,5-dimethyl-phenyl)-4-hydroxy-8-methoxy-1-methoxymethoxy-1,8-diaza-spiro[4.5]dec-3-en-2-one (Compound P2ii.2)

[Two-Steps (Hydroxamic Acid O-Alkylation and Cyclisation), One-Pot Procedure]

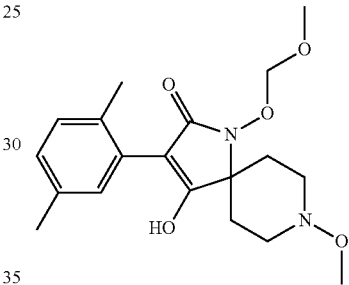

To a solution of 4-{[2-(2,5-dimethyl-phenyl)-acetyl]-hydroxy-amino}-1-methoxy-piperidine-4-carboxylic acid methyl ester (35 g, 100.0 mmol) in dimethylformamide (300 ml) at 0° C. was added sodium hydride (5.02 g, 55% w/w dispersion in mineral oil, 115.0 mmol) in 5 portions. The reaction mixture was stirred at 0° C. for 30 minutes, treated with chloromethyl methyl ether (8.96 ml, 9.5 g, 118.0 mmol) dropwise, and further stirred at 0° C. for one hour and at room temperature for 1.5 hours. To the mixture recooled at 0° C. was added sodium methoxide (8.1 g, 150 mmol) in one portion, and stirring continued at room temperature for 2.5 hours. The reaction mixture was poured on ice water (500 ml), acidified to pH 5-6 with an aqueous HCl solution and thoroughly extracted with ethyl acetate. The combined organic layers were washed with brine, dried over sodium sulfate and concentrated. The crude oily product was triturated with a cold diethyl ether/hexane 1:1 solution, filtered and dried to afford 15.8 g as a white solid. The mother liquor was concentrated and purified by chromatography on silica gel (ethyl acetate/hexane 2:1) to further afford 2.1 g of product. Yield: 17.9 g of 3-(2,5-dimethyl-phenyl)-4-hydroxy-8-methoxy-1-methoxymethoxy-1,8-diaza-spiro[4.5]dec-3-en-2-one (compound P2ii.2), mp 136-138° C.

$^1$H-NMR (CDCl$_3$): 1.44-2.72 (br signals, total 4H), 2.27 (s, 3H), 2.30 (s, 3H), 2.78-3.48 (br signals, total 4H), 3.59 (s, 3H), 3.64 (s, 3H), 4.41 (s, 1H), 5.12 (br m, 2H), 6.76 (s, 1H), 7.02 (d, 1H), 7.10 (d, 1H) (mixture of keto-enol tautomers, signals of major diketo-form isomer shown).

LC/MS (ES+): 363 (M+H)$^+$, LC/MS (ES−): 361 (M−H)$^−$

Step 6: Preparation of carbonic acid 3-(2,5-dimethyl-phenyl)-8-methoxy-1-methoxy-methoxy-2-oxo-1,8-diaza-spiro[4.5]dec-3-en-4-yl ester ethyl ester (Title Compound P1ii.2)

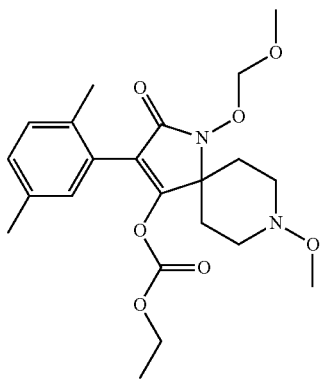 [SMILES: CCOC(=O)OC1=C(c2cc(C)ccc2C)C(=O)N(OCOC)C12CCN(OC)CC2]

To a solution of 3-(2,5-dimethyl-phenyl)-4-hydroxy-8-methoxy-1-methoxymethoxy-1,8-diaza-spiro[4.5]dec-3-en-2-one (9.0 g, 24.83 mmol), triethylamine (6.9 ml, 5.0 g, 49.66 mmol) and 4-dimethylaminopyridine (100 mg, 0.82 mmol) in tetrahydrofuran (250 ml) at 0° C. was added a solution of ethyl chloroformate (3.09 ml, 3.5 g, 32.28 mmol) in tetrahydrofuran (20 ml) dropwise. The suspension was stirred at 0° C. for one hour, and at room temperature for one hour. The reaction mixture was evaporated, diluted with ethyl acetate and filtered to remove salts. The filtrate was washed with a saturated aqueous sodium hydrogen carbonate solution (2×100 ml) and brine, dried over sodium sulfate and concentrated. The oily residue was purified by chromatography on silica gel (ethyl acetate/hexane 1:1). Yield: 9.63 g of carbonic acid 3-(2,5-dimethyl-phenyl)-8-methoxy-1-methoxy-methoxy-2-oxo-1,8-diaza-spiro[4.5]dec-3-en-4-yl ester ethyl ester (title compound P1ii.2) as a white solid, mp 109-111° C.

$^1$H-NMR (CDCl$_3$): 1.06 (t, 3H), 1.75-2.05 (br m, 2H), 2.20 (s, 3H), 2.28 (s, 3H), 2.47 (br m, 2H), 2.89 (br m, 1H), 3.15-3.45 (br m, 3H), 3.59 (s, 3H), 3.64 (s, 3H), 3.99 (q, 2H), 5.07 (br s, 2H), 6.96 (s, 1H), 7.03 (d, 1H), 7.09 (d, 1H).

LC/MS (ES+): 435 (M+H)$^+$

EXAMPLE 12

Preparation of 4-Hydroxy-8-methoxy-1-prop-2-ynyloxy-3-(2,4,6-trimethyl-phenyl)-1,8-diaza-spiro[4.5]dec-3-en-2-one (Compound P2ii.8)

(stepwise hydroxamic acid O-alkylation and cyclisation)

Step 1: Preparation of 1-methoxy-4-{prop-2-ynyloxy-[2-(2,4,6-trimethyl-phenyl)-acetyl]-amino}-piperidine-4-carboxylic acid methyl ester (Compound P3ii.4)

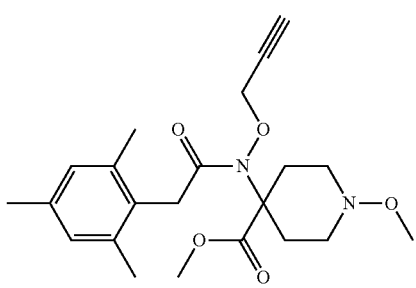

To a solution of 4-{hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (500 mg, 1.37 mmol) in tetrahydrofuran (3 ml) at 0° C. was added sodium hydride (66 mg, 55% w/w dispersion in mineral oil, 1.51 mmol) in 2 portions. The reaction mixture was stirred at 0° C. for one hour, treated with propargyl bromide (202 mg, 1.65 mmol) dropwise, and further stirred at room temperature overnight. The reaction mixture was evaporated, diluted with ethyl acetate and filtered to remove salts. The filtrate was washed twice with brine, dried over sodium sulfate and concentrated. The oily residue was purified by chromatography on silica gel (ethyl acetate/hexane 1:2). Yield: 321 mg of 1-methoxy-4-{prop-2-ynyloxy-[2-(2,4,6-trimethyl-phenyl)-acetyl]-amino}-piperidine-4-carboxylic acid methyl ester (compound P3ii.4) as a colorless gum.

$^1$H-NMR (CDCl$_3$): 1.90-3.34 (br signals, total 8H), 2.21 (s, 6H), 2.24 (s, 3H), 2.68 (t, 1H), 3.53 (s, 3H), 3.68 (s, 3H), 3.77 (d, 1H), 4.03 (m, 1H), 4.65-4.89 (br m, 2H), 6.84 (s, 2H).

LC/MS (ES+): 403 (M+H)$^+$

Step 2: Preparation of 4-hydroxy-8-methoxy-1-prop-2-ynyloxy-3-(2,4,6-trimethyl-phenyl)-1,8-diaza-spiro[4.5]dec-3-en-2-one (Title Compound P2ii.8)

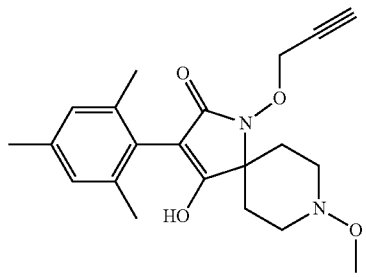

To a solution of 1-methoxy-4-{prop-2-ynyloxy-[2-(2,4,6-trimethyl-phenyl)-acetyl]-amino}-piperidine-4-carboxylic acid methyl ester (150 mg, 0.41 mmol) in dimethylformamide (2 ml) at 0° C. was added sodium methoxide (33 mg, 0.62 mmol) in one portion and stirring continued at room temperature for 4 hours. The reaction mixture was poured on ice water, acidified to pH 5-6 with an aqueous HCl solution, saturated with sodium chloride and thoroughly extracted with ethyl acetate. The combined organic layers were washed with brine, dried over sodium sulfate and concentrated. The residue was purified by chromatography on silica gel (ethyl acetate/hexane 2:1). Yield: 14 mg of 4-hydroxy-8-methoxy-1-prop-2-ynyloxy-3-(2,4,6-trimethyl-phenyl)-1,8-diaza-spiro[4.5]dec-3-en-2-one (title compound P2ii.8) as a tan solid.

$^1$H-NMR (CD$_3$OD): 1.97-2.08 (m, 2H), 2.10 (s, 6H), 2.25 (s, 3H), 2.23-2.32 (m, 2H), 3.04 (br s, 1H), 3.20 (m, 2H), 3.38 (m, 2H), 3.54 (s, 3H), 4.76 (br s, 2H), 6.89 (s, 2H).

LC/MS (ES+): 371 (M+H)$^+$

EXAMPLE 13

Preparation of Carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (Compound P1ii.9)

Step 1: Preparation of carbonic acid ethyl ester 1-hydroxy-8-methoxy-2-oxo-3-(2,4,6-trimethyl-phenyl)-1,8-diaza-spiro[4.5]dec-3-en-4-yl ester (Compound P1ii.11)

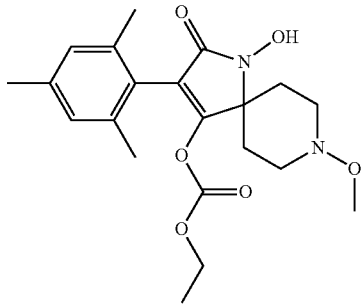

To a solution of carbonic acid ethyl ester 8-methoxy-1-methoxymethoxy-2-oxo-3-(2,4,6-trimethyl-phenyl)-1,8-diaza-spiro[4.5]dec-3-en-4-yl ester (compound P1ii.7 obtained in analogy to preparation example 11, step 6) (1.0 g, 2.23 mmol) in bromotrimethylsilane (4.33 ml, 5.12 g, 33.44 mmol) under argon atmosphere was added 3 Å molecular sieves (0.5 g) and the reaction mixture was stirred at 75° C. overnight. The mixture was diluted with dichloromethane, filtered, the filtrate evaporated, the residue triturated with cold diethyl ether, filtered and dried. The crude product was purified by chromatography on silica gel (gradient dichloromethane→dichloromethane/methanol 20:1→10:1). Yield: 580 mg of carbonic acid ethyl ester 1-hydroxy-8-methoxy-2-oxo-3-(2,4,6-trimethyl-phenyl)-1,8-diaza-spiro[4.5]dec-3-en-4-yl ester (compound P1ii.11) as a white solid, mp 154-155° C.

$^1$H-NMR (CD$_3$OD): 1.03 (t, 3H), 2.03 (br m, 2H), 2.13 (s, 6H), 2.22 (br m, 2H), 2.25 (s, 3H), 2.94 (br m, 1H), 3.28 (br m, 2H), 3.44 (br m, 1H), 3.54 (s, 3H), 4.00 (q, 2H), 6.87 (s, 2H).

LC/MS (ES+): 405 (M+H)$^+$

Step 2: Preparation of carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (Title Compound P1ii.9)

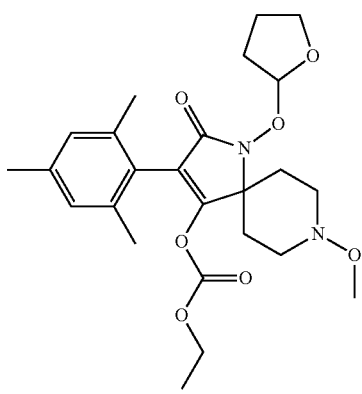

To a solution of carbonic acid ethyl ester 1-hydroxy-8-methoxy-2-oxo-3-(2,4,6-trimethyl-phenyl)-1,8-diaza-spiro[4.5]dec-3-en-4-yl ester (150 mg, 0.37 mmol) in dichloromethane (3 ml) under argon atmosphere was added 2,3-dihydro-furan (56 μl, 52 mg, 0.74 mmol) and a catalytic amount of p-toluenesulfonic acid monohydrate (2 mg). The reaction mixture was stirred at room temperature for 4 hours, diluted with dichloromethane, washed twice with brine, dried over sodium sulfate and concentrated. The residue was purified by chromatography on silica gel (ethyl acetate/hexane 2:1). Yield: 114 mg of carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (title compound P1ii.9) as a colorless gum.

$^1$H-NMR (CD$_3$OD): 1.02 (t, 3H), 1.70-2.22 (br signals, total 6H), 2.12 (s, 3H), 2.13 (s, 3H), 2.25 (s, 3H), 2.31-2.68 (br m, 2H), 2.86 (br m, 1H), 3.20 (br m, 1H), 3.39 (br m, 2H), 3.54 (s, 3H), 3.96 (m, 1H), 4.00 (q, 2H), 4.18 (q, 1H), 5.62 (br s, 1H), 6.88 (s, 2H).

LC/MS (ES+): 475 (M+H)$^+$

EXAMPLE 14

Preparation of 1,4-Dihydroxy-8-methoxy-3-(2,4,6-trimethyl-phenyl)-1,8-diaza-spiro[4.5]dec-3-en-2-one (Compound P2ii.4)

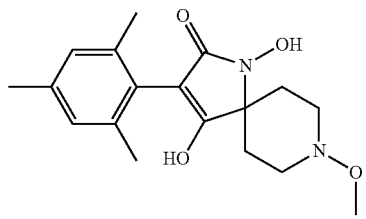

To a solution of 4-hydroxy-8-methoxy-1-methoxymethoxy-3-(2,4,6-trimethyl-phenyl)-1,8-diaza-spiro[4.5]dec-3-en-2-one (compound P2ii.6 obtained in analogy to preparation example 11, step 5) (500 mg, 1.33 mmol) in dichloromethane (10 ml) under argon atmosphere at 0° C. was added 3 Å molecular sieves (0.5 g), followed by bromotrimethylsilane (1.72 ml, 2.03 g, 13.28 mmol) dropwise and the reaction mixture was stirred at 0° C. for one hour and at room temperature for 48 hours. The mixture was poured on cold water, the water layer saturated with sodium chloride and thoroughly extracted with dichloromethane. The combined organic layers were washed with brine, dried over sodium sulfate and concentrated. The residue was purified by chromatography on silica gel (ethyl acetate). Yield: 40 mg of 1,4-dihydroxy-8-methoxy-3-(2,4,6-trimethyl-phenyl)-1,8-diaza-spiro[4.5]dec-3-en-2-one (title compound P2ii.4) as a white solid, mp 152-154° C.

$^1$H-NMR (CDCl$_3$): 1.82-2.58 (br signals, total 4H), 2.12 (s, 6H), 2.27 (s, 3H), 2.93-3.46 (br signals, total 4H), 3.57 (br s, 3H), 6.89 (s, 2H), 9.97 (br s, 1H).

LC/MS (ES+): 333 (M+H)$^+$

EXAMPLE 15

Preparation of Carbonic acid ethyl ester 8-methoxy-1-methoxycarbonyloxy-2-oxo-3-(2,4,6-trimethyl-phenyl)-1,8-diaza-spiro[4.5]dec-3-en-4-yl ester (Compound P1 ii. 13)

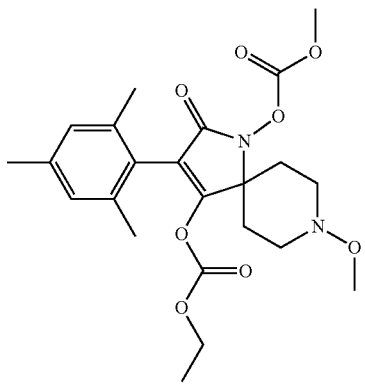

To a solution of carbonic acid ethyl ester 1-hydroxy-8-methoxy-2-oxo-3-(2,4,6-trimethyl-phenyl)-1,8-diaza-spiro[4.5]dec-3-en-4-yl ester (preparation example 13, step 1; compound P1ii.11) (140 mg, 0.33 mmol), triethylamine (93 µl, 68 mg, 0.67 mmol) and 4-dimethylaminopyridine (2 mg) in tetrahydrofuran (3 ml) at 0° C. was added a solution of methyl chloroformate (33 µl, 41 mg, 0.43 mmol) in tetrahydrofuran (2 ml) dropwise. The suspension was stirred at 0° C. for one hour, and at room temperature for one hour. The reaction mixture was evaporated, diluted with ethyl acetate and filtered to remove salts. The filtrate was washed with a saturated aqueous sodium hydrogen carbonate solution (2×15 ml) and brine, dried over sodium sulfate and concentrated. The oily residue was purified by chromatography on silica gel (ethyl acetate/hexane 1:2). Yield: 30 mg of carbonic acid ethyl ester 8-methoxy-1-methoxycarbonyloxy-2-oxo-3-(2,4,6-trimethyl-phenyl)-1,8-diaza-spiro[4.5]dec-3-en-4-yl ester (title compound P1ii.13) as a colorless gum.

$^1$H-NMR (CDCl$_3$): 1.06 (t, 3H), 2.16 (s, 6H), 2.20 (m, 4H), 2.25 (s, 3H), 2.75-3.16 (br m, total 2H), 3.34 (br m, 2H), 3.55 (s, 3H), 3.96 (s, 3H), 3.99 (q, 2H), 6.85 (s, 2H). LC/MS (ES+): 463 (M+H)$^+$

EXAMPLE 16

Alternative preparation of 4-{[2-(2,5-Dimethyl-phenyl)-acetyl]-hydroxy-amino}-1-methoxy-piperidine-4-carboxylic acid methyl ester (Compound P3ii.1)

Step 1: Preparation of N-(4-cyano-1-methoxy-piperidin-4-yl)-2-(2,5-dimethyl-phenyl)-N-hydroxy-acetamide (Compound P3ii.2)

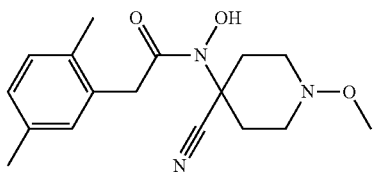

To a solution of 4-hydroxyamino-1-methoxy-piperidine-4-carbonitrile (preparation example 11, step 2) (4.0 g, 23.4 mmol) and sodium hydrogen carbonate (3.0 g, 35.7 mmol) in ethyl acetate (35 ml) and water (25 ml) at 0° C. was added a solution of (2,5-dimethyl-phenyl)-acetyl chloride (4.2 g, 23.0 mmol) in ethyl acetate (35 ml) dropwise over one hour. The reaction mixture was stirred at 0° C. for one hour and at room temperature for two hours. The layers of the biphasic system were separated, the aqueous phase extracted with ethyl acetate (3×), the combined organic layers washed with brine, dried over sodium sulfate and concentrated. The oily residue was purified by chromatography on silica gel (gradient ethyl acetate/hexane 1:2→1:1→2:1). Yield: 1.55 g of N-(4-cyano-1-methoxy-piperidin-4-yl)-2-(2,5-dimethyl-phenyl)-N-hydroxy-acetamide (compound P3ii.2) as a white solid, mp 153-156° C.

$^1$H-NMR (CDCl$_3$): 2.11 (br m, 2H), 2.21 (s, 3H), 2.28 (s, 3H), 2.56 (br m, 2H), 2.77 (br m, 1H), 3.10 (br m, 2H), 3.31 (br m, 1H), 3.50 (s, 3H), 3.77 (s, 2H), 6.83 (br s, 1H), 6.97 (s, 1H), 6.98 (d, 1H), 7.06 (d, 1H).

IR(CN): ν 2238.0 cm$^{-1}$. LC/MS (ES+): 318 (M+H)$^+$

Step 2: Preparation of 4-{[2-(2,5-dimethyl-phenyl)-acetyl]-hydroxy-amino}-1-methoxy-piperidine-4-carboxylic acid methyl ester (Title Compound P3ii.1)

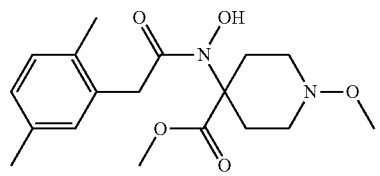

To a solution of N-(4-cyano-1-methoxy-piperidin-4-yl)-2-(2,5-dimethyl-phenyl)-N-hydroxy-acetamide (1.5 g, 4.73 mmol) in methanol (15 ml) at 0° C. was added concentrated sulfuric acid (1.26 ml, 2.3 g, 23.64 mmol) slowly dropwise and the reaction mixture was stirred at reflux for 40 hours. The mixture was poured on ice (50 g), neutralized carefully with a saturated aqueous sodium hydrogen carbonate solution and extracted with ethyl acetate (5×). The combined organic layers were washed with brine, dried over sodium sulfate and concentrated. The oily residue was purified by chromatography on silica gel (ethyl acetate/hexane 2:1) to afford 136 mg of an off-white solid. This material was triturated with a tert-butyl methyl ether/hexane 1:4 solution (2-3 ml), filtered and dried. Yield: 82 mg of 4-{[2-(2,5-dimethyl-phenyl)-acetyl]-hydroxy-amino}-1-methoxy-piperidine-4-carboxylic acid methyl ester (title compound P3ii.1) as a white solid, mp 140-142° C.

The spectral data were identical to those described above under preparation example 11, step 4.

EXAMPLE 17

Preparation of 4-Hydroxy-8-methoxy-1-(tetrahydrofuran-2-yloxy)-3-(2,4,6-trimethyl-phenyl)-1,8-diaza-spiro[4,5]dec-3-en-2-one (Compound P2ii.18)

(stepwise hydroxamic acid O-tetrahydrofuranylation and cyclisation)

Step 1: Preparation of 1-methoxy-4-{(tetrahydro-furan-2-yloxy)-[2-(2,4,6-trimethyl-phenyl)-acetyl]-amino}-piperidine-4-carboxylic acid methyl ester (Compound P3ii.6)

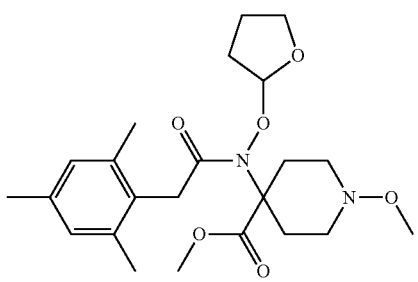

To a solution of 4-{hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (70 g, 192.1 mmol) in dichloromethane (1500 ml) under argon atmosphere was added 2,3-dihydro-furan (29.1 ml, 26.9 g, 384.1 mmol) and a catalytic amount of p-toluenesulfonic acid monohydrate (1.94 g, 19.2 mmol). The reaction mixture was stirred at reflux for 7 hours, filtered and concentrated. The residue was triturated with hexane, filtered and the solid dried in vacuo. Yield: 70.0 g of 1-methoxy-4-{(tetrahydro-furan-2-yloxy)-[2-(2,4,6-trimethyl-phenyl)-acetyl]-amino}-piperidine-4-carboxylic acid methyl ester (compound P3ii.6) as a solid, mp 107-109° C. This material was used without further purification in the next step.

$^1$H-NMR (CD$_3$OD): 1.79-2.36 (br signals, total 6H), 2.15 (br s, 6H), 2.21 (s, 3H), 2.42 (m, 1H), 2.65 (m, 1H), 2.80 (m, 1H), 3.10 (m, 1H), 3.26 (br m, 2H), 3.53 (s, 3H), 3.63 (s, 3H), 3.77 (m, 1H), 4.01 (m, 1H), 4.10 (m, 2H), 5.68 (br m, 1H), 6.80 (s, 2H).

LC/MS (ES+): 435 (M+H)$^+$

Step 2: Preparation of 4-hydroxy-8-methoxy-1-(tetrahydro-furan-2-yloxy)-3-(2,4,6-trimethyl-phenyl)-1,8-diaza-spiro[4.5]dec-3-en-2-one (Title Compound P2ii.18)

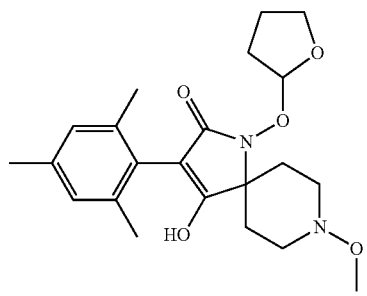

To a solution of 1-methoxy-4-{(tetrahydro-furan-2-yloxy)-[2-(2,4,6-trimethyl-phenyl)-acetyl]-amino}-piperidine-4-carboxylic acid methyl ester (70 g, 161.1 mmol) in dimethylformamide (350 ml) at 10° C. was added sodium methoxide (26.9 g, 483.3 mmol) in four portions and stirring continued at 10° C. for 30 minutes, then at room temperature for 2 hours. The reaction mixture was poured on cold saturated aqueous ammonium chloride and thoroughly extracted with ethyl acetate (6×100 ml). The combined organic layers were washed with brine, dried over sodium sulfate, concentrated and dried in vacuo. The residue was triturated with hexane, filtered and the solid dried. Yield: 51.0 g of 4-hydroxy-8-methoxy-1-(tetrahydro-furan-2-yloxy)-3-(2,4,6-trimethyl-phenyl)-1,8-diaza-spiro[4.5]dec-3-en-2-one (title compound P2ii.18) as a tan solid, mp 144-146° C.

$^1$H-NMR (CD$_3$OD): 1.75-2.19 (br signals, total 6H), 2.11 (s, 6H), 2.24 (s, 3H), 2.28-2.55 (m, 2H), 3.13-3.30 (m, 2H), 3.30-3.48 (m, 2H), 3.54 (s, 3H), 3.92 (m, 1H), 4.17 (m, 1H), 5.58 (m, 1H), 6.87 (s, 2H).

LC/MS (ES+): 403 (M+H)$^+$

EXAMPLE 18

Preparation of 1-Cyclohexyloxy-4-hydroxy-8-methoxy-3-(2,4,6-trimethyl-phenyl)-1,8-diaza-spiro[4.5]dec-3-en-2-one (Compound P2ii.26)

(stepwise hydroxamic acid O-alkylation via Mitsunobu and cyclisation)

Step 1: Preparation of 4-{cyclohexyloxy-[2-(2,4,6-trimethyl-phenyl)-acetyl]-amino}-1-methoxy-piperidine-4-carboxylic acid methyl ester (Compound P3ii.8)

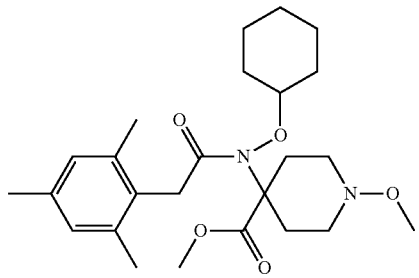

To a solution of triphenylphosphine (0.81 g, 3.09 mmol) in THF (20 ml) at 0° C. was added diisopropyl azodicarboxylate (0.64 ml, 0.66 g, 3.10 mmol) dropwise and the resulting precipitate was stirred at 0° C. for 30 minutes. 4-{Hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (1.0 g, 2.74 mmol) was further added in one portion, followed by a solution of cyclohexanol (0.33 ml, 0.31 g, 3.10 mmol) in THF (2 ml) dropwise at 0° C. The reaction mixture was stirred at room temperature for two hours and concentrated in vacuo. The residue was purified by chromatography on silica gel (ethyl acetate/cyclohexane 1:3). Yield: 690 mg of 4-{cyclohexyloxy-[2-(2,4,6-trimethyl-phenyl)-acetyl]-amino}-1-methoxy-piperidine-4-carboxylic acid methyl ester (compound P3ii.8) as a colorless gum.

$^1$H-NMR (CD$_3$OD): 1.17-1.59 (br signals, total 7H), 1.68 (m, 1H), 1.91 (m, 2H), 2.03 (m, 1H), 2.17 (br s, 6H), 2.21 (s, 3H), 2.32 (m, 2H), 2.44 (m, 1H), 2.69 (m, 1H), 3.09 (m, 1H), 3.25 (m, 2H), 3.51 (s, 3H), 3.61 (s, 3H), 3.69 (m, 1H), 3.92-4.12 (m, 2H), 6.80 (s, 2H).

LC/MS (ES+): 447 (M+H)$^+$

125

Step 2: Preparation of 1-cyclohexyloxy-4-hydroxy-8-methoxy-3-(2,4,6-trimethyl-phenyl)-1,8-diaza-spiro[4.5]dec-3-en-2-one (Title Compound P2ii.26)

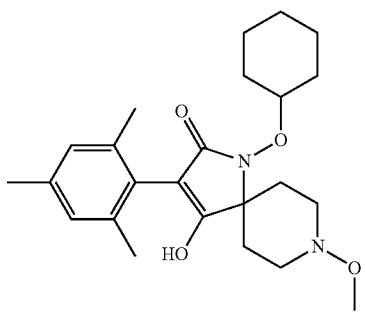

To a solution of 4-{cyclohexyloxy-[2-(2,4,6-trimethyl-phenyl)-acetyl]-amino}-1-methoxy-piperidine-4-carboxylic acid methyl ester (600 mg, 1.34 mmol) in dimethylformamide (10 ml) at 0° C. was added sodium methoxide (217 mg, 4.02 mmol) in one portion and the mixture was stirred at room temperature overnight. The reaction mixture was poured on cold saturated aqueous ammonium chloride and thoroughly extracted with ethyl acetate (4×25 ml). The combined organic layers were washed with water and brine, dried over sodium sulfate and concentrated. The residue was purified by chromatography on silica gel (ethyl acetate/cyclohexane 1:1). Yield: 329 mg of 1-cyclohexyloxy-4-hydroxy-8-methoxy-3-(2,4,6-trimethyl-phenyl)-1,8-diaza-spiro[4.5]dec-3-en-2-one (title compound P2ii.26) as a slight tan foam. Trituration with hexane gave a white solid, mp 115-118° C.

$^1$H-NMR (CD$_3$OD): 1.20-1.38 (m, 3H), 1.47 (m, 2H), 1.58 (m, 1H), 1.85 (m, 4H), 2.06 (m, 2H), 2.11 (s, 6H), 2.25 (s, 3H), 2.39 (m, 2H), 3.12-3.29 (m, 2H), 3.30-3.48 (m, 2H), 3.55 (s, 3H), 3.98 (m, 1H), 6.90 (s, 2H).

LC/MS (ES+): 415 (M+H)$^+$.

EXAMPLE 19

Preparation of 1-Methoxy-4-{(1-methoxy-piperidin-4-yloxy)-[2-(2,4,6-trimethyl-phenyl)-acetyl]-amino}-piperidine-4-carboxylic acid methyl ester (Compound P3ii.26)

Step 1: Preparation of 1-methoxy-piperidin-4-ol

To a solution of 1-methoxy-piperidin-4-one [prepared according to Journal of Organic Chemistry (1961), 26, 1867-74](15.0 g, 116.1 mmol) in ethanol (430 ml) was added sodium borohydride 96% (2.29 g, 58.1 mmol) in portions. The reaction mixture was stirred at room temperature for 5 hours, evaporated to half of its volume, poured on cold saturated aqueous ammonium chloride and thoroughly extracted with ethyl acetate. The combined organic layers were washed with brine, dried over sodium sulfate and concentrated. The residue was purified by chromatography on silica gel (ethyl acetate). Yield: 10.9 g of 1-methoxy-piperidin-4-ol as a liquid.

$^1$H-NMR (CDCl$_3$): 1.46-2.06 (br signals, total 5H), 2.34-3.40 (br signals, total 4H), 3.53 (s, 3H), 3.59-3.96 (br signals, total 1H).

LC/MS (ES+): 132 (M+H)$^+$

126

Step 2: Preparation of 1-methoxy-4-{(1-methoxy-piperidin-4-yloxy)-[2-(2,4,6-trimethyl-phenyl)-acetyl]-amino}-piperidine-4-carboxylic acid methyl ester (Title Compound P3ii.26)

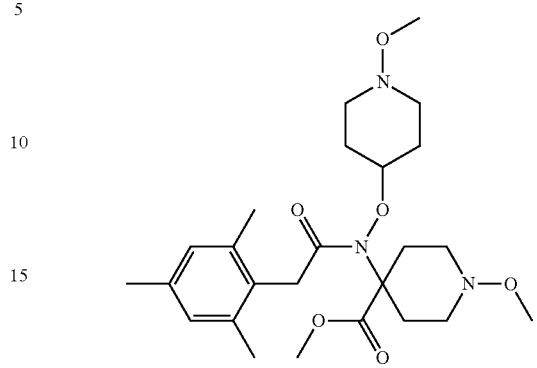

To a solution of triphenylphosphine (1.11 g, 4.23 mmol) in THF (20 ml) at 0° C. was added diisopropyl azodicarboxylate (0.83 ml, 0.85 g, 4.24 mmol) dropwise and the resulting precipitate was stirred at 0° C. for 30 minutes. 4-{Hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (1.3 g, 3.57 mmol) was further added in one portion, followed by a solution of 1-methoxy-piperidin-4-ol (0.53 g, 4.04 mmol) in THF (6 ml) dropwise at 0° C. The reaction mixture was stirred at room temperature for two hours and concentrated in vacuo. The residue was triturated with hexane and filtered to remove part of the insoluble triphenylphosphine oxide. The filtrate was evaporated and the residue purified by chromatography on silica gel (gradient ethyl acetate/heptane 3:7-ethyl acetate). Yield: 861 mg of pure 1-methoxy-4-{(1-methoxy-piperidin-4-yloxy)-[2-(2,4,6-trimethyl-phenyl)-acetyl]-amino}-piperidine-4-carboxylic acid methyl ester (title compound P3ii.26) as a colorless gum, followed by a second fraction of compound P3ii.26 (701 mg) slightly contaminated with triphenylphosphine oxide.

$^1$H-NMR (CD$_3$OD, selected signals only): 2.19 (s, 6H, mesityl CH$_3$), 2.23 (s, 3H, mesityl CH$_3$), 3.52 (br s, 3H, NOCH$_3$), 3.54 (br s, 3H, NOCH$_3$), 3.65 (s, 3H, COOCH$_3$), 6.82 (s, 2H, mesityl H$_{arom}$).

LC/MS (ES+): 478 (M+H)$^+$

EXAMPLE 20

Preparation of Carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (Compound P1ii.115)

Step 1: Preparation of 4-{[2-(4-chloro-2,6-dimethyl-phenyl)-acetyl]-hydroxy-amino}-1-methoxy-piperidine-4-carboxylic acid methyl ester (Compound P3ii.34)

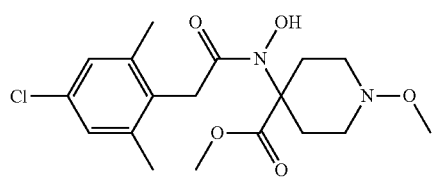

To a solution of (4-chloro-2,6-dimethyl-phenyl)-acetyl chloride (2.90 g, 13.4 mmol) in THF (25 ml) was added sodium hydrogen carbonate (1.90 g, 22.7 mmol) at 0° C., followed by 4-hydroxyamino-1-methoxy-piperidine-4-carboxylic acid methyl ester (preparation example 11, step 3; compound P4ii.2) (2.73 g, 13.4 mmol) dissolved in THF (25 ml) dropwise. The reaction mixture was stirred at 0° C. for 30 minutes, then further 30 minutes at room temperature. After completion of the reaction indicated by TLC and LC/MS, the reaction mixture was filtered and the residue (NaCl) washed with THF. The filtrate was concentrated to dryness and stirred several times with little amounts of an ether/hexane mixture (1:1) to remove side products. Finally, the compound was washed with ether to yield pure 4-{[2-(4-chloro-2,6-dimethyl-phenyl)-acetyl]-hydroxy-amino}-1-methoxy-piperidine-4-carboxylic acid methyl ester (compound P3ii.34) as white solid. Yield: 3.7 g, mp 228-231° C.

$^1$H-NMR (DMSO-$d_6$): 1.77-1.91 (br m, 1H), 1.91-2.05 (br m, 1H), 2.13 (s, 6H), 2.30-2.42 (br m, 1H), 2.45-2.55 (br m, 1H; covered by DMSO solvent peak), 2.62-2.80 (br m, 2H), 3.05-3.21 (br m, 2H), 3.40 (s, 3H), 3.55 (s, 3H), 3.70-3.85 (br m, 2H), 7.05 (s, 2H).

LC/MS (ES+): 385/387 (M+H)$^+$

Step 2: Preparation of 3-(4-chloro-2,6-dimethyl-phenyl)-1,4-dihydroxy-8-methoxy-1,8-diaza-spiro[4.5]dec-3-en-2-one (Compound P2ii.103)

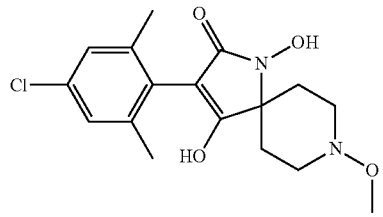 [SMILES: CON1CCC2(CC1)C(O)=C(c1c(C)cc(Cl)cc1C)C(=O)N2O]

To a suspension of 4-{[2-(4-chloro-2,6-dimethyl-phenyl)-acetyl]-hydroxy-amino}-1-methoxy-piperidine-4-carboxylic acid methyl ester (0.40 g, 1.04 mmol) in dimethylformamide (3 ml) at 0° C. was added potassium tert-butoxide (0.35 g, 3.12 mmol) in portions. After completion of the addition, stirring was continued at 0° C. for 30 minutes and at room temperature overnight. The reaction mixture was poured into cold water (0° C.), the pH adjusted to ca 5.5 by adding 1 N HCl and then thoroughly extracted with ethyl acetate (three times). The combined organic layers were washed with water and brine, dried over sodium sulfate and concentrated. The resulting crude material was purified by column chromatography on silica gel (gradient ethyl acetate/cyclohexane 1:1→ethyl acetate). Yield: 0.14 g of 3-(4-chloro-2,6-dimethyl-phenyl)-1,4-dihydroxy-8-methoxy-1,8-diaza-spiro[4.5]dec-3-en-2-one (compound P2ii.103) as a white solid.

$^1$H-NMR (CD$_3$OD): 1.95-2.10 (br m, 2H), 2.15-2.30 (br m, 2H), 2.18 (s, 6H), 3.20-3.50 (br m, total 4H), 3.55 (s, 3H), 7.14 (s, 2H).

LC/MS (ES+): 353/355 (M+H)$^+$

Step 3: Preparation of carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (Title Ccompound P1ii. 115)

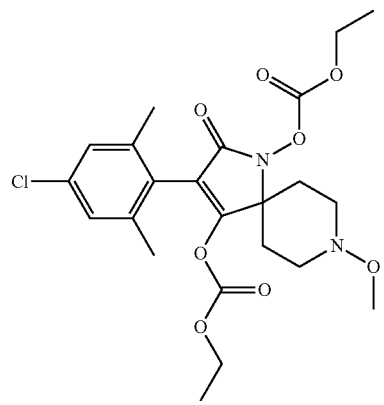 [SMILES: CCOC(=O)OC1=C(c2c(C)cc(Cl)cc2C)C(=O)N(OC(=O)OCC)C12CCN(OC)CC2]

To a solution of 3-(4-chloro-2,6-dimethyl-phenyl)-1,4-dihydroxy-8-methoxy-1,8-diaza-spiro[4.5]dec-3-en-2-one (140 mg, 0.40 mmol) and triethylamine (0.1 ml, 72 mg, 0.71 mmol) in THF (3 ml) at 0° C. was added a solution of ethyl chloroformate (0.05 ml, 52 mg, 0.48 mmol) dissolved in THF (2 ml) dropwise. The suspension was stirred at 0° C. for 30 minutes. Then the reaction mixture was poured into cold (0° C.) water and thoroughly extracted three times with ethyl acetate. The combined organic layers were washed with water and brine, dried over sodium sulfate and concentrated. The raw material was purified by column chromatography on silica gel (ethyl acetate/cyclohexane 1:4). Yield: 70 mg of carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (title compound P1ii. 115) as a colorless gum.

$^1$H-NMR (CDCl$_3$): 1.09 (t, 3H), 1.39 (t, 3H), 2.08-2.30 (br m, 4H), 2.19 (s, 6H), 2.70-3.13 (br m, total 2H), 3.20-3.42 (br m, 2H), 3.55 (s, 3H), 4.03 (q, 2H), 4.38 (br q, 2H), 7.05 (s, 2H).

LC/MS (ES+): 497/499 (M+H)$^+$

EXAMPLE 21

Preparation of Cyclopropanecarboxylic acid 3-(2,5-dimethyl-phenyl)-8-methoxy-1-methoxymethoxy-2-oxo-1,8-diaza-spiro[4.5]dec-3-en-4-yl ester (Compound P1ii.4)

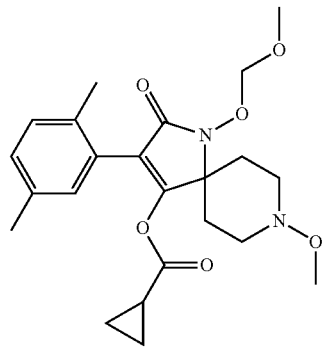 [SMILES: COCON1C(=O)C(c2cc(C)ccc2C)=C(OC(=O)C2CC2)C12CCN(OC)CC2]

To a solution of 3-(2,5-dimethyl-phenyl)-4-hydroxy-8-methoxy-1-methoxymethoxy-1,8-diaza-spiro[4.5]dec-3-en-2-one (compound P2ii.2) (200 mg, 0.55 mmol), triethylamine (0.153 ml, 111 mg, 1.10 mmol) and a catalytic amount of 4-dimethylaminopyridine in tetrahydrofuran (6 ml) at 0° C. was added cyclopropanecarboxylic acid chloride (0.066 ml, 75 mg, 0.72 mmol) dropwise. The suspension was stirred at 0° C. for 10 minutes, and at room temperature for one hour. The reaction mixture was evaporated, diluted with ethyl acetate and filtered to remove salts. The filtrate was washed with a saturated aqueous sodium hydrogen carbonate solution and brine, dried over sodium sulfate and concentrated. The residue was purified by chromatography on silica gel (ethyl acetate/hexane 1:2) to afford 200 mg of an oily product. This material was triturated with diethyl ether, filtered and dried. Yield: 190 mg of cyclopropanecarboxylic acid 3-(2,5-dimethyl-phenyl)-8-methoxy-1-methoxymethyl-2-oxo-1,8-diaza-spiro[4.5]dec-3-en-4-yl ester (title compound P1ii.4) as a white solid, mp 114-116° C.

$^1$H-NMR (CDCl$_3$): 0.75-0.92 (br m, 4H), 1.63 (br m, 1H), 1.72-2.03 (br m, 2H), 2.19 (s, 3H), 2.28 (s, 3H), 2.47 (br m, 2H), 2.88 (br m, 1H), 3.16-3.45 (br m, 3H), 3.56 (s, 3H), 3.64 (s, 3H), 5.07 (br s, 2H), 6.91 (s, 1H), 7.02 (d, 1H), 7.08 (d, 1H).

LC/MS (ES+): 431 (M+H)$^+$

EXAMPLE 22

Preparation of Carbonic acid ethyl ester 1-(2-methanesulfinyl-ethoxy)-8-methoxy-2-oxo-3-(2,4,6-trimethyl-phenyl)-1,8-diaza-spiro[4.5]dec-3-en-4-yl ester (Compound P1ii.111)

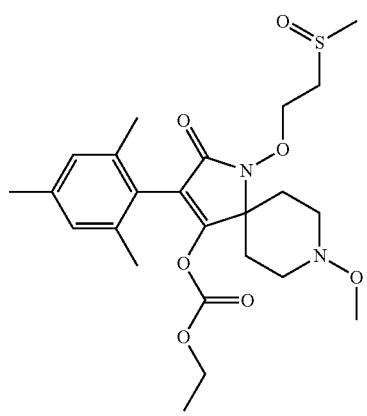

To a solution of carbonic acid ethyl ester 8-methoxy-1-(2-methylsulfanyl-ethoxy)-2-oxo-3-(2,4,6-trimethyl-phenyl)-1,8-diaza-spiro[4.5]dec-3-en-4-yl ester (compound P1ii.110) (400 mg, 0.84 mmol) in dichloromethane (10 ml) at 0° C. was added 3-chloroperbenzoic acid (210 mg, MCPBA ~70%, 0.85 mmol). The reaction mixture was stirred at room temperature overnight, then poured on saturated aqueous sodium metabisulfite and the layers separated. The aqueous phase was extracted with dichloromethane (3×), the combined organic layers were washed with water and brine, dried over sodium sulfate and concentrated. The residue was purified by chromatography on silica gel (ethyl acetate/methanol 20:1). Yield: 220 mg of carbonic acid ethyl ester 1-(2-methanesulfinyl-ethoxy)-8-methoxy-2-oxo-3-(2,4,6-trimethyl-phenyl)-1,8-diaza-spiro[4.5]dec-3-en-4-yl ester (title compound P1ii.111) as a colorless gum.

$^1$H-NMR (CD$_3$OD): 1.03 (t, 3H), 2.05 (br m, 2H), 2.13 (s, 3H), 2.14 (s, 3H), 2.26 (s, 3H), 2.33 (m, 2H), 2.75 (s, 3H), 2.96 (br m, 1H), 3.09-3.46 (br m, total 5H), 3.55 (s, 3H), 4.01 (q, 2H), 4.59 (m, 2H), 6.89 (s, 2H).

LC/MS (ES+): 495 (M+H)$^+$

EXAMPLE 23

Preparation of 2-(4-Chloro-2,6-dimethyl-phenyl)-N-(4-cyano-1-methoxy-piperidin-4-yl)-N-ethoxy-acetamide (Compound P3ii.49)

Step 1: Preparation of 1-methoxy-piperidin-4-one O-ethyl-oxime

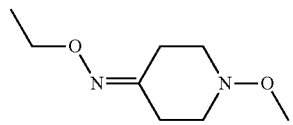

Obtained from 1-methoxy-piperidin-4-one (20 g, 154.85 mmol), triethylamine (47.4 ml, 34.5 g, 340.66 mmol) and O-ethyl-hydroxylamine hydrochloride (30.2 g, 309.69 mmol) in methanol (300 ml) according to procedure 'EXAMPLE 11, Step 1'. Yield: 22.02 g of 1-methoxy-piperidin-4-one O-ethyl-oxime as a colorless, viscous liquid. This material was used without further purification in the next step.

$^1$H-NMR (CDCl$_3$): 1.25 (t, 3H), 2.20-3.40 (br signals, total 8H), 3.55 (s, 3H), 4.07 (q, 2H).

LC/MS (ES+): 173 (M+H)$^+$

Step 2: Preparation of 4-ethoxyamino-1-methoxy-piperidine-4-carbonitrile (Compound P4ii.3)

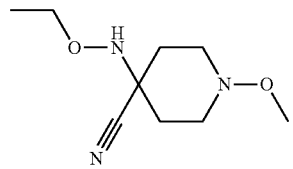

Obtained from 1-methoxy-piperidin-4-one O-ethyl-oxime (10 g, 58.06 mmol), potassium dihydrogen phosphate (31.6 g, 232.20 mmol) in water (50 ml) at 0-5° C. to which was added a solution of potassium cyanide (6.81 g, 104.58 mmol) in water (50 ml) according to procedure 'EXAMPLE 11, Step 2'. The reaction mixture was stirred at room temperature for 2 days [treated in between with another portion of potassium dihydrogen phosphate (7.9 g) and potassium cyanide (1.9 g)] and at 40° C. for 4 days [again treated in between with another portion of potassium dihydrogen phosphate (7.9 g) and potassium cyanide (1.9 g)]. The mixture was flushed with nitrogen, the aqueous layer saturated with sodium chloride and extracted with diethyl ether (4×150 ml). The combined organic layers were washed with brine, dried over sodium sulfate and concentrated. The residue was purified by chromatography on silica gel (ethyl acetate/cyclohexane 1:2). Yield: 5.1 g of 4-ethoxyamino-1-methoxy-piperidine-4-carbonitrile (compound P4ii.3) as a pale yellow oil.

¹H-NMR (CDCl₃): 1.19 (t, 3H), 1.59-2.29 (br signals, total 4H), 2.64-3.43 (br signals, total 4H), 3.52 (s, 3H), 3.80 (q, 2H), 5.37 (br s, 1H).

IR(CN): v2235.3 cm⁻¹. LC/MS (ES+): 200 (M+H)⁺

Step 3: Preparation of 2-(4-chloro-2,6-dimethyl-phenyl)-N-(4-cyano-1-methoxy-piperidin-4-yl)-N-ethoxy-acetamide (Title Compound P3ii.49)

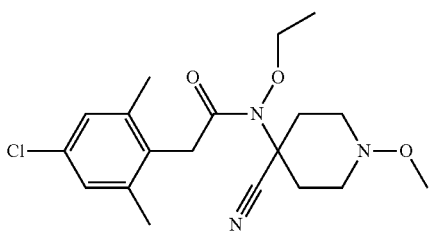 [SMILES: CCON(C(=O)Cc1c(C)cc(Cl)cc1C)C1(C#N)CCN(OC)CC1]

To a solution of 4-ethoxyamino-1-methoxy-piperidine-4-carbonitrile (2.0 g, 10.04 mmol), triethylamine (3.49 ml, 2.54 g, 25.09 mmol) and a catalytic amount of 4-dimethyl-amino-pyridine in tetrahydrofuran (10 ml) at 0° C. was added a solution of (4-chloro-2,6-dimethyl-phenyl)-acetyl chloride (2.18 g, 10.04 mmol) in tetrahydrofuran (1 ml) dropwise. The suspension was stirred at 0° C. for 15 minutes, and at room temperature overnight. The reaction mixture was evaporated, diluted with ethyl acetate and water, and the layers separated. The aqueous phase was extracted with ethyl acetate, the combined organic layers washed with brine, dried over sodium sulfate and concentrated. The crude material was triturated with diisopropyl ether, filtered and the filtrate concentrated. The oily residue was purified by chromatography on silica gel (ethyl acetate/hexane 1:1). Yield: 1.53 g of 2-(4-chloro-2,6-dimethyl-phenyl)-N-(4-cyano-1-methoxy-piperidin-4-yl)-N-ethoxy-acetamide (title compound P3ii.49) as a colorless oil, which solidified upon standing, mp 100-103° C.

¹H-NMR (CDCl₃): 1.36 (t, 3H), 2.00-3.44 (br signals, total 8H), 2.24 (s, 6H), 3.51 (br s, 3H), 3.63 (br d, 1H), 4.04 (br d, 1H), 4.13 (br q, 2H), 7.04 (s, 2H).

IR(CN): v 2243.4 cm⁻¹. LC/MS (ES+): 380/382 (M+H)⁺

EXAMPLE 24

Preparation of 3-(4'-Chloro-3,5-dimethyl-biphenyl-4-yl)-4-hydroxy-8-methoxy-1-methoxymethyl-1,8-diaza-spiro[4.5]dec-3-en-2-one (Compound P2ii.15)

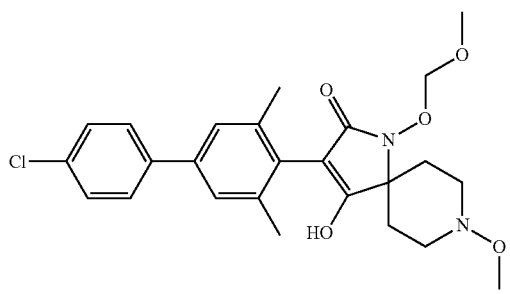 [SMILES: COCON1C(=O)C(c2c(C)cc(-c3ccc(Cl)cc3)cc2C)=C(O)C12CCN(OC)CC2]

To a suspension of 3-(4-bromo-2,6-dimethyl-phenyl)-4-hydroxy-8-methoxy-1-methoxymethyl-1,8-diaza-spiro[4.5]dec-3-en-2-one (compound P2ii. 14) (500 mg, 1.13 mmol) in dimethoxyethane (22 ml) under nitrogen atmosphere was added tetrakis(triphenylphosphine)palladium(0) (65 mg, 0.056 mmol) and the mixture stirred at room temperature for 15 minutes. After further addition of water (4.3 ml), 4-chlorophenylboronic acid (213 mg, 1.36 mmol) and sodium carbonate (410 mg, 3.87 mmol), the mixture was heated at reflux for 3 hours. The reaction mixture was acidified at room temperature with 1 N hydrochloric acid and extracted with ethyl acetate (3×). The combined organic layers were washed with brine, dried over sodium sulfate and concentrated. The residue was purified by chromatography on silica gel (ethyl acetate/heptane 5:3) to afford 150 mg of an gummy product. This material was triturated with methanol, filtered and dried. Yield: 90 mg of 3-(4'-chloro-3,5-dimethyl-biphenyl-4-yl)-4-hydroxy-8-methoxy-1-methoxymethyl-1,8-diaza-spiro[4.5]dec-3-en-2-one (compound P2ii. 15) as a white solid, mp 128° C. (dec).

¹H-NMR (CDCl₃, selected signals only): 2.27 (br s, 6H, mesityl CH₃), 3.60 (br s, 3H, OCH₃), 3.62 (br s, 3H, OCH₃), 5.05 (s, 2H, OCH₂OCH₃), 7.26 (s, 2H, H_{arom}), 7.39 (d, 2H, H_{arom}), 7.49 (d, 2H, H_{arom}).

LC/MS (ES+): 473/475 (M+H)⁺

EXAMPLE 25

Alternative preparation of 4-Hydroxyamino-1-methoxy-piperidine-4-carboxylic acid methyl ester (compound P4ii.2)

Step 1: Preparation of 4-hydroxyamino-1-methoxy-piperidine-4-carboxylic acid (Compound P4ii.4)

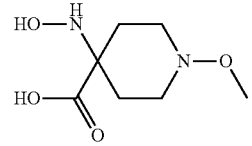

4-Hydroxyamino-1-methoxy-piperidine-4-carbonitrile (compound P4ii.1) (1.5 g, 8.76 mmol) was added in two portions to concentrated sulfuric acid (15 ml) at 0° C. After stirring for 20 minutes, a yellow solution was obtained which was kept at room temperature for two days. The reaction mixture was diluted with ice water (30 ml), heated at reflux for 4 hours, then poured on ice (25 g) and neutralised with 25% aqueous ammonia under cooling to pH 7-8. The reaction mixture was evaporated and the white solid residue triturated with warm (40° C.) methanol (3×50 ml), filtered and the combined methanol phases concentrated. The residue was treated with toluene (3×50 ml) to remove water azeotropically until constant weight, then triturated with tetrahydrofuran, filtered and dried. Yield: 1.58 g of 4-hydroxyamino-1-methoxy-piperidine-4-carboxylic acid (compound P4ii.4) as a white solid, mp 180° C. (dec).

¹H-NMR (CD₃OD): 1.54-2.29 (br signals, total 4H), 2.82 (br m, 2H), 3.07-3.26 (br signals, total 2H), 3.49 (s, 3H).

LC/MS (ES+): 191 (M+H)⁺

Step 2: Preparation of 4-hydroxyamino-1-methoxy-piperidine-4-carboxylic acid methyl ester (Title Compound P4ii.2)

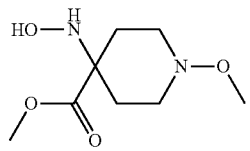

To a suspension of 4-hydroxyamino-1-methoxy-piperidine-4-carboxylic acid (1.0 g, 5.26 mmol) in methanol (25 ml) at 0-10° C. was added thionyl chloride (1.14 ml, 1.88 g, 15.77 mmol) and the reaction mixture was heated at reflux for 48 hours. After cooling, the mixture was concentrated, the residue diluted with ice water (20 ml) and neutralised with aqueous sodium bicarbonate. The aqueous phase was extracted with diethyl ether (3×25 ml), the combined organic layers washed with aqueous sodium bicarbonate and brine, dried over sodium sulfate and concentrated. Yield: 0.53 g of 4-hydroxyamino-1-methoxy-piperidine-4-carboxylic acid methyl ester (title compound P4ii.2) as a viscous, yellowish oil. This material was identical to the compound described above under preparation 'EXAMPLE 11, Step 3'. LC/MS (ES+): 205 (M+H)$^+$ Compounds of the formula I from Table P1ii, compounds from Table P2ii and intermediates listed in Tables P3ii and P4ii can be prepared by analogous procedures. Either one of the following LC-MS methods was used to characterize the compounds:

Method A

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B

MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 μm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v:v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

The characteristic values obtained for each compound were the retention time ("R$_t$", recorded in minutes) and the molecular ion as listed in Table P1 ii, Table P2ii, Table P3ii and in Table P4ii.

TABLE P1ii

Physical data of compounds of formula I:

| Compound No. | Structures | Melting Point | MS/NMR |
|---|---|---|---|
| P1ii.1 | 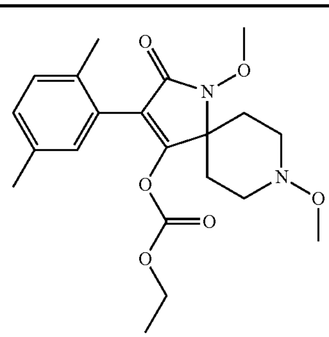 | gum | LC/MS: 405 (M + H)$^+$<br>R$_t$ = 1.88 min |

TABLE P1ii-continued

Physical data of compounds of formula I:

| Compound No. | Structures | Melting Point | MS/NMR |
|---|---|---|---|
| P1ii.2 | EXAMPLE 11, step 6 | 109-111° C. | LC/MS: 435 (M + H)$^+$<br>$R_t$ = 1.90 min |
| P1ii.3 | 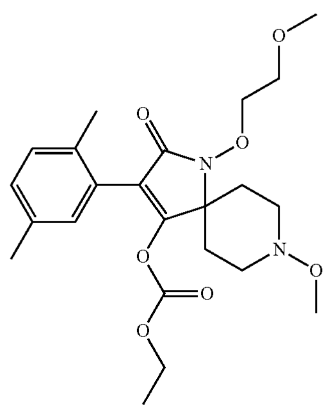 [SMILES: CCOC(=O)OC1=C(c2cc(C)ccc2C)C(=O)N(OCCOC)C12CCN(OC)CC2] | gum | LC/MS: 449 (M + H)$^+$<br>$R_t$ = 1.91 min |
| P1ii.4 | EXAMPLE 21 | 114-116° C. | LC/MS: 431 (M + H)$^+$<br>$R_t$ = 1.87 min |

TABLE P1ii-continued

Physical data of compounds of formula I:

| Compound No. | Structures | Melting Point | MS/NMR |
|---|---|---|---|
| P1ii.5 | 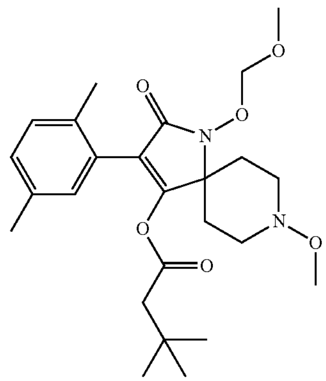 [SMILES: COCON1C(=O)C(c2cc(C)ccc2C)=C(OC(=O)CC(C)(C)C)C12CCN(OC)CC2] | 93-95° C. | LC/MS: 461 (M + H)+<br>$R_t$ = 2.12 min |
| P1ii.6 | 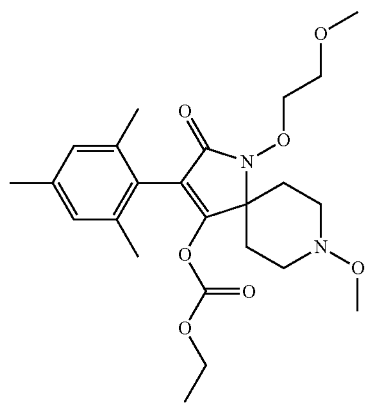 | gum | LC/MS: 463 (M + H)+<br>$R_t$ = 1.95 min |
| P1ii.7 | 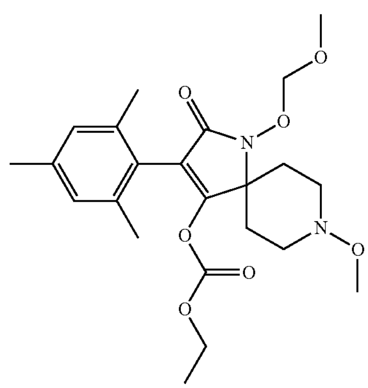 | 109-111° C. | LC/MS: 449 (M + H)+<br>$R_t$ = 1.95 min |
| P1ii.8 | 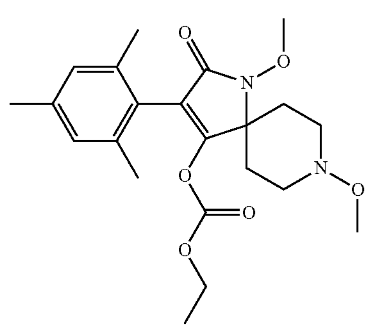 | 96-97° C. | LC/MS: 419 (M + H)+<br>$R_t$ = 1.91 min |

TABLE P1ii-continued

Physical data of compounds of formula I:

| Compound No. | Structures | Melting Point | MS/NMR |
|---|---|---|---|
| P1ii.9 | EXAMPLE 13, step 2 | 100-102° C. | LC/MS: 475 (M + H)$^+$<br>R$_t$ = 1.97 min |
| P1ii.10 | 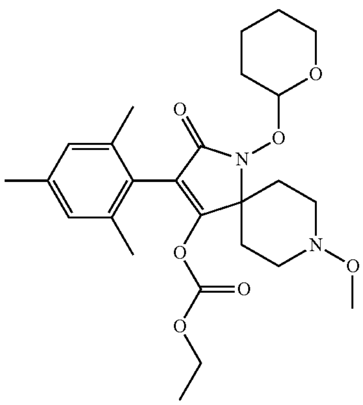 | 130-132° C. | LC/MS: 489 (M + H)$^+$<br>R$_t$ = 2.05 min |
| P1ii.11 | EXAMPLE 13, step 1 | 154-155° C. | LC/MS: 405 (M + H)$^+$<br>R$_t$ = 1.79 min |
| P1ii.12 | 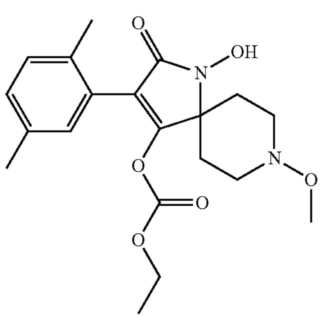 [SMILES: CCOC(=O)OC1=C(c2cc(C)ccc2C)C(=O)N(O)C12CCN(OC)CC2] | 78-81° C. | LC/MS: 391 (M + H)$^+$<br>R$_t$ = 1.67 min |

TABLE P1ii-continued
Physical data of compounds of formula I:
| Compound No. | Structures | Melting Point | MS/NMR |
|---|---|---|---|
| P1ii.13 | 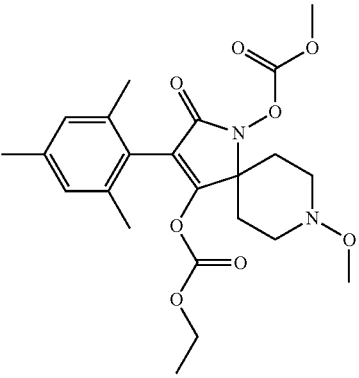<br>EXAMPLE 15 | gum | LC/MS: 463 (M + H)$^+$<br>R$_t$ = 1.98 min |
| P1ii.14 | 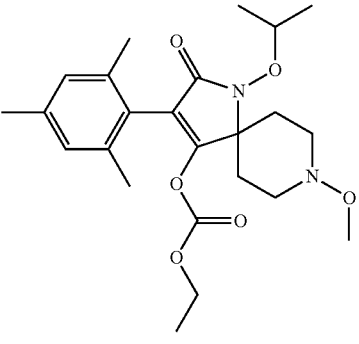 | gum | LC/MS: 447 (M + H)$^+$<br>R$_t$ = 2.07 min |
| P1ii.15 | 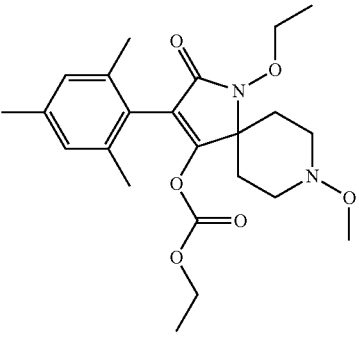 | 84-86° C. | LC/MS: 433 (M + H)$^+$<br>R$_t$ = 1.98 min |
| P1ii.16 | 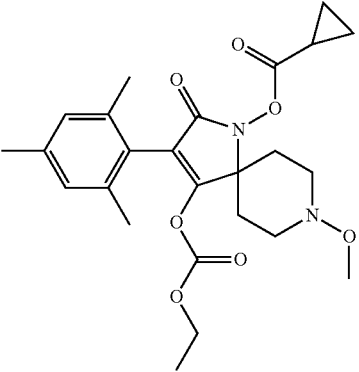 [SMILES: CCOC(=O)OC1=C(c2c(C)cc(C)cc2C)C(=O)N(OC(=O)C2CC2)C12CCN(OC)CC2] | gum | LC/MS: 473 (M + H)$^+$<br>R$_t$ = 2.03 min |

TABLE P1ii-continued

Physical data of compounds of formula I:

| Compound No. | Structures | Melting Point | MS/NMR |
|---|---|---|---|
| P1ii.17 | 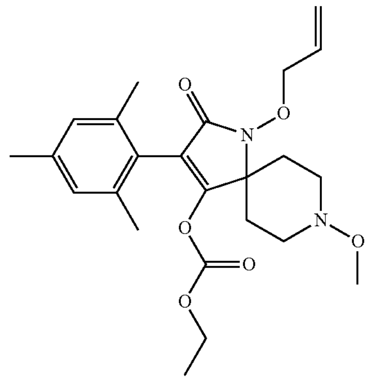 | gum | LC/MS: 445 (M + H)+<br>$R_t$ = 2.04 min |
| P1ii.18 | 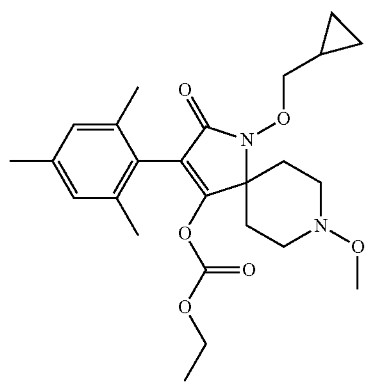 [SMILES: CCOC(=O)OC1=C(c2c(C)cc(C)cc2C)C(=O)N(OCC2CC2)C12CCN(OC)CC2] | gum | LC/MS: 459 (M + H)+<br>$R_t$ = 2.09 min |
| P1ii.19 | 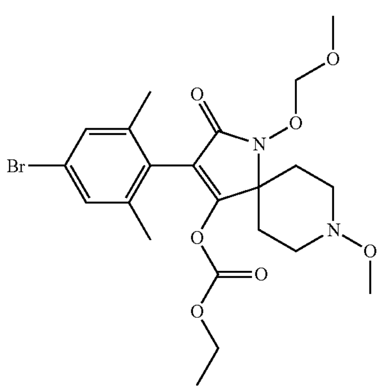 [SMILES: CCOC(=O)OC1=C(c2c(C)cc(Br)cc2C)C(=O)N(OCOC)C12CCN(OC)CC2] | 83-85° C. | LC/MS: 513/515 (M + H)+<br>$R_t$ = 2.03 min |
| P1ii.20 | 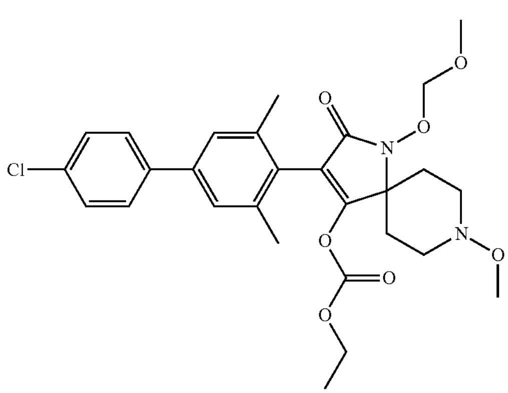 [SMILES: CCOC(=O)OC1=C(c2c(C)cc(-c3ccc(Cl)cc3)cc2C)C(=O)N(OCOC)C12CCN(OC)CC2] | 110-113° C. | LC/MS: 545/547 (M + H)+<br>$R_t$ = 2.20 min |

TABLE P1ii-continued

Physical data of compounds of formula I:

| Compound No. | Structures | Melting Point | MS/NMR |
|---|---|---|---|
| P1ii.21 | 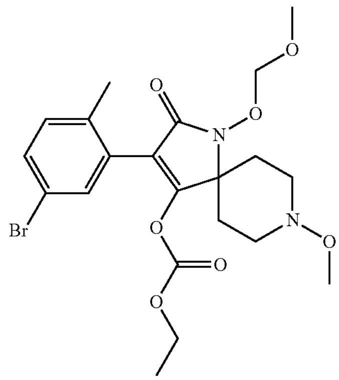 [SMILES: CCOC(=O)OC1=C(c2cc(Br)ccc2C)C(=O)N(OCOC)C12CCN(OC)CC2] | 118-121° C. | LC/MS: 499/501 (M + H)⁺<br>$R_t$ = 1.96 min |
| P1ii.22 | 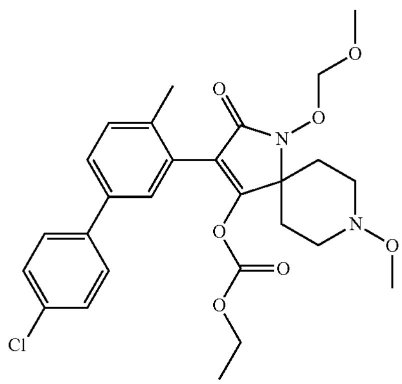 [SMILES: CCOC(=O)OC1=C(c2cc(-c3ccc(Cl)cc3)ccc2C)C(=O)N(OCOC)C12CCN(OC)CC2] | gum | LC/MS: 531/533 (M + H)⁺<br>$R_t$ = 2.15 min |
| P1ii.23 | 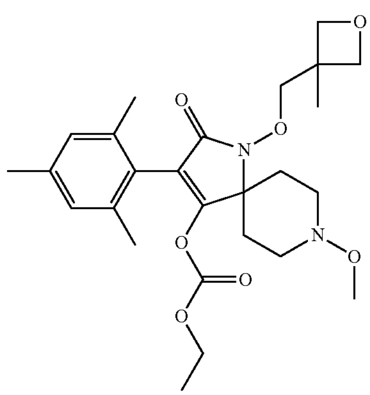 [SMILES: CCOC(=O)OC1=C(c2c(C)cc(C)cc2C)C(=O)N(OCC2(C)COC2)C12CCN(OC)CC2] | 132-134° C. | LC/MS: 489 (M + H)⁺<br>$R_t$ = 1.99 min |
| P1ii.24 | 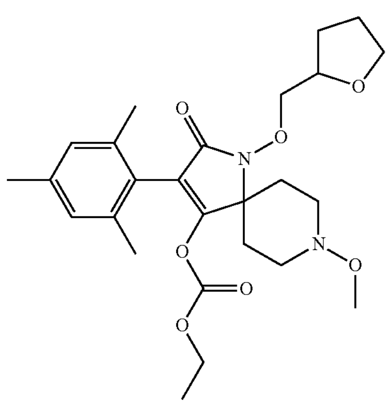 | 53-55° C. | LC/MS: 489 (M + H)⁺<br>$R_t$ = 2.04 min |

TABLE P1ii-continued

Physical data of compounds of formula I:

| Compound No. | Structures | Melting Point | MS/NMR |
|---|---|---|---|
| P1ii.25 | 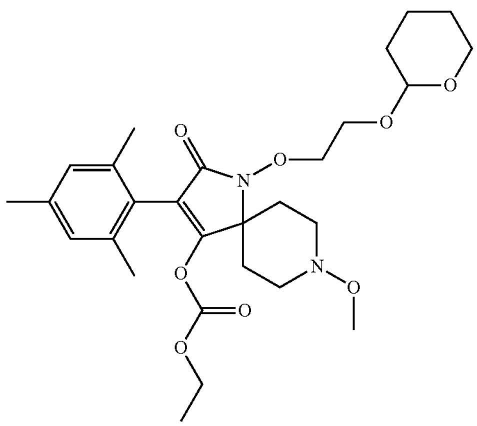 [SMILES: CCOC(=O)OC1=C(c2c(C)cc(C)cc2C)C(=O)N(OCCOC2CCCCO2)C12CCN(OC)CC2] | gum | LC/MS: 533 (M + H)$^+$<br>R$_t$ = 2.12 min |
| P1ii.26 | 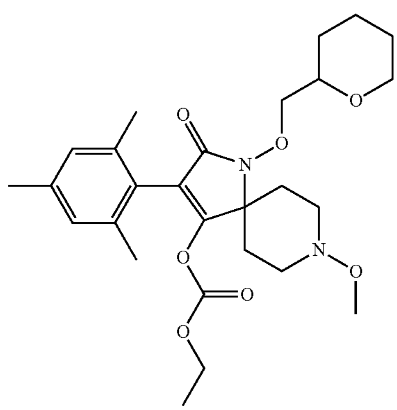 | 74-76° C. | LC/MS: 503 (M + H)$^+$<br>R$_t$ = 2.10 min |
| P1ii.27 | 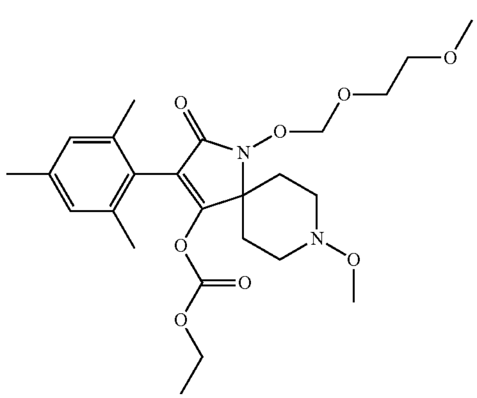 | 57-59° C. | LC/MS: 493 (M + H)$^+$<br>R$_t$ = 1.96 min |

TABLE P1ii-continued

Physical data of compounds of formula I:

| Compound No. | Structures | Melting Point | MS/NMR |
|---|---|---|---|
| P1ii.28 | 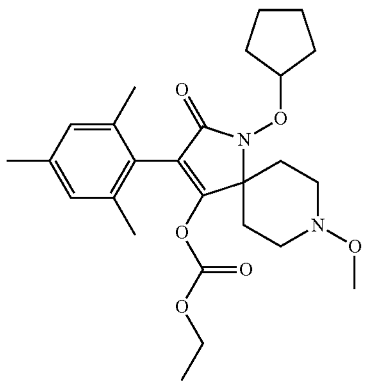 | gum | LC/MS: 473 (M + H)$^+$<br>R$_t$ = 2.17 min |
| P1ii.29 | 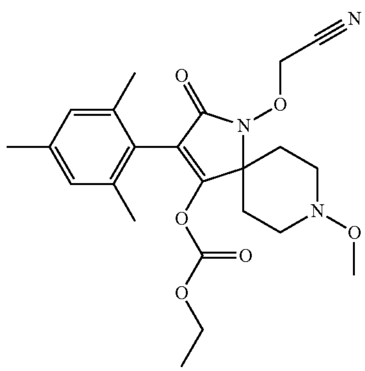 [SMILES: CCOC(=O)OC1=C(c2c(C)cc(C)cc2C)C(=O)N(OCC#N)C12CCN(OC)CC2] | gum | LC/MS: 443 (M + H)$^+$<br>R$_t$ = 1.99 min |
| P1ii.30 | 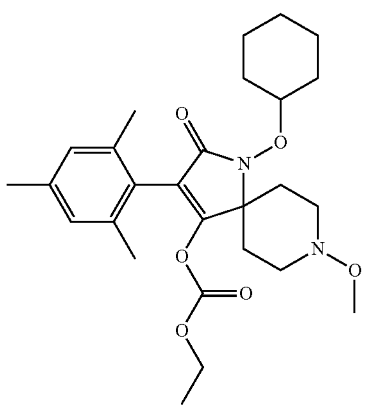 | gum | LC/MS: 487 (M + H)$^+$<br>R$_t$ = 2.19 min |
| P1ii.31 | 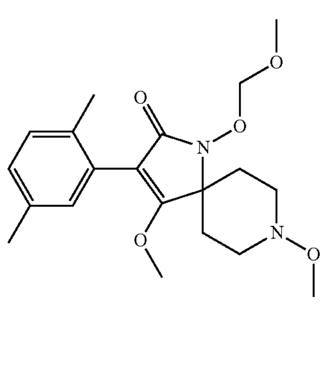 [SMILES: COCON1C(=O)C(c2cc(C)ccc2C)=C(OC)C12CCN(OC)CC2] | 91-93° C. | LC/MS: 377 (M + H)$^+$<br>R$_t$ = 1.79 min |

TABLE P1ii-continued
Physical data of compounds of formula I:
| Compound No. | Structures | Melting Point | MS/NMR |
|---|---|---|---|
| P1ii.32 | 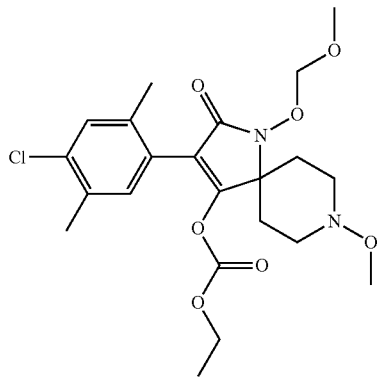 [SMILES: CCOC(=O)OC1=C(c2cc(C)c(Cl)cc2C)C(=O)N(OCOC)C12CCN(OC)CC2] | gum | LC/MS: 469/471 (M + H)+<br>R$_t$ = 1.94 min |
| P1ii.33 | 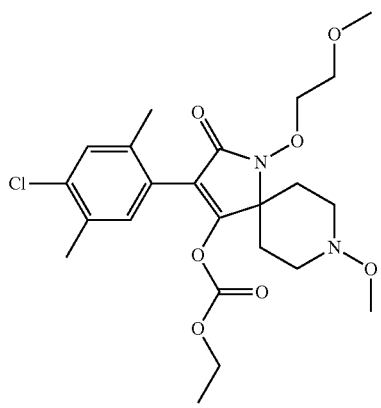 [SMILES: CCOC(=O)OC1=C(c2cc(C)c(Cl)cc2C)C(=O)N(OCCOC)C12CCN(OC)CC2] | gum | LC/MS: 483/485 (M + H)+<br>R$_t$ = 1.93 min |
| P1ii.34 | 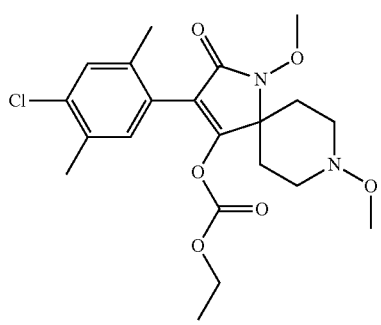 [SMILES: CCOC(=O)OC1=C(c2cc(C)c(Cl)cc2C)C(=O)N(OC)C12CCN(OC)CC2] | gum | LC/MS: 439/441 (M + H)+<br>R$_t$ = 1.91 min |
| P1ii.35 | 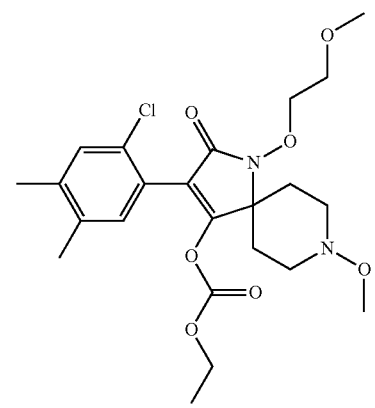 | solid | LC/MS: 483/485 (M + H)+<br>R$_t$ = 1.87 min |

TABLE P1ii-continued

Physical data of compounds of formula I:

| Compound No. | Structures | Melting Point | MS/NMR |
|---|---|---|---|
| P1ii.36 | 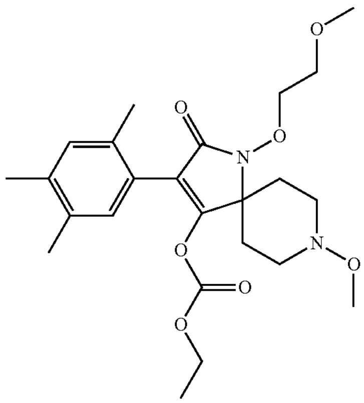 | gum | LC/MS: 463 (M + H)$^+$<br>R$_t$ = 1.91 min |
| P1ii.37 | 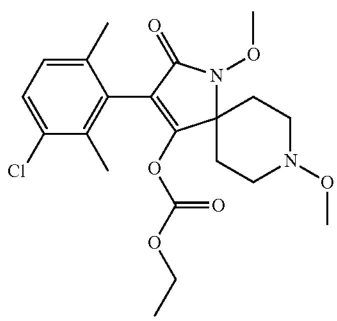 [SMILES: CCOC(=O)OC1=C(c2c(C)ccc(Cl)c2C)C(=O)N(OC)C12CCN(OC)CC2] | gum | LC/MS: 439/441 (M + H)$^+$<br>R$_t$ = 1.91 min |
| P1ii.38 | 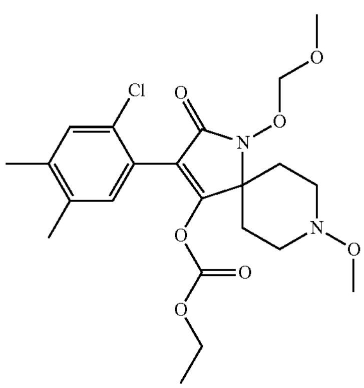 | solid | LC/MS: 469/471 (M + H)$^+$<br>R$_t$ = 1.90 min |
| P1ii.39 | 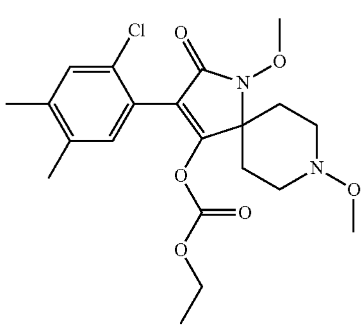 | gum | LC/MS: 449/441 (M + H)$^+$<br>R$_t$ = 1.84 min |

TABLE P1ii-continued

Physical data of compounds of formula I:

| Compound No. | Structures | Melting Point | MS/NMR |
|---|---|---|---|
| P1ii.40 | 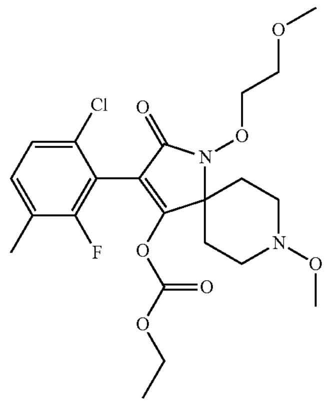 | gum | LC/MS: 487/489 (M + H)+<br>$R_t$ = 1.84 min |
| P1ii.41 | 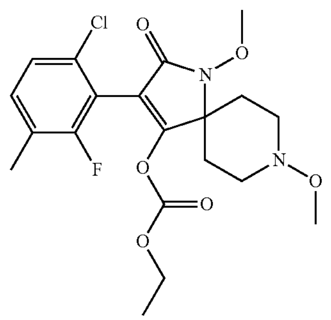 [SMILES: CCOC(=O)OC1=C(c2c(Cl)ccc(C)c2F)C(=O)N(OC)C12CCN(OC)CC2] | solid | LC/MS: 443/445 (M + H)+<br>$R_t$ = 1.82 min |
| P1ii.42 | 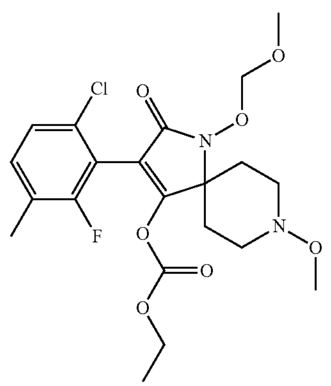 | 119-123° C. | LC/MS: 473/475 (M + H)+<br>$R_t$ = 1.85 min |
| P1ii.43 | 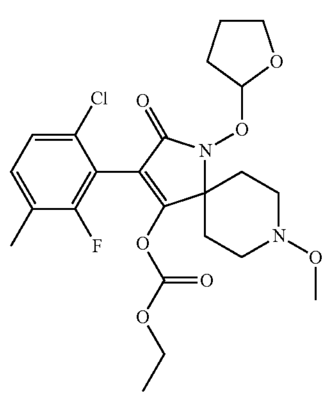 [SMILES: CCOC(=O)OC1=C(c2c(Cl)ccc(C)c2F)C(=O)N(OC2CCCO2)C12CCN(OC)CC2] | 135-137° C. | LC/MS: 499/501 (M + H)+<br>$R_t$ = 1.89 min |

TABLE P1ii-continued

Physical data of compounds of formula I:

| Compound No. | Structures | Melting Point | MS/NMR |
|---|---|---|---|
| P1ii.44 | 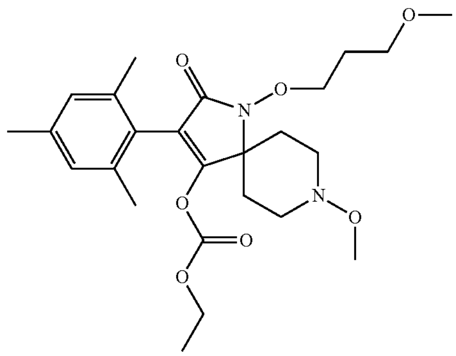 | 122-125° C. | LC/MS: 477 (M + H)+<br>R$_t$ = 1.97 min |
| P1ii.45 | 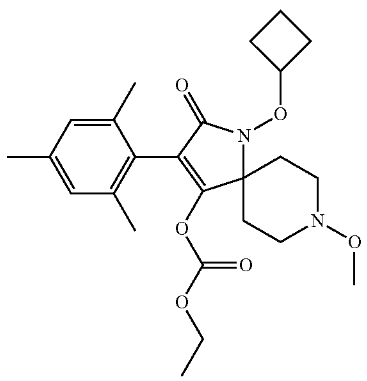 | gum | LC/MS: 459 (M + H)+<br>R$_t$ = 2.07 min |
| P1ii.46 | 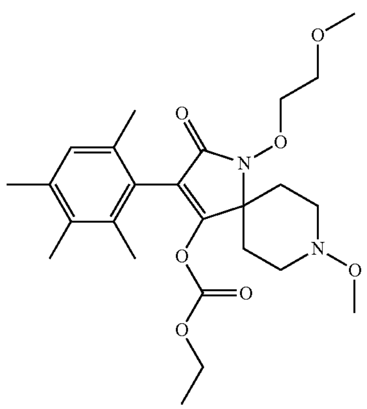 | gum | LC/MS: 477 (M + H)+<br>R$_t$ = 1.95 min |
| P1ii.47 | 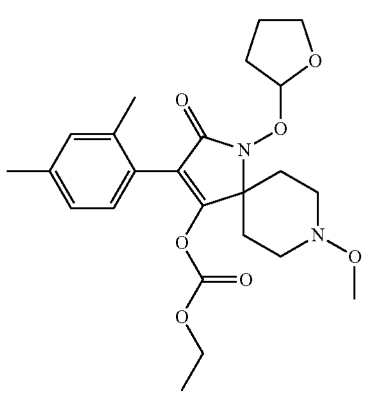 | gum | LC/MS: 461 (M + H)+<br>R$_t$ = 1.92 min |

TABLE P1ii-continued

Physical data of compounds of formula I:

| Compound No. | Structures | Melting Point | MS/NMR |
|---|---|---|---|
| P1ii.48 | 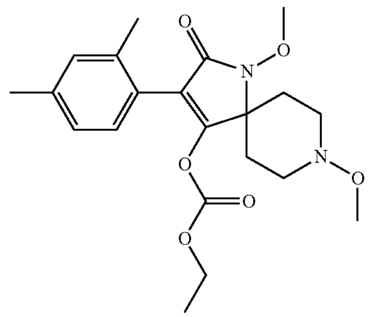 | gum | LC/MS: 405 (M + H)+<br>$R_t$ = 1.83 min |
| P1ii.49 | 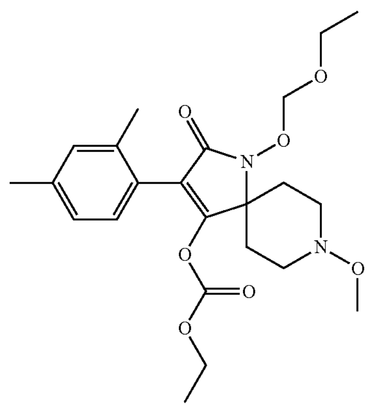 [SMILES: CCOCON1C(=O)C(c2ccc(C)cc2C)=C(OC(=O)OCC)C12CCN(OC)CC2] | powder | LC/MS: 449 (M + H)+<br>$R_t$ = 1.95 min |
| P1ii.50 | 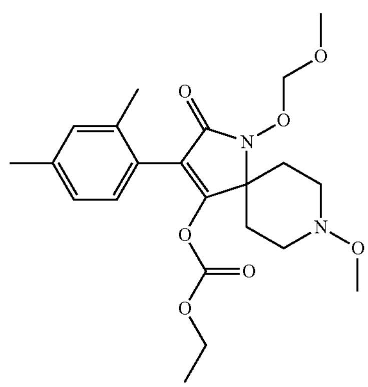 | 128-130° C. | LC/MS: 435 (M + H)+<br>$R_t$ = 1.87 min |
| P1ii.51 | 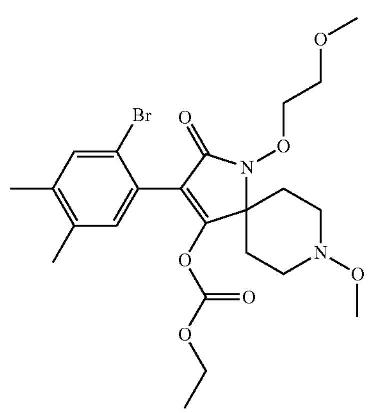 | gum | $^1$H-NMR (CDCl$_3$):<br>1.17 (t, 3H), 2.02-2.31 (br m, total 4H), 2.20 (s, 3H), 2.22 (s, 3H), 2.91-3.47 (br m, total 4H),<br>3.43 (s, 3H), 3.56 (s, 3H), 3.72 (br m, 2H), 4.08 (q, 2H), 4.35 (br m, 2H), 7.06 (s, 1H), 7.35 (s, 1H) |

TABLE P1ii-continued

Physical data of compounds of formula I:

| Compound No. | Structures | Melting Point | MS/NMR |
|---|---|---|---|
| P1ii.52 | 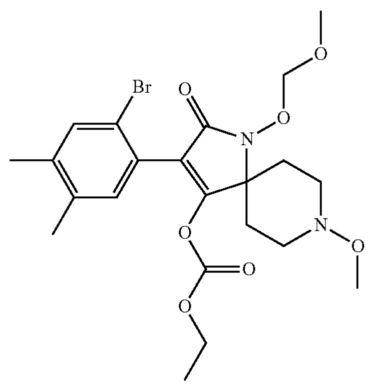 | gum | LC/MS: 513/515 (M + H)$^+$<br>$R_t$ = 1.92 min |
| P1ii.53 | 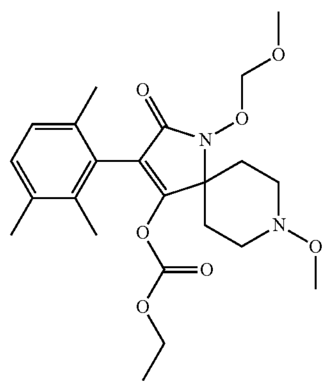 [SMILES: CCOC(=O)OC1=C(c2c(C)ccc(C)c2C)C(=O)N(OCOC)C12CCN(OC)CC2] | gum | LC/MS: 449 (M + H)$^+$<br>$R_t$ = 1.90 min |
| P1ii.54 | 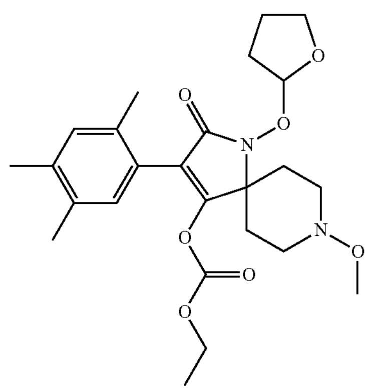 | gum | LC/MS: 475 (M + H)$^+$<br>$R_t$ = 1.96 min |
| P1ii.55 | 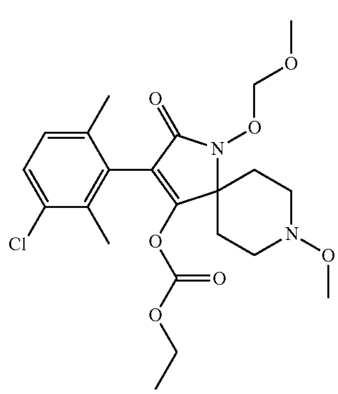 [SMILES: CCOC(=O)OC1=C(c2c(C)ccc(Cl)c2C)C(=O)N(OCOC)C12CCN(OC)CC2] | gum | LC/MS: 469/471 (M + H)$^+$<br>$R_t$ = 1.96 min |

TABLE P1ii-continued

Physical data of compounds of formula I:

| Compound No. | Structures | Melting Point | MS/NMR |
|---|---|---|---|
| P1ii.56 | 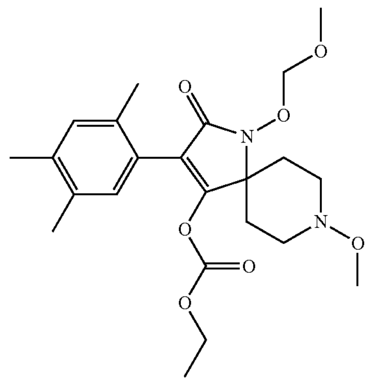 | gum | LC/MS: 449 (M + H)+<br>R$_t$ = 1.88 min |
| P1ii.57 | 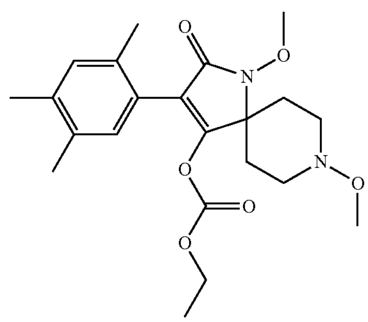 | gum | LC/MS: 419 (M + H)+<br>R$_t$ = 1.90 min |
| P1ii.58 | 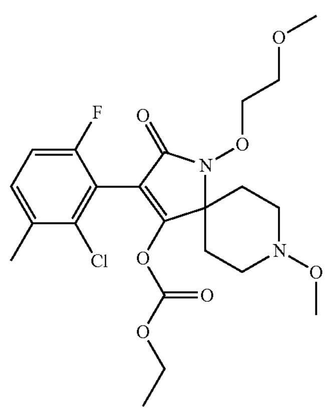 [SMILES: CCOC(=O)OC1=C(c2c(F)ccc(C)c2Cl)C(=O)N(OCCOC)C12CCN(OC)CC2] | gum | LC/MS: 487/489 (M + H)+<br>R$_t$ = 1.84 min |
| P1ii.59 | 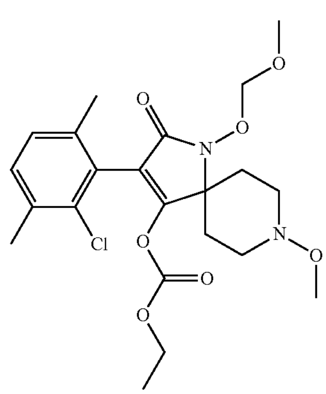 [SMILES: CCOC(=O)OC1=C(c2c(C)ccc(C)c2Cl)C(=O)N(OCOC)C12CCN(OC)CC2] | gum | LC/MS: 469/471 (M + H)+<br>R$_t$ = 1.87 min |

TABLE P1ii-continued

Physical data of compounds of formula I:

| Compound No. | Structures | Melting Point | MS/NMR |
|---|---|---|---|
| P1ii.60 | 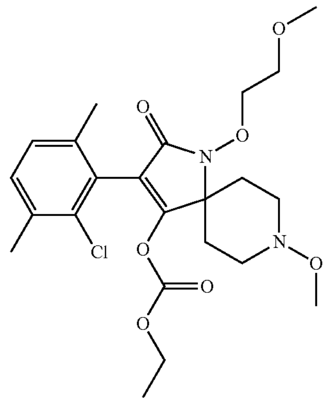 [SMILES: CCOC(=O)OC1=C(c2c(C)ccc(C)c2Cl)C(=O)N(OCCOC)C12CCN(OC)CC2] | gum | LC/MS: 483/485 (M + H)$^+$<br>$R_t$ = 1.86 min |
| P1ii.61 | 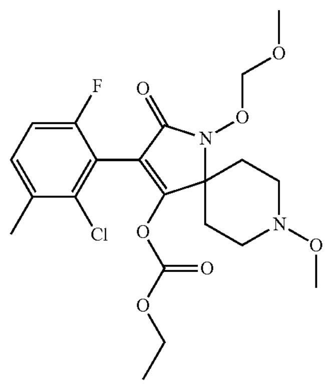 [SMILES: CCOC(=O)OC1=C(c2c(F)ccc(C)c2Cl)C(=O)N(OCOC)C12CCN(OC)CC2] | 116-119° C. | LC/MS: 473/475 (M + H)$^+$<br>$R_t$ = 1.80 min |
| P1ii.62 | 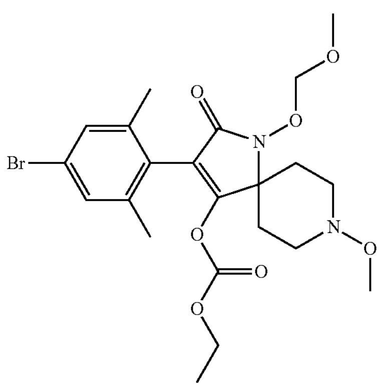 [SMILES: CCOC(=O)OC1=C(c2c(C)cc(Br)cc2C)C(=O)N(OCOC)C12CCN(OC)CC2] | gum | LC/MS: 513/515 (M + H)$^+$<br>$R_t$ = 2.01 min |
| P1ii.63 | 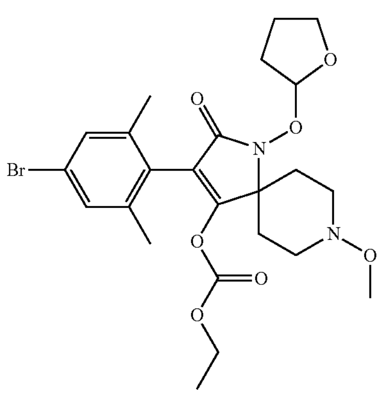 [SMILES: CCOC(=O)OC1=C(c2c(C)cc(Br)cc2C)C(=O)N(OC2CCCO2)C12CCN(OC)CC2] | gum | LC/MS: 539/541 (M + H)$^+$<br>$R_t$ = 2.01 min |

TABLE P1ii-continued

Physical data of compounds of formula I:

| Compound No. | Structures | Melting Point | MS/NMR |
|---|---|---|---|
| P1ii.64 | 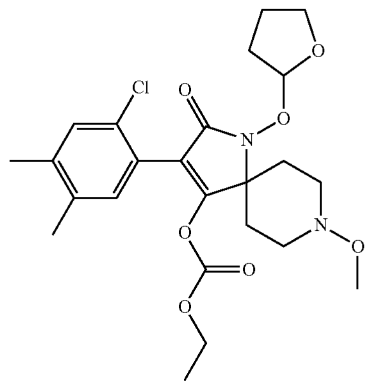 | gum | LC/MS: 495/497 (M + H)$^+$<br>R$_t$ = 1.95 min |
| P1ii.65 | 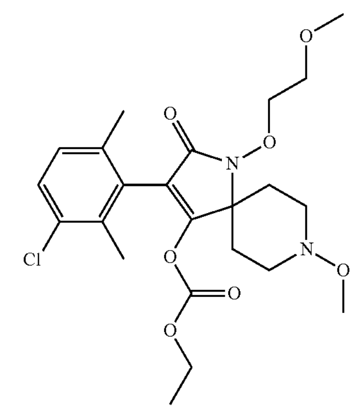 [SMILES: CCOC(=O)OC1=C(c2c(C)ccc(Cl)c2C)C(=O)N(OCCOC)C12CCN(OC)CC2] | gum | LC/MS: 483/485 (M + H)$^+$<br>R$_t$ = 1.94 min |
| P1ii.66 | 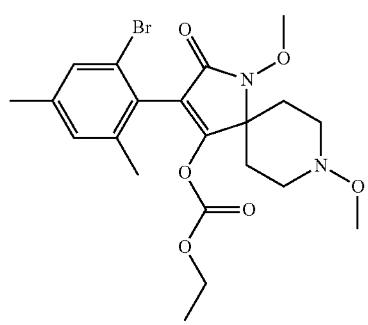 | 90-94° C. | LC/MS: 483/485 (M + H)$^+$<br>R$_t$ = 1.89 min |
| P1ii.67 | 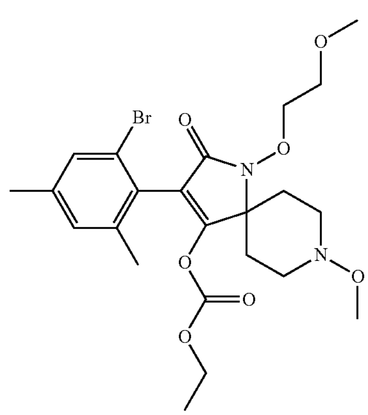 | gum | LC/MS: 527/529 (M + H)$^+$<br>R$_t$ = 1.92 min |

TABLE P1ii-continued

Physical data of compounds of formula I:

| Compound No. | Structures | Melting Point | MS/NMR |
|---|---|---|---|
| P1ii.68 | 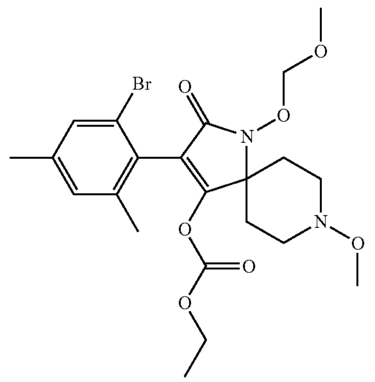 | gum | LC/MS: 513/515 (M + H)+<br>$R_t$ = 1.91 min |
| P1ii.69 | 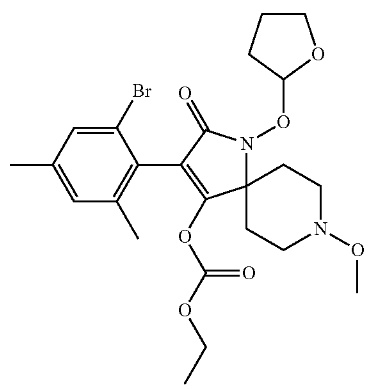 | gum | LC/MS: 539/541 (M + H)+<br>$R_t$ = 1.97 min |
| P1ii.70 | 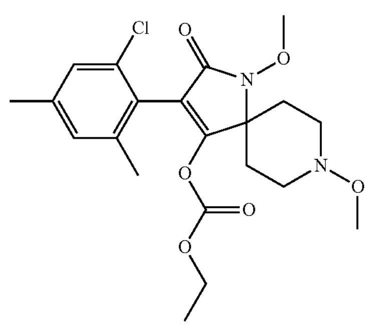 | gum | LC/MS: 439/441 (M + H)+<br>$R_t$ = 1.88 min |
| P1ii.71 | 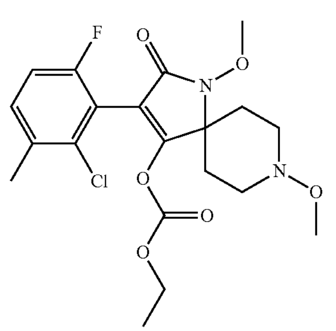 [SMILES: CCOC(=O)OC1=C(c2c(F)ccc(C)c2Cl)C(=O)N(OC)C12CCN(OC)CC2] | gum | LC/MS: 443/445 (M + H)+<br>$R_t$ = 1.79 min |

TABLE P1ii-continued

Physical data of compounds of formula I:

| Compound No. | Structures | Melting Point | MS/NMR |
|---|---|---|---|
| P1ii.72 | 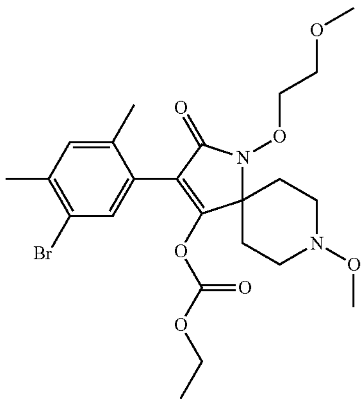 | gum | LC/MS: 527/529 (M + H)+<br>$R_t$ = 1.97 min |
| P1ii.73 | 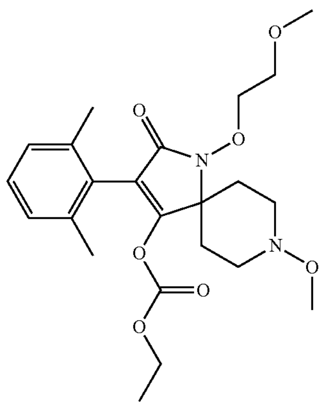 [SMILES: CCOC(=O)OC1=C(c2c(C)cccc2C)C(=O)N(OCCOC)C12CCN(OC)CC2] | gum | LC/MS: 449 (M + H)+<br>$R_t$ = 1.84 min |
| P1ii.74 | 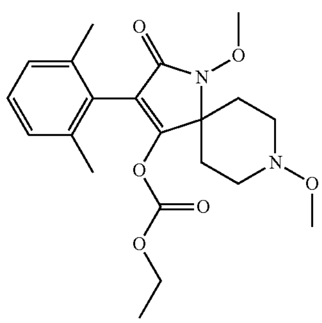 [SMILES: CCOC(=O)OC1=C(c2c(C)cccc2C)C(=O)N(OC)C12CCN(OC)CC2] | gum | LC/MS: 405 (M + H)+<br>$R_t$ = 1.81 min |
| P1ii.75 | 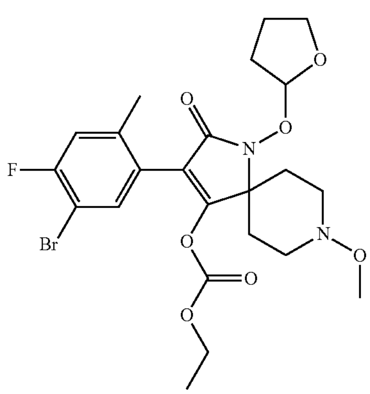 [SMILES: CCOC(=O)OC1=C(c2cc(Br)c(F)cc2C)C(=O)N(OC2CCCO2)C12CCN(OC)CC2] | gum | LC/MS: 543/545 (M + H)+<br>$R_t$ = 1.97 min |

TABLE P1ii-continued

Physical data of compounds of formula I:

| Compound No. | Structures | Melting Point | MS/NMR |
|---|---|---|---|
| P1ii.76 | 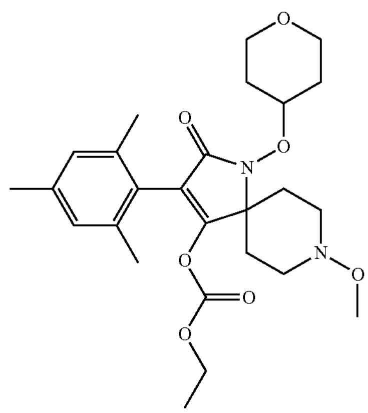 | gum | LC/MS: 489 (M + H)+<br>R$_t$ = 1.93 min |
| P1ii.77 | 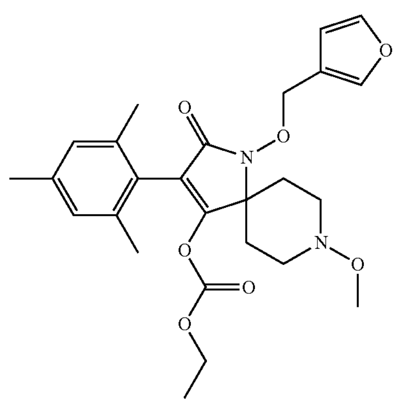 [SMILES: CCOC(=O)OC1=C(c2c(C)cc(C)cc2C)C(=O)N(OCc2ccoc2)C12CCN(OC)CC2] | gum | LC/MS: 485 (M + H)+<br>R$_t$ = 2.02 min |
| P1ii.78 | 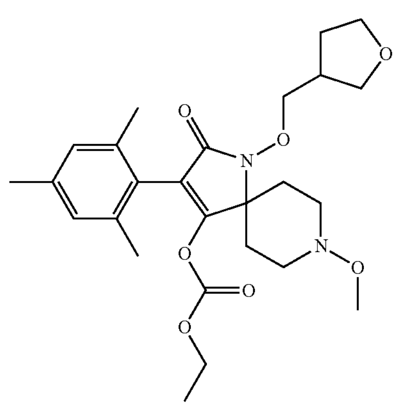 [SMILES: CCOC(=O)OC1=C(c2c(C)cc(C)cc2C)C(=O)N(OCC2CCOC2)C12CCN(OC)CC2] | gum | LC/MS: 489 (M + H)+<br>R$_t$ = 1.95 min |

TABLE P1ii-continued

Physical data of compounds of formula I:

| Compound No. | Structures | Melting Point | MS/NMR |
|---|---|---|---|
| P1ii.79 | 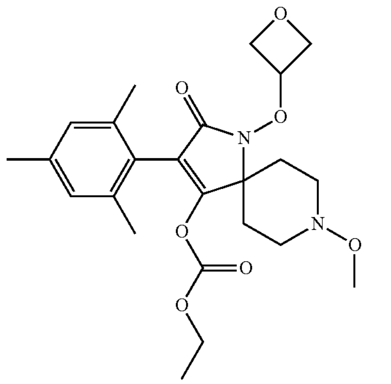 | gum | LC/MS: 461 (M + H)$^+$<br>$R_t$ = 1.87 min |
| P1ii.80 | 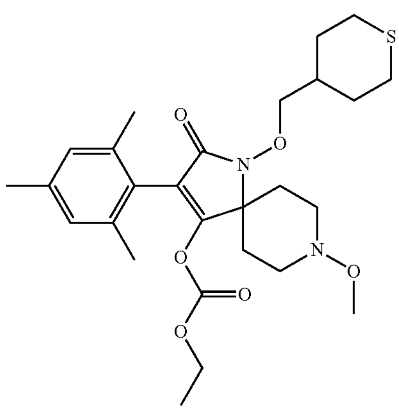 [SMILES: CCOC(=O)OC1=C(c2c(C)cc(C)cc2C)C(=O)N(OCC2CCSCC2)C12CCN(OC)CC2] | gum | LC/MS: 519 (M + H)$^+$<br>$R_t$ = 2.14 min |
| P1ii.81 | 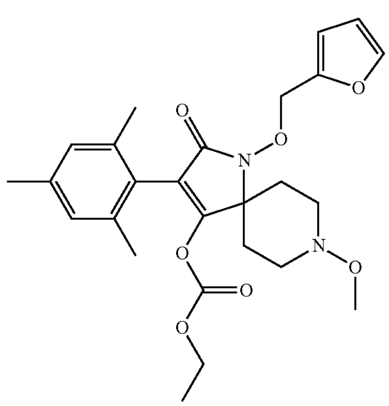 [SMILES: CCOC(=O)OC1=C(c2c(C)cc(C)cc2C)C(=O)N(OCc2ccco2)C12CCN(OC)CC2] | gum | LC/MS: 485 (M + H)$^+$<br>$R_t$ = 2.03 min |

TABLE P1ii-continued

Physical data of compounds of formula I:

| Compound No. | Structures | Melting Point | MS/NMR |
|---|---|---|---|
| P1ii.82 | 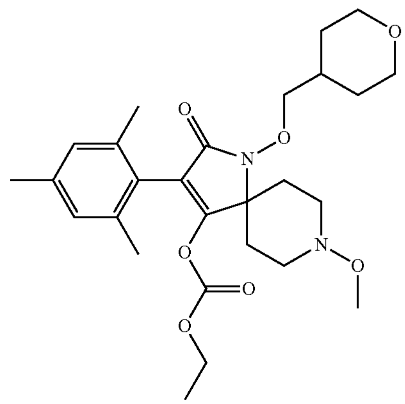 [SMILES: CCOC(=O)OC1=C(c2c(C)cc(C)cc2C)C(=O)N(OCC2CCOCC2)C12CCN(OC)CC2] | gum | LC/MS: 503 (M + H)+<br>$R_t$ = 1.98 min |
| P1ii.83 | 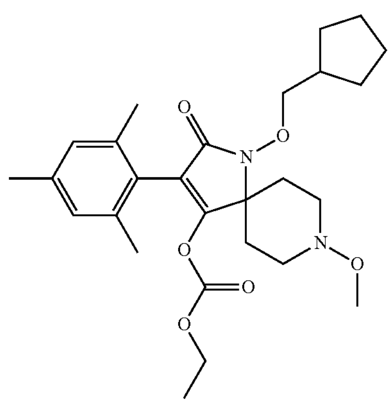 [SMILES: CCOC(=O)OC1=C(c2c(C)cc(C)cc2C)C(=O)N(OCC2CCCC2)C12CCN(OC)CC2] | gum | LC/MS: 487 (M + H)+<br>$R_t$ = 2.23 min |
| P1ii.84 | 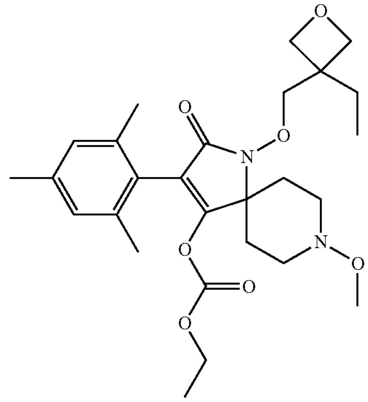 [SMILES: CCOC(=O)OC1=C(c2c(C)cc(C)cc2C)C(=O)N(OCC2(CC)COC2)C12CCN(OC)CC2] | 105-107° C. | LC/MS: 503 (M + H)+<br>$R_t$ = 2.03 min |

TABLE P1ii-continued

Physical data of compounds of formula I:

| Compound No. | Structures | Melting Point | MS/NMR |
|---|---|---|---|
| P1ii.85 | 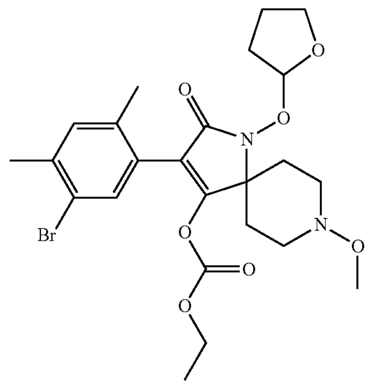 | gum | LC/MS: 539/541 (M + H)+<br>$R_t$ = 2.03 min |
| P1ii.86 | 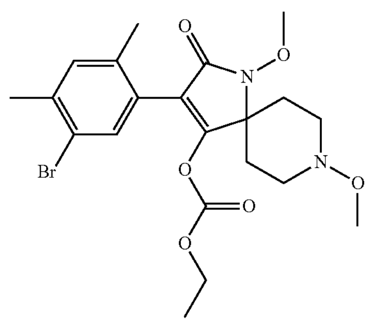 | gum | LC/MS: 483/485 (M + H)+<br>$R_t$ = 1.94 min |
| P1ii.87 | 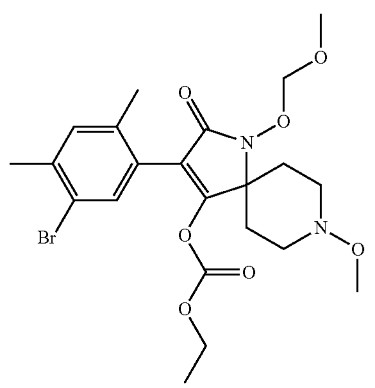 | gum | LC/MS: 513/515 (M + H)+<br>$R_t$ = 1.95 min |
| P1ii.88 | 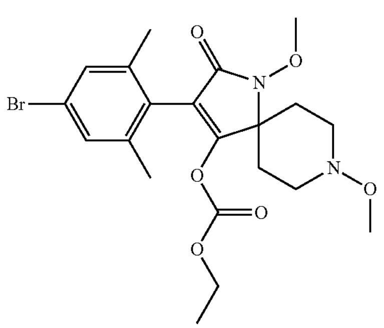 [SMILES: CCOC(=O)OC1=C(c2c(C)cc(Br)cc2C)C(=O)N(OC)C12CCN(OC)CC2] | 113-116° C. | LC/MS: 483/485 (M + H)+<br>$R_t$ = 1.96 min |

TABLE P1ii-continued

Physical data of compounds of formula I:

| Compound No. | Structures | Melting Point | MS/NMR |
|---|---|---|---|
| P1ii.89 | 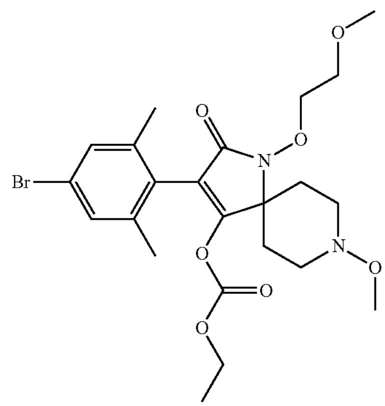 [SMILES: CCOC(=O)OC1=C(c2c(C)cc(Br)cc2C)C(=O)N(OCCOC)C12CCN(OC)CC2] | gum | LC/MS: 527/529 (M + H)+<br>R$_t$ = 1.98 min |
| P1ii.90 | 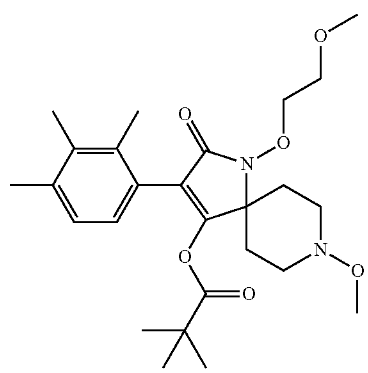 | gum | LC/MS: 475 (M + H)+<br>R$_t$ = 2.05 min |
| P1ii.91 | 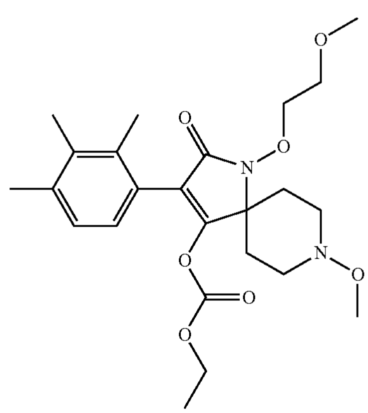 | gum | LC/MS: 463 (M + H)+<br>R$_t$ = 1.89 min |

TABLE P1ii-continued

Physical data of compounds of formula I:

| Compound No. | Structures | Melting Point | MS/NMR |
|---|---|---|---|
| P1ii.92 | 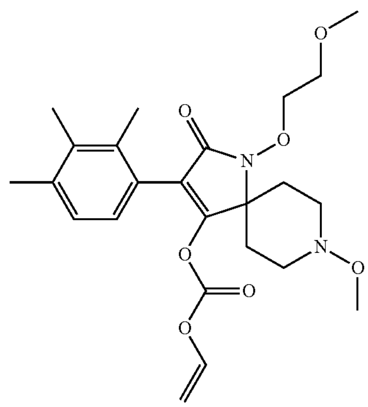 | solid | LC/MS: 461 (M + H)+<br>R$_t$ = 1.95 min |
| P1ii.93 | 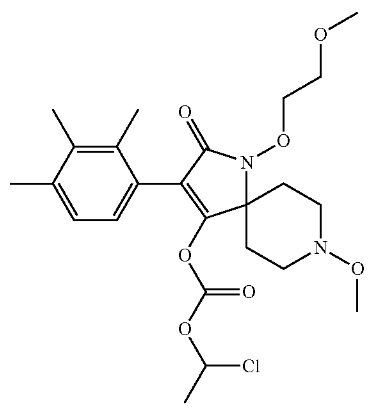 | gum | LC/MS: 497/499 (M + H)+<br>R$_t$ = 1.97 min |
| P1ii.94 | 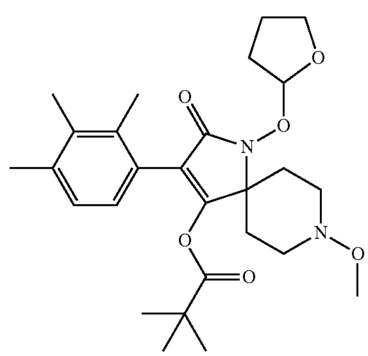 | gum | LC/MS: 487 (M + H)+<br>R$_t$ = 2.12 min |
| P1ii.95 | 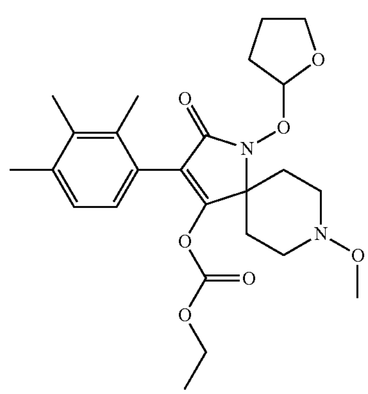 | gum | LC/MS: 475 (M + H)+<br>R$_t$ = 1.95 min |

TABLE P1ii-continued

Physical data of compounds of formula I:

| Compound No. | Structures | Melting Point | MS/NMR |
|---|---|---|---|
| P1ii.96 | 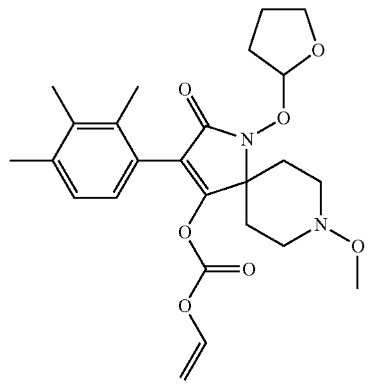 | gum | LC/MS: 473 (M + H)⁺<br>$R_t$ = 2.00 min |
| P1ii.97 | 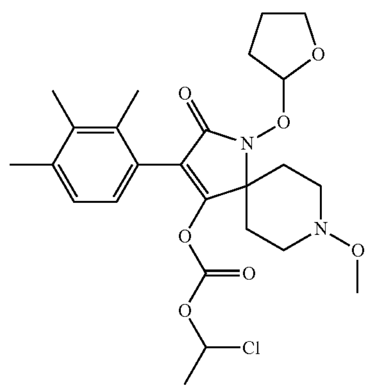 | gum | LC/MS: 509/511 (M + H)⁺<br>$R_t$ = 2.02 min |
| P1ii.98 | 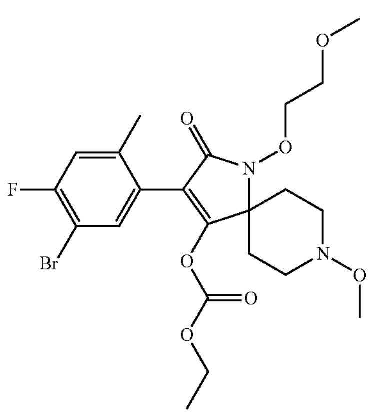 [SMILES: CCOC(=O)OC1=C(c2cc(Br)c(F)cc2C)C(=O)N(OCCOC)C12CCN(OC)CC2] | gum | LC/MS: 531/533 (M + H)⁺<br>$R_t$ = 1.92 min |
| P1ii.99 | 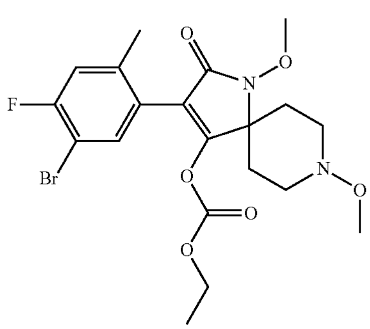 [SMILES: CCOC(=O)OC1=C(c2cc(Br)c(F)cc2C)C(=O)N(OC)C12CCN(OC)CC2] | gum | LC/MS: 487/489 (M + H)⁺<br>$R_t$ = 1.93 min |

TABLE P1ii-continued
Physical data of compounds of formula I:
| Compound No. | Structures | Melting Point | MS/NMR |
|---|---|---|---|
| P1ii.100 | 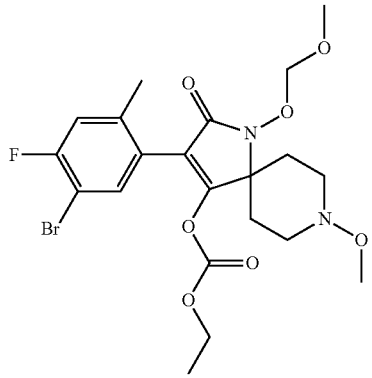 [SMILES: CCOC(=O)OC1=C(c2cc(Br)c(F)cc2C)C(=O)N(OCOC)C12CCN(OC)CC2] | gum | LC/MS: 517/519 (M + H)$^+$<br>$R_t$ = 1.94 min |
| P1ii.101 | 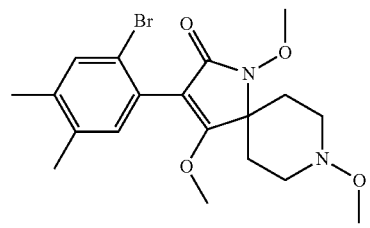 | gum | LC/MS: 425/427 (M + H)$^+$<br>$R_t$ = 1.83 min |
| P1ii.102 | 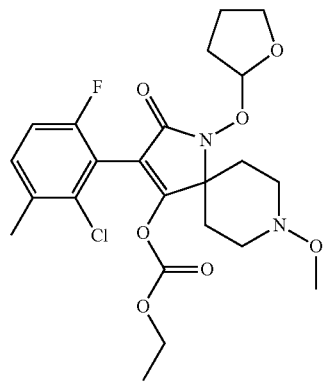 [SMILES: CCOC(=O)OC1=C(c2c(F)ccc(C)c2Cl)C(=O)N(OC2CCCO2)C12CCN(OC)CC2] | 134-138° C. | LC/MS: 499/501 (M + H)$^+$<br>$R_t$ = 1.90 min |
| P1ii.103 | 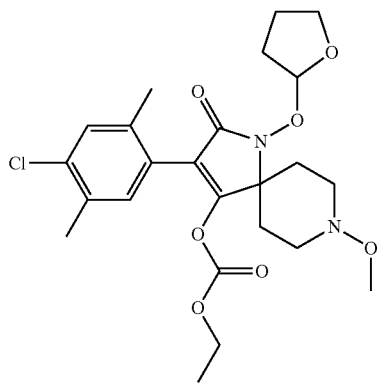 [SMILES: CCOC(=O)OC1=C(c2cc(C)c(Cl)cc2C)C(=O)N(OC2CCCO2)C12CCN(OC)CC2] | gum | LC/MS: 495/497 (M + H)$^+$<br>$R_t$ = 2.03 min |

TABLE P1ii-continued

Physical data of compounds of formula I:

| Compound No. | Structures | Melting Point | MS/NMR |
|---|---|---|---|
| P1ii.104 | 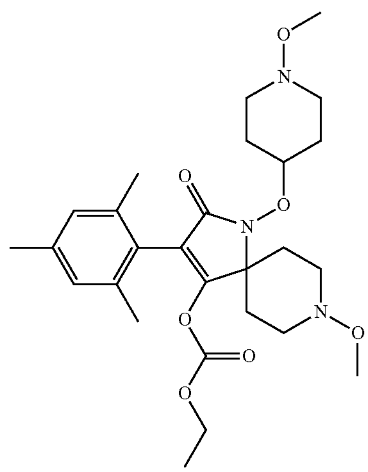 | gum | LC/MS: 518 (M + H)+<br>R$_t$ = 1.97 min |
| P1ii.105 | 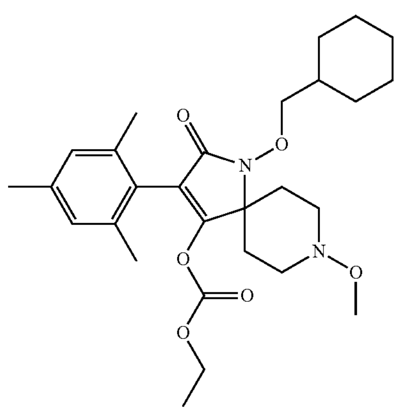 [SMILES: CCOC(=O)OC1=C(c2c(C)cc(C)cc2C)C(=O)N(OCC2CCCCC2)C12CCN(OC)CC2] | gum | LC/MS: 501 (M + H)+<br>R$_t$ = 2.26 min |
| P1ii.106 | 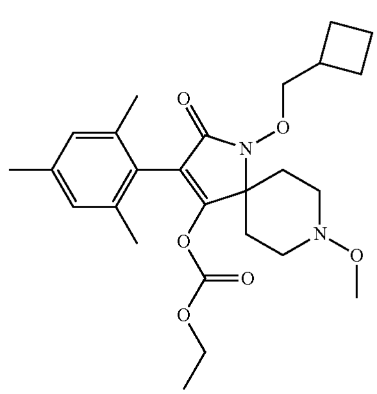 [SMILES: CCOC(=O)OC1=C(c2c(C)cc(C)cc2C)C(=O)N(OCC2CCC2)C12CCN(OC)CC2] | gum | LC/MS: 473 (M + H)+<br>R$_t$ = 2.15 min |

TABLE P1ii-continued

Physical data of compounds of formula I:

| Compound No. | Structures | Melting Point | MS/NMR |
|---|---|---|---|
| P1ii.107 | 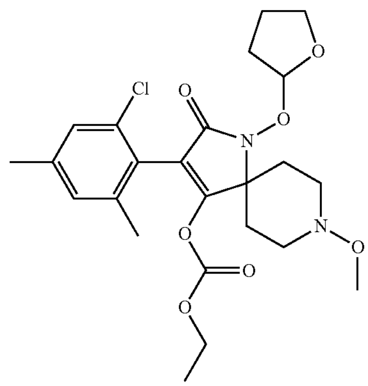 | gum | LC/MS: 495/497 (M + H)+<br>$R_t$ = 1.95 min |
| P1ii.108 | 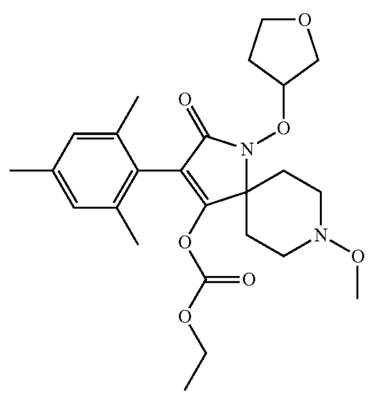 | gum | LC/MS: 475 (M + H)+<br>$R_t$ = 1.94 min |
| P1ii.109 | 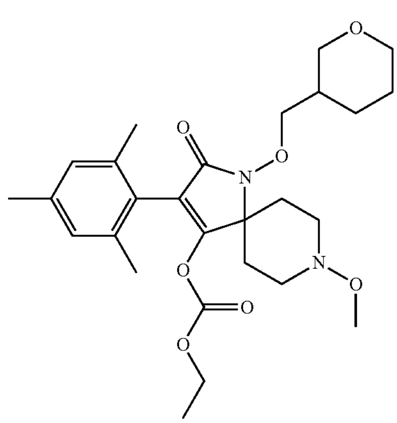 [SMILES: CCOC(=O)OC1=C(c2c(C)cc(C)cc2C)C(=O)N(OCC2CCCOC2)C12CCN(OC)CC2] | gum | LC/MS: 503 (M + H)+<br>$R_t$ = 2.04 min |

TABLE P1ii-continued
Physical data of compounds of formula I:
| Compound No. | Structures | Melting Point | MS/NMR |
|---|---|---|---|
| P1ii.110 | 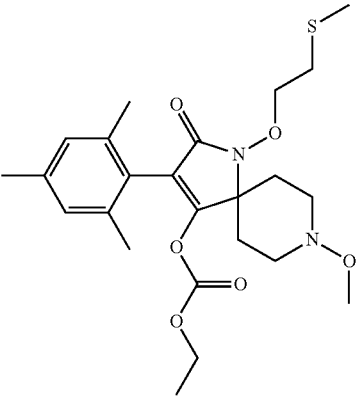 | gum | LC/MS: 479 (M + H)$^+$<br>$R_t$ = 2.03 min |
| P1ii.111 | 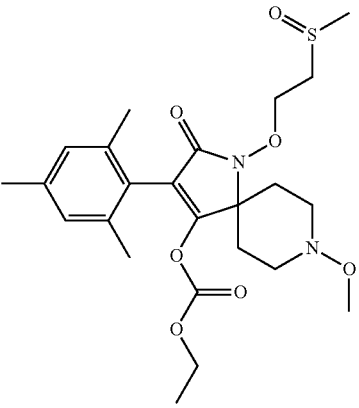<br>EXAMPLE 22 | gum | LC/MS: 495 (M + H)$^+$<br>$R_t$ = 1.74 min |
| P1ii.112 | 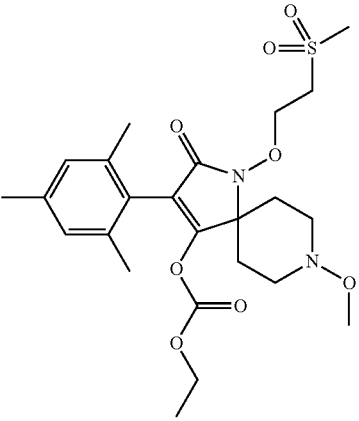 | | |

TABLE P1ii-continued

Physical data of compounds of formula I:

| Compound No. | Structures | Melting Point | MS/NMR |
|---|---|---|---|
| P1ii.113 | 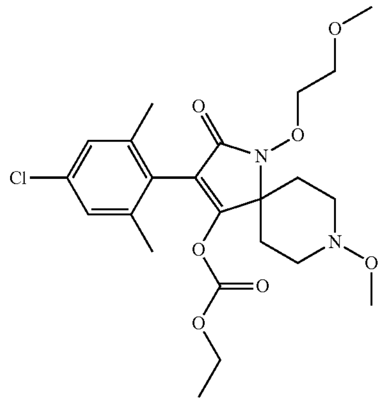 [SMILES: CCOC(=O)OC1=C(c2c(C)cc(Cl)cc2C)C(=O)N(OCCOC)C12CCN(OC)CC2] | gum | LC/MS: 483/485 (M + H)+<br>$R_t$ = 1.94 min |
| P1ii.114 | 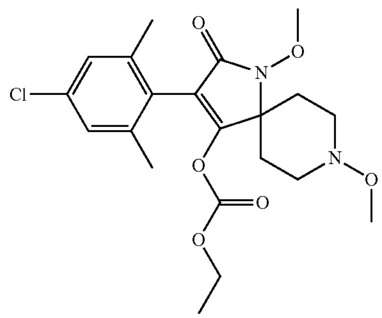 [SMILES: CCOC(=O)OC1=C(c2c(C)cc(Cl)cc2C)C(=O)N(OC)C12CCN(OC)CC2] | 122-125° C. | LC/MS: 439/441 (M + H)+<br>$R_t$ = 1.92 min |
| P1ii.115 | EXAMPLE 20, step 3 | gum | LC/MS: 497/499 (M + H)+<br>$R_t$ = 2.02 min |
| P1ii.116 | 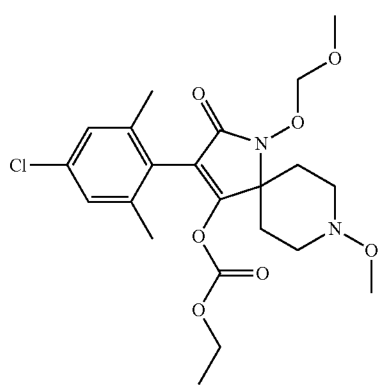 [SMILES: CCOC(=O)OC1=C(c2c(C)cc(Cl)cc2C)C(=O)N(OCOC)C12CCN(OC)CC2] | gum | LC/MS: 469/471 (M + H)+<br>$R_t$ = 1.97 min |

TABLE P1ii-continued
Physical data of compounds of formula I:
| Compound No. | Structures | Melting Point | MS/NMR |
|---|---|---|---|
| P1ii.117 | 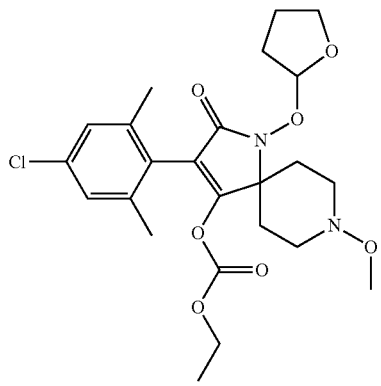 [SMILES: CCOC(=O)OC1=C(c2c(C)cc(Cl)cc2C)C(=O)N(OC2CCCO2)C12CCN(OC)CC2] | gum | LC/MS: 495/497 (M + H)+<br>$R_t$ = 2.02 min |
TABLE P2ii
Physical data of compounds of formula II
| Compound No. | Structures | Melting Point | MS/NMR |
|---|---|---|---|
| P2ii.1 | 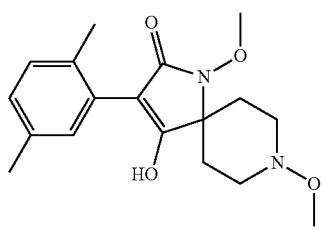 [SMILES: CON1CCC2(CC1)C(O)=C(c1cc(C)ccc1C)C(=O)N2OC] | gum | LC/MS: 333 (M + H)+<br>$R_t$ = 1.54 min |
| P2ii.2 | 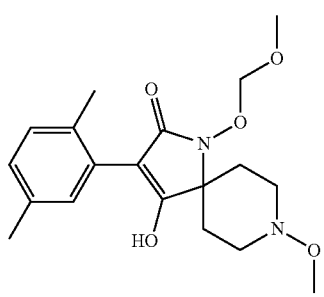 [SMILES: COCON1C(=O)C(c2cc(C)ccc2C)=C(O)C12CCN(OC)CC2]<br>EXAMPLE 11, step 5 | 136-138° C. | LC/MS: 363 (M + H)+<br>$R_t$ = 1.55 min |
| P2ii.3 | 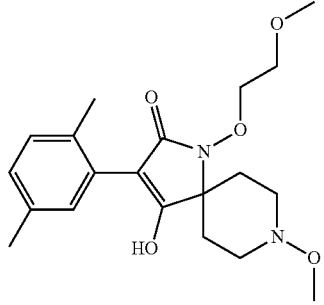 [SMILES: COCCON1C(=O)C(c2cc(C)ccc2C)=C(O)C12CCN(OC)CC2] | gum | LC/MS: 377 (M + H)+<br>$R_t$ = 1.58 min |

TABLE P2ii-continued

Physical data of compounds of formula II

| Compound No. | Structures | Melting Point | MS/NMR |
|---|---|---|---|
| P2ii.4 | EXAMPLE 14 | 152-154° C. | LC/MS: 333 (M + H)+ $R_t$ = 1.40 min |
| P2ii.5 | 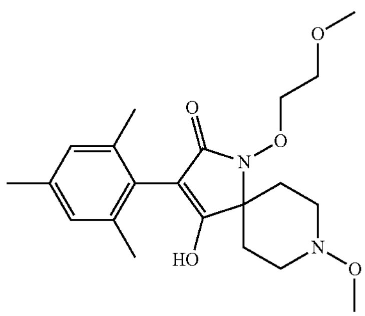 | 139-142° C. | LC/MS: 391 (M + H)+ $R_t$ = 1.61 min |
| P2ii.6 | 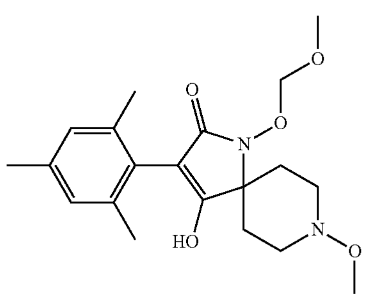 | 163-165° C. | LC/MS: 377 (M + H)+ $R_t$ = 1.64 min |
| P2ii.7 | 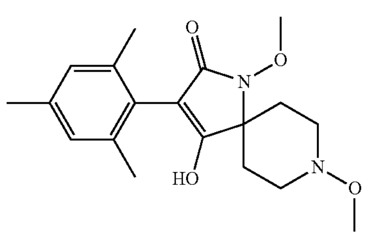 | 70° C. (dec) | LC/MS: 347 (M + H)+ $R_t$ = 1.60 min |
| P2ii.8 | EXAMPLE 12, step 2 | 167-169° C. | LC/MS: 371 (M + H)+ $R_t$ = 1.66 min |

TABLE P2ii-continued
Physical data of compounds of formula II
| Compound No. | Structures | Melting Point | MS/NMR |
|---|---|---|---|
| P2ii.9 | 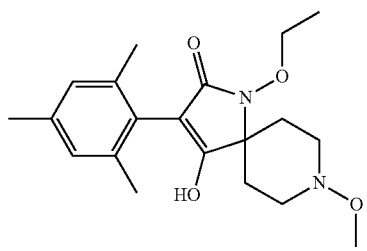 | 168-170° C. | LC/MS: 361 (M + H)+<br>R$_t$ = 1.67 min |
| P2ii.10 | 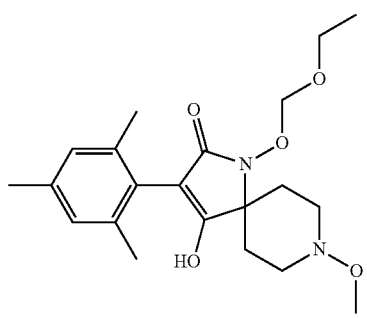 [SMILES: CCOCON1C(=O)C(c2c(C)cc(C)cc2C)=C(O)C12CCN(OC)CC2] | gum | LC/MS: 391 (M + H)+<br>R$_t$ = 1.71 min |
| P2ii.11 | 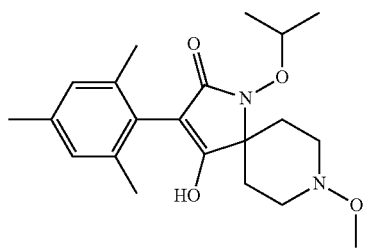 | 153-156° C. | LC/MS: 375 (M + H)+<br>R$_t$ = 1.78 min |
| P2ii.12 | 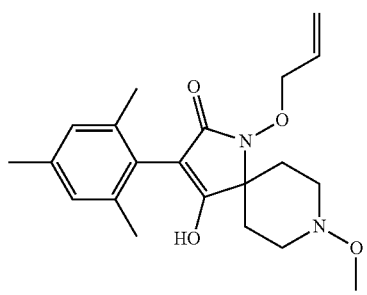 | 162-164° C. | LC/MS: 373 (M + H)+<br>R$_t$ = 1.73 min |
| P2ii.13 | 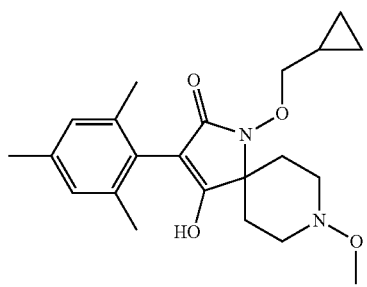 [SMILES: CON1CCC2(CC1)C(O)=C(c1c(C)cc(C)cc1C)C(=O)N2OCC1CC1] | 150-153° C. | LC/MS: 387 (M + H)+<br>R$_t$ = 1.81 min |

TABLE P2ii-continued
Physical data of compounds of formula II
| Compound No. | Structures | Melting Point | MS/NMR |
|---|---|---|---|
| P2ii.14 | 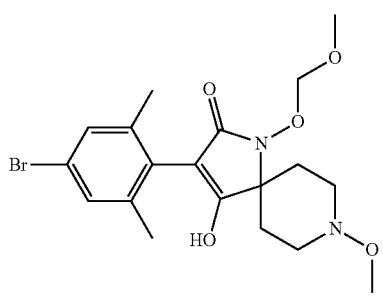 | 190-191° C. | LC/MS: 441/443 (M + H)+<br>$R_t$ = 1.62 min |
| P2ii.15 | 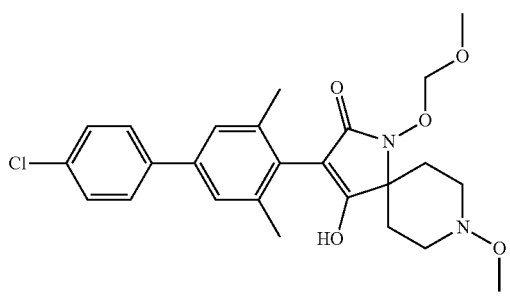 [SMILES: COCON1C(=O)C(c2c(C)cc(-c3ccc(Cl)cc3)cc2C)=C(O)C12CCN(OC)CC2]<br>EXAMPLE 24 | 128° C. (dec) | LC/MS: 473/475 (M + H)+<br>$R_t$ = 1.97 min |
| P2ii.16 | 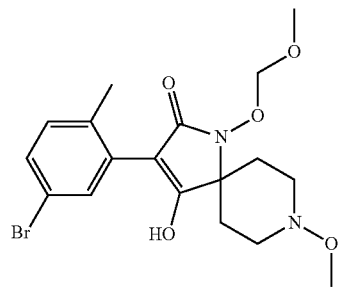 [SMILES: COCON1C(=O)C(c2cc(Br)ccc2C)=C(O)C12CCN(OC)CC2] | gum | LC/MS: 427/429 (M + H)+<br>$R_t$ = 1.63 min |
| P2ii.17 | 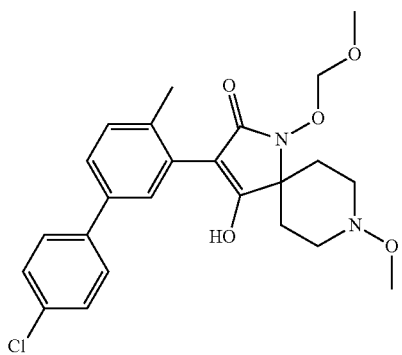 [SMILES: COCON1C(=O)C(c2cc(-c3ccc(Cl)cc3)ccc2C)=C(O)C12CCN(OC)CC2] | 68-71° C. | LC/MS: 459/461 (M + H)+<br>$R_t$ = 1.93 min |

TABLE P2ii-continued

Physical data of compounds of formula II

| Compound No. | Structures | Melting Point | MS/NMR |
|---|---|---|---|
| P2ii.18 | EXAMPLE 17, step 2 | 144-146° C. | LC/MS: 403 (M + H)$^+$<br>R$_t$ = 1.66 min |
| P2ii.19 | 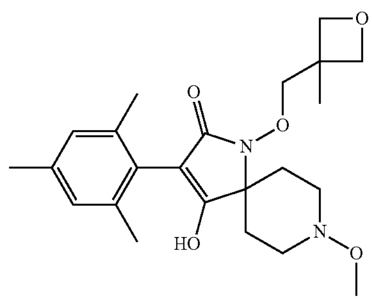 [SMILES: CON1CCC2(CC1)C(O)=C(c1c(C)cc(C)cc1C)C(=O)N2OCC1(C)COC1] | 108-111° C. | LC/MS: 417 (M + H)$^+$<br>R$_t$ = 1.68 min |
| P2ii.20 | 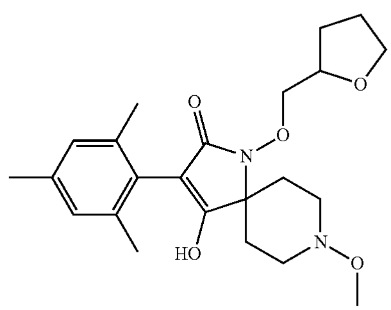 [SMILES: CON1CCC2(CC1)C(O)=C(c1c(C)cc(C)cc1C)C(=O)N2OCC1CCCO1] | gum | LC/MS: 417 (M + H)$^+$<br>R$_t$ = 1.72 min |
| P2ii.21 | 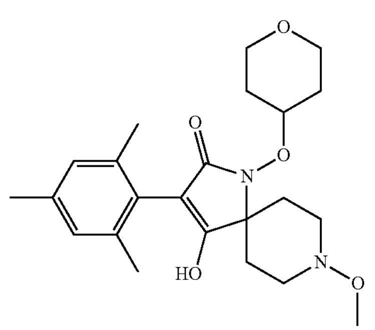 | 124-126° C. | LC/MS: 417 (M + H)$^+$<br>R$_t$ = 1.62 min |

TABLE P2ii-continued

Physical data of compounds of formula II

| Compound No. | Structures | Melting Point | MS/NMR |
|---|---|---|---|
| P2ii.22 | 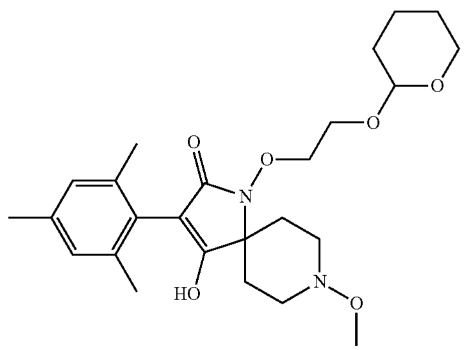 [SMILES: CON1CCC2(CC1)C(O)=C(c1c(C)cc(C)cc1C)C(=O)N2OCCOC1CCCCO1] | 135-137° C. | LC/MS: 461 (M + H)+<br>$R_t$ = 1.87 min |
| P2ii.23 | 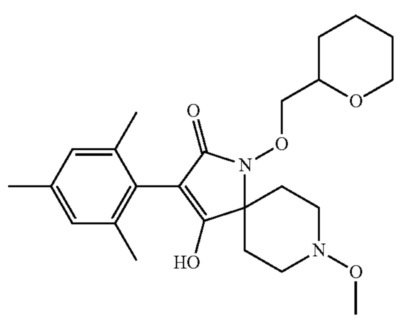 [SMILES: CON1CCC2(CC1)C(O)=C(c1c(C)cc(C)cc1C)C(=O)N2OCC1CCCCO1] | 90-93° C. | LC/MS: 431 (M + H)+<br>$R_t$ = 1.81 min |
| P2ii.24 | 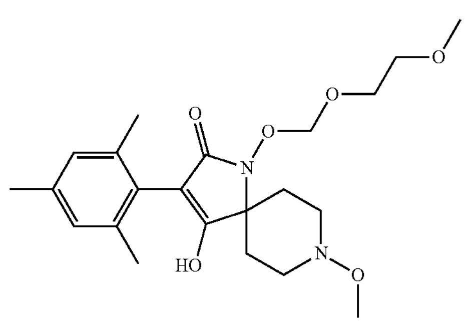 | 98-100° C. | LC/MS: 421 (M + H)+<br>$R_t$ = 1.62 min |
| P2ii.25 | 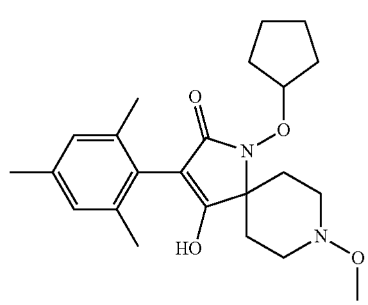 | 144-147° C. | LC/MS: 401 (M + H)+<br>$R_t$ = 1.92 min |

TABLE P2ii-continued

Physical data of compounds of formula II

| Compound No. | Structures | Melting Point | MS/NMR |
|---|---|---|---|
| P2ii.26 | EXAMPLE 18, step 2 | 115-118° C. | LC/MS: 415 (M + H)$^+$<br>R$_t$ = 1.98 min |
| P2ii.27 | 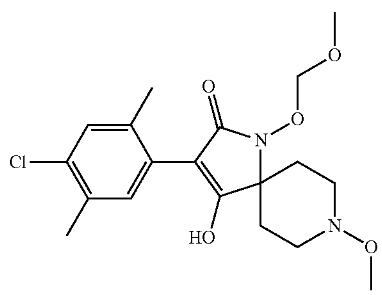 [SMILES: COCON1C(=O)C(c2cc(C)c(Cl)cc2C)=C(O)C12CCN(OC)CC2] | 139-143° C. | LC/MS: 397/399 (M + H)$^+$<br>R$_t$ = 1.67 min |
| P2ii.28 | 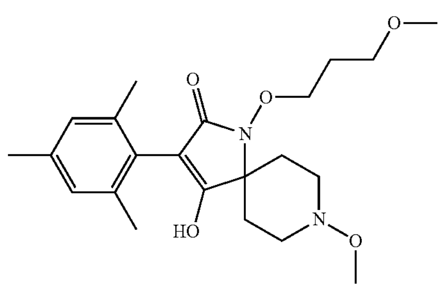 | 128-130° C. | LC/MS: 405 (M + H)$^+$<br>R$_t$ = 1.69 min |
| P2ii.29 | 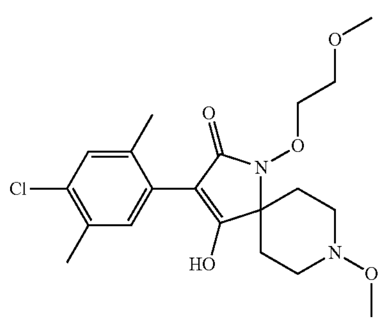 [SMILES: COCCON1C(=O)C(c2cc(C)c(Cl)cc2C)=C(O)C12CCN(OC)CC2] | 49-54° C. | LC/MS: 411/413 (M + H)$^+$<br>R$_t$ = 1.68 min |
| P2ii.30 | 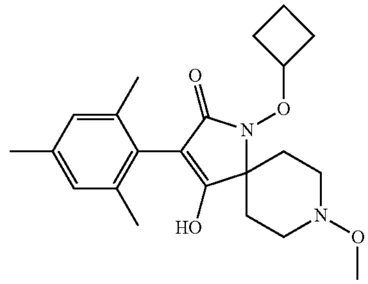 | gum | LC/MS: 387 (M + H)$^+$<br>R$_t$ = 1.82 min |

TABLE P2ii-continued

Physical data of compounds of formula II

| Compound No. | Structures | Melting Point | MS/NMR |
|---|---|---|---|
| P2ii.31 | 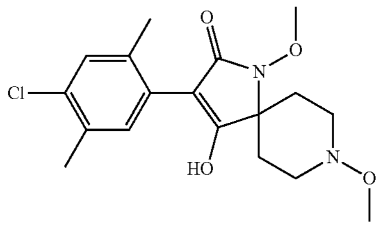 [SMILES: CON1CCC2(CC1)C(O)=C(c1cc(C)c(Cl)cc1C)C(=O)N2OC] | 92-95° C. | LC/MS: 367/369 (M + H)+ $R_t$ = 1.64 min |
| P2ii.32 | 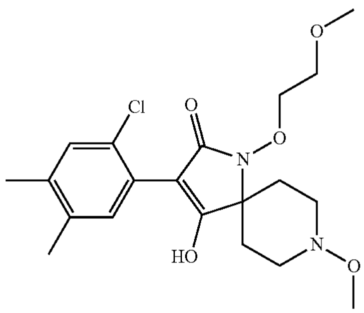 | solid | LC/MS: 411/413 (M + H)+ $R_t$ = 1.66 min |
| P2ii.33 | 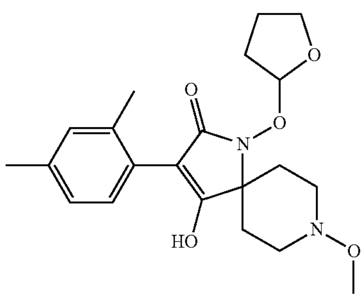 | solid | LC/MS: 389 (M + H)+ $R_t$ = 1.63 min |
| P2ii.34 | 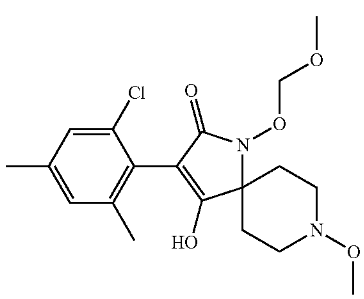 | 79-82° C. | LC/MS: 397/399 (M + H)+ $R_t$ = 1.55 min |
| P2ii.35 | 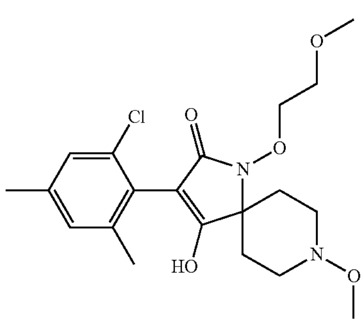 | 161-163° C. | LC/MS: 411/413 (M + H)+ $R_t$ = 1.55 min |

TABLE P2ii-continued

Physical data of compounds of formula II

| Compound No. | Structures | Melting Point | MS/NMR |
|---|---|---|---|
| P2ii.36 | 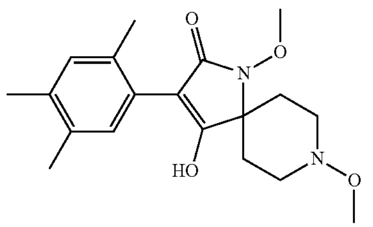 | gum | LC/MS: 347 (M + H)$^+$<br>$R_t$ = 1.59 min |
| P2ii.37 | 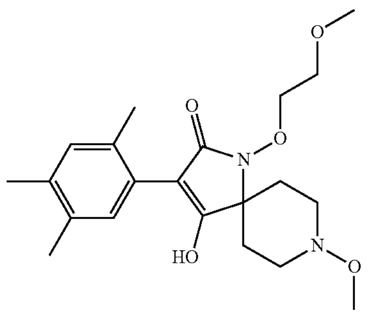 | gum | LC/MS: 391 (M + H)$^+$<br>$R_t$ = 1.65 min |
| P2ii.38 | 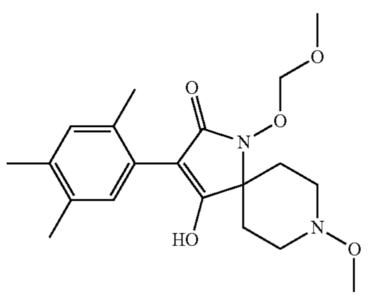 | gum | LC/MS: 377 (M + H)$^+$<br>$R_t$ = 1.60 min |
| P2ii.39 | 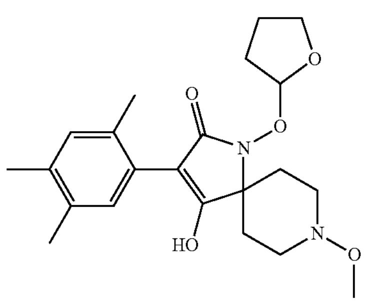 | gum | LC/MS: 403 (M + H)$^+$<br>$R_t$ = 1.72 min |
| P2ii.40 | 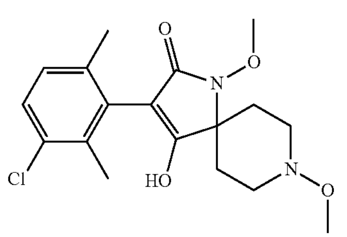 [SMILES: CON1CCC2(CC1)C(O)=C(c1c(C)ccc(Cl)c1C)C(=O)N2OC] | gum | LC/MS: 367/369 (M + H)$^+$<br>$R_t$ = 1.58 min |

TABLE P2ii-continued

Physical data of compounds of formula II

| Compound No. | Structures | Melting Point | MS/NMR |
|---|---|---|---|
| P2ii.41 | 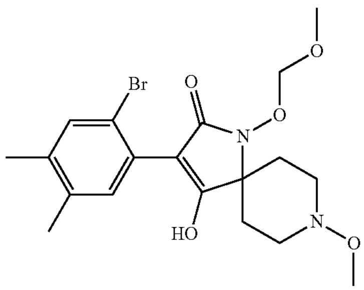 | solid | LC/MS: 441/443 (M + H)⁺<br>$R_t$ = 1.64 min |
| P2ii.42 | 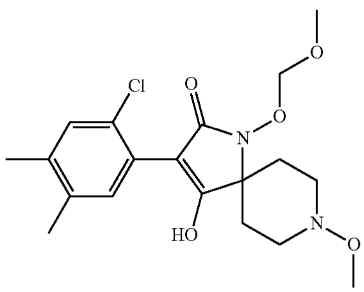 | solid | LC/MS: 395/397 (M − H)⁻<br>$R_t$ = 1.64 min |
| P2ii.43 | 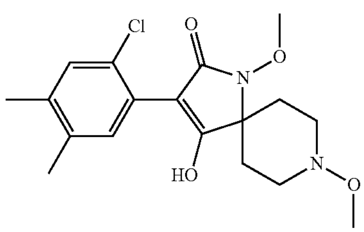 | solid | LC/MS: 367/369 (M + H)⁺<br>$R_t$ = 1.64 min |
| P2ii.44 | 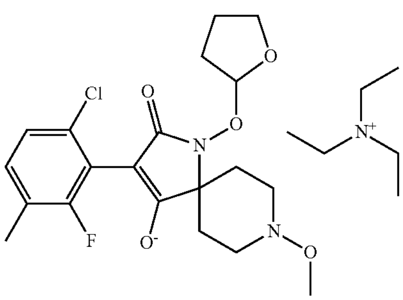 | gum | ¹H-NMR (CD₃OD, selected signals only): 1.29 (t, 9H, N(CH₂CH₃)₃), 2.23 (d, ⁴J(H,F) = 1.9 Hz, 3H, mesityl CH₃), 3.17 (q, 6H, N(CH₂CH₃)₃), 3.54 (s, 3H, NOCH₃), 5.82 (br m, 1H, tetrahydrofuranyl CH). |
| P2ii.45 | 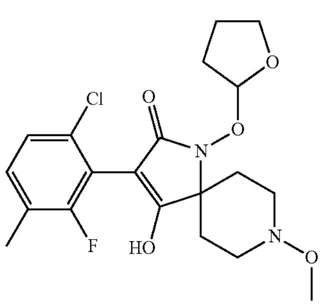 [SMILES: CON1CCC2(CC1)C(O)=C(c1c(Cl)ccc(C)c1F)C(=O)N2OC1CCCO1] | solid | LC/MS: 427/429 (M + H)⁺<br>$R_t$ = 1.62 min |

TABLE P2ii-continued

Physical data of compounds of formula II

| Compound No. | Structures | Melting Point | MS/NMR |
|---|---|---|---|
| P2ii.46 | 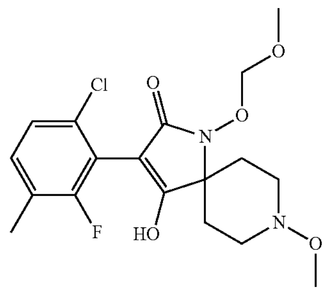 [SMILES: COCON1C(=O)C(c2c(Cl)ccc(C)c2F)=C(O)C12CCN(OC)CC2] | solid | LC/MS: 401/403 (M + H)+<br>$R_t$ = 1.54 min |
| P2ii.47 | 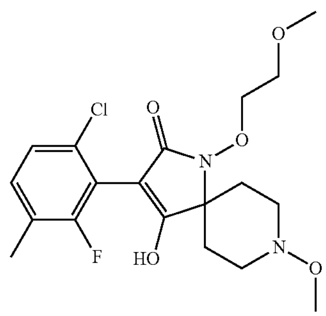 [SMILES: COCCON1C(=O)C(c2c(Cl)ccc(C)c2F)=C(O)C12CCN(OC)CC2] | gum | LC/MS: 415/417 (M + H)+<br>$R_t$ = 1.57 min |
| P2ii.48 | 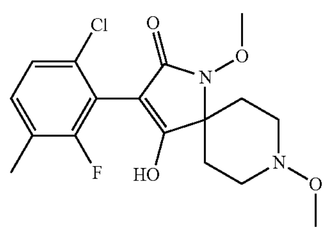 [SMILES: CON1CCC2(CC1)C(O)=C(c1c(Cl)ccc(C)c1F)C(=O)N2OC] | solid | LC/MS: 371/373 (M + H)+<br>$R_t$ = 1.55 min |
| P2ii.49 | 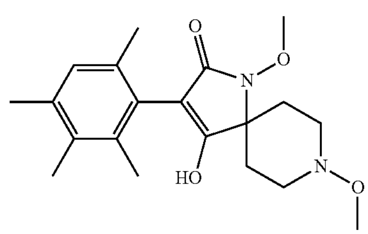 | gum | LC/MS: 361 (M + H)+<br>$R_t$ = 1.63 min |
| P2ii.50 | 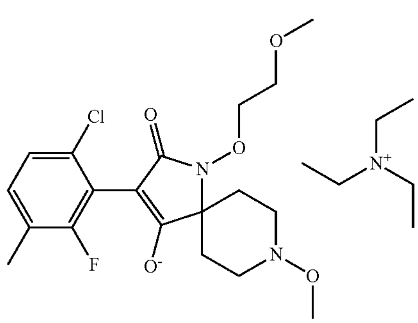 | gum | 1H-NMR (CD3OD, selected signals only): 1.29 (t, 9H, N(CH2CH3)3), 2.22 (d, 4J(H,F) = 2.2 Hz, 3H, mesityl CH3), 3.17 (q, 6H, N(CH2CH3)3), 3.39 (s, 3H, CH2CH2OCH3), 3.54 (s, 3H, NOCH3). |

TABLE P2ii-continued

Physical data of compounds of formula II

| Compound No. | Structures | Melting Point | MS/NMR |
|---|---|---|---|
| P2ii.51 | 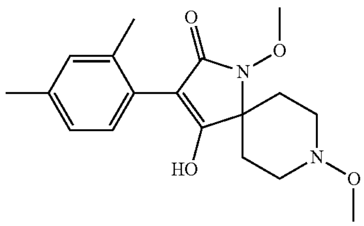 | powder | LC/MS: 333 (M + H)+ $R_t$ = 1.53 min |
| P2ii.52 | 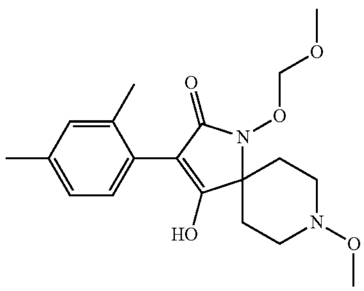 | 133-136° C. | |
| P2ii.53 | 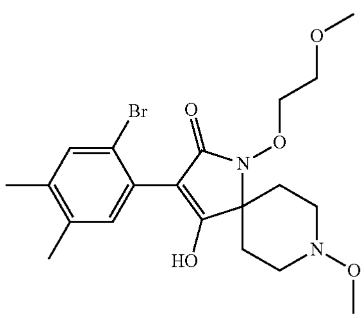 | solid | LC/MS: 455/457 (M + H)+ $R_t$ = 1.67 min |
| P2ii.54 | 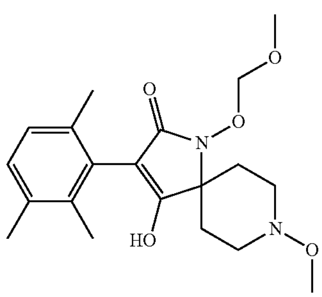 [SMILES: COCON1C(=O)C(c2c(C)ccc(C)c2C)=C(O)C12CCN(OC)CC2] | gum | LC/MS: 377 (M + H)+ $R_t$ = 1.57 min |
| P2ii.55 | 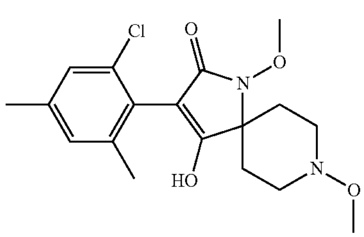 | 176-180° C. | LC/MS: 367/369 (M + H)+ $R_t$ = 1.55 min |

TABLE P2ii-continued

Physical data of compounds of formula II

| Compound No. | Structures | Melting Point | MS/NMR |
|---|---|---|---|
| P2ii.56 | 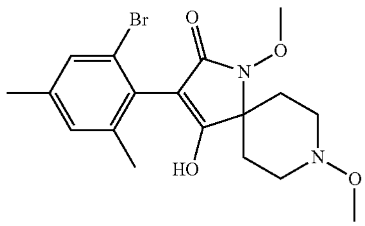 | 185-190° C. | LC/MS: 411/413 (M + H)+<br>$R_t$ = 1.56 min |
| P2ii.57 | 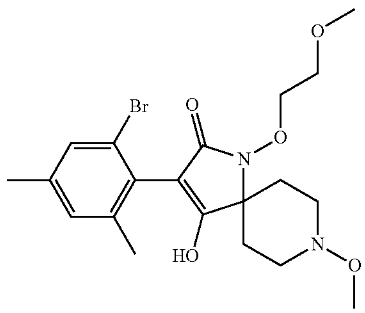 | 148-153° C. | LC/MS: 455/457 (M + H)+<br>$R_t$ = 1.60 min |
| P2ii.58 | 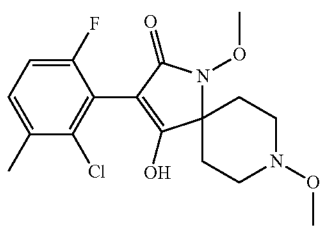 [SMILES: CON1CCC2(CC1)C(O)=C(c1c(F)ccc(C)c1Cl)C(=O)N2OC] | 83-86° C. | LC/MS: 371/373 (M + H)+<br>$R_t$ = 1.52 min |
| P2ii.59 | 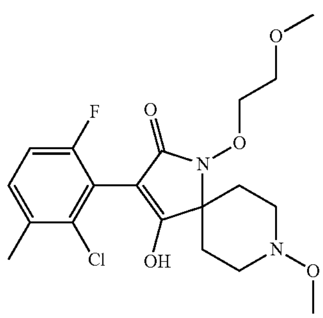 [SMILES: COCCON1C(=O)C(c2c(F)ccc(C)c2Cl)=C(O)C12CCN(OC)CC2] | 55-57° C. | LC/MS: 415/417 (M + H)+<br>$R_t$ = 1.53 min |
| P2ii.60 | 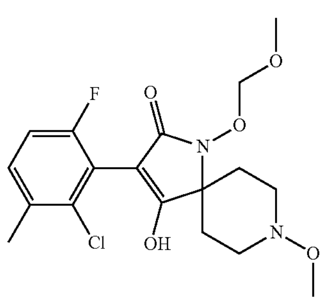 [SMILES: COCON1C(=O)C(c2c(F)ccc(C)c2Cl)=C(O)C12CCN(OC)CC2] | 155-158° C. | LC/MS: 401/403 (M + H)+<br>$R_t$ = 1.51 min |

TABLE P2ii-continued

Physical data of compounds of formula II

| Compound No. | Structures | Melting Point | MS/NMR |
|---|---|---|---|
| P2ii.61 | 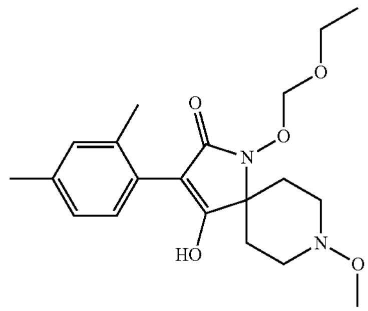 [SMILES: CCOCON1C(=O)C(c2ccc(C)cc2C)=C(O)C12CCN(OC)CC2] | powder | LC/MS: 377 (M + H)$^+$<br>$R_t$ = 1.66 min |
| P2ii.62 | 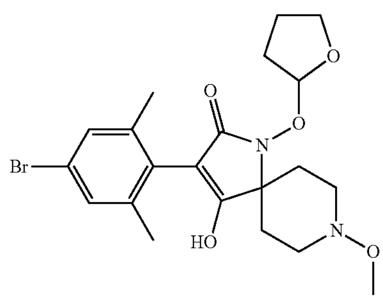 | 91-92° C. | LC/MS: 467/469 (M + H)$^+$<br>$R_t$ = 1.71 min |
| P2ii.63 | 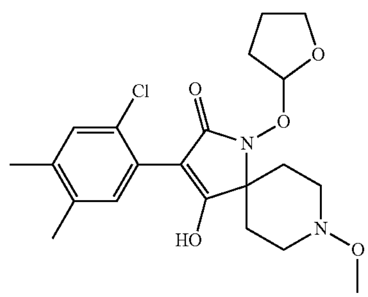 | 84-85° C. | LC/MS: 423/425 (M + H)$^+$<br>$R_t$ = 1.71 min |
| P2ii.64 | 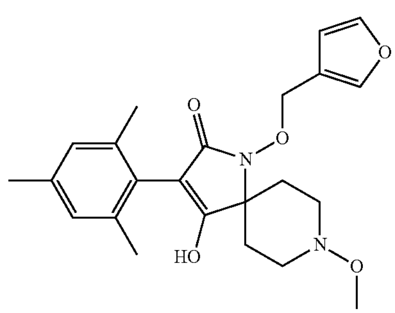 [SMILES: CON1CCC2(CC1)C(O)=C(c1c(C)cc(C)cc1C)C(=O)N2OCc1ccoc1] | 154-157° C. | LC/MS: 413 (M + H)$^+$<br>$R_t$ = 1.77 min |
| P2ii.65 | 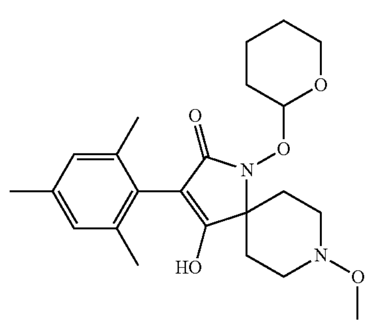 | 103-106° C. | LC/MS: 417 (M + H)$^+$<br>$R_t$ = 1.77 min |

TABLE P2ii-continued

Physical data of compounds of formula II

| Compound No. | Structures | Melting Point | MS/NMR |
|---|---|---|---|
| P2ii.66 | 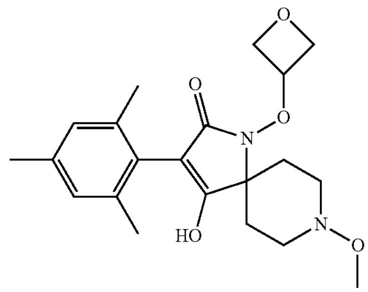 | 88-91° C. | LC/MS: 389 (M + H)$^+$<br>R$_t$ = 1.54 min |
| P2ii.67 | 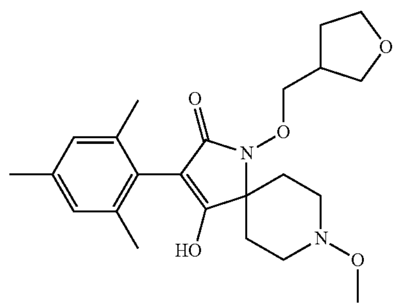 [SMILES: CON1CCC2(CC1)C(O)=C(c1c(C)cc(C)cc1C)C(=O)N2OCC1CCOC1] | 69-72° C. | LC/MS: 417 (M + H)$^+$<br>R$_t$ = 1.64 min |
| P2ii.68 | 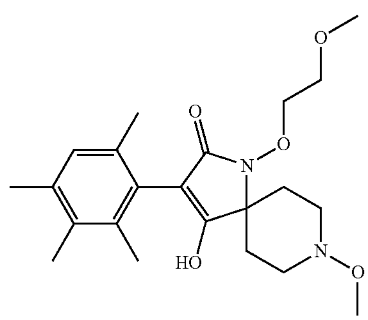 | gum | LC/MS: 405 (M + H)$^+$<br>R$_t$ = 1.65 min |
| P2ii.69 | 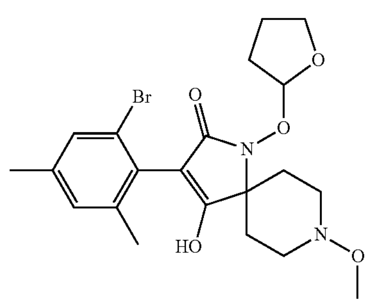 | gum | LC/MS: 467/469 (M + H)$^+$<br>R$_t$ = 1.66 min |
| P2ii.70 | 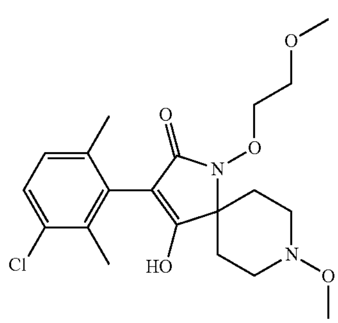 [SMILES: COCCON1C(=O)C(c2c(C)ccc(Cl)c2C)=C(O)C12CCN(OC)CC2] | gum | LC/MS: 411/413 (M + H)$^+$<br>R$_t$ = 1.61 min |

TABLE P2ii-continued

Physical data of compounds of formula II

| Compound No. | Structures | Melting Point | MS/NMR |
|---|---|---|---|
| P2ii.71 | 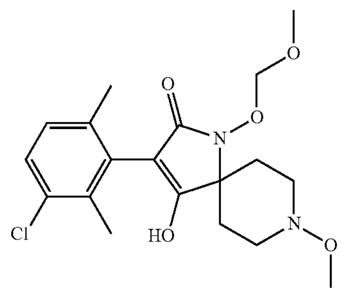 [SMILES: COCON1C(=O)C(c2c(C)ccc(Cl)c2C)=C(O)C12CCN(OC)CC2] | gum | LC/MS: 397/399 (M + H)+<br>$R_t$ = 1.60 min |
| P2ii.72 | 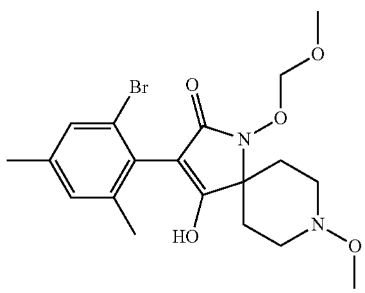 | 167-171° C. | LC/MS: 441/443 (M + H)+<br>$R_t$ = 1.58 min |
| P2ii.73 | 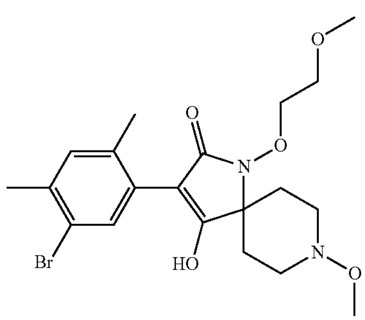 | 63-64° C. | LC/MS: 445/457 (M + H)+<br>$R_t$ = 1.72 min |
| P2ii.74 | 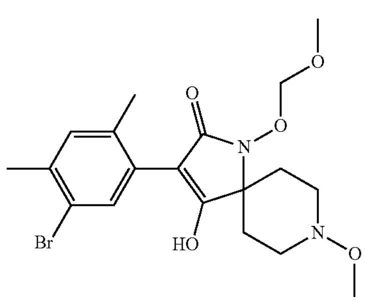 | 79-80° C. | LC/MS: 441/443 (M + H)+<br>$R_t$ = 1.70 min |
| P2ii.75 | 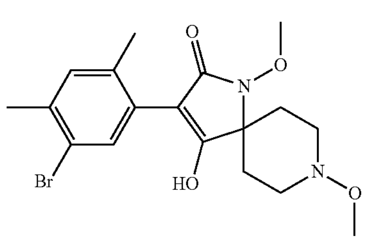 | 86-87° C. | LC/MS: 411/413 (M + H)+<br>$R_t$ = 1.69 min |

TABLE P2ii-continued

Physical data of compounds of formula II

| Compound No. | Structures | Melting Point | MS/NMR |
|---|---|---|---|
| P2ii.76 | 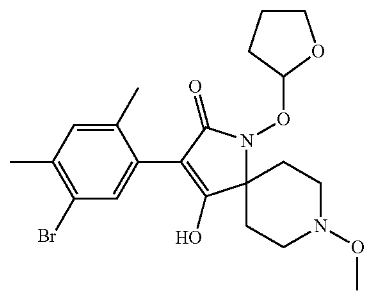 | 96-97° C. | LC/MS: 467/469 (M + H)+<br>$R_t$ = 1.78 min |
| P2ii.77 | 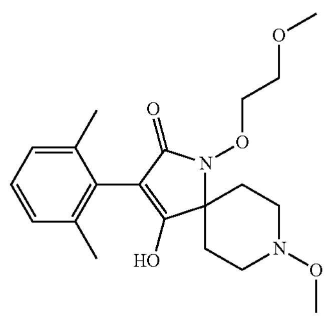 [SMILES: COCCON1C(=O)C(c2c(C)cccc2C)=C(O)C12CCN(OC)CC2] | 141-144° C. | LC/MS: 377 (M + H)+<br>$R_t$ = 1.49 min |
| P2ii.78 | 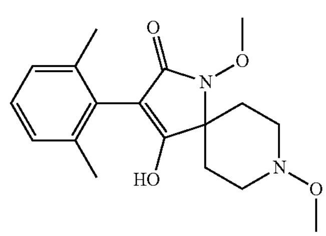 [SMILES: CON1CCC2(CC1)C(O)=C(c1c(C)cccc1C)C(=O)N2OC] | 153-155° C. | LC/MS: 333 (M + H)+<br>$R_t$ = 1.44 min |
| P2ii.79 | 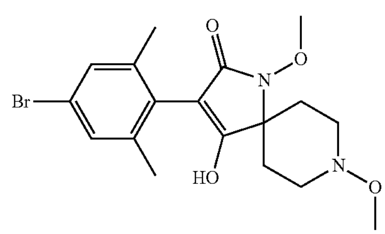 | 188-191° C. | LC/MS: 411/413 (M + H)+<br>$R_t$ = 1.63 min |
| P2ii.80 | 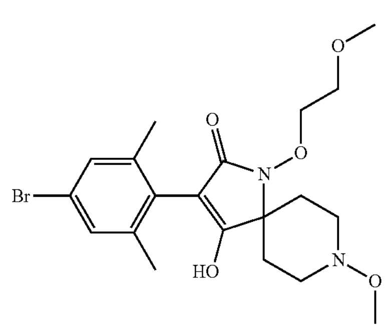 | 163-167° C. | LC/MS: 455/457 (M + H)+<br>$R_t$ = 1.67 min |

TABLE P2ii-continued

Physical data of compounds of formula II

| Compound No. | Structures | Melting Point | MS/NMR |
|---|---|---|---|
| P2ii.81 | 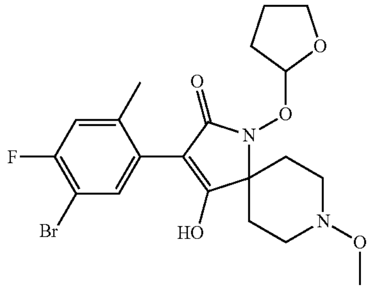 [SMILES: CON1CCC2(CC1)C(O)=C(c1cc(Br)c(F)cc1C)C(=O)N2OC1CCCO1] | gum | LC/MS: 471/473 (M + H)+<br>$R_t$ = 1.70 min |
| P2ii.82 | 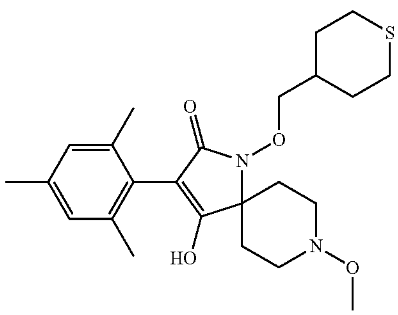 | 95-98° C. | LC/MS: 447 (M + H)+<br>$R_t$ = 1.89 min |
| P2ii.83 | 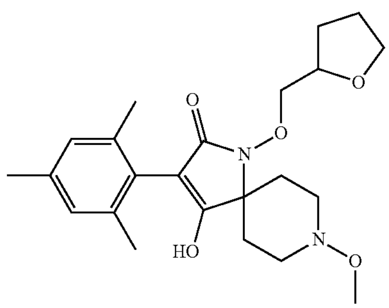 | 155-157° C. | LC/MS: 413 (M + H)+<br>$R_t$ = 1.75 min |
| P2ii.84 | 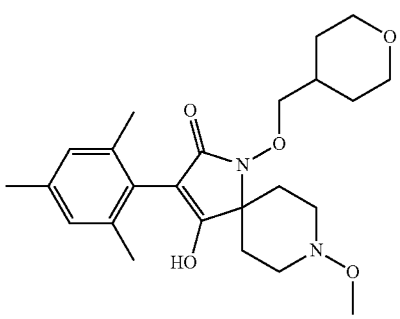 [SMILES: CON1CCC2(CC1)C(O)=C(c1c(C)cc(C)cc1C)C(=O)N2OCC1CCOCC1] | 100-103° C. | LC/MS: 431 (M + H)+<br>$R_t$ = 1.70 min |
| P2ii.85 | 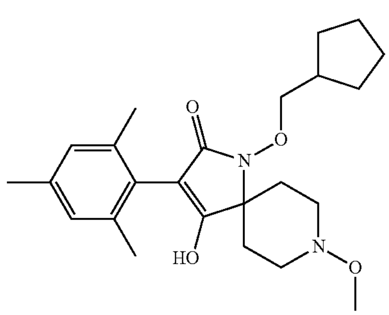 [SMILES: CON1CCC2(CC1)C(O)=C(c1c(C)cc(C)cc1C)C(=O)N2OCC1CCCC1] | 74-77° C. | LC/MS: 415 (M + H)+<br>$R_t$ = 1.98 min |

TABLE P2ii-continued

Physical data of compounds of formula II

| Compound No. | Structures | Melting Point | MS/NMR |
|---|---|---|---|
| P2ii.86 | 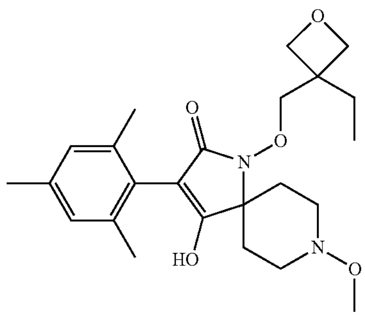 [SMILES: CCC1(CON2C(=O)C(c3c(C)cc(C)cc3C)=C(O)C23CCN(OC)CC3)COC1] | 88-91° C. | LC/MS: 431 (M + H)⁺ $R_t$ = 1.62 min |
| P2ii.87 | 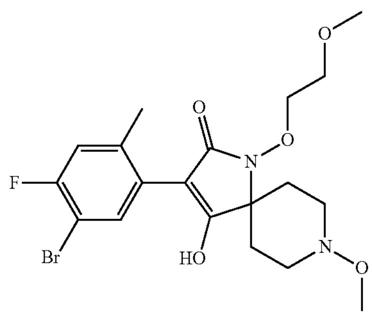 [SMILES: COCCON1C(=O)C(c2cc(Br)c(F)cc2C)=C(O)C12CCN(OC)CC2] | 71-74° C. | LC/MS: 459/461 (M + H)⁺ $R_t$ = 1.66 min |
| P2ii.88 | 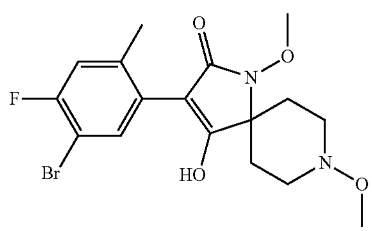 [SMILES: CON1CCC2(CC1)C(O)=C(c1cc(Br)c(F)cc1C)C(=O)N2OC] | solid | LC/MS: 415/417 (M + H)⁺ $R_t$ = 1.63 min |
| P2ii.89 | 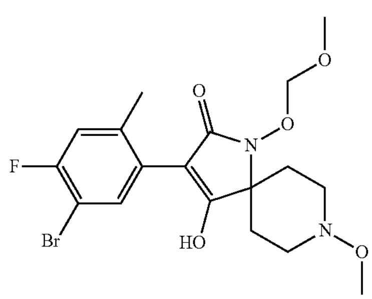 [SMILES: COCON1C(=O)C(c2cc(Br)c(F)cc2C)=C(O)C12CCN(OC)CC2] | 64-67° C. | LC/MS: 445/447 (M + H)⁺ $R_t$ = 1.65 min |
| P2ii.90 | 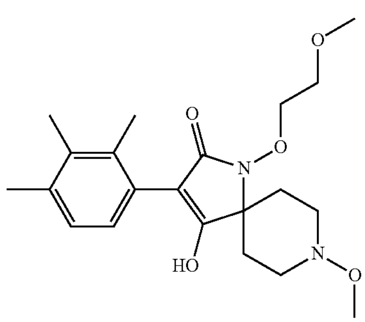 | solid | LC/MS: 391 (M + H)⁺ $R_t$ = 1.62 min |

TABLE P2ii-continued

Physical data of compounds of formula II

| Compound No. | Structures | Melting Point | MS/NMR |
|---|---|---|---|
| P2ii.91 | 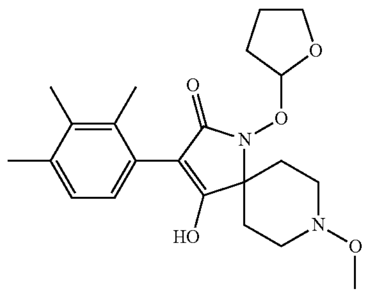 | foam | LC/MS: 403 (M + H)+<br>$R_t$ = 1.68 min |
| P2ii.92 | 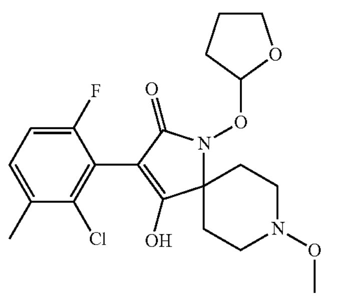 [SMILES: CON1CCC2(CC1)C(O)=C(c1c(F)ccc(C)c1Cl)C(=O)N2OC1CCCO1] | 86-89° C. | LC/MS: 427/429 (M + H)+<br>$R_t$ = 1.61 min |
| P2ii.93 | 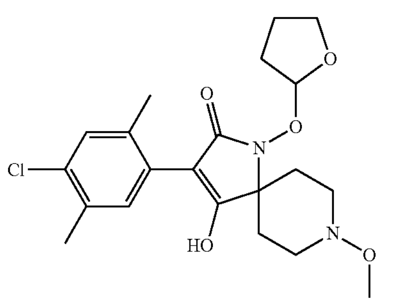 [SMILES: CON1CCC2(CC1)C(O)=C(c1cc(C)c(Cl)cc1C)C(=O)N2OC1CCCO1] | 88-91° C. | LC/MS: 423/425 (M + H)+<br>$R_t$ = 1.74 min |
| P2ii.94 | 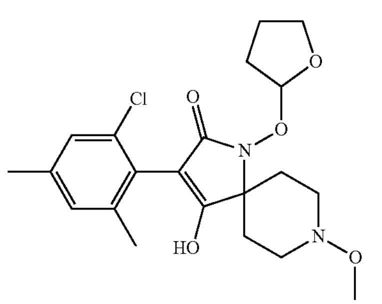 | 84-88° C. | LC/MS: 423/425 (M + H)+<br>$R_t$ = 1.63 min |

TABLE P2ii-continued
Physical data of compounds of formula II
| Compound No. | Structures | Melting Point | MS/NMR |
|---|---|---|---|
| P2ii.95 | 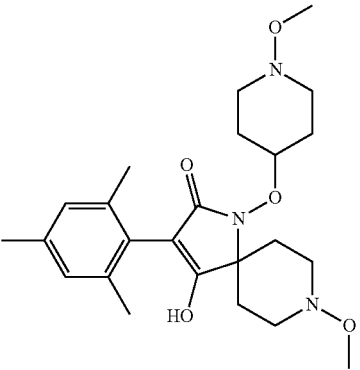 | solid | LC/MS: 446 (M + H)+ $R_t$ = 1.62 min |
| P2ii.96 | 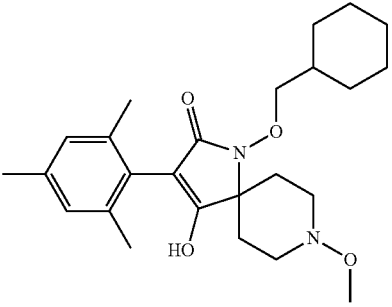 | 169-172° C. | LC/MS: 429 (M + H)+ $R_t$ = 2.05 min |
| P2ii.97 | 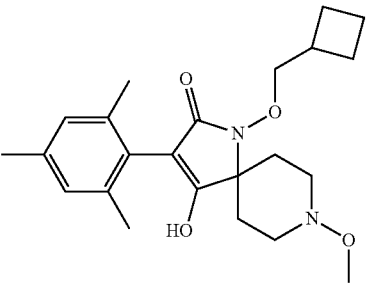 [SMILES: CON1CCC2(CC1)C(O)=C(c1c(C)cc(C)cc1C)C(=O)N2OCC1CCC1] | 113-115° C. | LC/MS: 401 (M + H)+ $R_t$ = 1.89 min |
| P2ii.98 | 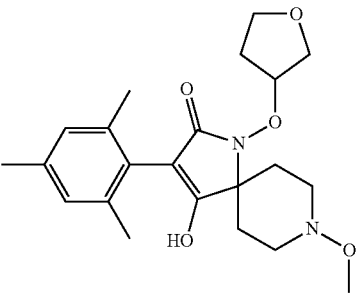 | 135-138° C. | LC/MS: 403 (M + H)+ $R_t$ = 1.57 min |

TABLE P2ii-continued

Physical data of compounds of formula II

| Compound No. | Structures | Melting Point | MS/NMR |
|---|---|---|---|
| P2ii.99 | 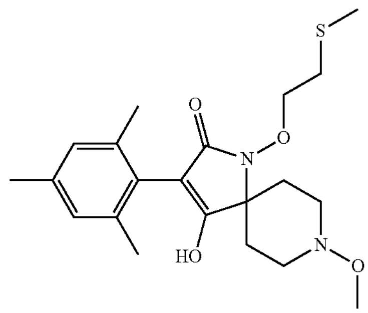 | 113-115° C. | LC/MS: 407 (M + H)+ $R_t$ = 1.72 min |
| P2ii.100 | 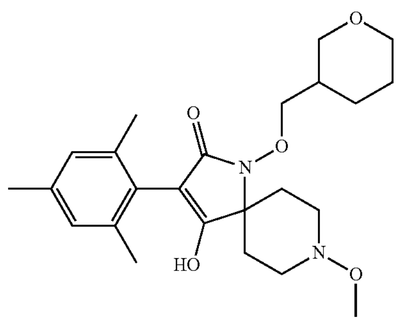 [SMILES: CON1CCC2(CC1)C(O)=C(c1c(C)cc(C)cc1C)C(=O)N2OCC1CCCOC1] | 98-101° C. | LC/MS: 431 (M + H)+ $R_t$ = 1.72 min |
| P2ii.101 | 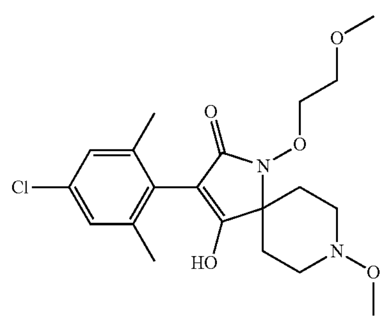 [SMILES: COCCON1C(=O)C(c2c(C)cc(Cl)cc2C)=C(O)C12CCN(OC)CC2] | 161-164° C. | LC/MS: 411/413 (M + H)+ $R_t$ = 1.63 min |
| P2ii.102 | 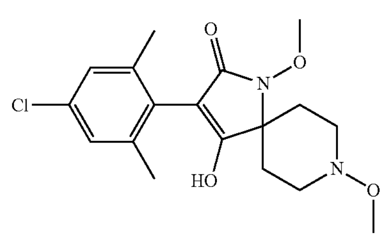 [SMILES: CON1CCC2(CC1)C(O)=C(c1c(C)cc(Cl)cc1C)C(=O)N2OC] | 88-92° C. | LC/MS: 367/369 (M + H)+ $R_t$ = 1.58 min |
| P2ii.103 | 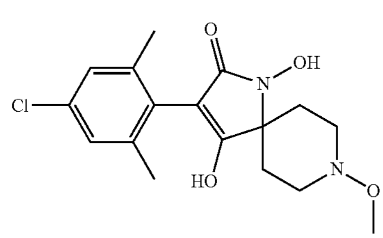 [SMILES: CON1CCC2(CC1)C(O)=C(c1c(C)cc(Cl)cc1C)C(=O)N2O] | solid | LC/MS: 353/355 (M + H)+ $R_t$ = 1.37 min |

EXAMPLE 20, step 2

TABLE P2ii-continued

Physical data of compounds of formula II

| Compound No. | Structures | Melting Point | MS/NMR |
|---|---|---|---|
| P2ii.104 | 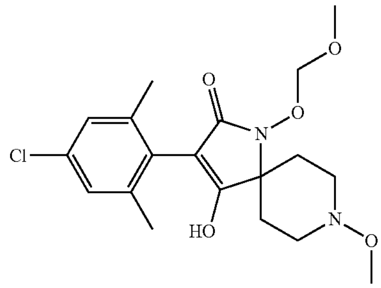 [SMILES: COCON1C(=O)C(c2c(C)cc(Cl)cc2C)=C(O)C12CCN(OC)CC2] | 176-178° C. | LC/MS: 397/399 (M + H)+<br>R$_t$ = 1.64 min |
| P2ii.105 | 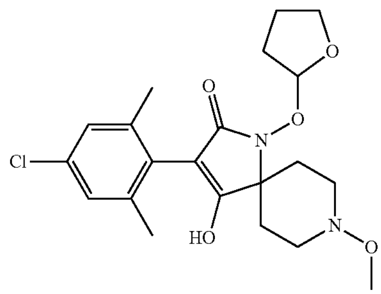 [SMILES: CON1CCC2(CC1)C(O)=C(c1c(C)cc(Cl)cc1C)C(=O)N2OC1CCCO1] | 137-139° C. | LC/MS: 421/423 (M − H)−<br>R$_t$ = 1.69 min |

Intermediates from Table P31i can be prepared by analogous procedures.

TABLE P3ii

Physical data of intermediates

| Compound No. | Structure | Melting Point | MS/NMR |
|---|---|---|---|
| P3ii.1 | EXAMPLE 11, step 4<br>EXAMPLE 16, step 2 | 140-142° C. | LC/MS: 351 (M + H)+<br>R$_t$ = 1.59 min |
| P3ii.2 | EXAMPLE 16, step 1 | 153-156° C. | LC/MS: 318 (M + H)+<br>R$_t$ = 1.66 min |
| P3ii.3 | 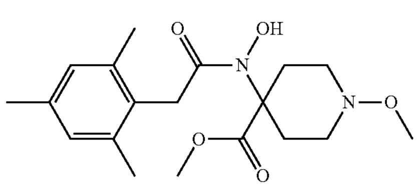 | 199-200° C. | LC/MS: 365 (M + H)+<br>R$_t$ = 1.68 min |

TABLE P3ii-continued

Physical data of intermediates

| Compound No. | Structure | Melting Point | MS/NMR |
|---|---|---|---|
| P3ii.4 | EXAMPLE 12, step 1 | 108-110° C. | LC/MS: 403 (M + H)+ $R_t$ = 1.98 min |
| P3ii.5 | 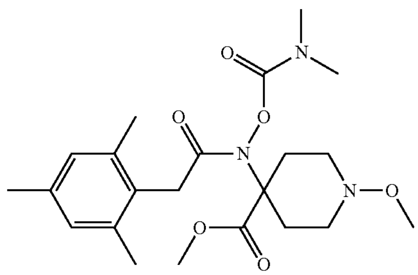 | gum | LC/MS: 436 (M + H)+ $R_t$ = 1.91 min |
| P3ii.6 | EXAMPLE 17, step 1 | 107-109° C. | LC/MS: 435 (M + H)+ $R_t$ = 2.03 min |
| P3ii.7 | 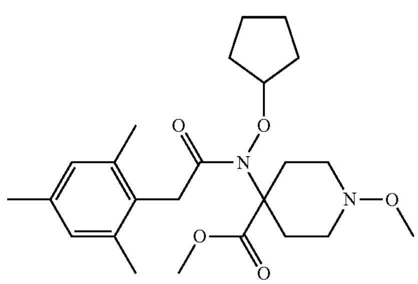 | gum | LC/MS: 433 (M + H)+ $R_t$ = 2.19 min |
| P3ii.8 | EXAMPLE 18, step 1 | gum | LC/MS: 447 (M + H)+ $R_t$ = 2.23 min |

TABLE P3ii-continued

Physical data of intermediates

| Compound No. | Structure | Melting Point | MS/NMR |
|---|---|---|---|
| P3ii.9 | 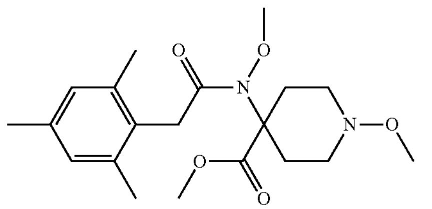 | gum | LC/MS: 379 (M + H)+ $R_t$ = 1.89 min |
| P3ii.10 | 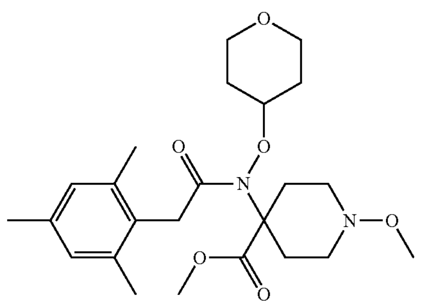 | gum | LC/MS: 449 (M + H)+ $R_t$ = 1.89 min |
| P3ii.11 | 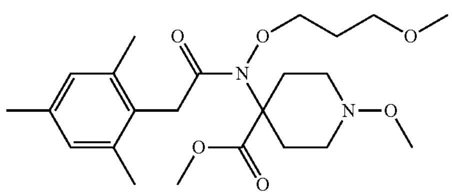 | 55-57° C. | LC/MS: 437 (M + H)+ $R_t$ = 1.95 min |
| P3ii.12 | 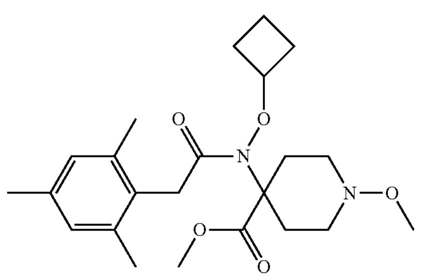 | gum | LC/MS: 419 (M + H)+ $R_t$ = 2.09 min |
| P3ii.13 | 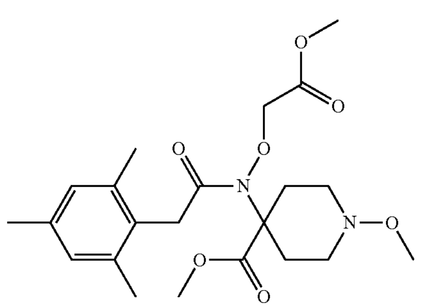 | gum | LC/MS: 437 (M + H)+ $R_t$ = 1.86 min |
| P3ii.14 | 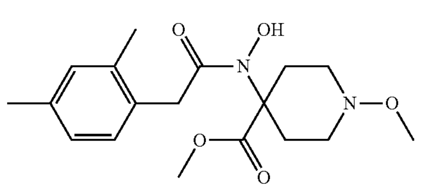 | solid | LC/MS: 351 (M + H)+ $R_t$ = 1.59 min |

TABLE P3ii-continued

Physical data of intermediates

| Compound No. | Structure | Melting Point | MS/NMR |
|---|---|---|---|
| P3ii.15 | 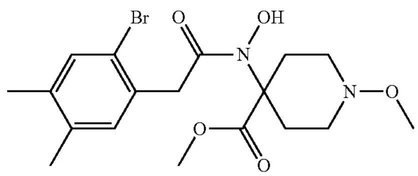 | 166-167° C. | LC/MS: 429/431 (M + H)$^+$<br>$R_t$ = 1.71 min |
| P3ii.16 | 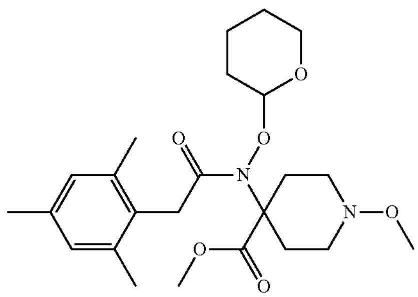 | gum | LC/MS: 449 (M + H)$^+$<br>$R_t$ = 2.08 min |
| P3ii.17 | 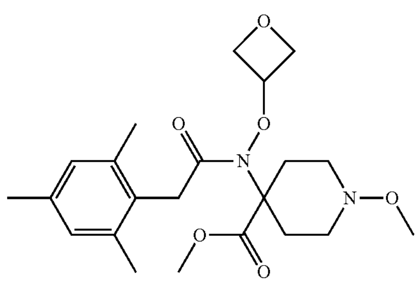 | gum | LC/MS: 421 (M + H)$^+$<br>$R_t$ = 1.80 min |
| P3ii.18 | 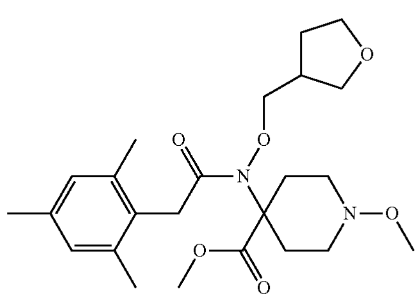 | gum | LC/MS: 449 (M + H)$^+$<br>$R_t$ = 1.88 min |
| P3ii.19 | 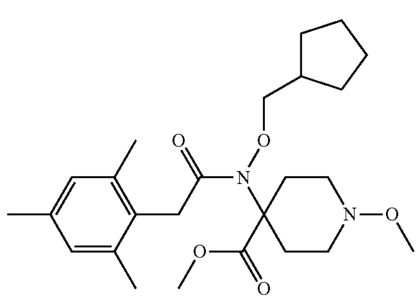 | gum | LC/MS: 447 (M + H)$^+$<br>$R_t$ = 2.25 min |

TABLE P3ii-continued

Physical data of intermediates

| Compound No. | Structure | Melting Point | MS/NMR |
|---|---|---|---|
| P3ii.20 | 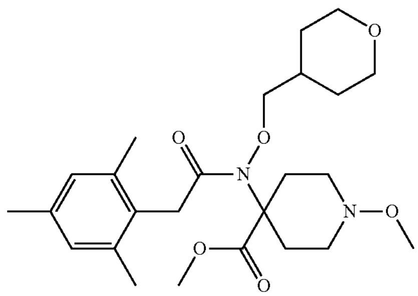 | gum | LC/MS: 463 (M + H)$^+$ R$_t$ = 1.93 min |
| P3ii.21 | 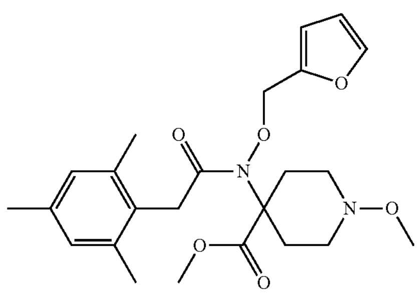 | gum | LC/MS: 445 (M + H)$^+$ R$_t$ = 2.05 min |
| P3ii.22 | 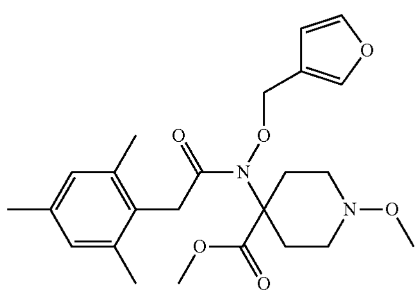 | gum | LC/MS: 445 (M + H)$^+$ R$_t$ = 1.98 min |
| P3ii.23 | 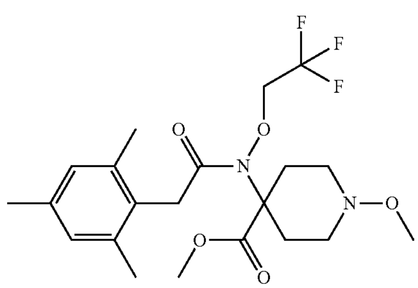 | gum | LC/MS: 447 (M + H)$^+$ R$_t$ = 2.03 min |
| P3ii.24 | 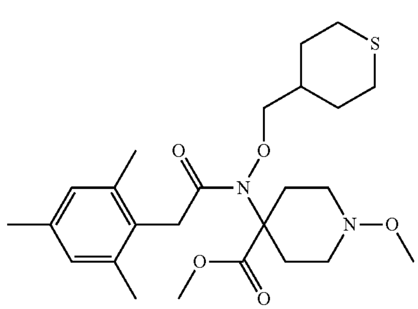 | gum | LC/MS: 479 (M + H)$^+$ R$_t$ = 2.10 min |

TABLE P3ii-continued
Physical data of intermediates
| Compound No. | Structure | Melting Point | MS/NMR |
|---|---|---|---|
| P3ii.25 | 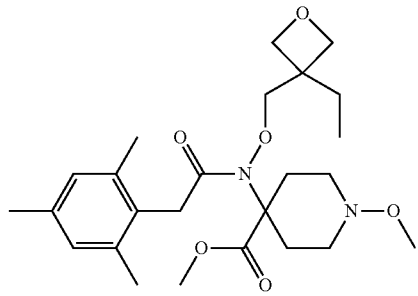 | gum | LC/MS: 463 (M + H)+<br>R$_t$ = 1.94 min |
| P3ii.26 | 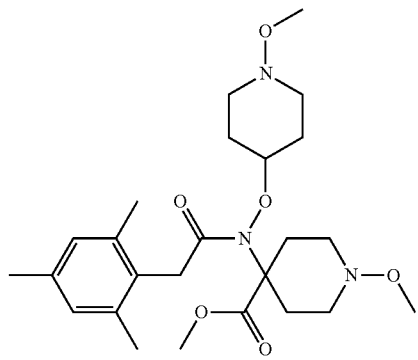<br>EXAMPLE 19, step 2 | gum | LC/MS: 478 (M + H)+<br>R$_t$ = 1.97 min |
| P3ii.27 | 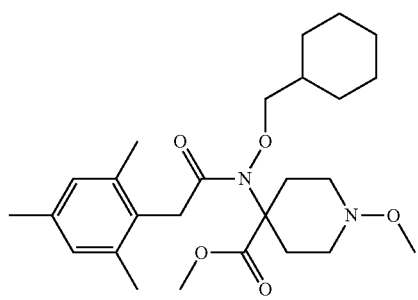 | gum | LC/MS: 461 (M + H)+<br>R$_t$ = 2.31 min |
| P3ii.28 | 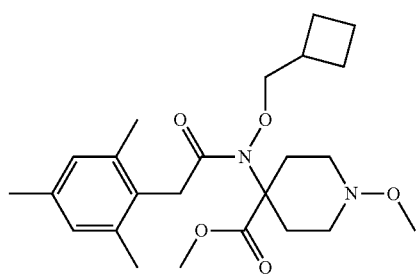 | gum | LC/MS: 433 (M + H)+<br>R$_t$ = 2.17 min |

TABLE P3ii-continued

Physical data of intermediates

| Compound No. | Structure | Melting Point | MS/NMR |
|---|---|---|---|
| P3ii.29 | 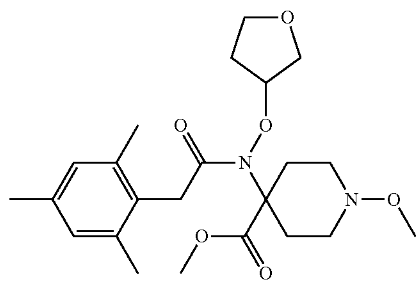 | 115-117° C. | LC/MS: 435 (M + H)+ $R_t$ = 1.85 min |
| P3ii.30 | 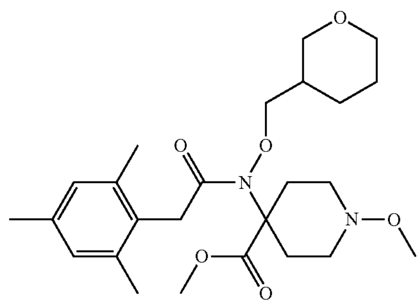 | gum | LC/MS: 463 (M + H)+ $R_t$ = 2.01 min |
| P3ii.31 | 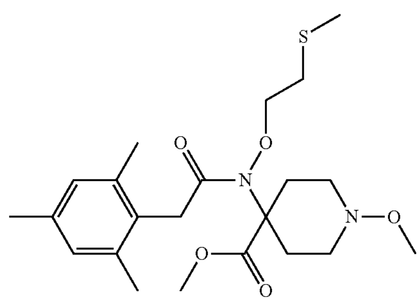 | gum | LC/MS: 439 (M + H)+ $R_t$ = 2.03 min |
| P3ii.32 | 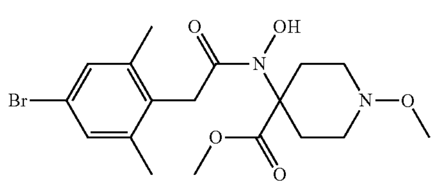 | solid | LC/MS: 429/431 (M + H)+ $R_t$ = 1.73 min |
| P3ii.33 | 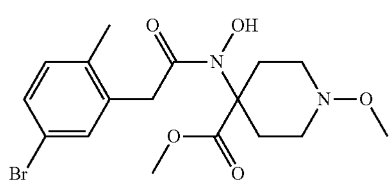 [SMILES: COC(=O)C1(N(O)C(=O)Cc2cc(Br)ccc2C)CCN(OC)CC1] | solid | LC/MS: 415/417 (M + H)+ $R_t$ = 1.67 min |
| P3ii.34 | 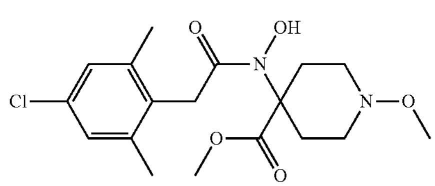 | 228-231° C. | LC/MS: 385/387 (M + H)+ $R_t$ = 1.71 min |

EXAMPLE 20, step 1

TABLE P3ii-continued

Physical data of intermediates

| Compound No. | Structure | Melting Point | MS/NMR |
|---|---|---|---|
| P3ii.35 | 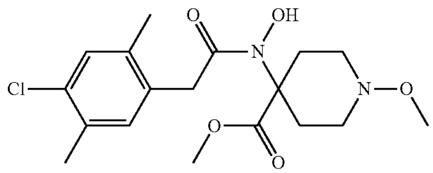 | | LC/MS: 385/387 (M + H)+<br>R$_t$ = 1.86 min |
| P3ii.36 | 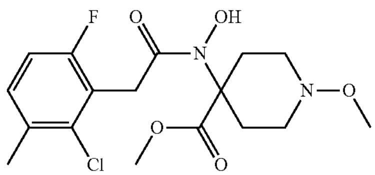 [SMILES: COC(=O)C1(N(O)C(=O)Cc2c(F)ccc(C)c2Cl)CCN(OC)CC1] | | LC/MS: 389/391 (M + H)+<br>R$_t$ = 1.59 min |
| P3ii.37 | 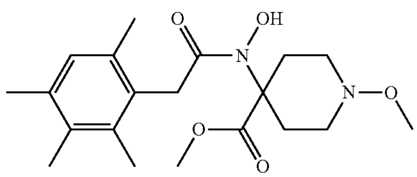 | | LC/MS: 379 (M + H)+<br>R$_t$ = 1.91 min |
| P3ii.38 | 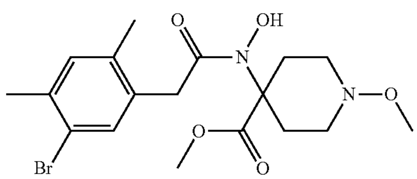 | 162-163° C. | LC/MS: 429/431 (M + H)+<br>R$_t$ = 1.76 min |
| P3ii.39 | 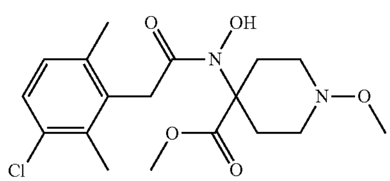 | | LC/MS: 385/387 (M + H)+<br>R$_t$ = 1.67 min |
| P3ii.40 | 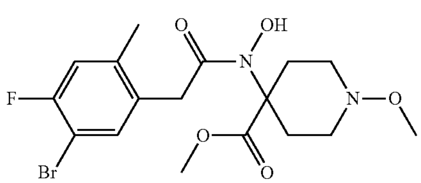 | | LC/MS: 433/435 (M + H)+<br>R$_t$ = 1.69 min |
| P3ii.41 | 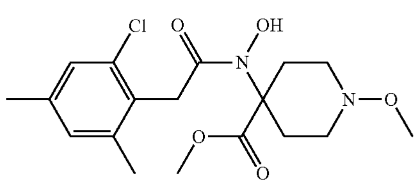 | | LC/MS: 385/387 (M + H)+<br>R$_t$ = 1.69 min |
| P3ii.42 | 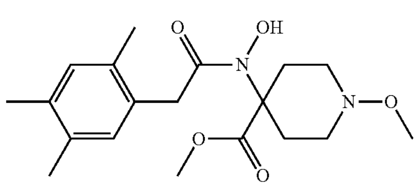 | | LC/MS: 365 (M + H)+<br>R$_t$ = 1.67 min |

TABLE P3ii-continued

Physical data of intermediates

| Compound No. | Structure | Melting Point | MS/NMR |
|---|---|---|---|
| P3ii.43 | 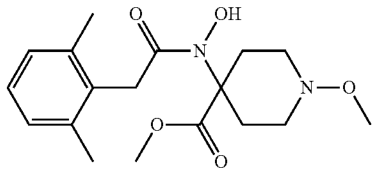 [SMILES: COC(=O)C1(N(O)C(=O)Cc2c(C)cccc2C)CCN(OC)CC1] | | LC/MS: 351 (M + H)+<br>R$_t$ = 1.55 min |
| P3ii.44 | 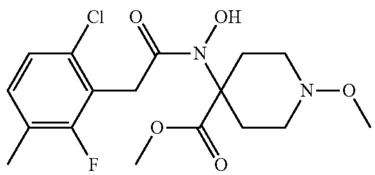 | | LC/MS: 389/391 (M + H)+<br>R$_t$ = 1.62 min |
| P3ii.45 | 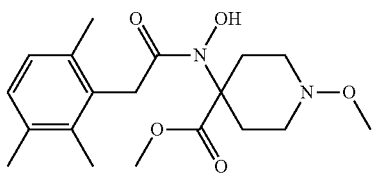 | | LC/MS: 365 (M + H)+<br>R$_t$ = 1.66 min |
| P3ii.46 | 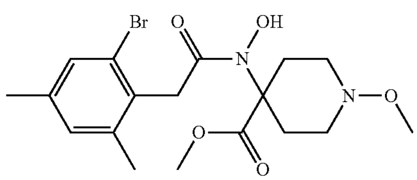 | | LC/MS: 429/431 (M + H)+<br>R$_t$ = 1.67 min |
| P3ii.47 | 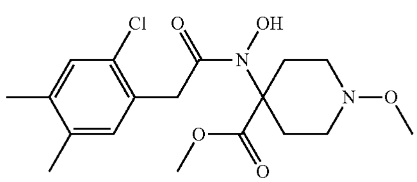 | | LC/MS: 385/387 (M + H)+<br>R$_t$ = 1.71 min |
| P3ii.48 | 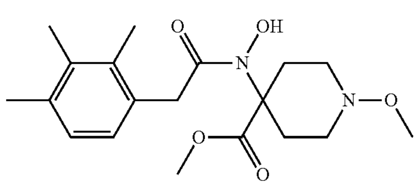 | | LC/MS: 365 (M + H)+<br>R$_t$ = 1.65 min |
| P3ii.49<br>EXAMPLE 23, step 3 | | 100-103° C. | LC/MS 380/382 (M + H)+<br>R$_t$ = 1.99 min |

Intermediates from Table P4ii can be prepared by analogous procedures.

TABLE P4ii

Physical data of intermediates

| Compound No. | Structures | Melting Point | MS/NMR |
|---|---|---|---|
| P4ii.1 | EXAMPLE 11, step 2 | 130-131° C. | $^1$H-NMR (CDCl$_3$): 1.55-2.35 (br signals, total 4H), 2.60-3.45 (br signals, total 4H), 3.52 (s, 3H), 5.19 (br s, 1H), 5.42 (br s, 1H). IR (CN): v 2227.8 cm$^{-1}$. LC/MS (ES+): 172 (M + H$^+$; R$_t$ = 0.31 min. |
| P4ii.2 | EXAMPLE 11, step 3 | Oil | $^1$H-NMR (CDCl$_3$): 1.50-2.40 (br signals, total 4H), 2.76 (br m, 2H), 3.01-3.32 (br m, 2H), 3.52 (s, 3H), 3.76 (s, 3H), 5.58 (br s, 2H). IR (COOMe): v 1731.3 cm$^{-1}$. LC/MS (ES+): 205 (M + H)$^+$; R$_t$ = 0.31 min. |
| P4ii.3 | EXAMPLE 23, step 2 | Oil | $^1$H-NMR (CDCl$_3$): 1.19 (t, 3H), 1.59-2.29 (br signals, total 4H), 2.64-3.43 (br signals, total 4H), 3.52 (s, 3H), 3.80 (q, 2H), 5.37 (br s, 1H). IR (CH): v 2235.3 cm$^{-1}$. LC/MS (ES+): 200 (M + H)$^+$; R$_t$ = 1.21 min. |
| P4ii.4 | example 25, step 1 | 180° C. | $^1$H-NMR (CD$_3$OD): 1.54-2.29 (br signals, total 4H), 2.82 (br m, 2H), 3.07-3.26 (br signals, total 2H), 3.49 (s, 3H). LC/MS (ES+): 191 (M + H)$^+$; R$_t$ = 0.22 min. |

Examples of compounds of formula I where Q is iii are disclosed in WO2009/049851.

BIOLOGICAL EXAMPLES

Example B1

Activity Against *Rhopalosiphum padi* (Cereal Aphid) and Crop Safety

The experiment was divided into two parts, one half of the plants was used for the aphid bioassay the other half was not infested with aphids and kept for plant growth evaluation. One replicate consisted of 4 wheat plants per pot. 5 replicates were infested with a mixed population of cereal aphids 6 days after seeding. 9 days after seeding all wheat plants (10replicates) were sprayed with respective test solutions. Test solutions contained the formulated test compound (25 ppm), the adjuvant Mero (0.1% v/v), and the safener cloquintocet. 6 days after application aphid mortality and phytotoxicity were evaluated. Efficacy was calculated with the aid of Abbott's formula. Assessment on phytotoxicity was done by counting the number of leaves bent down due to necrosis per pot. Additionally the average plant height per replicate was measured.

TABLE B1-1

Efficacy (% mortality) against cereal aphids (*Rhopalosiphum padi*)

| | % mortality | |
|---|---|---|
| ratio AI: safener | Cpd. P1.2 of Table P1 | Cpd. P1.29 of Table P1 |
| | 97.4 | 97.0 |
| 1:2 | 94.4 | 96.9 |
| 1:1 | 93.4 | 96.6 |

Tank mixing of the safener cloquintocet with these insecticides does not adversely affect the aphid control of test compounds.

TABLE B1-2 plant safety on wheat, 6 DAA

| ratio Al: safener | Check | Cpd. P1.2 of Table P1 | Cpd. P1.29 of Table P1 |
|---|---|---|---|
| | mean stem height (cm) | | |
| | 24.2 | 14.8 | 19.8 |
| 1:2 | 23.8 | 23.4 | 20.8 |
| 1:1 | 23.4 | 22.8 | 23.0 |
| | no. of leaves bent down (necrotic) | | |
| | 0 | 3.8 | 1.3 |
| 1:2 | 0 | 0 | 0 |
| 1:1 | 0 | 0 | 0 |

In combination with the safener cloquintocet no leaf with necrosis occurred on treated plants and the stunting effect was reduced resulting in plants with normal heights.

Example B2

Activity Against *Nilaparvata lugens* (Brown Plant Hopper, BPH) and Crop Safety

The experiment was divided into two parts, one half of the plants was used for the plant hoppers bioassay the other half was not infested with insects and kept for plant growth evaluation. Eight replicates (pots with rice plants) were sprayed with respective test solutions. Test solutions contained the formulated test compound and the safener cloquintocet and N-(2-methoxybenzoyl)-4-[(methylaminocarbonyl)amino]-benzenesulfonamide at different ratios. 4 pots were infested with plant hopper nymphs right after application. 7d after application BPH mortality and plant safety were evaluated. Efficacy was calculated with the aid of Abbott's formula. Assessment on plant safety was done by measuring the average plant height per replicate.

TABLE B2-1

Efficacy (% mortality) against brown plant hopper (*Nilaparvata lugens*)

| | ratio Al: safener | ppm Al | Cpd. P1.2 of Table P1 | Cpd P1.29 of Table P1 | Cpd T1.067 of Table 1 of WO2009/049851, wherein G is COOCH$_2$CH$_3$ |
|---|---|---|---|---|---|
| | | 200 | 90 | 100 | 100 |
| | | 100 | 80 | 100 | 98 |
| | | 50 | 62 | 100 | 100 |
| | | 25 | 37 | 98 | 97 |
| | | 12.5 | 65 | 98 | 98 |
| Cloquintocet | 15:1 | 200 | 93 | 100 | 100 |
| | 7.5:1 | 100 | 78 | 100 | 100 |
| | 1.25:1 | 50 | 57 | 98 | 100 |
| | 1.9:1 | 25 | 30 | 100 | 100 |
| | 0.9:1 | 12.5 | 5 | 98 | 98 |
| Safener 2 | 15:1 | 200 | 85 | 100 | 100 |
| | 7.5:1 | 100 | 68 | 100 | 100 |
| | 1.25:1 | 50 | 42 | 100 | 98 |
| | 1.9:1 | 25 | 3 | 95 | 100 |
| | 0.9:1 | 12.5 | 0 | 65 | 100 |

Safener 2 = N-(2-methoxybenzoyl)-4-[(methylaminocarbonyl)amino]benzenesulfonamide Tank mixing of these insecticides with these safeners at different mixture ratios did not adversely affect the BPH control of test compounds.

TABLE B2-2 plant safety on rice
Stem height (mean of 4 reps)

mean plant height [cm]

| | ratio Al: safener | ppm Al | Cpd. P1.2 of Table P1 | Cpd P1.29 of Table P1 | Cpd T1.067 of Table 1 of WO2009/049851, wherein G is COOCH$_2$CH$_3$ | Check |
|---|---|---|---|---|---|---|
| | | 200 | 17 | 19 | 17 | 29 |
| | | 100 | 18 | 19 | 17 | |
| | | 50 | 20 | 25 | 19 | |
| | | 25 | 27 | 27 | 23 | |
| | | 12.5 | 29 | 29 | 29 | |
| Cloquintocet | 15:1 | 200 | 18 | 19 | 18 | 28 |
| | 7.5:1 | 100 | 18 | 22 | 18 | |
| | 1.25:1 | 50 | 22 | 29 | 19 | |
| | 1.9:1 | 25 | 27 | 30 | 20 | |
| | 0.9:1 | 12.5 | 27 | 28 | 24 | |
| Safener 2 | 15:1 | 200 | 18 | 20 | 20 | 30 |
| | 7.5:1 | 100 | 18 | 23 | 20 | |
| | 1.25:1 | 50 | 22 | 31 | 20 | |
| | 1.9:1 | 25 | 28 | 29 | 20 | |
| | 0.9:1 | 12.5 | 31 | 30 | 29 | |

Safener 2 = N-(2-methoxybenzoyl)-4-[(methylaminocarbonyl)amino]benzenesulfonamide Data demonstrate that test compounds caused a dose dependent effect on plant growth. Combining test compounds with safeners at various mixture ratios caused accordingly different degrees of reduced stunting effects.

Example B3

Activity Against *Rhopalosiphum padi* (Cereal Aphid) and Crop Safety

The experiment was divided into two parts, one half of the plants was used for the aphid bioassay (one AI rate) the other half was not infested with aphids and kept for plant growth evaluation (two AI rates). One replicate consisted of 4 wheat plants per pot. 5 replicates were infested with a mixed population of cereal aphids 6 days after seeding. 9 days after seeding all wheat plants (10 replicates) were sprayed with respective test solutions. Test solutions contained the formulated test compounds, the adjuvant Mero (0.1% v/v), and selected safeners at different mixture ratios. 7d after application aphid mortality and was evaluated.

Efficacy was calculated with the aid of Abbott's formula. Evaluation on phytotoxicity was done by assessing the percentage of leaves demonstrating chlorotic lesions per pot 14DAA.

TABLE B3-1

Efficacy (% mortality) against cereal aphids (*Rhopalosiphum padi*) 7DAA AI rate: 12.5 ppm

|  | ratio AI: safener | Cpd. P1.2 of Table P1 | Cpd T1.067 of Table 1 of WO2009/049851, wherein G is COOCH$_2$CH$_3$ |
|---|---|---|---|
|  |  | 98 | 98 |
| Cloquintocet-mexyl | 1:2 | 94 | 98 |
|  | 1:4 | 91 | 98 |
|  | 1:8 | 91 | 99 |
| Mefenpyr-diethyl | 1:2 | 97 | 98 |
|  | 1:4 | 92 | 97 |
|  | 1:8 | 92 | 97 |
| Safener 2 | 1:2 | 97 | 98 |
|  | 1:4 | 95 | 99 |
|  | 1:8 | 97 | 98 |

Safener 2 = N-(2-methoxybenzoyl)-4-[(methylaminocarbonyl)amino]benzenesulfonamide

TABLE B3-2 plant safety on wheat (% phytotoxicity), 14 DAA

| AI rate | Safener | ratio AI: safener | Cpd. P1.2 of Table P1 | Cpd T1.067 of Table 1 of Wo2009/049851, wherein G is COOCH$_2$CH$_3$ |
|---|---|---|---|---|
| 12.5 ppm |  |  | 5 | 66 |
|  | Cloquintocet-mexyl | 1:2 | 0 | 36 |
|  |  | 1:4 | 0 | 20 |
|  |  | 1:8 | 0 | 10 |
|  | Mefenpyr-diethyl | 1:2 | 0 | 30 |
|  |  | 1:4 | 0 | 20 |
|  |  | 1:8 | 0 | 20 |
|  | Safener 2 | 1:2 | 0 | 50 |
|  |  | 1:4 | 0 | 42 |
|  |  | 1:8 | 0 | 30 |
| 25 ppm |  |  | 12 | 80 |
|  | Cloquintocet-mexyl | 1:1 | 0 | 50 |
|  |  | 1:2 | 0 | 46 |
|  |  | 1:4 | 0 | 34 |

TABLE B3-2-continued plant safety on wheat (% phytotoxicity), 14 DAA

| AI rate | Safener | ratio AI: safener | Cpd. P1.2 of Table P1 | Cpd T1.067 of Table 1 of Wo2009/049851, wherein G is COOCH$_2$CH$_3$ |
|---|---|---|---|---|
|  | Mefenpyr-diethyl | 1:1 | 0 | 50 |
|  |  | 1:2 | 0 | 42 |
|  |  | 1:4 | 0 | 38 |
|  | Safener 2 | 1:1 | 0 | 70 |
|  |  | 1:2 | 0 | 60 |
|  |  | 1:4 | 0 | 60 |

Safener 2 = N-(2-methoxybenzoyl)-4-[(methylaminocarbonyl)amino]benzenesulfonamide Results demonstrate that the combination with safeners reduced the phytotoxicity. Degree of reduction is related to type of safener and AI:safener mixture ratio.

Example B4

Reduction of Phytotoxicity by the Use of Safeners Applied as Seed Treatment with a Compounds of Formula I on Wheat Test compounds: compound P1.2 according to Table P1, as SC 050; Safener 1=cloquintocet-mexyl, as WP 25, Safener 2=mefenpyr-diethyl as WP 25, Safener 3=N-(2-methoxybenzoyl)-4-[(methylaminocarbonyl)amino]benzenesulfonamide, as SC 100.

Plants: Wheat, *Triticium durum* (Poaceae) var. *Arina*

Seed treatment: The seeds were treated by shaking the seeds with a slurry for 30 seconds in a glass flask. Treatments were 10% overdosed to compensate for substance adhering to the flask. In a first step, compound P1.2 was treated on the seeds. Afterwards the safeners were treated on the dried seeds. Loading rates: The loading rate of compound P1.2 was 0.1 mg a.i./seed. The loading rates of the safeners were 0.5, 0.1 and 0.025 mg a.i./seed. Soil: "Drench soil", loamy sand, prefertilised with 1 g/l soil of Landor 13.1.3.21.

Procedures: 9-cm pots were filled with 330 ml of Drench soil loamy sand and the seeds were placed into the soil in about 5 mm beneath the soil surface.

Conditions: During the growth period the plants were kept in a randomised fashion in a greenhouse chamber at 25° C. during daytime, 23° C. during night, 50-60% rH, a 14-hour photoperiod and artificial lighting when natural light fell below 20 kLux. During the exposure the assay was kept at 22° C.

Assessments: 14 days after emergence, the phytotoxicity was recorded. The seed safety results are given in Table 2.

TABLE 2

Phytotoxicity (%) of compound P2.1 with safeners on wheat

| mg safener/ seed | 1 mg compound P1.2 + safener 1 | 1 mg compound P1.2 + safener 2 | 1 mg compound P1.2 + safener 3 |
|---|---|---|---|
| 0.025 | 35.7 | 7.1 | 28.6 |
| 0.1 | 14.3 | 14.3 | 42.9 |
| 0.5 | 7.1 | 0 | 64.3 |

Control: application of 1 mg compound P1.2. without safener results in 64.3% phytotoxicity The safeners protect the plants from the adverse effects of the compound P1.2 in all three treatments.

The invention claimed is:

1. A pesticidal composition comprising
(a) a pesticidal effective amount of at least one compound of formula I

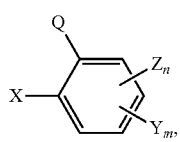

(I)

in which Q is
i

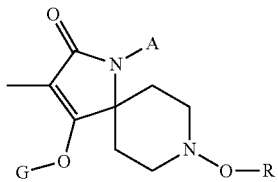

i

X, Y and Z independently of each other are $C_{1-4}$alkyl, $C_{3-6}$cycloalkyl, $C_{1-4}$haloalkyl, $C_{1-4}$ alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, an ammonium, a sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G;

A is $C_{1-6}$alkyl;

or an agrochemically acceptable salt or an N-oxide thereof, and (b) a safener, where the ratio of compound of formula I to safener is from 20:1 to 0.5:15.

2. A composition according to claim 1, wherein the safener is cloquintocet-mexyl, cloquintocet acid or salts thereof, mefenpyr-diethyl, mefenpyr diacid, isoxadifen-ethyl, isoxadifen acid, cyprosulfamide or N-(2-methoxybenzoyl)-4-[(methylaminocarbonyl)amino]-benzenesulfonamide.

3. A composition according to claim 2, wherein the safener is cloquintocet-mexyl, cloquintocet acid or salts thereof, mefenpyr-diethyl, mefenpyr diacid or N-(2-methoxybenzoyl)-4-[(methylaminocarbonyl)amino]-benzenesulfonamide.

4. A composition according to claim 1, wherein the ratio compound of formula I to safener is from 15:1 to 1:10.

5. A method of combating and controlling pests which comprises treating the pests or the locus of the pests or the plant susceptible to attack by a pest or the seeds thereof with an insecticidally, nematicidally or mollusicidally effective amount of a composition according to claim 1.

* * * * *